US009442114B2

(12) United States Patent
Despres et al.

(10) Patent No.: US 9,442,114 B2
(45) Date of Patent: Sep. 13, 2016

(54) ISOLATED AND PURIFIED STRAINS OF CHIKUNGUNYA VIRUS AND POLYNUCLEOTIDES AND POLYPEPTIDES SEQUENCES, DIAGNOSTIC AND IMMUNOGENICAL USES THEREOF

(71) Applicant: INSTITUT PASTEUR, Paris (FR)

(72) Inventors: Philippe Despres, La Garenne Colombes (FR); Anne-Claire Brehin, Paris (FR); Valerie Marechal, Chatillon (FR); Pierre Charneau, Paris (FR); Philippe Souque, Plaisir (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 14/335,065

(22) Filed: Jul. 18, 2014

(65) Prior Publication Data

US 2015/0111197 A1 Apr. 23, 2015

Related U.S. Application Data

(66) Division of application No. 12/225,111, filed on Sep. 29, 2009, now abandoned, Substitute for application No. PCT/IB2007/001716, filed on Mar. 15, 2007.

(30) Foreign Application Priority Data

Mar. 15, 2006 (CA) ..................................... 2538898
Apr. 4, 2006 (CA) ..................................... 2545597

(51) Int. Cl.

| | |
|---|---|
| ***G01N 33/569*** | (2006.01) |
| ***C07K 14/005*** | (2006.01) |
| ***C12N 7/00*** | (2006.01) |
| ***C07K 16/10*** | (2006.01) |
| *A61K 38/00* | (2006.01) |
| *A61K 39/00* | (2006.01) |

(52) U.S. Cl.

CPC ....... *G01N 33/56983* (2013.01); *C07K 14/005* (2013.01); *C07K 16/1081* (2013.01); *C12N 7/00* (2013.01); *A61K 38/00* (2013.01); *A61K 39/00* (2013.01); *C12N 2770/36121* (2013.01); *C12N 2770/36122* (2013.01); *C12N 2770/36131* (2013.01); *G01N 2333/181* (2013.01); *G01N 2800/32* (2013.01)

(58) Field of Classification Search

None

See application file for complete search history.

(56) References Cited

U.S. PATENT DOCUMENTS

2010/0233209 A1* 9/2010 Higgs .................... A61K 39/00 424/218.1
2015/0111197 A1* 4/2015 Despres ............... C07K 14/005 435/5

OTHER PUBLICATIONS

Tsetsarkin et al. (Vector-Borne and Zoonotic Diseases. 2006; 6 (4): 325-337).*

Khan, A.H., Complete nucleotide sequence of chikungunya virus and evidence for an inernal polyadenylation site, *Journal of General Virology* (2002), 83: 3075-3084.

Powers, Ann M., Re-emergence of chikungunya virus and o'nyong-nyong viruses: evidence for distinct geographical lineages and distant evolutionary relationships, *Journal of General Virology* (2000), 81:471-479.

Schuffenecker, I., Genome Microevolution of Chikungunya viruses Causing the Indian Ocean Outbreak, *PLoS Medicine*, (2006) 3:1058-1070.

Kan, A.H., NCBI Sequence No. AF369024 Report (Jan. 14, 2003), pp. 1-6.

Yuzhen, Z., Abstract, Susceptibility of GC32 cell to three strains of arbovirus, (Sep. 1998).

* cited by examiner

*Primary Examiner* — Shanon A Foley

(74) *Attorney, Agent, or Firm* — Law Office of Salvatore Arrigo and Scott Lee, LLP

(57) ABSTRACT

The present invention concerns wild-strains of Chikungunya virus isolated from patients exhibiting severe forms of infection and stemming from a human arbovirosis epidemy. The present invention also concerns polypeptide sequences and fragment thereof derived from their genome, the polynucleotide encoding same and their use as diagnostic products, as vaccine and/or as immunogenic compositions.

17 Claims, 70 Drawing Sheets

FIGURE 1
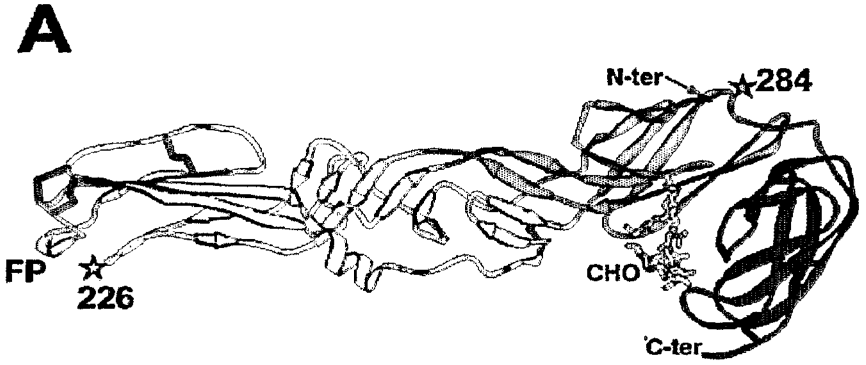
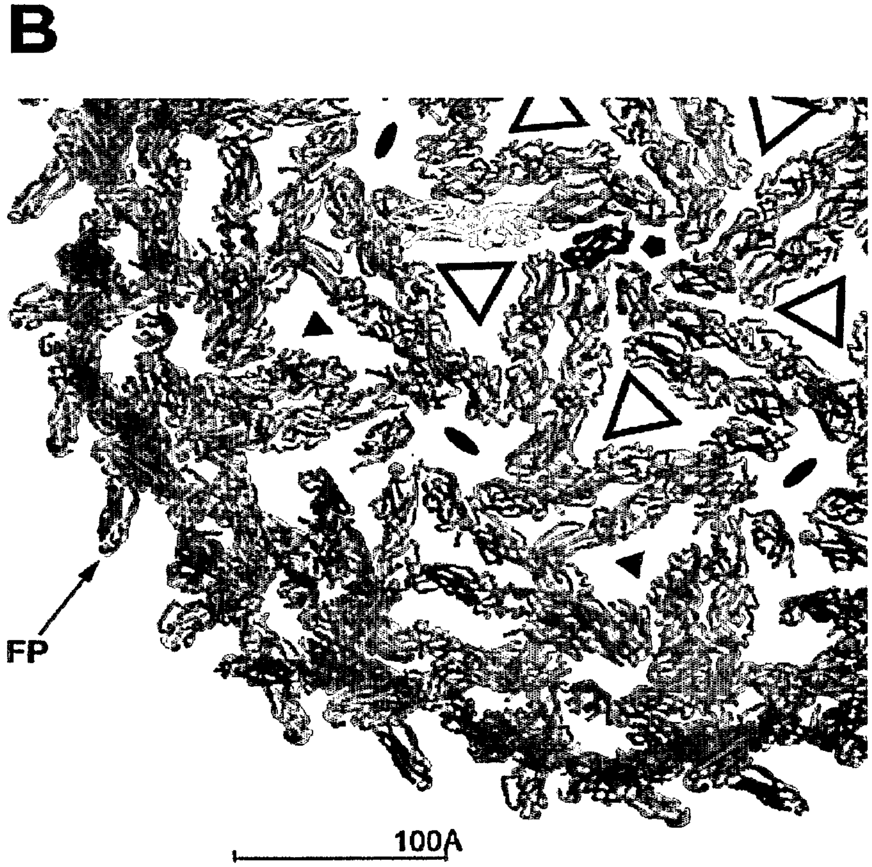

FIGURE 4

```
caaagcaaga gattaataac ccatcatgga tcctgtgtac gtggacatag acgctgacag      60
cgcctttttg aaggccctgc aacgtgcgta ccccatgttt gaggtggaac caaggcaggt     120
cacaccgaat gaccatgcta atgctagagc gttctcgcat ctagctataa aactaataga     180
gcaggaaatt gacccccgact caaccatcct ggatatcggc agtgcgccag caaggaggat     240
gatgtcggac aggaagtacc actgcgtctg cccgatgcgc agtgcggaag atcccgagag     300
actcgccaat tatgcgagaa agctagcatc tgccgcagga aaagtcctgg acagaaacat     360
ctctggaaag atcggggact tacaagcagt aatggccgtg ccagacacgg agacgccaac     420
attctgctta cacacagacg tctcatgtag acagagagca gacgtcgcta tataccaaga     480
cgtctatgct gtacacgcac ccacgtcgct ataccaccag gcgattaaag ggtccgagt      540
ggcgtactgg gttgggttcg acacaacccc gttcatgtac aatgccatgg cgggtgccta     600
cccctcatac tcgacaaact gggcagatga gcaggtactg aaggctaaga acataggatt     660
atgttcaaca gacctgacgg aaggtagacg aggcaagttg tctattatga gagggaaaaa     720
gctaaaaccg tgcgaccgtg tgctgttctc agtagggtca acgctctacc cggaaagccg     780
caagctactt aagagctggc acctgccatc ggtgttccat ttaaagggca aactcagctt     840
cacatgccgc tgtgatacag tggtttcgtg tgagggctac gtcgttaaga gaataacgat     900
gagcccaggc ctttatggaa aaaccacagg gtatgcggta acccaccacg cagacggatt     960
cctgatgtgc aagactaccg acacggttga cggcgaaaga gtgtcattct cggtgtgcac    1020
atacgtgccg gcgaccattt gtgatcaaat gaccggcatc cttgctacag aagtcacgcc    1080
ggaggatgca cagaagctgt tggtggggct gaaccagaga atagtggtta acggcagaac    1140
gcaacggaat acgaacacca tgaaaaatta tctgcttccc gtggtcgccc aagccttcag    1200
taagtgggca aaggagtgcc ggaaagacat ggaagatgaa aaactcctgg gggtcagaga    1260
aagaacactg acctgctgct gtctatgggc attcaagaag cagaaaacac acacggtcta    1320
caagaggcct gatacccagt caattcagaa ggttcaggcc gagtttgaca gctttgtggt    1380
accgagtctg tggtcgtccg ggttgtcaat ccctttgagg actagaatca aatggttgtt    1440
aagcaaggtg ccaaaaaccg acctgatccc atacagcgga gacgcccgag aagcccggga    1500
cgcagaaaaa gaagcagagg aagaacgaga agcagaactg actcgcgaag ccctaccacc    1560
tctacaggca gcacaggaag atgttcaggt cgaaatcgac gtggaacagc ttgaggacag    1620
agcgggcgca ggaataatag agactccgag aggagctatc aaagttactg cccaaccaac    1680
agaccacgtc gtgggagagt acctggtact ctccccgcag accgtactac gtagccagaa    1740
gctcagtctg attcacgctt tggcggagca agtgaagacg tgcacgcaca acggacgagc    1800
agggaggtat gcggtcgaag cgtacgacgg ccgagtccta gtgccctcag gctatgcaat    1860
ctcgcctgaa gacttccaga gtctaagcga aagcgcaacg atggtgtata acgaaagaga    1920
gttcgtaaac agaaagctac accatattgc gatgcacgga ccagccctga acaccgacga    1980
agagtcgtat gagctggtga gggcagagag gacagaacac gagtacgtct acgacgtgga    2040
tcagagaaga tgctgtaaga aggaagaagc cgcaggactg gtactggtgg gcgacttgac    2100
taatccgccc taccacgaat tcgcatatga agggctaaaa atccgccctg cctgcccata    2160
caaaattgca gtcataggag tcttcggagt accgggatct ggcaagtcag ctattatcaa    2220
gaacctagtt accaggcagg acctggtgac tagcggaaag aaagaaaact gccaagaaat    2280
caccaccgac gtgatgagac agagaggtct agagatatct gcacgtacgg ttgactcgct    2340
gctcttgaat ggatgcaaca gaccagtcga cgtgttgtac gtagacgagg cgtttgcgtg    2400
ccactctgga acgctacttg ctttgatcgc cttggtgaga ccaaggcaga aagttgtact    2460
ttgtggtgac ccgaagcagt gcggcttctt caatatgatg cagatgaaag tcaactataa    2520
tcacaacatc tgcacccaag tgtaccacaa aagtatctcc aggcggtgta cactgcctgt    2580
gaccgccatt gtgtcatcgt tgcattacga aggcaaaatg cgcactacga atgagtacaa    2640
caagccgatt gtagtggaca ctacaggctc aacaaaacct gaccctggag acctcgtgtt    2700
aacgtgcttc agagggtggg ttaaacaact gcaaattgac tatcgtggat acgaggtcat    2760
```

FIGURE 4 (con't)

```
gacagcagcc gcatcccaag ggttaaccag aaaaggagtt tacgcagtta gacaaaaagt    2820
taatgaaaac ccgctctatg catcaacgtc agagcacgtc aacgtactcc taacgcgtac    2880
ggaaggtaaa ctggtatgga agacactttc cggcgacccg tggataaaga cgctgcagaa    2940
cccaccgaaa ggaaacttca aagcaactat taaggagtgg gaggtggagc atgcatcaat    3000
aatggcgggc atctgcagtc accaaatgac cttcgataca ttccaaaata aagccaacgt    3060
ttgttgggct aagagcttgg tccctatcct cgaaacagcg gggataaaac taaatgatag    3120
gcagtggtct cagataattc aagccttcaa agaagacaaa gcatactcac ctgaagtagc    3180
cctgaatgaa atatgtacgc gcatgtatgg ggtggatcta gacagcgggc tattttctaa    3240
accgttggtg tctgtgtatt acgcggataa ccactgggat aataggcctg gagggaaaat    3300
gttcggattt aaccccgagg cagcatccat tctagaaaga aagtatccat tcacaaaagg    3360
gaagtggaac atcaacaagc agatctgcgt gactaccagg aggatagaag actttaaccc    3420
taccaccaac atcataccgg ccaacaggag actaccacac tcattagtgg ccgaacaccg    3480
cccagtaaaa ggggaaagaa tggaatggct ggttaacaag ataaacggcc accacgtgct    3540
cctggtcagt ggctataacc ttgcactgcc tactaagaga gtcacttggg tagcgccgtt    3600
aggtgtccgc ggagcggact acacatacaa cctagagttg ggtctgccag caacgcttgg    3660
taggtatgac ctagtggtca taaacatcca cacacctttt cgcatacacc attaccaaca    3720
gtgcgtcgac cacgcaatga aactgcaaat gctcgggggt gactcattga gactgctcaa    3780
accgggcggc tctctattga tcagagcata tggttacgca gatagaacca gtgaacgagt    3840
catctgcgta ttgggacgca agtttagatc gtctagagcg ttgaaaccac catgtgtcac    3900
cagcaacact gagatgtttt tcctattcag caactttgac aatggcagaa ggaatttcac    3960
aactcatgtc atgaacaatc aactgaatgc agccttcgta ggacaggtca cccgagcagg    4020
atgtgcaccg tcgtaccggg taaaacgcat ggacatcgcg aagaacgatg aagagtgcgt    4080
agtcaacgcc gctaaccctc gcgggttacc gggtgacggt gtttgcaagg cagtatacaa    4140
aaaatggccg gagtccttta agaacagtgc aacaccagtg ggaaccgcaa aaacagttat    4200
gtgcggtacg tatccagtaa tccacgctgt tggaccaaac ttctctaatt attcggagtc    4260
tgaaggggac cgggaattgg cagctgccta tcgagaagtc gcaaaggaag taactaggct    4320
gggagtaaat agtgtagcta tacctctcct ctccacaggt gtatactcag gagggaaaga    4380
caggctgacc cagtcactga accacctctt tacagccatg gactcgacgg atgcagacgt    4440
ggtcatctac tgccgcgaca aagaatggga gaagaaaata tctgaggcca tacagatgcg    4500
gacccaagta gagctgctgg atgagcacat ctccatagac tgcgatattg ttcgcgtgca    4560
ccctgacagc agcttggcag gcagaaaagg atacagcacc acggaaggcg cactgtactc    4620
atatctagaa gggacccgtt ttcatcagac ggctgtggat atggcggaga tacatactat    4680
gtggccaaag caaacagagg ccaatgagca agtctgccta tatgccctgg gggaaagtat    4740
tgaatcgatc aggcagaaat gcccggtgga tgatgcagac gcatcatctc cccccaaaac    4800
tgtcccgtgc ctttgccgtt acgctatgac tccagaacgc gtcacccggc ttcgcatgaa    4860
ccacgtcaca agcataattg tgtgttcttc gtttcccctc ccaaagtaca aaatagaagg    4920
agtgcaaaaa gtcaaatgct ctaaggtaat gctatttgac cacaacgtgc catcgcgcgt    4980
aagtccaagg gaatatagat cttcccagga gtctgcacag gaggcgagta caatcacgtc    5040
actgacgcat agtcaattcg acctaagcgt tgatggcgag atactgcccg tcccgtcaga    5100
cctggatgct gacgccccag ccctagaacc agcactagac gacggggcga cacacacgct    5160
gccatccaca accggaaacc ttgcggccgt gtctgattgg gtaatgagca ccgtacctgt    5220
cgcgccgccc agaagaaggc gagggagaaa cctgactgtg acatgtgacg agagagaagg    5280
gaatataaca cccatggcta gcgtccgatt ctttagggca gagctgtgtc cggtcgtaca    5340
agaaacagcg gagacgcgtg acacagcaat gtctcttcag gcaccaccga gtaccgccac    5400
ggaaccgaat catccgccga tctccttcgg agcatcaagc gagacgttcc ccattacatt    5460
tggggacttc aacgaaggag aaatcgaaag cttgtcttct gagctactaa ctttcggaga    5520
```

FIGURE 4 (con't)

```
cttcttacca ggagaagtgg atgacttgac agacagcgac tggtccacgt gctcagacac     5580
ggacgacgag ttatgactag acagggcagg tgggtatata ttctcgtcgg acaccggtcc     5640
aggtcattta caacagaagt cagtacgcca gtcagtgctg ccggtgaaca ccctggagga     5700
agtccacgag gagaagtgtt acccacctaa gctggatgaa gcaaaggagc aactattact     5760
taagaaactc caggagagtg catccatggc caacagaagc aggtatcagt cgcgcaaagt     5820
agaaaacatg aaagcagcaa tcatccagag actaaagaga ggctgtagac tatacttaat     5880
gtcagagacc ccaaaagtcc ctacttaccg gactacatat ccggcgcctg tgtactcgcc     5940
tccgatcaac gtccgattgt ccaatcccga gtccgcagtg gcagcatgca atgagttctt     6000
agctagaaac tatccaactg tctcatcata ccaaattacc gacgagtatg atgcatatct     6060
agacatggtg gacgggtcgg agagttgcct ggaccgagcg acattcaatc cgtcaaaact     6120
caggagctac ccgaaacagc acgcttacca cgcgccctcc atcagaagcg ctgtaccgtc     6180
cccattccag aacacactac agaatgtact ggcagcagcc acgaaaagaa actgcaacgt     6240
cacacagatg agggaattac ccactttgga ctcagcagta ttcaacgtgg agtgtttcaa     6300
aaaattcgca tgcaaccaag aatactggga agaatttgct gccagcccta ttaggataac     6360
aactgagaat ttagcaacct atgttactaa actaaaaggg ccaaaagcag cagcgctatt     6420
cgcaaaaacc cataatctac tgccactaca ggaagtacca atggataggt tcacagtaga     6480
tatgaaaagg gacgtgaagg tgactcctgg tacaaagcat acagaggaaa gacctaaggt     6540
gcaggttata caggcggctg aacccttggc gacagcatac ctatgtggga ttcacagaga     6600
gctggttagg aggctgaacg ccgtcctcct acccaatgta catacactat ttgacatgtc     6660
tgccgaggat ttcgatgcca tcatagccgc acactttaag ccaggagaca ctgttttgga     6720
aacggacata gcctcctttg ataagagcca agatgattca cttgcgctta ctgctttgat     6780
gctgttagag gatttagggg tggatcactc cctgctggac ttgatagagg ctgctttcgg     6840
agagatttcc agctgtcacc taccgacagg tacgcgcttc aagttcggcg ccatgatgaa     6900
atcaggtatg ttcctaactc tgttcgtcaa cacattgtta aacatcacca tcgccagccg     6960
agtgctggaa gatcgtctga caaaatccgc gtgcgcggcc ttcatcggcg acgacaacat     7020
aatacatgga gtcgtctccg atgaattgat ggcagccaga tgtgccactt ggatgaacat     7080
ggaagtgaag atcatagatg cagttgtatc cttgaaagcc ccttactttt gtggagggtt     7140
tatactgcac gatactgtga caggaacagc ttgcagagtg gcagacccgc taaaaaggct     7200
ttttaaactg ggcaaaccgc tagcggcagg tgacgaacaa gatgaagata gaagacgagc     7260
gctggctgac gaagtgatca gatggcaacg aacagggcta attgatgagc tggagaaagc     7320
ggtatactct aggtacgaag tgcagggtat atcagttgtg gtaatgtcca tggccacctt     7380
tgcaagctcc agatccaact tcgagaagct cagaggaccc gtcataactt tgtacggcgg     7440
tcctaaatag gtacgcacta cagctaccta ttttgcagaa gccgacagca agtatctaaa     7500
cactaatcag ctacaatgga gttcatccca acccaaactt tttacaatag gaggtaccag     7560
cctcgaccct ggactccgcg ccctactatc caagtcatca ggcccagacc gcgccctcag     7620
aggcaagctg ggcaacttgc ccagctgatc tcagcagtta ataaactgac aatgcgcgcg     7680
gtaccccaac agaagccacg caggaatcgg aagaataaga agcaaaagca aaaacaacag     7740
gcgccacaaa acaacacaaa tcaaaagaag cagccaccta aaaagaaacc ggctcaaaag     7800
aaaaagaagc cgggccgcag agagaggatg tgcatgaaaa tcgaaaatga ttgtattttc     7860
gaagtcaagc acgaaggtaa ggtaacaggt tacgcgtgcc tggtggggga caaagtaatg     7920
aaaccagcac acgtaaaggg gaccatcgat aacgcggacc tggccaaact ggcctttaag     7980
cggtcatcta agtatgacct tgaatgcgcg cagataccgg tgcacatgaa gtccgacgct     8040
tcgaagttca cccatgagaa accggagggg tactacaact ggcaccacgg agcagtacag     8100
tactcaggag gccggttcac catccctaca ggtgctggca aaccagggga cagcggcaga     8160
ccgatcttcg acaacaaggg acgcgtggtg gccatagtct taggaggagc taatgaagga     8220
gcccgtacag ccctctcggt ggtgacctgg aataaagaca ttgtcactaa aatcaccccc     8280
gaggggggccg aagagtggag tcttgccatc ccagttatgt gcctgttggc aaacaccacg     8340
ttcccctgct cccagccccc ttgcacgccc tgctgctacg aaaaggaacc ggaggaaacc     8400
```

FIGURE 4 (con't)

```
ctacgcatgc ttgaggacaa cgtcatgaga cctgggtact atcagctgct acaagcatcc    8460
ttaacatgtt ctccccaccg ccagcgacgc agcaccaagg acaacttcaa tgtctataaa    8520
gccacaagac catacttagc tcactgtccc gactgtggag aagggcactc gtgccatagt    8580
cccgtagcac tagaacgcat cagaaatgaa gcgacagacg ggacgctgaa aatccaggtc    8640
tccttgcaaa tcggaataaa gacggatgac agccacgatt ggaccaagct gcgttatatg    8700
gacaaccaca tgccagcaga cgcagagagg gcggggctat ttgtaagaac atcagcaccg    8760
tgtacgatta ctggaacaat gggacacttc atcctggccc gatgtccaaa aggggaaact    8820
ctgacggtgg gattcactga cagtaggaag attagtcact catgtacgca cccatttcac    8880
cacgaccctc ctgtgatagg tcgggaaaaa ttccattccc gaccgcagca cggtaaagag    8940
ctaccttgca gcacgtacgt gcagagcacc gccgcaacta ccgaggagat agaggtacac    9000
atgcccccag acacccctga tcgcacatta atgtcacaac agtccggcaa cgtaaagatc    9060
acagtcaatg gccagacggt gcggtacaag tgtaattgcg gtggctcaaa tgaaggacta    9120
acaactacag acaaagtgat taataactgc aaggttgatc aatgtcatgc cgcggtcacc    9180
aatcacaaaa agtggcagta taactcccct ctggtcccgc gtaatgctga acttggggac    9240
cgaaaaggaa aaattcacat cccgtttccg ctggcaaatg taacatgcag ggtgcctaaa    9300
gcaaggaacc ccaccgtgac gtacgggaaa aaccaagtca tcatgctact gtatcctgac    9360
cacccaacac tcctgtccta ccggaatatg ggagaagaac caaactatca agaagagtgg    9420
gtgatgcata agaaggaagt cgtgctaacc gtgccgactg aagggctcga ggtcacgtgg    9480
ggcaacaacg agccgtataa gtattggccg cagttatcta caaacggtac agcccatggc    9540
cacccgcatg agataattct gtattattat gagctgtacc ccactatgac tgtagtagtt    9600
gtgtcagtgg ccacgttcat actcctgtcg atggtgggta tggcagcggg gatgtgcatg    9660
tgtgcacgac gcagatgcat cacaccgtat gaactgacac caggagctac cgtccctttc    9720
ctgcttagcc taatatgctg catcagaaca gctaaagcgg ccacatacca agaggctgcg    9780
atatacctgt ggaacgagca gcaacctttg ttttggctac aagcccttat tccgctggca    9840
gccctgattg ttctatgcaa ctgtctgaga ctcttaccat gctgctgtaa aacgttggct    9900
tttttagccg taatgagcgt cggtgcccac actgtgagcg cgtacgaaca cgtaacagtg    9960
atcccgaaca cggtgggagt accgtataag actctagtca atagacctgg ctacagcccc   10020
atggtattgg agatggaact actgtcagtc actttggagc caacactatc gcttgattac   10080
atcacgtgcg agtacaaaac cgtcatcccg tctccgtacg tgaagtgctg cggtacagca   10140
gagtgcaagg acaaaaacct acctgactac agctgtaagg tcttcaccgg cgtctaccca   10200
tttatgtggg gcggcgccta ctgcttctgc gacgctgaaa acacgcagtt gagcgaagca   10260
cacgtggaga agtccgaatc atgcaaaaca gaatttgcat cagcatacag ggctcatacc   10320
gcatctgcat cagctaagct ccgcgtcctt taccaaggaa ataacatcac tgtaactgcc   10380
tatgcaaacg gcgaccatgc cgtcacagtt aaggacgcca aattcattgt ggggccaatg   10440
tcttcagcct ggacaccttt cgacaacaaa attgtggtgt acaaaggtga cgtctataac   10500
atggactacc cgccctttgg cgcaggaaga ccaggacaat ttggcgatat ccaaagtcgc   10560
acacctgaga gtaaagacgt ctatgctaat acacaactgg tactgcagag accggctgcg   10620
ggtacggtac acgtgccata ctctcaggca ccatctggct ttaagtattg gctaaaagaa   10680
cgcggggcgt cgctgcagca cacagcacca tttggctgcc aaatagcaac aaacccggta   10740
agagcggtga actgcgccgt agggaacatg cccatctcca tcgacatacc ggaagcggcc   10800
ttcactaggg tcgtcgacgc gccctcttta acggacatgt cgtgcgaggt accagcctgc   10860
acccattcct cagactttgg gggcgtcgcc attattaaat atgcagccag caagaaaggc   10920
aagtgtgcgg tgcattcgat gactaacgcc gtcactattc gggaagctga gatagaagtt   10980
gaagggaatt ctcagctgca aatctctttc tcgacggcct tagccagcgc cgaattccgc   11040
gtacaagtct gttctacaca agtacactgt gcagccgagt gccacccccc gaaggaccac   11100
atagtcaact acccggcgtc acataccacc ctcggggtcc aggacatctc cgctacggcg   11160
atgtcatggg tgcagaagat cacgggaggt gtgggactgg ttgttgctgt tgccgcactg   11220
attctaatcg tggtgctatg cgtgtcgttc agcaggcact aacttgacaa ttaagtatga   11280
```

FIGURE 4 (con't)

```
aggtatatgt gtcccctaag agacacactg tacatagcaa ataatctata gatcaaaggg   11340
ctacgcaacc cctgaatagt aacaaaatac aaaatcacta aaaattataa aaacagaaaa   11400
atacataaat aggtatacgt gtcccctaag agacacattg tatgtaggtg ataagtatag   11460
atcaaagggc cgaataaccc ctgaatagta acaaaatatg aaaatcaata aaaatcataa   11520
aatagaaaaa ccataaacag aagtagttca aagggctata aaacccctga atagtaacaa   11580
aacataaaat taataaaaat c                                             11601
```

FIGURE 5

```
caaagcaaga gattaataac ccatcatgga tcctgtgtac gtggacatag acgctgacag     60
cgcctttttg aaggccctgc aacgtgcgta ccccatgttt gaggtggaac caaggcaggt    120
cacaccgaat gaccatgcta atgctagagc gttctcgcat ctagctataa aactaataga    180
gcaggaaatt gaccccgact caaccatcct ggatatcggc agtgcgccag caaggaggat    240
gatgtcggac aggaagtacc actgcgtctg cccgatgcgc agtgcggaag atcccgagag    300
actcgccaat tatgcgagaa agctagcatc tgccgcagga aaagtcctgg acagaaacat    360
ctctggaaag atcggggact tacaagcagt aatggccgtg ccagacacgg agacgccaac    420
attctgctta cacacagacg tctcatgtag acagagagca gacgtcgcta tataccaaga    480
cgtctatgct gtacacgcac ccacgtcgct ataccaccag gcgattaaag ggtccgagt    540
ggcgtactgg gttgggttcg acacaacccc gttcatgtac aatgccatgg cgggtgccta    600
cccctcatac tcgacaaact gggcagatga gcaggtactg aaggctaaga acataggatt    660
atgttcaaca gacctgacgg aaggtagacg aggcaagttg tctattatga gagggaaaaa    720
gctaaaaccg tgcgaccgtg tgctgttctc agtagggtca acgctctacc cggaaagccg    780
caagctactt aagagctggc acctgccatc ggtgttccat ttaaagggca aactcagctt    840
cacatgccgc tgtgatacag tggtttcgtg tgagggctac gtcgttaaga gaataacgat    900
gagcccaggc ctttatggaa aaaccacagg gtatgcggta acccaccacg cagacggatt    960
cctgatgtgc aagactaccg acacggttga cggcgaaaga gtgtcattct cggtgtgcac   1020
atacgtgccg gcgaccattt gtgatcaaat gaccggcatc cttgctacag aagtcacgcc   1080
ggaggatgca cagaagctgt tggtggggct gaaccagaga atagtggtta acggcagaac   1140
gcaacggaat acgaacacca tgaaaaatta tctgcttccc gtggtcgccc aagccttcag   1200
taagtgggca aaggagtgcc ggaaagacat ggaagatgaa aaactcctgg gggtcagaga   1260
aagaacactg acctgctgct gtctatgggc attcaagaag cagaaaacac acacggtcta   1320
caagaggcct gatacccagt caattcagaa ggttcaggcc gagtttgaca gctttgtggt   1380
accgagtctg tggtcgtccg ggttgtcaat ccctttgagg actagaatca aatggttgtt   1440
aagcaaggtg ccaaaaaccg acctgatccc atacagcgga gacgcccgag aagcccggga   1500
cgcagaaaaa gaagcagagg aagaacgaga agcagaactg actcgcgaag ccctaccacc   1560
tctacaggca gcacaggaag atgttcaggt cgaaatcgac gtggaacagc ttgaggacag   1620
agcgggcgca ggaataatag agactccgag aggagctatc aaagttactg cccaaccaac   1680
agaccacgtc gtgggagagt acctggtact ctccccgcag accgtactac gtagccagaa   1740
gctcagtctg attcacgctt tggcggagca agtgaagacg tgcacgcaca acggacgagc   1800
agggaggtat gcggtcgaag cgtacgacgg ccgagtccta gtgccctcag gctatgcaat   1860
ctcgcctgaa gacttccaga gtctaagcga aagcgcaacg atggtgtata acgaaagaga   1920
gttcgtaaac agaaagctac accatattgc gatgcacgga ccagccctga acaccgacga   1980
agagtcgtat gagctggtga gggcagagag gacagaacac gagtacgtct acgacgtgga   2040
tcagagaaga tgctgtaaga aggaagaagc cgcaggactg gtactggtgg gcgacttgac   2100
taatccgccc taccacgaat tcgcatatga agggctaaaa atccgccctg cctgcccata   2160
caaaattgca gtcataggag tcttcggagt accgggatct ggcaagtcag ctattatcaa   2220
gaacctagtt accaggcagg acctggtgac tagcggaaag aaagaaaact gccaagaaat   2280
caccaccgac gtgatgagac agagaggtct agagatatct gcacgtacgg ttgactcgct   2340
gctcttgaat ggatgcaaca gaccagtcga cgtgttgtac gtagacgagg cgtttgcgtg   2400
ccactctgga acgctacttg ctttgatcgc cttggtgaga ccaaggcaga aagttgtact   2460
ttgtggtgac ccgaagcagt gcggcttctt caatatgatg cagatgaaag tcaactataa   2520
tcacaacatc tgcacccaag tgtaccacaa aagtatctcc aggcggtgta cactgcctgt   2580
gaccgccatt gtgtcatcgt tgcattacga aggcaaaatg cgcactacga atgagtacaa   2640
caagccgatt gtagtggaca ctacaggctc aacaaaacct gaccctggag acctcgtgtt   2700
aacgtgcttc agagggtggg ttaaacaact gcaaattgac tatcgtggat acgaggtcat   2760
gacagcagcc gcatcccaag ggttaaccag aaaaggagtt tacgcagtta gacaaaaagt   2820
```

FIGURE 5 (con't)

```
taatgaaaac ccgctctatg catcaacgtc agagcacgtc aacgtactcc taacgcgtac     2880
ggaaggtaaa ctggtatgga agacactttc cggcgacccg tggataaaga cgctgcagaa     2940
cccaccgaaa ggaaacttca aagcaactat taaggagtgg gaggtggagc atgcatcaat     3000
aatggcgggc atctgcagtc accaaatgac cttcgataca ttccaaaata aagccaacgt     3060
ttgttgggct aagagcttgg tccctatcct cgaaacagcg gggataaaac taaatgatag     3120
gcagtggtct cagataattc aagccttcaa agaagacaaa gcatactcac ctgaagtagc     3180
cctgaatgaa atatgtacgc gcatgtatgg ggtggatcta gacagcgggc tattttctaa     3240
accgttggtg tctgtgtatt acgcggataa ccactgggat aataggcctg gagggaaaat     3300
gttcggattt aaccccgagg cagcatccat tctagaaaga aagtatccat tcacaaaagg     3360
gaagtggaac atcaacaagc agatctgcgt gactaccagg aggatagaag actttaaccc     3420
taccaccaac atcataccgg ccaacaggag actaccacac tcattagtgg ccgaacaccg     3480
cccagtaaaa ggggaaagaa tggaatggct ggttaacaag ataaacggcc accacgtgct     3540
cctggtcagt ggctataacc ttgcactgcc tactaagaga gtcacttggg tagcgccgtt     3600
aggtgtccgc ggagcggact acacatacaa cctagagttg ggtctgccag caacgcttgg     3660
taggtatgac ctagtggtca taaacatcca cacacctttt cgcatacacc attaccaaca     3720
gtgcgtcgac cacgcaatga aactgcaaat gctcgggggt gactcattga gactgctcaa     3780
accgggcggc tctctattga tcagagcata tggttacgca gatagaacca gtgaacgagt     3840
catctgcgta ttgggacgca agtttagatc gtctagagcg ttgaaaccac catgtgtcac     3900
cagcaacact gagatgtttt tcctattcag caactttgac aatggcagaa ggaatttcac     3960
aactcatgtc atgaacaatc aactgaatgc agccttcgta ggacaggtca cccgagcagg     4020
atgtgcaccg tcgtaccggg taaaacgcat ggacatcgcg aagaacgatg aagagtgcgt     4080
agtcaacgcc gctaaccctc gcgggttacc gggtgacggt gtttgcaagg cagtatacaa     4140
aaaatggccg gagtccttta agaacagtgc aacaccagtg ggaaccgcaa aaacagttat     4200
gtgcggtacg tatccagtaa tccacgctgt tggaccaaac ttctctaatt attcggagtc     4260
tgaaggggac cgggaattgg cagctgccta tcgagaagtc gcaaaggaag taactaggct     4320
gggagtaaat agtgtagcta tacctctcct ctccacaggt gtatactcag gagggaaaga     4380
caggctgacc cagtcactga accacctctt tacagccatg gactcgacgg atgcagacgt     4440
ggtcatctac tgccgcgaca aagaatggga gaagaaaata tctgaggcca tacagatgcg     4500
gacccaagta gagctgctgg atgagcacat ctccatagac tgcgatattg ttcgcgtgca     4560
ccctgacagc agcttggcag gcagaaaagg atacagcacc acggaaggcg cactgtactc     4620
atatctagaa gggacccgtt ttcatcagac ggctgtggat atggcggaga tacatactat     4680
gtggccaaag caaacagagg ccaatgagca agtctgccta tatgccctgg gggaaagtat     4740
tgaatcgatc aggcagaaat gcccggtgga tgatgcagac gcatcatctc cccccaaaac     4800
tgtcccgtgc ctttgccgtt acgctatgac tccagaacgc gtcacccggc ttcgcatgaa     4860
ccacgtcaca agcataattg tgtgttcttc gtttcccctc ccaaagtaca aaatagaagg     4920
agtgcaaaaa gtcaaatgct ctaaggtaat gctatttgac cacaacgtgc catcgcgcgt     4980
aagtccaagg gaatatagat cttcccagga gtctgcacag gaggcgagta caatcacgtc     5040
actgacgcat agtcaattcg acctaagcgt tgatggcgag atactgcccg tcccgccaga     5100
cctggatgct gacgccccag ccctagaacc agcactagac gacggggcga cacacacgct     5160
gccatccaca accggaaacc ttgcggccgt gtctgattgg gtaatgagca ccgtacctgt     5220
cgcgccgccc agaagaaggc gagggagaaa cctgactgtg acatgtgacg agagagaagg     5280
gaatataaca cccatggcta gcgtccgatt ctttagggca gagctgtgtc cggtcgtaca     5340
agaaacagcg gagacgcgtg acacagcaat gtctcttcag gcaccaccga gtaccgccac     5400
ggaaccgaat catccgccga tctccttcgg agcatcaagc gagacgttcc ccattacatt     5460
tggggacttc aacgaaggag aaatcgaaag cttgtcttct gagctactaa ctttcggaga     5520
cttcttacca ggagaagtgg atgacttgac agacagcgac tggtccacgt gctcagacac     5580
ggacgacgag ttatgactag acagggcagg tgggtatata ttctcgtcgg acaccggtcc     5640
```

FIGURE 5 (con't)

```
aggtcattta caacagaagt cagtacgcca gtcagtgctg ccggtgaaca ccctggagga    5700
agtccacgag gagaagtgtt acccacctaa gctggatgaa gcaaaggagc aactattact    5760
taagaaactc caggagagtg catccatggc caacagaagc aggtatcagt cgcgcaaagt    5820
agaaaacatg aaagcagcaa tcatccagag actaaagaga ggctgtagac tatacttaat    5880
gtcagagacc ccaaaagtcc ctacttaccg gactacatat ccggcgcctg tgtactcgcc    5940
tccgatcaac gtccgattgt ccaatcccga gtccgcagtg gcagcatgca atgagttctt    6000
agctagaaac tatccaactg tctcatcata ccaaattacc gacgagtatg atgcatatct    6060
agacatggtg gacgggtcgg agagttgcct ggaccgagcg acattcaatc cgtcaaaact    6120
caggagctac ccgaaacagc acgcttacca cgcgccctcc atcagaagcg ctgtaccgtc    6180
cccattccag aacacactac agaatgtact ggcagcagcc acgaaaagaa actgcaacgt    6240
cacacagatg agggaattac ccactttgga ctcagcagta ttcaacgtgg agtgtttcaa    6300
aaaattcgca tgcaaccaag aatactggga agaatttgct gccagcccta ttaggataac    6360
aactgagaat ttagcaacct atgttactaa actaaaaggg ccaaaagcag cagcgctatt    6420
cgcaaaaacc cataatctac tgccactaca ggaagtacca atggataggt tcacagtaga    6480
tatgaaaagg gacgtgaagg tgactcctgg tacaaagcat acagaggaaa gacctaaggt    6540
gcaggttata caggcggctg aacccttggc gacagcatac ctatgtggga ttcacagaga    6600
gctggttagg aggctgaacg ccgtcctcct acccaatgta catacactat ttgacatgtc    6660
tgccgaggat ttcgatgcca tcatagccgc acactttaag ccaggagaca ctgttttgga    6720
aacggacata gcctcctttg ataagagcca agatgattca cttgcgctta ctgctttgat    6780
gctgttagag gatttagggg tggatcactc cctgctggac ttgatagagg ctgctttcgg    6840
agagatttcc agctgtcacc taccgacagg tacgcgcttc aagttcggcg ccatgatgaa    6900
atcaggtatg ttcctaactc tgttcgtcaa cacattgtta aacatcacca tcgccagccg    6960
agtgctggaa gatcgtctga caaaatccgc gtgtgcggcc ttcatcggcg acgacaacat    7020
aatacatgga gtcgtctccg atgaattgat ggcagccaga tgtgccactt ggatgaacat    7080
ggaagtgaag atcatagatg cagttgtatc cttgaaagcc ccttactttt gtggagggtt    7140
tatactgcac gatactgtga caggaacagc ttgcagagtg gcagacccgc taaaaaggct    7200
ttttaaactg ggcaaaccgc tagcggcagg tgacgaacaa gatgaagata gaagacgagc    7260
gctggctgac gaagtgatca gatggcaacg aacagggcta attgatgagc tggagaaagc    7320
ggtatactct aggtacgaag tgcagggtat atcagttgtg gtaatgtcca tggccacctt    7380
tgcaagctcc agatccaact tcgagaagct cagaggaccc gtcataactt tgtacggcgg    7440
tcctaaatag gtacgcacta cagctaccta ttttgcagaa gccgacagca agtatctaaa    7500
cactaatcag ctacaatgga gttcatccca acccaaactt tttacaatag gaggtaccag    7560
cctcgaccct ggactccgcg ccctactatc caagtcatca ggcccagacc gcgccctcag    7620
aggcaagctg ggcaacttgc ccagctgatc tcagcagtta ataaactgac aatgcgcgcg    7680
gtaccccaac agaagccacg caggaatcgg aagaataaga agcaaaagca aaaacaacag    7740
gcgccacaaa acaacacaaa tcaaaagaag cagccaccta aaaagaaacc ggctcaaaag    7800
aaaaagaagc cgggccgcag agagaggatg tgcatgaaaa tcgaaaatga ttgtattttc    7860
gaagtcaagc acgaaggtaa ggtaacaggt tacgcgtgcc tggtggggga caaagtaatg    7920
aaaccagcac acgtaaaggg gaccatcgat aacgcggacc tggccaaact ggcctttaag    7980
cggtcatcta agtatgacct tgaatgcgcg cagatacccg tgcacatgaa gtccgacgct    8040
tcgaagttca cccatgagaa accggagggg tactacaact ggcaccacgg agcagtacag    8100
tactcaggag gccggttcac catccctaca ggtgctggca aaccagggga cagcggcaga    8160
ccgatcttcg acaacaaggg acgcgtggtg gccatagtct taggaggagc taatgaagga    8220
gcccgtacag ccctctcggt ggtgacctgg aataaagaca ttgtcactaa aatcaccccc    8280
gaggggggccg aagagtggag tcttgccatc ccagttatgt gcctgttggc aaacaccacg    8340
ttcccctgct cccagccccc ttgcacgccc tgctgctacg aaaaggaacc ggaggaaacc    8400
ctacgcatgc ttgaggacaa cgtcatgaga cctgggtact atcagctgct acaagcatcc    8460
ttaacatgtt ctccccaccg ccagcgacgc agcaccaagg acaacttcaa tgtctataaa    8520
```

FIGURE 5 (con't)

```
gccacaagac catacttagc tcactgtccc gactgtggag aagggcactc gtgccatagt     8580
cccgtagcac tagaacgcat cagaaatgaa gcgacagacg ggacgctgaa aatccaggtc     8640
tccttgcaaa tcggaataaa gacggatgac agccacgatt ggaccaagct gcgttatatg     8700
gacaaccaca tgccagcaga cgcagagagg gcggggctat ttgtaagaac atcagcaccg     8760
tgtacgatta ctggaacaat gggacacttc atcctggccc gatgtccaaa aggggaaact     8820
ctgacggtgg gattcactga cagtaggaag attagtcact catgtacgca cccatttcac     8880
cacgaccctc ctgtgatagg tcgggaaaaa ttccattccc gaccgcggca cggtaaagag     8940
ctaccttgca gcacgtacgt gcagagcacc gccgcaacta ccgaggagat agaggtacac     9000
atgcccccag acacccctga tcgcacatta atgtcacaac agtccggcaa cgtaaagatc     9060
acagtcaatg gccagacggt gcggtacaag tgtaattgcg gtggctcaaa tgaaggacta     9120
acaactacag acaaagtgat taataactgc aaggttgatc aatgtcatgc cgcggtcacc     9180
aatcacaaaa agtggcagta taactcccct ctggtcccgc gtaatgctga acttggggac     9240
cgaaaaggaa aaattcacat cccgtttccg ctggcaaatg taacatgcag ggtgcctaaa     9300
gcaaggaacc ccaccgtgac gtacgggaaa aaccaagtca tcatgctact gtatcctgac     9360
cacccaacac tcctgtccta ccggaatatg ggagaagaac caaactatca agaagagtgg     9420
gtgatgcata agaaggaagt cgtgctaacc gtgccgactg aagggctcga ggtcacgtgg     9480
ggcaacaacg agccgtataa gtattggccg cagttatcta caaacggtac agcccatggc     9540
cacccgcatg agataattct gtattattat gagctgtacc ccactatgac tgtagtagtt     9600
gtgtcagtgg ccacgttcat actcctgtcg atggtgggta tggcagcggg gatgtgcatg     9660
tgtgcacgac gcagatgcat cacaccgtat gaactgacac caggagctac cgtccctttc     9720
ctgcttagcc taatatgctg catcagaaca gctaaagcgg ccacatacca agaggctgcg     9780
atatacctgt ggaacgagca gcaacctttg ttttggctac aagcccttat tccgctggca     9840
gccctgattg ttctatgcaa ctgtctgaga ctcttaccat gctgctgtaa aacgttggct     9900
tttttagccg taatgagcgt cggtgcccac actgtgagcg cgtacgaaca cgtaacagtg     9960
atcccgaaca cggtgggagt accgtataag actctagtca atagacctgg ctacagcccc    10020
atggtattgg agatggaact actgtcagtc actttggagc caacactatc gcttgattac    10080
atcacgtgcg agtacaaaac cgtcatcccg tctccgtacg tgaagtgctg cggtacagca    10140
gagtgcaagg acaaaaacct acctgactac agctgtaagg tcttcaccgg cgtctaccca    10200
tttatgtggg gcggcgccta ctgcttctgc gacgctgaaa acacgcagtt gagcgaagca    10260
cacgtggaga agtccgaatc atgcaaaaca gaatttgcat cagcatacag ggctcatacc    10320
gcatctgcat cagctaagct ccgcgtcctt taccaaggaa ataacatcac tgtaactgcc    10380
tatgcaaacg gcgaccatgc cgtcacagtt aaggacgcca aattcattgt ggggccaatg    10440
tcttcagcct ggacaccttt cgacaacaaa attgtggtgt acaaaggtga cgtctataac    10500
atggactacc cgccctttgg cgcaggaaga ccaggacaat ttggcgatat ccaaagtcgc    10560
acacctgaga gtaaagacgt ctatgctaat acacaactgg tactgcagag accggctgcg    10620
ggtacggtac acgtgccata ctctcaggca ccatctggct ttaagtattg gctaaaagaa    10680
cgcggggcgt cgctgcagca cacagcacca tttggctgcc aaatagcaac aaacccggta    10740
agagcggtga actgcgccgt agggaacatg cccatctcca tcgacatacc ggaagcggcc    10800
ttcactaggg tcgtcgacgc gccctcttta acggacatgt cgtgcgaggt accagcctgc    10860
acccattcct cagactttgg gggcgtcgcc attattaaat atgcagccag caagaaaggc    10920
aagtgtgcgg tgcattcgat gactaacgcc gtcactattc gggaagctga gatagaagtt    10980
gaagggaatt ctcagctgca aatctctttc tcgacggcct tagccagcgc cgaattccgc    11040
gtacaagtct gttctacaca agtacactgt gcagccgagt gccacccccc gaaggaccac    11100
atagtcaact acccggcgtc acataccacc ctcggggtcc aggacatctc cgctacggcg    11160
atgtcatggg tgcagaagat cacgggaggt gtgggactgg ttgttgctgt tgccgcactg    11220
attctaatcg tggtgctatg cgtatcgttc agcaggcact aacttgacaa ttaagtatga    11280
aggtatatgt gtcccctaag agacacactg tacatagcaa ataatctata gatcaaaggg    11340
ctacgcaacc cctgaatagt aacaaaatac aaaatcacta aaaattataa aaacagaaaa    11400
```

FIGURE 5 (con't)

```
atacataaat aggtatacgt gtcccctaag agacacattg tatgtaggtg ataagtatag   11460
atcaaagggc cgaataaccc ctgaatagta acaaaatatg aaaatcaata aaaatcataa   11520
aatagaaaaa ccataaacag aagtagttca aagggctata aaacccctga atagtaacaa   11580
aacataaaat taataaaaat c                                             11601
```

FIGURE 6

```
caaagcaaga gattaataac ccatcatgga tcctgtgtac gtggacatag acgctgacag      60
cgcctttttg aaggccctgc aacgtgcgta ccccatgttt gaggtggaac caaggcaggt     120
cacaccgaat gaccatgcta atgctagagc gttctcgcat ctagctataa aactaataga     180
gcaggaaatt gaccccgact caaccatcct ggatatcggc agtgcgccag caaggaggat     240
gatgtcggac aggaagtacc actgcgtctg cccgatgcgc agtgcggaag atcccgagag     300
actcgccaat tatgcgagaa agctagcatc tgccgcagga aaagtcctgg acagaaacat     360
ctctggaaag atcggggact tacaagcagt aatggccgtg ccagacacgg agacgccaac     420
attctgctta cacacagacg tctcatgtag acagagagca gacgtcgcta tataccaaga     480
cgtctatgct gtacacgcac ccacgtcgct ataccaccag gcgattaaag ggtccgagt     540
ggcgtactgg gttgggttcg acacaacccc gttcatgtac aatgccatgg cgggtgccta     600
cccctcatac tcgacaaact gggcagatga gcaggtactg aaggctaaga acataggatt     660
atgttcaaca gacctgacgg aaggtagacg aggcaagttg tctattatga gagggaaaaa     720
gctaaaaccg tgcgaccgtg tgctgttctc agtagggtca acgctctacc cggaaagccg     780
caagctactt aagagctggc acctgccatc ggtgttccat ttaaagggca aactcagctt     840
cacatgccgc tgtgatacag tggtttcgtg tgagggctac gtcgttaaga gaataacgat     900
gagcccaggc ctttatggaa aaaccacagg gtatgcggta acccaccacg cagacggatt     960
cctgatgtgc aagactaccg acacggttga cggcgaaaga gtgtcattct cggtgtgcac    1020
atacgtgccg gcgaccattt gtgatcaaat gaccggcatc cttgctacag aagtcacgcc    1080
ggaggatgca cagaagctgt tggtggggct gaaccagaga atagtggtta acggcagaac    1140
gcaacggaat acgaacacca tgaaaaatta tctgcttccc gtggtcgccc aagccttcag    1200
taagtgggca aaggagtgcc ggaaagacat ggaagatgaa aaactcctgg gggtcagaga    1260
aagaacactg acctgctgct gtctatgggc attcaagaag cagaaaacac acacggtcta    1320
caagaggcct gatacccagt caattcagaa ggttcaggcc gagtttgaca gctttgtggt    1380
accgagtctg tggtcgtccg ggttgtcaat ccctttgagg actagaatca aatggttgtt    1440
aagcaaggtg ccaaaaaccg acctgatccc atacagcgga gacgcccgag aagcccggga    1500
cgcagaaaaa gaagcagagg aagaacgaga agcagaactg actcgcgaag ccctaccacc    1560
tctacaggca gcacaggaag atgttcaggt cgaaatcgac gtggaacagc ttgaggacag    1620
agcgggcgca ggaataatag agactccgag aggagctatc aaagttactg cccaaccaac    1680
agaccacgtc gtgggagagt acctggtact ctccccgcag accgtactac gtagccagaa    1740
gctcagtctg attcacgctt tggcggagca agtgaagacg tgcacgcaca acggacgagc    1800
agggaggtat gcggtcgaag cgtacgacgg ccgagtccta gtgccctcag gctatgcaat    1860
ctcgcctgaa gacttccaga gtctaagcga aagcgcaacg atggtgtata acgaaagaga    1920
gttcgtaaac agaaagctac accatattgc gatgcacgga ccagccctga acaccgacga    1980
agagtcgtat gagctggtga gggcagagag gacagaacac gagtacgtct acgacgtgga    2040
tcagagaaga tgctgtaaga aggaagaagc cgcaggactg gtactggtgg gcgacttgac    2100
taatccgccc taccacgaat tcgcatatga agggctaaaa atccgccctg cctgcccata    2160
caaaattgca gtcataggag tcttcggagt accgggatct ggcaagtcag ctattatcaa    2220
gaacctagtt accaggcagg acctggtgac tagcggaaag aaagaaaact gccaagaaat    2280
caccaccgac gtgatgagac agagaggtct agagatatct gcacgtacgg ttgactcgct    2340
gctcttgaat ggatgcaaca gaccagtcga cgtgttgtac gtagacgagg cgtttgcgtg    2400
ccactctgga acgctacttg ctttgatcgc cttggtgaga ccaaggcaga aagttgtact    2460
ttgtggtgac ccgaagcagt gcggcttctt caatatgatg cagatgaaag tcaactataa    2520
tcacaacatc tgcacccaag tgtaccacaa aagtatctcc aggcggtgta cactgcctgt    2580
gaccgccatt gtgtcatcgt tgcattacga aggcaaaatg cgcactacga atgagtacaa    2640
caagccgatt gtagtggaca ctacaggctc aacaaaacct gaccctggag acctcgtgtt    2700
aacgtgcttc agagggtggg ttaaacaact gcaaattgac tatcgtggat acgaggtcat    2760
gacagcagcc gcatcccaag ggttaaccag aaaaggagtt tacgcagtta gacaaaagt     2820
```

FIGURE 6 (con't)

```
taatgaaaac ccgctctatg catcaacgtc agagcacgtc aacgtactcc taacgcgtac 2880
ggaaggtaaa ctggtatgga agacactttc cggcgacccg tggataaaga cgctgcagaa 2940
cccaccgaaa ggaaacttca aagcaactat taaggagtgg gaggtggagc atgcatcaat 3000
aatggcgggc atctgcagtc accaaatgac cttcgataca ttccaaaata aagccaacgt 3060
ttgttgggct aagagcttgg tccctatcct cgaaacagcg ggataaaac taaatgatag 3120
gcagtggtct cagataattc aagccttcaa agaagacaaa gcatactcac ctgaagtagc 3180
cctgaatgaa atatgtacgc gcatgtatgg ggtggatcta gacagcgggc tattttctaa 3240
accgttggtg tctgtgtatt acgcggataa ccactgggat aataggcctg gagggaaaat 3300
gttcggattt aaccccgagg cagcatccat tctagaaaga aagtatccat tcacaaaagg 3360
gaagtggaac atcaacaagc agatctgcgt gactaccagg aggatagaag actttaaccc 3420
taccaccaac atcataccgg ccaacaggag actaccacac tcattagtgg ccgaacaccg 3480
cccagtaaaa ggggaaagaa tggaatggct ggttaacaag ataaacggcc accacgtgct 3540
cctggtcagt ggctataacc ttgcactgcc tactaagaga gtcacttggg tagcgccgtt 3600
aggtgtccgc ggagcggact acacatacaa cctagagttg ggtctgccag caacgcttgg 3660
taggtatgac ctagtggtca taaacatcca cacacctttt cgcatacacc attaccaaca 3720
gtgcgtcgac cacgcaatga aactgcaaat gctcgggggt gactcattga gactgctcaa 3780
accgggcggc tctctattga tcagagcata tggttacgca gatagaacca gtgaacgagt 3840
catctgcgta ttgggacgca agtttagatc gtctagagcg ttgaaaccac catgtgtcac 3900
cagcaacact gagatgtttt tcctattcag caactttgac aatggcagaa ggaatttcac 3960
aactcatgtc atgaacaatc aactgaatgc agccttcgta ggacaggtca cccgagcagg 4020
atgtgcaccg tcgtaccggg taaaacgcat ggacatcgcg aagaacgatg aagagtgcgt 4080
agtcaacgcc gctaaccctc gcgggttacc gggtgacggt gtttgcaagg cagtatacaa 4140
aaaatggccg gagtccttta agaacagtgc aacaccagtg ggaaccgcaa aaacagttat 4200
gtgcggtacg tatccagtaa tccacgctgt tggaccaaac ttctctaatt attcggagtc 4260
tgaaggggac cgggaattgg cagctgccta tcgagaagtc gcaaaggaag taactaggct 4320
gggagtaaat agtgtagcta tacctctcct ctccacaggt gtatactcag gagggaaaga 4380
caggctgacc cagtcactga accacctctt tacagccatg gactcgacgg atgcagacgt 4440
ggtcatctac tgccgcgaca aagaatggga gaagaaaata tctgaggcca tacagatgcg 4500
gacccaagta gagctgctgg atgagcacat ctccatagac tgcgatattg ttcgcgtgca 4560
ccctgacagc agcttggcag gcagaaaagg atacagcacc acggaaggcg cactgtactc 4620
atatctagaa gggacccgtt ttcatcagac ggctgtggat atggcggaga tacatactat 4680
gtggccaaag caaacagagg ccaatgagca agtctgccta tatgccctgg gggaaagtat 4740
tgaatcgatc aggcagaaat gcccggtgga tgatgcagac gcatcatctc cccccaaaac 4800
tgtcccgtgc ctttgccgtt acgctatgac tccagaacgc gtcacccggc ttcgcatgaa 4860
ccacgtcaca agcataattg tgtgttcttc gtttcccctc ccaaagtaca aaatagaagg 4920
agtgcaaaaa gtcaaatgct ctaaggtaat gctatttgac cacaacgtgc catcgcgcgt 4980
aagtccaagg gaatatagat cttcccagga gtctgcacag gaggcgagta caatcacgtc 5040
actgacgcat agtcaattcg acctaagcgt tgatggcgag atactgcccg tcccgtcaga 5100
cctggatgct gacgccccag ccctagaacc agcactagac gacggggcga cacacacgct 5160
gccatccaca accggaaacc ttgcggccgt gtctgattgg gtaatgagca ccgtacctgt 5220
cgcgccgccc agaagaaggc gagggagaaa cctgactgtg acatgtgacg agagagaagg 5280
gaatataaca cccatggcta gcgtccgatt ctttagggca gagctgtgtc cggtcgtaca 5340
agaaacagcg gagacgcgtg acacagcaat gtctcttcag gcaccaccga gtaccgccac 5400
ggaaccgaat catccgccga tctccttcgg agcatcaagc gagacgttcc ccattacatt 5460
tggggacttc aacgaaggag aaatcgaaag cttgtcttct gagctactaa ctttcggaga 5520
cttcttacca ggagaagtgg atgacttgac agacagcgac tggtccacgt gctcagacac 5580
ggacgacgag ttatgactag acagggcagg tgggtatata ttctcgtcgg acaccggtcc 5640
aggtcattta caacagaagt cagtacgcca gtcagtgctg ccggtgaaca ccctggagga 5700
```

FIGURE 6 (con't)

```
agtccacgag gagaagtgtt acccacctaa gctggatgaa gcaaaggagc aactattact    5760
taagaaactc caggagagtg catccatggc caacagaagc aggtatcagt cgcgcaaagt    5820
agaaaacatg aaagcagcaa tcatccagag actaaagaga ggctgtagac tatacttaat    5880
gtcagagacc ccaaaagtcc ctacttaccg gactacatat ccggcgcctg tgtactcgcc    5940
tccgatcaac gtccgattgt ccaatcccga gtccgcagtg gcagcatgca atgagttctt    6000
agctagaaac tatccaactg tctcatcata ccaaattacc gacgagtatg atgcatatct    6060
agacatggtg gacgggtcgg agagttgcct ggaccgagcg acattcaatc cgtcaaaact    6120
caggagctac ccgaaacagc acgcttacca cgcgccctcc atcagaagcg ctgtaccgtc    6180
cccattccag aacacactac agaatgtact ggcagcagcc acgaaaagaa actgcaacgt    6240
cacacagatg agggaattac ccactttgga ctcagcagta ttcaacgtgg agtgtttcaa    6300
aaaattcgca tgcaaccaag aatactggga agaatttgct gccagcccta ttaggataac    6360
aactgagaat ttagcaacct atgttactaa actaaaaggg ccaaaagcag cagcgctatt    6420
cgcaaaaacc cataatctac tgccactaca ggaagtacca atggataggt tcacagtaga    6480
tatgaaaagg gacgtgaagg tgactcctgg tacaaagcat acagaggaaa gacctaaggt    6540
gcaggttata caggcggctg aacccttggc gacagcatac ctatgtggga ttcacagaga    6600
gctggttagg aggctgaacg ccgtcctcct acccaatgta catacactat ttgacatgtc    6660
tgccgaggat ttcgatgcca tcatagccgc acactttaag ccaggagaca ctgttttgga    6720
aacggacata gcctcctttg ataagagcca agatgattca cttgcgctta ctgctttgat    6780
gctgttagag gatttagggg tggatcactc cctgctggac ttgatagagg ctgctttcgg    6840
agagatttcc agctgtcacc taccgacagg tacgcgcttc aagttcggcg ccatgatgaa    6900
atcaggtatg ttcctaactc tgttcgtcaa cacattgtta aacatcacca tcgccagccg    6960
agtgctggaa gatcgtctga caaaatccgc gtgcgcggcc ttcatcggcg acgacaacat    7020
aatacatgga gtcgtctccg atgaattgat ggcagccaga tgtgccactt ggatgaacat    7080
ggaagtgaag atcatagatg cagttgtatc cttgaaagcc ccttactttt gtggagggtt    7140
tatactgcac gatactgtga caggaacagc ttgcagagtg gcagacccgc taaaaaggct    7200
ttttaaactg ggcaaaccgc tagcggcagg tgacgaacaa gatgaagata gaagacgagc    7260
gctggctgac gaagtgatca gatggcaacg aacagggcta attgatgagc tggagaaagc    7320
ggtatactct aggtacgaag tgcagggtat atcagttgtg gtaatgtcca tggccacctt    7380
tgcaagctcc agatccaact tcgagaagct cagaggaccc gtcataactt tgtacggcgg    7440
tcctaaatag gtacgcacta cagctaccta ttttgcagaa gccgacagca agtatctaaa    7500
cactaatcag ctacaatgga gttcatccca acccaaactt tttacaatag gaggtaccag    7560
cctcgaccct ggactccgcg ccctactatc caagtcatca ggcccagacc gcgccctcag    7620
aggcaagctg ggcaacttgc ccagctgatc tcagcagtta ataaactgac aatgcgcgcg    7680
gtaccccaac agaagccacg caggaatcgg aagaataaga agcaaaagca aaaacaacag    7740
gcgccacaaa acaacacaaa tcaaaagaag cagccaccta aaaagaaacc ggctcaaaag    7800
aaaaagaagc cgggccgcag agagaggatg tgcatgaaaa tcgaaaatga ttgtattttc    7860
gaagtcaagc acgaaggtaa ggtaacaggt tacgcgtgcc tggtgggga caaagtaatg    7920
aaaccagcac acgtaaaggg gaccatcgat aacgcggacc tggccaaact ggcctttaag    7980
cggtcatcta agtatgacct tgaatgcgcg cagataccccg tgcacatgaa gtccgacgct    8040
tcgaagttca cccatgagaa accggagggg tactacaact ggcaccacgg agcagtacag    8100
tactcaggag gccggttcac catccctaca ggtgctggca aaccagggga cagcggcaga    8160
ccgatcttcg acaacaaggg acgcgtggtg gccatagtct taggaggagc taatgaagga    8220
gcccgtacag ccctctcggt ggtgacctgg aataaagaca ttgtcactaa aatcaccccc    8280
gagggggccg aagagtggag tcttgccatc ccagttatgt gcctgttggc aaacaccacg    8340
ttcccctgct cccagccccc ttgcacgccc tgctgctacg aaaaggaacc ggaggaaacc    8400
ctacgcatgc ttgaggacaa cgtcatgaga cctgggtact atcagctgct acaagcatcc    8460
ttaacatgtt ctccccaccg ccagcgacgc agcaccaagg acaacttcaa tgtctataaa    8520
gccacaagac catacttagc tcactgtccc gactgtggag aagggcactc gtgccatagt    8580
```

FIGURE 6 (con't)

```
cccgtagcac tagaacgcat cagaaatgaa gcgacagacg ggacgctgaa aatccaggtc 8640
tccttgcaaa tcggaataaa gacggatgac agccacgatt ggaccaagct gcgttatatg 8700
gacaaccaca tgccagcaga cgcagagagg gcggggctat ttgtaagaac atcagcaccg 8760
tgtacgatta ctggaacaat gggacacttc atcctggccc gatgtccaaa aggggaaact 8820
ctgacggtgg gattcactga cagtaggaag attagtcact catgtacgca cccatttcac 8880
cacgaccctc ctgtgatagg tcgggaaaaa ttccattccc gaccgcagca cggtaaagag 8940
ctaccttgca gcacgtacgt gcagagcacc gccgcaacta ccgaggagat agaggtacac 9000
atgcccccag acacccctga tcgcacatta atgtcacaac agtccggcaa cgtaaagatc 9060
acagtcaatg gccagacggt gcggtacaag tgtaattgcg gtggctcaaa tgaaggacta 9120
acaactacag acaaagtgat taataactgc aaggttgatc aatgtcatgc cgcggtcacc 9180
aatcacaaaa agtggcagta taactcccct ctggtcccgc gtaatgctga acttggggac 9240
cgaaaaggaa aaattcacat cccgtttccg ctggcaaatg taacatgcag ggtgcctaaa 9300
gcaaggaacc ccaccgtgac gtacgggaaa aaccaagtca tcatgctact gtatcctgac 9360
caccccaacac tcctgtccta ccggaatatg ggagaagaac caaactatca agaagagtgg 9420
gtgatgcata agaaggaagt cgtgctaacc gtgccgactg aagggctcga ggtcacgtgg 9480
ggcaacaacg agccgtataa gtattggccg cagttatcta caaacggtac agcccatggc 9540
cacccgcatg agataattct gtattattat gagctgtacc ccactatgac tgtagtagtt 9600
gtgtcagtgg ccacgttcat actcctgtcg atggtgggta tggcagcggg gatgtgcatg 9660
tgtgcacgac gcagatgcat cacaccgtat gaactgacac caggagctac cgtccctttc 9720
ctgcttagcc taatatgctg catcagaaca gctaaagcgg ccacatacca agaggctgcg 9780
atatacctgt ggaacgagca gcaacctttg ttttggctac aagcccttat tccgctggca 9840
gccctgattg ttctatgcaa ctgtctgaga ctcttaccat gctgctgtaa aacgttggct 9900
tttttagccg taatgagcgt cggtgcccac actgtgagcg cgtacgaaca cgtaacagtg 9960
atcccgaaca cggtgggagt accgtataag actctagtca atagacctgg ctacagcccc 10020
atggtattgg agatggaact actgtcagtc actttggagc caacactatc gcttgattac 10080
atcacgtgcg agtacaaaac cgtcatcccg tctccgtacg tgaagtgctg cggtacagca 10140
gagtgcaagg acaaaaacct acctgactac agctgtaagg tcttcaccgg cgtctaccca 10200
tttatgtggg gcggcgccta ctgcttctgc gacgctgaaa acacgcagtt gagcgaagca 10260
cacgtggaga agtccgaatc atgcaaaaca gaatttgcat cagcatacag ggctcatacc 10320
gcatctgcat cagctaagct ccgcgtcctt taccaaggaa ataacatcac tgtaactgcc 10380
tatgcaaacg gcgaccatgc cgtcacagtt aaggacgcca aattcattgt ggggccaatg 10440
tcttcagcct ggacaccttt cgacaacaaa attgtggtgt acaaaggtga cgtctataac 10500
atggactacc cgccctttgg cgcaggaaga ccaggacaat ttggcgatat ccaaagtcgc 10560
acacctgaga gtaaagacgt ctatgctaat acacaactgg tactgcagag accggctgtg 10620
ggtacggtac acgtgccata ctctcaggca ccatctggct ttaagtattg gctaaaagaa 10680
cgcggggcgt cgctgcagca cacagcacca tttggctgcc aaatagcaac aaacccggta 10740
agagcggtga actgcgccgt agggaacatg cccatctcca tcgacatacc ggaagcggcc 10800
ttcactaggg tcgtcgacgc gccctcttta acggacatgt cgtgcgaggt accagcctgc 10860
acccattcct cagactttgg gggcgtcgcc attattaaat atgcagccag caagaaaggc 10920
aagtgtgcgg tgcattcgat gactaacgcc gtcactattc gggaagctga gatagaagtt 10980
gaagggaatt ctcagctgca aatctctttc tcgacggcct tagccagcgc cgaattccgc 11040
gtacaagtct gttctacaca agtacactgt gcagccgagt gccacccccc gaaggaccac 11100
atagtcaact acccggcgtc acataccacc ctcggggtcc aggacatctc cgctacggcg 11160
atgtcatggg tgcagaagat cacgggaggt gtgggactgg ttgttgctgt tgccgcactg 11220
attctaatcg tggtgctatg cgtgtcgttc agcaggcact aacttgacaa ttaagtatga 11280
aggtatatgt gtcccctaag agacacactg tacatagcaa ataatctata gatcaaaggg 11340
ctacgcaacc cctgaatagt aacaaaatac aaaatcacta aaaattataa aaacagaaaa 11400
atacataaat aggtatacgt gtcccctaag agacacattg tatgtaggtg ataagtatag 11460
```

FIGURE 6 (con't)

```
atcaaagggc cgaataaccc ctgaatagta acaaaatatg aaaatcaata aaaatcataa   11520
aatagaaaaa ccataaacag aagtagttca aagggctata aaacccctga atagtaacaa   11580
aacataaaat taataaaaat c                                             11601
```

FIGURE 7

```
caaagcaaga gattaataac ccatcatgga tcctgtgtac gtggacatag acgctgacag     60
cgcctttttg aaggccctgc aacgtgcgta ccccatgttt gaggtggaac caaggcaggt    120
cacaccgaat gaccatgcta atgctagagc gttctcgcat ctagctataa aactaataga    180
gcaggaaatt gaccccgact caaccatcct ggatatcggc agtgcgccag caaggaggat    240
gatgtcggac aggaagtacc actgcgtctg cccgatgcgc agtgcggaag atcccgagag    300
actcgccaat tatgcgagaa agctagcatc tgccgcagga aaagtcctgg acagaaacat    360
ctctggaaag atcggggact tacaagcagt aatggccgtg ccagacacgg agacgccaac    420
attctgctta cacacagacg tctcatgtag acagagagca gacgtcgcta tataccaaga    480
cgtctatgct gtacacgcac ccacgtcgct ataccaccag gcgattaaag ggtccgagt     540
ggcgtactgg gttgggttcg acacaacccc gttcatgtac aatgccatgg cgggtgccta    600
cccctcatac tcgacaaact gggcagatga gcaggtactg aaggctaaga acataggatt    660
atgttcaaca gacctgacgg aaggtagacg aggcaagttg tctattatga gagggaaaaa    720
gctaaaaccg tgcgaccgtg tgctgttctc agtagggtca acgctctacc cggaaagccg    780
caagctactt aagagctggc acctgccatc ggtgttccat ttaaagggca aactcagctt    840
cacatgccgc tgtgatacag tggtttcgtg tgagggctac gtcgttaaga gaataacgat    900
gagcccaggc ctttatggaa aaaccatagg gtatgcggta acccaccacg cagacggatt    960
cctgatgtgc aagactaccg acacggttga cggcgaaaga gtgtcattct cggtgtgcac   1020
atacgtgccg gcgaccattt gtgatcaaat gaccggcatc cttgctacag aagtcacgcc   1080
ggaggatgca cagaagctgt tggtggggct gaaccagaga atagtggtta acggcagaac   1140
gcaacggaat acgaacacca tgaaaaatta tctgcttccc gtggtcgccc aagccttcag   1200
taagtgggca aaggagtgcc ggaaagacat ggaagatgaa aaactcctgg gggtcagaga   1260
aagaacactg acctgctgct gtctatgggc attcaagaag cagaaaacac acacggtcta   1320
caagaggcct gatacccagt caattcagaa ggttcaggcc gagtttgaca gctttgtggt   1380
accgagtctg tggtcgtccg ggttgtcaat ccctttgagg actagaatca aatggttgtt   1440
aagcaaggtg ccaaaaaccg acctgatccc atacagcgga gacgcccgag aagcccggga   1500
cgcagaaaaa gaagcagagg aagaacgaga agcagaactg actcgcgaag ccctaccacc   1560
tctacaggca gcacaggaag atgttcaggt cgaaatcgac gtggaacagc ttgaggacag   1620
agcgggcgca ggaataatag agactccgag aggagctatc aaagttactg cccaaccaac   1680
agaccacgtc gtgggagagt acctggtact ctccccgcag accgtactac gtagccagaa   1740
gctcagtctg attcacgctt tggcggagca agtgaagacg tgcacgcaca acggacgagc   1800
agggaggtat gcggtcgaag cgtacgacgg ccgagtccta gtgccctcag gctatgcaat   1860
ctcgcctgaa gacttccaga gtctaagcga aagcgcaacg atggtgtata acgaaagaga   1920
gttcgtaaac agaaagctac accatattgc gatgcacgga ccagccctga acaccgacga   1980
agagtcgtat gagctggtga gggcagagag gacagaacac gagtacgtct acgacgtgga   2040
tcagagaaga tgctgtaaga aggaagaagc cgcaggactg gtactggtgg gcgacttgac   2100
taatccgccc taccacgaat tcgcatatga agggctaaaa atccgccctg cctgcccata   2160
caaaattgca gtcataggag tcttcggagt accgggatct ggcaagtcag ctattatcaa   2220
gaacctagtt accaggcagg acctggtgac tagcggaaag aaagaaaact gccaagaaat   2280
caccaccgac gtgatgagac agagaggtct agagatatct gcacgtacgg ttgactcgct   2340
gctcttgaat ggatgcaaca gaccagtcga cgtgttgtac gtagacgagg cgtttgcgtg   2400
ccactctgga acgctacttg ctttgatcgc cttggtgaga ccaaggcaga aagttgtact   2460
ttgtggtgac ccgaagcagt gcggcttctt caatatgatg cagatgaaag tcaactataa   2520
tcacaacatc tgcacccaag tgtaccacaa aagtatctcc aggcggtgta cactgcctgt   2580
gaccgccatt gtgtcatcgt tgcattacga aggcaaaatg cgcactacga atgagtacaa   2640
caagccgatt gtagtggaca ctacaggctc aacaaaacct gaccctggag acctcgtgtt   2700
aacgtgcttc agagggtggg ttaaacaact gcaaattgac tatcgtggat acgaggtcat   2760
```

FIGURE 7 (con't)

```
gacagcagcc gcatcccaag ggttaaccag aaaaggagtt tacgcagtta gacaaaaagt    2820
taatgaaaac ccgctctatg catcaacgtc agagcacgtc aacgtactcc taacgcgtac    2880
ggaaggtaaa ctggtatgga agacactttc cggcgacccg tggataaaga cgctgcagaa    2940
cccaccgaaa ggaaacttca aagcaactat taaggagtgg gaggtggagc atgcatcaat    3000
aatggcgggc atctgcagtc accaaatgac cttcgataca ttccaaaata aagccaacgt    3060
ttgttgggct aagagcttgg tccctatcct cgaaacagcg gggataaaac taaatgatag    3120
gcagtggtct cagataattc aagccttcaa agaagacaaa gcatactcac ctgaagtagc    3180
cctgaatgaa atatgtacgc gcatgtatgg ggtggatcta gacagcgggc tattttctaa    3240
accgttggtg tctgtgtatt acgcggataa ccactgggat aataggcctg gagggaaaat    3300
gttcggattt aaccccgagg cagcatccat tctagaaaga aagtatccat tcacaaaagg    3360
gaagtggaac atcaacaagc agatctgcgt gactaccagg aggatagaag actttaaccc    3420
taccaccaac atcataccgg ccaacaggag actaccacac tcattagtgg ccgaacaccg    3480
cccagtaaaa ggggaaagaa tggaatggct ggttaacaag ataaacggcc accacgtgct    3540
cctggtcagt ggcaataacc ttgcactgcc tactaagaga gtcacttggg tagcgccgtt    3600
aggtgtccgc ggagcggact acacatacaa cctagagttg ggtctgccag caacgcttgg    3660
taggtatgac ctagtggtca taaacatcca cacacctttt cgcatacacc attaccaaca    3720
gtgcgtcgac cacgcaatga aactgcaaat gctcgggggt gactcattga gactgctcaa    3780
accgggcggc tctctattga tcagagcata tggttacgca gatagaacca gtgaacgagt    3840
catctgcgta ttgggacgca agtttagatc gtctagagcg ttgaaaccac catgtgtcac    3900
cagcaacact gagatgtttt tcctattcag caactttgac aatggcagaa ggaatttcac    3960
aactcatgtc atgaacaatc aactgaatgc agccttcgta ggacaggtca cccgagcagg    4020
atgtgcaccg tcgtaccggg taaaacgcat ggacatcgcg aagaacgatg aagagtgcgt    4080
agtcaacgcc gctaaccctc gcgggttacc gggtgacggt gtttgcaagg cagtatacaa    4140
aaaatggccg gagtccttta agaacagtgc aacaccagtg ggaaccgcaa aaacagttat    4200
gtgcggtacg tatccagtaa tccacgctgt tggaccaaac ttctctaatt attcggagtc    4260
tgaaggggac cgggaattgg cagctgccta tcgagaagtc gcaaaggaag taactaggct    4320
gggagtaaat agtgtagcta tacctctcct ctccacaggt gtatactcag gagggaaaga    4380
caggctgacc cagtcactga accacctctt tacagccatg gactcgacgg atgcagacgt    4440
ggtcatctac tgccgcgaca aagaatggga gaagaaaata tctgaggcca tacagatgcg    4500
gacccaagta gagctgctgg atgagcacat ctccatagac tgcgatattg ttcgcgtgca    4560
ccctgacagc agcttggcag gcagaaaagg atacagcacc acggaaggcg cactgtactc    4620
atatctagaa gggacccgtt ttcatcagac ggcagtggat atggcggaga tacatactat    4680
gtggccaaag caaacagagg ccaatgagca agtctgccta tatgccctgg gggaaagtat    4740
tgaatcgatc aggcagaaat gcccggtgga tgatgcagac gcatcatctc cccccaaaac    4800
tgtcccgtgc ctttgccgtt acgctatgac tccagaacgc gtcacccggc ttcgcatgaa    4860
ccacgtcaca agcataattg tgtgttcttc gtttcccctc ccaaagtaca aaatagaagg    4920
agtgcaaaaa gtcaaatgct ctaaggtaat gctatttgac cacaacgtgc catcgcgcgt    4980
aagtccaagg gaatatagat cttcccagga gtctgcacag gaggcgagta caatcacgtc    5040
actgacgcat agtcaattcg acctaagcgt tgatggcgag atactgcccg tcccgtcaga    5100
cctggatgct gacgccccag ccctagaacc agcactagac gacggggcga cacacacgct    5160
gccatccaca accggaaacc ttgcggccgt gtctgattgg gtaatgagca ccgtacctgt    5220
cgcgccgccc agaagaaggc gagggagaaa cctgactgtg acatgtgacg agagagaagg    5280
gaatataaca cccatggcta gcgtccgatt ctttagggca gagctgtgtc cggtcgtaca    5340
agaaacagcg gagacgcgtg acacagcaat gtctcttcag gcaccaccga gtaccgccac    5400
accgaatcat ccgccgatct ccttcggagc atcaagcgag acgttcccca ttacatttgg    5460
ggacttcaac gaaggagaaa tcgaaagctt gtcttctgag ctactaactt tcggagactt    5520
cttaccagga gaagtggatg acttgacaga cagcgactgg tccacgtgct cagacacgga    5580
cgacgagtta tgactagaca gggcaggtgg gtatatattc tcgtcggaca ccggtccagg    5640
```

FIGURE 7 (con't)

```
tcatttacaa cagaagtcag tacgccagtc agtgctgccg gtgaacaccc tggaggaagt     5700
ccacgaggag aagtgttacc cacctaagct ggatgaagca aaggagcaac tattacttaa     5760
gaaactccag gagagtgcat ccatggccaa cagaagcagg tatcagtcgc gcaaagtaga     5820
aaacatgaaa gcagcaatca tccagagact aaagagaggc tgtagactat acttaatgtc     5880
agagacccca aaagtcccta cttaccggac tacatatccg gcgcctgtgt actcgcctcc     5940
gatcaacgtc cgattgtcca atcccgagtc cgcagtggca gcatgcaatg agttcttagc     6000
tagaaactat ccaactgtct catcatacca aattaccgac gagtatgatg catatctaga     6060
catggtggac gggtcggaga gttgcctgga ccgagcgaca ttcaatccgt caaaactcag     6120
gagctacccg aaacagcacg cttaccacgc gccctccatc agaagcgctg taccgtcccc     6180
attccagaac acactacaga atgtactggc agcagccacg aaaagaaact gcaacgtcac     6240
acagatgagg gaattaccca ctttggactc agcagtattc aacgtggagt gtttcaaaaa     6300
attcgcatgc aaccaagaat actgggaaga atttgctgcc agccctatta ggataacaac     6360
tgagaattta gcaacctatg ttactaaact aaaagggcca aaagcagcag cgctattcgc     6420
aaaaacccat aatctactgc cactacagga agtaccaatg gataggttca cagtagatat     6480
gaaaagggac gtaaaggtga ctcctggtac aaagcataca gaggaaagac ctaaggtgca     6540
ggttatacag gcggctgaac ccttggcgac agcataccta tgtgggattc acagagagct     6600
ggttaggagg ctgaacgccg tcctcctacc caatgtacat acactatttg acatgtctgc     6660
cgaggatttc gatgccatca tagccgcaca ctttaagcca ggagacactg ttttggaaac     6720
ggacatagcc tcctttgata agagccaaga tgattcactt gcgcttactg ctttgatgct     6780
gttagaggat ttaggggtgg atcactccct gctggacttg atagaggctg ctttcggaga     6840
gatttccagc tgtcacctac cgacaggtac gcgcttcaag ttcggcgcca tgatgaaatc     6900
aggtatgttc ctaactctgt tcgtcaacac attgttaaac atcaccatcg ccagccgagt     6960
gctggaagat cgtctgacaa aatccgcgtg cgcggccttc atcggcgacg acaacataat     7020
acatggagtc gtctccgatg aattgatggc agccagatgt gccacttgga tgaacatgga     7080
agtgaagatc atagatgcag ttgtatcctt gaaagcccct tacttttgtg gagggtttat     7140
actgcacgat actgtgacag gaacagcttg cagagtggca gacccgctaa aaaggctttt     7200
taaactgggc aaaccgctag cggcaggtga cgaacaagat gaagatagaa gacgagcgct     7260
ggctgacgaa gtgatcagat ggcaacgaac agggctaatt gatgagctgg agaaagcggt     7320
atactctagg tacgaagtgc agggtatatc agttgtggta atgtccatgg ccacctttgc     7380
aagctccaga tccaacttcg agaagctcag aggacccgtc ataactttgt acggcggtcc     7440
taaataggta cgcactacag ctacctattt tgcagaagcc gacagcaagt atctaaacac     7500
taatcagcta caatggagtt catcccaacc caaacttttt acaataggag gtaccagcct     7560
cgaccctgga ctccgcgccc tactatccaa gtcatcaggc ccagaccgcg ccctcagagg     7620
caagctgggc aacttgccca gctgatctca gcagttaata aactgacaat gcgcgcggta     7680
ccccaacaga agccacgcag gaatcggaag aataagaagc aaaagcaaaa acaacaggcg     7740
ccacaaaaca acacaaatca aaagaagcag ccacctaaaa agaaaccggc tcaaaagaaa     7800
aagaagccgg gccgcagaga gaggatgtgc atgaaaatcg aaaatgattg tatttcgaa     7860
gtcaagcacg aaggtaaggt aacaggttac gcgtgcctgg tggggacaa agtaatgaaa     7920
ccagcacacg taaaggggac catcgataac gcggacctgg ccaaactggc ctttaagcgg     7980
tcatctaagt atgaccttga atgcgcgcag atacccgtgc acatgaagtc cgacgcttcg     8040
aagttcaccc atgagaaacc ggaggggtac tacaactggc accacggagc agtacagtac     8100
tcaggaggcc ggttcaccat ccctacaggt gctggcaaac caggggacag cggcagaccg     8160
atcttcgaca acaagggacg cgtggtggcc atagtcttag gaggagctaa tgaaggagcc     8220
cgtacagccc tctcggtggt gacctggaat aaagacattg tcactaaaat cacccccgag     8280
ggggccgaag agtggagtct tgccatccca gttatgtgcc tgttggcaaa caccacgttc     8340
ccctgctccc agcccccttg cacgccctgc tgctacgaaa aggaaccgga ggaaacccta     8400
cgcatgcttg aggacaacgt catgagacct gggtactatc agctgctaca agcatcctta     8460
acatgttctc cccaccgcca gcgacgcagc accaaggaca acttcaatgt ctataaagcc     8520
```

FIGURE 7 (con't)

```
acaagaccat acttagctca ctgtcccgac tgtggagaag ggcactcgtg ccatagtccc     8580
gtagcactag aacgcatcag aaatgaagcg acagacggga cgctgaaaat ccaggtctcc     8640
ttgcaaatcg gaataaagac ggatgacagc cacgattgga ccaagctgcg ttatatggac     8700
aaccacatgc cagcagacgc agagagggcg gggctatttg taagaacatc agcaccgtgt     8760
acgattactg gaacaatggg acacttcatc ctggcccgat gtccaaaagg ggaaactctg     8820
acggtgggat tcactgacag taggaagatt agtcactcat gtacgcaccc atttcaccac     8880
gaccctcctg tgataggtcg ggaaaaattc cattcccgac cgcagcacgg taaagagcta     8940
ccttgcagca cgtacgtgca gagcaccgcc gcaactaccg aggagataga ggtacacatg     9000
cccccagaca cccctgatcg cacattaatg tcacaacagt ccggcaacgt aaagatcaca     9060
gtcaatggcc agacggtgcg gtacaagtgt aattgcggtg gctcaaatga aggactaaca     9120
actacagaca aagtgattaa taactgcaag gttgatcaat gtcatgccgc ggtcaccaat     9180
cacaaaaagt ggcagtataa ctcccctctg gtcccgcgta atgctgaact tggggaccga     9240
aaaggaaaaa ttcacatccc gtttccgctg gcaaatgtaa catgcagggt gcctaaagca     9300
aggaacccca ccgtgacgta cgggaaaaac caagtcatca tgctactgta tcctgaccac     9360
ccaacactcc tgtcctaccg gaatatggga gaagaaccaa actatcaaga agagtgggtg     9420
atgcataaga aggaagtcgt gctaaccgtg ccgactgaag ggctcgaggt cacgtggggc     9480
aacaacgagc cgtataagta ttggccgcag ttatctacaa acggtacagc ccatggccac     9540
ccgcatgaga taattctgta ttattatgag ctgtacccca ctatgactgt agtagttgtg     9600
tcagtggcca cgttcatact cctgtcgatg gtgggtatgg cagcggggat gtgcatgtgt     9660
gcacgacgca gatgcatcac accgtatgaa ctgacaccag gagctaccgt ccctttcctg     9720
cttagcctaa tatgctgcat cagaacagct aaagcggcca cataccaaga ggctgcgata     9780
tacctgtgga acgagcagca acctttgttt tggctacaag cccttattcc gctggcagcc     9840
ctgattgttc tatgcaactg tctgagactc ttaccatgct gctgtaaaac gttggctttt     9900
ttagccgtaa tgagcgtcgg tgcccacact gtgagcgcgt acgaacacgt aacagtgatc     9960
ccgaacacgg tgggagtacc gtataagact ctagtcaata gacctggcta cagccccatg    10020
gtattggaga tggaactact gtcagtcact ttggagccaa cactatcgct tgattacatc    10080
acgtgcgagt acaaaaccgt catcccgtct ccgtacgtga agtgctgcgg tacagcagag    10140
tgcaaggaca aaaacctacc tgactacagc tgtaaggtct tcaccggcgt ctacccattt    10200
atgtggggcg gcgcctactg cttctgcgac gctgaaaaca cgcagttgag cgaagcacac    10260
gtggagaagt ccgaatcatg caaaacagaa tttgcatcag catacagggc tcataccgca    10320
tctgcatcag ctaagctccg cgtcctttac caaggaaata acatcactgt aactgcctat    10380
gcaaacggcg accatgccgt cacagttaag gacgccaaat tcattgtggg gccaatgtct    10440
tcagcctgga cacctttcga caacaaaatt gtggtgtaca aaggtgacgt ctataacatg    10500
gactacccgc cctttggcgc aggaagacca ggacaatttg gcgatatcca aagtcgcaca    10560
cctgagagta aagacgtcta tgctaataca caactggtac tgcagagacc ggctgtgggt    10620
acggtacacg tgccatactc tcaggcacca tctggcttta agtattggct aaaagaacgc    10680
ggggcgtcgc tgcagcacac agcaccattt ggctgccaaa tagcaacaaa cccggtaaga    10740
gcggtgaact gcgccgtagg gaacatgccc atctccatcg acataccgga agcggccttc    10800
actagggtcg tcgacgcgcc ctctttaacg gacatgtcgt gcgaggtacc agcctgcacc    10860
cattcctcag actttggggg cgtcgccatt attaaatatg cagccagcaa gaaaggcaag    10920
tgtgcggtgc attcgatgac taacgccgtc actattcggg aagctgagat agaagttgaa    10980
gggaattctc agctgcaaat ctctttctcg acggccttag ccagcgccga attccgcgta    11040
caagtctgtt ctacacaagt acactgtgca gccgagtgcc acccccgaa ggaccacata    11100
gtcaactacc cggcgtcaca taccaccctc ggggtccagg acatctccgc tacggcgatg    11160
tcatgggtgc agaagatcac gggaggtgtg ggactggttg ttgctgttgc cgcactgatt    11220
ctaatcgtgg tgctatgcgt gtcgttcagc aggcactaac ttgacaatta agtatgaagg    11280
tatatgtgtc ccctaagaga cacactgtac atagcaaata atctatagat caaagggcta    11340
cgcaacccct gaatagtaac aaaatacaaa atcactaaaa attataaaaa cagaaaata     11400
```

FIGURE 7 (con't)

```
cataaatagg tatacgtgtc ccctaagaga cacattgtat gtaggtgata agtatagatc   11460
aaagggccga ataacccctg aatagtaaca aaatatgaaa atcaataaaa atcataaaat   11520
agaaaaacca taaacagaag tagttcaaag ggctataaaa cccctgaata gtaacaaaac   11580
ataaaattaa taaaaatc                                                 11598
```

FIGURE 8

| | | | | | | |
|---|---|---|---|---|---|---|
| caaagcaaga | gattaataac | ccatcatgga | tcctgtgtac | gtggacatag | acgctgacag | 60 |
| cgcctttttg | aaggccctgc | aacgtgcgta | ccccatgttt | gaggtggaac | caaggcaggt | 120 |
| cacaccgaat | gaccatgcta | atgctagagc | gttctcgcat | ctagctataa | aactaataga | 180 |
| gcaggaaatt | gaccccgact | caaccatcct | ggatatcggc | agtgcgccag | caaggaggat | 240 |
| gatgtcggac | aggaagtacc | actgcgtctg | cccgatgcgc | agtgcggaag | atcccgagag | 300 |
| actcgccaat | tatgcgagaa | agctagcatc | tgccgcagga | aaagtcctgg | acagaaacat | 360 |
| ctctggaaag | atcggggact | tacaagcagt | aatggccgtg | ccagacacgg | agacgccaac | 420 |
| attctgctta | cacacagacg | tctcatgtag | acagagagca | gacgtcgcta | tataccaaga | 480 |
| cgtctatgct | gtacacgcac | ccacgtcgct | ataccaccag | gcgattaaag | ggtccgagt | 540 |
| ggcgtactgg | gttgggttcg | acacaacccc | gttcatgtac | aatgccatgg | cgggtgccta | 600 |
| cccctcatac | tcgacaaact | gggcagatga | gcaggtactg | aaggctaaga | acataggatt | 660 |
| atgttcaaca | gacctgacgg | aaggtagacg | aggcaagttg | tctattatga | gagggaaaaa | 720 |
| gctaaaaccg | tgcgaccgtg | tgctgttctc | agtagggtca | acgctctacc | cggaaagccg | 780 |
| caagctactt | aagagctggc | acctgccatc | ggtgttccat | ttaaagggca | aactcagctt | 840 |
| cacatgccgc | tgtgatacag | tggtttcgtg | tgagggctac | gtcgttaaga | gaataacgat | 900 |
| gagcccaggc | ctttatggaa | aaaccacagg | gtatgcggta | acccaccacg | cagacggatt | 960 |
| cctgatgtgc | aagactaccg | acacggttga | cggcgaaaga | gtgtcattct | cggtgtgcac | 1020 |
| atacgtgccg | gcgaccattt | gtgatcaaat | gaccggcatc | cttgctacag | aagtcacgcc | 1080 |
| ggaggatgca | cagaagctgt | tggtggggct | gaaccagaga | atagtggtta | acggcagaac | 1140 |
| gcaacggaat | acgaacacca | tgaaaaatta | tctgcttccc | gtggtcgccc | aagccttcag | 1200 |
| taagtgggca | aaggagtgcc | ggaaagacat | ggaagatgaa | aaactcctgg | gggtcagaga | 1260 |
| aagaacactg | acctgctgct | gtctatgggc | attcaagaag | cagaaaacac | acacggtcta | 1320 |
| caagagacct | gatacccagt | caattcagaa | ggttcaggcc | gagtttgaca | gctttgtggt | 1380 |
| accgagtctg | tggtcgtccg | ggttgtcaat | ccctttgagg | actagaatca | aatggttgtt | 1440 |
| aagcaaggtg | ccaaaaaccg | acctgatccc | atacagcgga | gacgcccgag | aagcccggga | 1500 |
| cgcagaaaaa | gaagcagagg | aagaacgaga | agcagaactg | actcgcgaag | ccctaccacc | 1560 |
| tctacaggca | gcacaggaag | atgttcaggt | cgaaatcgac | gtggaacagc | ttgaggacag | 1620 |
| agcgggcgca | ggaataatag | agactccgag | aggagctatc | aaagttactg | cccaaccaac | 1680 |
| agaccacgtc | gtgggagagt | acctggtact | ctccccgcag | accgtactac | gtagccagaa | 1740 |
| gctcagtctg | attcacgctt | tggcggagca | agtgaagacg | tgcacgcaca | acggacgagc | 1800 |
| agggaggtat | gcggtcgaag | cgtacgacgg | ccgagtccta | gtgccctcag | gctatgcaat | 1860 |
| ctcgcctgaa | gacttccaga | gtctaagcga | aagcgcaacg | atggtgtata | acgaaagaga | 1920 |
| gttcgtaaac | agaaagctac | accatattgc | gatgcacgga | ccagccctga | acaccgacga | 1980 |
| agagtcgtat | gagctggtga | gggcagagag | gacagaacac | gagtacgtct | acgacgtgga | 2040 |
| tcagagaaga | tgctgtaaga | aggaagaagc | cgcaggactg | gtactggtgg | gcgacttgac | 2100 |
| taatccgccc | taccacgaat | tcgcatatga | agggctaaaa | atccgccctg | cctgcccata | 2160 |
| caaaattgca | gtcataggag | tcttcggagt | accgggatct | ggcaagtcag | ctattatcaa | 2220 |
| gaacctagtt | accaggcagg | acctggtgac | tagcggaaag | aaagaaaact | gccaagaaat | 2280 |
| caccaccgac | gtgatgagac | agagaggtct | agagatatct | gcacgtacgg | ttgactcgct | 2340 |
| gctcttgaat | ggatgcaaca | gaccagtcga | cgtgttgtac | gtagacgagg | cgtttgcgtg | 2400 |
| ccactctgga | acgctacttg | ctttgatcgc | cttggtgaga | ccaaggcaga | aagttgtact | 2460 |
| ttgtggtgac | ccgaagcagt | gcggcttctt | caatatgatg | cagatgaaag | tcaactataa | 2520 |
| tcacaacatc | tgcacccaag | tgtaccacaa | aagtatctcc | aggcggtgta | cactgcctgt | 2580 |
| gaccgccatt | gtgtcatcgt | tgcattacga | aggcaaaatg | cgcactacga | atgagtacaa | 2640 |
| caagccgatt | gtagtggaca | ctacaggctc | aacaaaacct | gaccctggag | acctcgtgtt | 2700 |
| aacgtgcttc | agagggtggg | ttaaacaact | gcaaattgac | tatcgtggat | acgaggtcat | 2760 |
| gacagcagcc | gcatcccaag | ggttaaccag | aaaaggagtt | tacgcagtta | gacaaaaagt | 2820 |

FIGURE 8 (con't)

```
taatgaaaac ccgctctatg catcaacgtc agagcacgtc aacgtactcc taacgcgtac 2880
ggaaggtaaa ctggtatgga agacactttc cggcgacccg tggataaaga cgctgcagaa 2940
cccaccgaaa ggaaacttca aagcaactat taaggagtgg gaggtggagc atgcatcaat 3000
aatggcgggc atctgcagtc accaaatgac cttcgataca ttccaaaata aagccaacgt 3060
ttgttgggct aagagcttgg tccctatcct cgaaacagcg ggataaaac taaatgatag 3120
gcagtggtct cagataattc aagccttcaa agaagacaaa gcatactcac ctgaagtagc 3180
cctgaatgaa atatgtacgc gcatgtatgg ggtggatcta gacagcgggc tattttctaa 3240
accgttggtg tctgtgtatt acgcggataa ccactgggat aataggcctg gagggaaaat 3300
gttcggattt aaccccgagg cagcatccat tctagaaaga aagtatccat tcacaaaagg 3360
gaagtggaac atcaacaagc agatctgcgt gactaccagg aggatagaag actttaaccc 3420
taccaccaac atcataccgg ccaacaggag actaccacac tcattagtgg ccgaacaccg 3480
cccagtaaaa ggggaaagaa tggaatggct ggttaacaag ataaacggcc accacgtgct 3540
cctggtcagt ggctataacc ttgcactgcc tactaagaga gtcacttggg tagcgccgtt 3600
aggtgtccgc ggagcggact acacatacaa cctagagttg ggtctgccag caacgcttgg 3660
taggtatgac ctagtggtca taaacatcca cacacctttt cgcatacacc attaccaaca 3720
gtgcgtcgac cacgcaatga aactgcaaat gctcgggggt gactcattga gactgctcaa 3780
accgggcggc tctctattga tcagagcata tggttacgca gatagaacca gtgaacgagt 3840
catctgcgta ttgggacgca agtttagatc gtctagagcg ttgaaaccac catgtgtcac 3900
cagcaacact gagatgtttt tcctattcag caactttgac aatggcagaa ggaatttcac 3960
aactcatgtc atgaacaatc aactgaatgc agccttcgta ggacaggtca cccgagcagg 4020
atgtgcaccg tcgtaccggg taaaacgcat ggacatcgcg aagaacgatg aagagtgcgt 4080
agtcaacgcc gctaaccctc gcgggttacc gggtgacggt gtttgcaagg cagtatacaa 4140
aaaatggccg gagtccttta agaacagtgc aacaccagtg ggaaccgcaa aaacagttat 4200
gtgcggtacg tatccagtaa tccacgctgt tggaccaaac ttctctaatt attcggagtc 4260
tgaaggggac cgggaattgg cagctgccta tcgagaagtc gcaaaggaag taactaggct 4320
gggagtaaat agtgtagcta tacctctcct ctccacaggt gtatactcag gagggaaaga 4380
caggctgacc cagtcactga accacctctt tacagccatg gactcgacgg atgcagacgt 4440
ggtcatctac tgccgcgaca aagaatggga gaagaaaata tctgaggcca tacagatgcg 4500
gacccaagta gagctgctgg atgagcacat ctccatagac tgcgatattg ttcgcgtgca 4560
ccctgacagc agcttggcag gcagaaaagg atacagcacc acggaaggcg cactgtactc 4620
atatctagaa gggacccgtt ttcatcagac ggctgtggat atggcggaga tacatactat 4680
gtggccaaag caaacagagg ccaatgagca agtctgccta tatgccctgg gggaaagtat 4740
tgaatcgatc aggcagaaat gcccggtgga tgatgcagac gcatcatctc cccccaaaac 4800
tgtcccgtgc ctttgccgtt acgctatgac tccagaacgc gtcacccggc ttcgcatgaa 4860
ccacgtcaca agcataattg tgtgttcttc gtttcccctc ccaaagtaca aaatagaagg 4920
agtgcaaaaa gtcaaatgct ctaaggtaat gctatttgac cacaacgtgc catcgcgcgt 4980
aagtccaagg gaatatagat cttcccagga gtctgcacag gaggcgagta caatcacgtc 5040
actgacgcat agtcaattcg acctaagcgt tgatggcgag atactgcccg tcccgtcaga 5100
cctggatgct gacgccccag ccctagaacc agcactagac gacgggggcga cacacacgct 5160
gccatccaca accggaaacc ttgcggccgt gtctgattgg gtaatgagca ccgtacctgt 5220
cgcgccgccc agaagaaggc gagggagaaa cctgactgtg acatgtgacg agagagaagg 5280
gaatataaca cccatggcta gcgtccgatt ctttagggca gagctgtgtc cggtcgtaca 5340
agaaacagcg gagacgcgtg acacagcaat gtctcttcag gcaccaccga gtaccgccac 5400
ggaaccgaat catccgccga tctccttcgg agcatcaagc gagacgttcc ccattacatt 5460
tggggacttc aacgaaggag aaatcgaaag cttgtcttct gagctactaa ctttcggaga 5520
cttcttacca ggagaagtgg atgacttgac agacagcgac tggtccacgt gctcagacac 5580
ggacgacgag ttatgactag acagggcagg tgggtatata ttctcgtcgg acaccggtcc 5640
```

FIGURE 8 (con't)

```
aggtcattta caacagaagt cagtacgcca gtcagtgctg ccggtgaaca ccctggagga 5700
agtccacgag gagaagtgtt acccacctaa gctggatgaa gcaaaggagc aactattact 5760
taagaaactc caggagagtg catccatggc caacagaagc aggtatcagt cgcgcaaagt 5820
agaaaacatg aaagcagcaa tcatccagag actaaagaga ggctgtagac tatacttaat 5880
gtcagagacc ccaaaagtcc ctacttaccg gactacatat ccggcgcctg tgtactcgcc 5940
tccgatcaac gtccgattgt ccaatcccga gtccgcagtg gcagcatgca atgagttctt 6000
agctagaaac tatccaactg tctcatcata ccaaattacc gacgagtatg atgcatatct 6060
agacatggtg gacgggtcgg agagttgcct ggaccgagcg acattcaatc cgtcaaaact 6120
caggagctac ccgaaacagc acgcttacca cgcgccctcc atcagaagcg ctgtaccgtc 6180
cccattccag aacacactac agaatgtact ggcagcagcc acgaaaagaa actgcaacgt 6240
cacacagatg agggaattac ccactttgga ctcagcagta ttcaacgtgg agtgtttcaa 6300
aaaattcgca tgcaaccaag aatactggga agaatttgct gccagcccta ttaggataac 6360
aactgagaat ttagcaacct atgttactaa actaaaaggg ccaaaagcag cagcgctatt 6420
cgcaaaaacc cataatctac tgccactaca ggaagtacca atggataggt tcacagtaga 6480
tatgaaaagg gacgtaaagg tgactcctgg tacaaagcat acagaggaaa gacctaaggt 6540
gcaggttata caggcggctg aacccttggc gacagcatac ctatgtggga ttcacagaga 6600
gctggttagg aggctgaacg ccgtcctcct acccaatgta catacactat ttgacatgtc 6660
tgccgaggat ttcgatgcca tcatagccgc acactttaag ccaggagaca ctgttttgga 6720
aacggacata gcctcctttg ataagagcca agatgattca cttgcgctta ctgctttgat 6780
gctgttagag gatttagggg tggatcactc cctgctggac ttgatagagg ctgctttcgg 6840
agagatttcc agctgtcacc taccgacagg tacgcgcttc aagttcggcg ccatgatgaa 6900
atcaggtatg ttcctaactc tgttcgtcaa cacattgtta aacatcacca tcgccagccg 6960
agtgctggaa gatcgtctga caaaatccgc gtgcgcggcc ttcatcggcg acgacaacat 7020
aatacatgga gtcgtctccg atgaattgat ggcagccaga tgtgccactt ggatgaacat 7080
ggaagtgaag atcatagatg cagttgtatc cttgaaagcc ccttactttt gtggagggtt 7140
tatactgcac gatactgtga caggaacagc ttgcagagtg gcagacccgc taaaaaggct 7200
ttttaaactg ggcaaaccgc tagcggcagg tgacgaacaa gatgaagata gaagacgagc 7260
gctggctgac gaagtgatca gatggcaacg aacagggcta attgatgagc tggagaaagc 7320
ggtatactct aggtacgaag tgcagggtat atcagttgtg gtaatgtcca tggccacctt 7380
tgcaagctcc agatccaact tcgagaagct cagaggaccc gtcataactt tgtacggcgg 7440
tcctaaatag gtacgcacta cagctaccta ttttgcagaa gccgacagca agtatctaaa 7500
cactaatcag ctacaatgga gttcatccca acccaaactt tttacaatag gaggtaccag 7560
cctcgaccct ggactccgcg ccctactatc caagtcatca ggcccagacc gcgccctcag 7620
aggcaagctg ggcaacttgc ccagctgatc tcagcagtta ataaactgac aatgcgcgcg 7680
gtaccccaac agaagccacg caggaatcgg aagaataaga agcaaaagca aaaacaacag 7740
gcgccacaaa acaacacaaa tcaaaagaag cagccaccta aaaagaaacc ggctcaaaag 7800
aaaaagaagc cgggccgcag agagaggatg tgcatgaaaa tcgaaaatga ttgtattttc 7860
gaagtcaagc acgaaggtaa ggtaacaggt tacgcgtgcc tggtggggga caaagtaatg 7920
aaaccagcac acgtaaaggg gaccatcgat aacgcggacc tggccaaact ggcctttaag 7980
cggtcatcta agtatgacct tgaatgcgcg cagatacccg tgcacatgaa gtccgacgct 8040
tcgaagttca cccatgagaa accggagggg tactacaact ggcaccacgg agcagtacag 8100
tactcaggag gccggttcac catccctaca ggtgctggca aaccagggga cagcggcaga 8160
ccgatcttcg acaacaaggg acgcgtggtg gccatagtct taggaggagc taatgaagga 8220
gcccgtacag ccctctcggt ggtgacctgg aataaagaca ttgtcactaa aatcaccccc 8280
gagggggccg aagagtggag tcttgccatc ccagttatgt gcctgttggc aaacaccacg 8340
ttcccctgct cccagccccc ttgcacgccc tgctgctacg aaaaggaacc ggaggaaacc 8400
ctacgcatgc ttgaggacaa cgtcatgaga cctgggtact atcagctgct acaagcatcc 8460
```

FIGURE 8 (con't)

```
ttaacatgtt ctccccaccg ccagcgacgc agcaccaagg acaacttcaa tgtctataaa     8520
gccacaagac catacttagc tcactgtccc gactgtggag aagggcactc gtgccatagt     8580
cccgtagcac tagaacgcat cagaaatgaa gcgacagacg ggacgctgaa aatccaggtc     8640
tccttgcaaa tcggaataaa gacggatgac agccacgatt ggaccaagct gcgttatatg     8700
gacaaccaca tgccagcaga cgcagagagg gcggggctat ttgtaagaac atcagcaccg     8760
tgtacgatta ctggaacaat gggacacttc atcctggccc gatgtccaaa aggggaaact     8820
ctgacggtgg gattcactga cagtaggaag attagtcact catgtacgca cccatttcac     8880
cacgaccctc ctgtgatagg tcgggaaaaa ttccattccc gaccgcagca cggtaaagag     8940
ctaccttgca gcacgtacgt gcagagcacc gccgcaacta ccgaggagat agaggtacac     9000
atgcccccag acacccctga tcgcacatta atgtcacaac agtccggcaa cgtaaagatc     9060
acagtcaatg gccagacggt gcggtacaag tgtaattgcg gtggctcaaa tgaaggacta     9120
acaactacag acaaagtgat taataactgc aaggttgatc aatgtcatgc cgcggtcacc     9180
aatcacaaaa agtggcagta taactcccct ctggtcccgc gtaatgctga acttggggac     9240
cgaaaaggaa aaattcacat cccgtttccg ctggcaaatg taacatgcag ggtgcctaaa     9300
gcaaggaacc ccaccgtgac gtacggaaaa aaccaagtca tcatgctact gtatcctgac     9360
cacccaacac tcctgtccta ccggaatatg ggagaagaac caaactatca agaagagtgg     9420
gtgatgcata agaaggaagt cgtgctaacc gtgccgactg aagggctcga ggtcacgtgg     9480
ggcaacaacg agccgtataa gtattggccg cagttatcta caaacggtac agcccatggc     9540
cacccgcacg agataattct gtattattat gagctgtacc ccactatgac tgtagtagtt     9600
gtgtcagtgg ccacgttcat actcctgtcg atggtgggta tggcagcggg gatgtgcatg     9660
tgtgcacgac gcagatgcat cacaccgtat gaactgacac caggagctac cgtccctttc     9720
ctgcttagcc taatatgctg catcagaaca gctaaagcgg ccacatacca agaggctgcg     9780
atatacctgt ggaacgagca gcaacctttg ttttggctac aagcccttat tccgctggca     9840
gccctgattg ttctatgcaa ctgtctgaga ctcttaccat gctgctgtaa aacgttggct     9900
tttttagccg taatgagcgt cggtgcccac actgtgagcg cgtacgaaca cgtaacagtg     9960
atcccgaaca cggtgggagt accgtataag actctagtca atagacctgg ctacagcccc    10020
atggtattgg agatggaact actgtcagtc actttggagc caacactatc gcttgattac    10080
atcacgtgcg agtacaaaac cgtcatcccg tctccgtacg tgaagtgctg cggtacagca    10140
gagtgcaagg acaaaaacct acctgactac agctgtaagg tcttcaccgg cgtctaccca    10200
tttatgtggg gcggcgccta ctgcttctgc gacgctgaaa acacgcagtt gagcgaagca    10260
cacgtggaga agtccgaatc atgcaaaaca gaatttgcat cagcatacag ggctcatacc    10320
gcatctgcat cagctaagct ccgcgtcctt taccaaggaa ataacatcac tgtaactgcc    10380
tatgcaaacg gcgaccatgc cgtcacagtt aaggacgcca aattcattgt ggggccaatg    10440
tcttcagcct ggacaccttt cgacaacaaa attgtggtgt acaaaggtga cgtctataac    10500
atggactacc cgccctttgg cgcaggaaga ccaggacaat ttggcgatat ccaaagtcgc    10560
acacctgaga gtaaagacgt ctatgctaat acacaactgg tactgcagag accggctgtg    10620
ggtacggtac acgtgccata ctctcaggca ccatctggct ttaagtattg gctaaaagaa    10680
cgcggggcgt cgctgcagca cacagcacca tttggctgcc aaatagcaac aaacccggta    10740
agagcggtga actgcgccgt agggaacatg cccatctcca tcgacatacc ggaagcggcc    10800
ttcactaggg tcgtcgacgc gccctcttta acggacatgt cgtgcgaggt accagcctgc    10860
acccattcct cagactttgg gggcgtcgcc attattaaat atgcagccag caagaaaggc    10920
aagtgtgcgg tgcattcgat gactaacgcc gtcactattc gggaagctga gatagaagtt    10980
gaagggaatt ctcagctgca aatctctttc tcgacggcct tagccagcgc cgaattccgc    11040
gtacaagtct gttctacaca agtacactgt gcagccgagt gccacccccc gaaggaccac    11100
atagtcaact acccggcgtc acataccacc ctcggggtcc aggacatctc cgctacggcg    11160
atgtcatggg tgcagaagat cacgggaggt gtgggactgg ttgttgctgt tgccgcactg    11220
attctaatcg tggtgctatg cgtgtcgttc agcaggcact aacttgacaa ttaagtatga    11280
```

FIGURE 8 (con't)

```
aggtatatgt gtcccctaag agacacactg tacatagcaa ataatctata gatcaaaggg   11340
ctacgcaacc cctgaatagt aacaaaatat aaaatcacta aaaattataa aaacagaaaa   11400
atacataaat aggtatacgt gtcccctaag agacacattg tatgtaggtg ataagtatag   11460
atcaaagggc cgaataaccc ctgaatagta acaaaatatg aaaatcaata aaaatcataa   11520
aatagaaaaa ccataaacag aagtagttca aagggctata aaacccctga atagtaacaa   11580
aacataaaat taataaaaat c                                             11601
```

FIGURE 9

```
cagtttctta ctgctctact ctgcaaagca agagattaat aacccatcat ggatcctgtg      60
tacgtggaca tagacgctga cagcgccttt ttgaaggccc tgcaacgtgc gtaccccatg     120
tttgaggtgg aaccaaggca ggtcacaccg aatgaccatg ctaatgctag agcgttctcg     180
catctagcta taaaactaat agagcaggaa attgaccccg actcaaccat cctggatatc     240
ggcagtgcgc cagcaaggag gatgatgtcg gacaggaagt accactgcgt ctgcccgatg     300
cgcagtgcgg aagatcccga gagactcgcc aattatgcga gaaagctagc atctgccgca     360
ggaaaagtcc tggacagaaa catctctgga aagatcgggg acttacaagc agtaatggcc     420
gtgccagaca cggagacgcc aacattctgc ttacacacag acgtctcatg tagacagaga     480
gcagacgtcg ctatatacca agacgtctat gctgtacacg cacccacgtc gctataccac     540
caggcgatta aaggggtccg agtggcgtac tgggttgggt tcgacacaac cccgttcatg     600
tacaatgcca tggcgggtgc ctacccctca tactcgacaa actgggcaga tgagcaggta     660
ctgaaggcta agaacatagg attatgttca acagacctga cggaaggtag acgaggcaag     720
ttgtctatta tgagagggaa aaagctaaaa ccgtgcgacc gtgtgctgtt ctcagtaggg     780
tcaacgctct acccggaaag ccgcaagcta cttaagagct ggcacctgcc atcggtgttc     840
catttaaagg gcaaactcag cttcacatgc cgctgtgata cagtggtttc gtgtgagggc     900
tacgtcgtta agagaataac gatgagccca ggcctttatg gaaaaaccac agggtatgcg     960
gtaacccacc acgcagacgg attcctgatg tgcaagacta ccgacacggt tgacggcgaa    1020
agagtgtcat tctcggtgtg cacatacgtg ccggcgacca tttgtgatca aatgaccggc    1080
atccttgcta cagaagtcac gccggaggat gcacagaagc tgttggtggg gctgaaccag    1140
agaatagtgg ttaacggcag aacgcaacgg aatacgaaca ccatgaaaaa ttatctgctt    1200
cccgtggtcg cccaagcctt cagtaagtgg gcaaaggagt gccggaaaga catggaagat    1260
gaaaaactcc tgggggtcag agaaagaaca ctgacctgct gctgtctatg ggcattcaag    1320
aagcagaaaa cacacacggt ctacaagagg cctgataccc agtcaattca gaaggttcag    1380
gccgagtttg acagctttgt ggtaccgagt ctgtggtcgt ccgggttgtc aatccctttg    1440
aggactagaa tcaaatggtt gttaagcaag gtgccaaaaa ccgacctgat cccatacagc    1500
ggagacgccc gagaagcccg ggacgcagaa aaagaagcag aggaagaacg agaagcagaa    1560
ctgactcgcg aagccctacc acctctacag gcagcacagg aagatgttca ggtcgaaatc    1620
gacgtggaac agcttgagga cagagcgggc gcaggaataa tagagactcc gagaggagct    1680
atcaaagtta ctgcccaacc aacagaccac gtcgtgggag agtacctggt actctccccg    1740
cagaccgtac tacgtagcca gaagctcagt ctgattcacg ctttggcgga gcaagtgaag    1800
acgtgcacgc acaacggacg agcagggagg tatgcggtcg aagcgtacga cggccgagtc    1860
ctagtgccct caggctatgc aatctcgcct gaagacttcc agagtctaag cgaaagcgca    1920
acgatggtgt ataacgaaag agagttcgta aacagaaagc tacaccatat tgcgatgcac    1980
ggaccagccc tgaacaccga cgaagagtcg tatgagctgg tgagggcaga gaggacagaa    2040
cacgagtacg tctacgacgt ggatcagaga agatgctgta agaaggaaga agccgcagga    2100
ctggtactgg tgggcgactt gactaatccg ccctaccacg aattcgcata tgaaggcgta    2160
aaaatccgcc ctgcctgccc atacaaaatt gcagtcatag gagtcttcgg agtaccggga    2220
tctggcaagt cagctattat caagaaccta gttaccaggc aggacctggt gactagcgga    2280
aagaaagaaa actgccaaga aatcaccacc gacgtgatga gacagagagg tctagagata    2340
tctgcacgta cggttgactc gctgctcttg aatggatgca acagaccagt cgacgtgttg    2400
tacgtagacg aggcgtttgc gtgccactct ggaacgctac ttgctttgat cgccttggtg    2460
agaccaaggc agaaagttgt actttgtggt gacccgaagc agtgcggctt cttcaatatg    2520
atgcagatga aagtcaacta taatcacaac atctgcaccc aagtgtacca caaaagtatc    2580
tccaggcggt gtacactgcc tgtgaccgcc attgtgtcat cgttgcatta cgaaggcaaa    2640
atgcgcacta cgaatgagta caacaagccg attgtagtgg acactacagg ctcaacaaaa    2700
cctgaccctg gagacctcgt gttaacgtgc ttcagagggt gggttaaaca actgcaaatt    2760
gactatcgtg gatacgaggt catgacagca gccgcatccc aagggttaac cagaaaagga    2820
```

FIGURE 9 (con't)

```
gtttacgcag ttagacaaaa agttaatgaa aacccgctct atgcatcaac gtcagagcac 2880
gtcaacgtac tcctaacgcg tacggaaggt aaactggtat ggaagacact ttccggcgac 2940
ccgtggataa agacgctgca gaacccaccg aaaggaaact tcaaagcaac tattaaggag 3000
tgggaggtgg agcatgcatc aataatggcg ggcatctgca gtcaccaaat gaccttcgat 3060
acattccaaa ataaagccaa cgtttgttgg gctaagagct tggtccctat cctcgaaaca 3120
gcggggataa aactaaatga taggcagtgg tctcagataa ttcaagcctt caaagaagac 3180
aaagcatact cacctgaagt agccctgaat gaaatatgta cgcgcatgta tggggtggat 3240
ctagacagcg ggctattttc taaaccgttg gtgtctgtgt attacgcgga taaccactgg 3300
gataataggc ctggagggaa aatgttcgga tttaaccccg aggcagcatc cattctagaa 3360
agaaagtatc cattcacaaa agggaagtgg aacatcaaca agcagatctg cgtgactacc 3420
aggaggatag aagactttaa ccctaccacc aacatcatac cggccaacag gagactacca 3480
cactcattag tggccgaaca ccgcccagta aaaggggaaa gaatggaatg gctggttaac 3540
aagataaacg gccaccacgt gctcctggtc agtggctata accttgcact gcctactaag 3600
agagtcactt gggtagcgcc gttaggtgtc cgcggagcgg actacacata caacctagag 3660
ttgggtctgc cagcaacgct tggtaggtat gacctagtgg tcataaacat ccacacacct 3720
tttcgcatac accattacca acagtgcgtc gaccacgcaa tgaaactgca aatgctcggg 3780
ggtgactcat tgagactgct caaaccgggc ggctctctat tgatcagagc atatggttac 3840
gcagatagaa ccagtgaacg agtcatctgc gtattgggac gcaagtttag atcgtctaga 3900
gcgttgaaac caccatgtgt caccagcaac actgagatgt ttttcctatt cagcaacttt 3960
gacaatggca gaaggaattt cacaactcat gtcatgaaca atcaactgaa tgcagccttc 4020
gtaggacagg tcacccgagc aggatgtgca ccgtcgtacc gggtaaaacg catggacatc 4080
gcgaagaacg atgaagagtg cgtagtcaac gccgctaacc ctcgcgggtt accgggtgac 4140
ggtgtttgca aggcagtata caaaaaatgg ccggagtcct ttaagaacag tgcaacacca 4200
gtgggaaccg caaaaacagt tatgtgcggt acgtatccag taatccacgc tgttggacca 4260
aacttctcta attattcgga gtctgaaggg gaccgggaat tggcagctgc ctatcgagaa 4320
gtcgcaaagg aagtaactag gctgggagta aatagtgtag ctatacctct cctctccaca 4380
ggtgtatact caggagggaa agacaggctg acccagtcac tgaaccacct ctttacagcc 4440
atggactcga cggatgcaga cgtggtcatc tactgccgcg acaaagaatg ggagaagaaa 4500
atatctgagg ccatacagat gcggacccaa gtagagctgc tggatgagca catctccata 4560
gactgcgata ttgttcgcgt gcaccctgac agcagcttgg caggcagaaa aggatacagc 4620
accacggaag gcgcactgta ctcatatcta gaagggaccc gttttcatca gacggctgtg 4680
gatatggcgg agatacatac tatgtggcca aagcaaacag aggccaatga gcaagtctgc 4740
ctatatgccc tgggggaaag tattgaatcg atcaggcaga aatgcccggt ggatgatgca 4800
gacgcatcat ctccccccaa aactgtcccg tgcctttgcc gttacgctat gactccagaa 4860
cgcgtcaccc ggcttcgcat gaaccacgtc acaagcataa ttgtgtgttc ttcgtttccc 4920
ctcccaaagt acaaaataga aggagtgcaa aaagtcaaat gctctaaggt aatgctattt 4980
gaccacaacg tgccatcgcg cgtaagtcca agggaatata gatcttccca ggagtctgca 5040
caggaggcga gtacaatcac gtcactgacg catagtcaat tcgacctaag cgttgatggc 5100
gagatactgc ccgtcccgtc agacctggat gctgacgccc cagccctaga accagcacta 5160
gacgacgggg cgacacacac gctgccatcc acaaccggaa accttgcggc cgtgtctaga 5220
cagggcaggt gggtatatat tctcgtcgga caccggtcca ggtcatttac aacagaagtc 5280
agtacgccag tcagtgctgc cggtgaacac cctggaggaa gtccacgagg agaagtgtta 5340
cccacctaag ctggatgaag caaaggagca actattactt aagaaactcc aggagagtgc 5400
atccatggcc aacagaagca ggtatcagtc gcgcaaagta gaaaacatga aagcagcaat 5460
catccagaga ctaaagagag gctgtagact atacttaatg tcagagaccc caaaagtccc 5520
tacttaccgg actacatatc cggcgcctgt gtactcgcct ccgatcaacg tccgattgtc 5580
caatcccgag tccgcagtgg cagcatgcaa tgagttctta gctagaaact atccaactgt 5640
```

FIGURE 9 (con't)

```
ctcatcatac caaattaccg acgagtatga tgcatatcta gacatggtgg acgggtcgga    5700
gagttgcctg gaccgagcga cattcaatcc gtcaaaactc aggagctacc cgaaacagca    5760
cgcttaccac gcgccctcca tcagaagcgc tgtaccgtcc ccattccaga acacactaca    5820
gaatgtactg gcagcagcca cgaaaagaaa ctgcaacgtc acacagatga gggaattacc    5880
cactttggac tcagcagtat tcaacgtgga gtgtttcaaa aaattcgcat gcaaccaaga    5940
atactgggaa gaatttgctg ccagccctat taggataaca actgagaatt tagcaaccta    6000
tgttactaaa ctaaaagggc caaaagcagc agcgctattc gcaaaaaccc ataatctact    6060
gccactacag gaagtaccaa tggataggtt cacagtagat atgaaaaggg acgtgaaggt    6120
gactcctggt acaaagcata cagaggaaag acctaaggtg caggttatac aggcggctga    6180
acccttggcg acagcatacc tatgtgggat tcacagagag ctggttagga ggctgaacgc    6240
cgtcctccta cccaatgtac atacactatt tgacatgtct gccgaggatt tcgatgccat    6300
catagccgca cactttaagc caggagacac tgttttggaa acggacatag cctcctttga    6360
taagagccaa gatgattcac ttgcgcttac tgctttgatg ctgttagagg atttaggggt    6420
ggatcactcc ctgctggact tgatagaggc tgctttcgga gagatttcca gctgtcacct    6480
accgacaggt acgcgcttca agttcggcgc catgatgaaa tcaggtatgt tcctaactct    6540
gttcgtcaac acattgttaa acatcaccat cgccagccga gtgctggaag atcgtctgac    6600
aaaatccgcg tgcgcggcct tcatcggcga cgacaacata atacatggag tcgtctccga    6660
tgaattgatg gcagccagat gtgccacttg gatgaacatg gaagtgaaga tcatagatgc    6720
agttgtatcc ttgaaagccc cttacttttg tggagggttt atactgcacg atactgtgac    6780
aggaacagct tgcagagtgg cagacccgct aaaaaggctt tttaaactgg gcaaaccgct    6840
agcggcaggt gacgaacaag atgaagatag aagacgagcg ctggctgacg aagtgatcag    6900
atggcaacga acagggctaa ttgatgagct ggagaaagcg gtatactcta ggtacgaagt    6960
gcagggtata tcagttgtgg taatgtccat ggccaccttt gcaagctcca gatccaactt    7020
cgagaagctc agaggacccg tcataacttt gtacggcggt cctaaatagg tacgcactac    7080
agctacctat tttgcagaag ccgacagcaa gtatctaaac actaatcagc tacaatggag    7140
ttcatcccaa cccaaacttt ttacaatagg aggtaccagc ctcgaccctg gactccgcgc    7200
cctactatcc aagtcatcag gcccagaccg cgccctcaga ggcaagctgg gcaacttgcc    7260
cagctgatct cagcagttaa taaactgaca atgcgcgcgg taccccaaca gaagccacgc    7320
aggaatcgga agaataagaa gcaaaagcaa aaacaacagg cgccacaaaa caacacaaat    7380
caaaagaagc agccacctaa aaagaaaccg gctcaaaaga aaaagaagcc gggccgcaga    7440
gagaggatgt gcatgaaaat cgaaaatgat tgtattttcg aagtcaagca cgaaggtaag    7500
gtaacaggtt acgcgtgcct ggtgggggac aaagtaatga aaccagcaca cgtaaagggg    7560
accatcgata acgcggacct ggccaaactg gcctttaagc ggtcatctaa gtatgacctt    7620
gaatgcgcgc agatacccgt gcacatgaag tccgacgctt cgaagttcac ccatgagaaa    7680
ccggaggggt actacaactg gcaccacgga gcagtacagt actcaggagg ccggttcacc    7740
atccctacag gtgctggcaa accaggggac agcggcagac cgatcttcga caacaaggga    7800
cgcgtggtgg ccatagtctt aggaggagct aatgaaggag cccgtacagc cctctcggtg    7860
gtgacctgga ataaagacat tgtcactaaa atcacccccg aggggggcga agagtggagt    7920
cttgccatcc cagttatgtg cctgttggca aacaccacgt tcccctgctc ccagcccccct    7980
tgcacgccct gctgctacga aaaggaaccg gaggaaaccc tacgcatgct tgaggacaac    8040
gtcatgagac ctgggtacta tcagctgcta caagcatcct taacatgttc tccccaccgc    8100
cagcgacgca gcaccaagga caacttcaat gtctataaag ccacaagacc atacttagct    8160
cactgtcccg actgtggaga agggcactcg tgccatagtc ccgtagcact agaacgcatc    8220
agaaatgaag cgacagacgg gacgctgaaa atccaggtct ccttgcaaat cggaataaag    8280
acggatgaca gccacgattg gaccaagctg cgttatatgg acaaccacat gccagcagac    8340
gcagagaggg cggggctatt tgtaagaaca tcagcaccgt gtacgattac tggaacaatg    8400
ggacacttca tcctggcccg atgtccaaaa ggggaaactc tgacggtggg attcactgac    8460
```

FIGURE 9 (con't)

```
agtaggaaga ttagtcactc atgtacgcac ccatttcacc acgaccctcc tgtgataggt     8520
cgggaaaaat tccattcccg accgcagcac ggtaaagagc taccttgcag cacgtacgtg     8580
cagagcaccg ccgcaactac cgaggagata gaggtacaca tgcccccaga cacccctgat     8640
cgcacattaa tgtcacaaca gtccggcaac gtaaagatca cagtcaatgg ccagacggtg     8700
cggtacaagt gtaattgcgg tggctcaaat gaaggactaa caactacaga caaagtgatt     8760
aataactgca aggttgatca atgtcatgcc gcggtcacca atcacaaaaa gtggcagtat     8820
aactcccctc tggtcccgcg taatgctgaa cttggggacc gaaaaggaaa aattcacatc     8880
ccgtttccgc tggcaaatgt aacatgcagg gtgcctaaag caaggaaccc caccgtgacg     8940
tacgggaaaa accaagtcat catgctactg tatcctgacc acccaacact cctgtcctac     9000
cggaatatgg gagaagaacc aaactatcaa gaagagtggg tgatgcataa gaaggaagtc     9060
gtgctaaccg tgccgactga agggctcgag gtcacgtggg gcaacaacga gccgtataag     9120
tattggccgc agttatctac aaacggtaca gcccatggcc acccgcatga gataattctg     9180
tattattatg agctgtaccc cactatgact gtagtagttg tgtcagtggc cacgttcata     9240
ctcctgtcga tggtgggtat ggcagcgggg atgtgcatgt gtgcacgacg cagatgcatc     9300
acaccgtatg aactgacacc aggagctacc gtccctttcc tgcttagcct aatatgctgc     9360
atcagaacag ctaaagcggc cacataccaa gaggctgcga tatacctgtg gaacgagcag     9420
caacctttgt tttggctaca agcccttatt ccgctggcag ccctgattgt tctatgcaac     9480
tgtctgagac tcttaccatg ctgctgtaaa acgttggctt ttttagccgt aatgagcgtc     9540
ggtgcccaca ctgtgagcgc gtacgaacac gtaacagtga tcccgaacac ggtgggagta     9600
ccgtataaga ctctagtcaa tagacctggc tacagcccca tggtattgga gatggaacta     9660
ctgtcagtca ctttggagcc aacactatcg cttgattaca tcacgtgcga gtacaaaacc     9720
gtcatcccgt ctccgtacgt gaagtgctgc ggtacagcag agtgcaagga caaaaaccta     9780
cctgactaca gctgtaaggt cttcaccggc gtctacccat ttatgtgggg cggcgcctac     9840
tgcttctgcg acgctgaaaa cacgcagttg agcgaagcac acgtggagaa gtccgaatca     9900
tgcaaaacag aatttgcatc agcatacagg gctcataccg catctgcatc agctaagctc     9960
cgcgtccttt accaaggaaa taacatcact gtaactgcct atgcaaacgg cgaccatgcc    10020
gtcacagtta aggacgccaa attcattgtg gggccaatgt cttcagcctg gacacctttc    10080
gacaacaaaa ttgtggtgta caaaggtgac gtctataaca tggactaccc gccctttggc    10140
gcaggaagac caggacaatt tggcgatatc caaagtcgca cacctgagag taaagacgtc    10200
tatgctaata cacaactggt actgcagaga ccggctgcgg gtacggtaca cgtgccatac    10260
tctcaggcac catctggctt taagtattgg ctaaaagaac gcggggcgtc gctgcagcac    10320
acagcaccat ttggctgcca aatagcaaca aacccggtaa gagcggtgaa ctgcgccgta    10380
gggaacatgc ccatctccat cgacataccg gaagcggcct tcactagggt cgtcgacgcg    10440
ccctctttaa cggacatgtc gtgcgaggta ccagcctgca cccattcctc agactttggg    10500
ggcgtcgcca ttattaaata tgcagccagc aagaaaggca agtgtgcggt gcattcgatg    10560
actaacgccg tcactattcg ggaagctgag atagaagttg aagggaattc tcagctgcaa    10620
atctctttct cgacggcctt agccagcgcc gaattccgcg tacaagtctg ttctacacaa    10680
gtacactgtg cagccgagtg ccaccccccg aaggaccaca tagtcaacta cccggcgtca    10740
cataccaccc tcggggtcca ggacatctcc gctacggcga tgtcatgggt gcagaagatc    10800
acgggaggtg tgggactggt tgttgctgtt gccgcactga ttctaatcgt ggtgctatgc    10860
gtgtcgttca gcaggcacta acttgacaat taagtatgaa ggtatatgtg tcccctaaga    10920
gacacactgt acatagcaaa taatctatag atcaaagggc tacgcaaccc ctgaatagta    10980
acaaaataca aaatcactaa aaattataaa aacagaaaaa tacataaata ggtatacgtg    11040
tcccctaaga gacacattgt atgtaggtga taagtataga tcaaagggcc gaataacccc    11100
tgaatagtaa caaaatatga aaatcaataa aaatcataaa atagaaaaac cataaacaga    11160
agtagttcaa agggctataa aacccctgaa tagtaacaaa acataaaatt aataaaaatc    11220
aaatgaatac catatgg                                                   11237
```

FIGURE 10

```
atacccgtgc acatgaagtc cgacgcttcg aagttcaccc atgagaaacc ggaggggtac      60
tacaactggc accacggagc agtacagtac tcaggaggcc ggttcaccat ccctacaggt     120
gctggcaaac caggggacag cggcagaccg atcttcgaca acaagggacg cgtggtggcc     180
atagtcttag gaggagctaa tgaaggagcc cgtacagccc tctcggtggt gacctggaat     240
aaagacattg tcactaaaat cacccccgag gggggccgaag agtggagtct tgccatccca     300
gttatgtgcc tgttggcaaa caccacgttc ccctgctccc agccccccttg cacgccctgc     360
tgctacgaaa aggaaccgga ggaaacccta cgcatgcttg aggacaacgt catgagacct     420
gggtactatc agctgctaca agcatcctta acatgttctc cccaccgcca gcgacgcagc     480
accaaggaca acttcaatgt ctataaagcc acaagaccat acttagctca ctgtcccgac     540
tgtggagaag ggcactcgtg ccatagtccc gtagcactag aacgcatcag aaatgaagcg     600
acagacggga cgctgaaaat ccaggtctcc ttgcaaatcg gaataaagac ggatgacagc     660
cacgattgga ccaagctgcg ttatatggac aaccacatgc cagcagacgc agagagggcg     720
gggctatttg taagaacatc agcaccgtgt acgattactg gaacaatggg acacttcatc     780
ctggcccgat gtccaaaagg ggaaactctg acggtgggat tcactgacag taggaagatt     840
agtcactcat gtacgcaccc atttcaccac gaccctcctg tgataggtcg ggaaaaattc     900
cattccccgac cgcagcacgg taaagagcta ccttgcagca cgtacgtgca gagcaccgcc     960
gcaactaccg aggagataga ggtacacatg cccccagaca cccctgatcg cacattaatg    1020
tcacaacagt ccggcaacgt aaagatcaca gtcaatggcc agacggtgcg gtacaagtgt    1080
aattgcggtg gctcaaatga aggactaaca actacagaca aagtgattaa taactgcaag    1140
gttgatcaat gtcatgccgc ggtcaccaat cacaaaaagt ggcagtataa ctcccctctg    1200
gtcccgcgta atgctgaact tggggaccga aaaggaaaaa ttcacatccc gtttccgctg    1260
gcaaatgtaa catgcagggt gcctaaagca aggaacccca ccgtgacgta cgggaaaaac    1320
caagtcatca tgctactgta tcctgaccac ccaacactcc tgtcctaccg gaatatggga    1380
gaagaaccaa actatcaaga agagtgggtg atgcataaga aggaagtcgt gctaaccgtg    1440
ccgactgaag ggctcgaggt cacgtggggc aacaacgagc cgtataagta ttggccgcag    1500
ttatctacaa acggtacagc ccatggccac ccgcatgaga taattctgta ttattatgag    1560
ctgtacccca ctatgactgt agtagttgtg tcagtggcca cgttcatact cctgtcgatg    1620
gtgggtatgg cagcggggat gtgcatgcgt gcacgacgca gatgcatcac accgtatgaa    1680
ctgacaccag gagctaccgt ccctttcctg cttagcctaa tatgctgcat cagaacagct    1740
aaagcggcca cataccaaga ggctgcgata tacctgtgga acgagcagca accttta       1797
```

FIGURE 11

```
atacccgtgc acatgaagtc cgacgcttcg aagttcaccc atgagaaacc ggaggggtac     60
tacaactggc accacggagc agtacagtac tcaggaggcc ggttcaccat ccctacaggt    120
gctggcaaac caggggacag cggcagaccg atcttcgaca acaagggacg cgtggtggcc    180
atagtcttag gaggagctaa tgaaggagcc cgtacagccc tctcggtggt gacctggaat    240
aaagacattg tcactaaaat cacccccgag gggccgaag agtggagtct tgccatccca     300
gttatgtgcc tgttggcaaa caccacgttc ccctgctccc agccccttg cacgccctgc     360
tgctacgaaa aggaaccgga ggaaacccta cgcatgcttg aggacaacgt catgagacct    420
gggtactatc agctgctaca agcatcctta acatgttctc cccaccgcca gcgacgcagc    480
accaaggaca acttcaatgt ctataaagcc acaagaccat acttagctca ctgtcccgac    540
tgtggagaag ggcactcgtg ccatagtccc gtagcactag aacgcatcag aaatgaagcg    600
acagacggga cgctgaaaat ccaggtctcc ttgcaaatcg gaataaagac ggatgacagc    660
cacgattgga ccaagctgcg ttatatggac aaccacatgc cagcagacgc agagagggcg    720
gggctatttg taagaacatc agcaccgtgt acgattactg gaacaatggg acacttcatc    780
ctggcccgat gtccaaaagg ggaaactctg acggtgggat tcactgacag taggaagatt    840
agtcactcat gtacgcaccc atttcaccac gaccctcctg tgataggtcg ggaaaaattc    900
cattcccgac cgcagcacgg taaagagcta ccttgcagca cgtacgtgca gagcaccgcc    960
gcaactaccg aggagataga ggtacacatg cccccagaca cccctgatcg cacattaatg   1020
tcacaacagt ccggcaacgt aaagatcaca gtcaatggcc agacggtgcg gtacaagtgt   1080
aattgcggtg gctcaaatga aggactaaca actacagaca aagtgattaa taactgcaag   1140
gttgatcaat gtcatgccgc ggtcaccaat cacaaaaagt ggcagtataa ctcccctctg   1200
gtcccgcgta atgctgaact tggggaccga aaaggaaaaa ttcacatccc gtttccgctg   1260
gcaaatgtaa catgcagggt gcctaaagca aggaacccca ccgtgacgta cgggaaaaac   1320
caagtcatca tgctactgta tcctgaccac ccaacactcc tgtcctaccg gaatatggga   1380
gaagaaccaa actatcaaga agagtgggtg atgcataaga aggaagtcgt gctaaccgtg   1440
ccgactgaag ggctcgaggt cacgtggggc aacaacgagc cgtataagta ttggccgcag   1500
ttatctacaa acggtacagc ccatggccac ccgcatgaga taattctgta ttattatgag   1560
ctgtacccca ctatgactgt agtagttgtg tcagtggcca cgttcatact cctgtcgatg   1620
gtgggtatgg cagcggggat gtgcatgtgt gcacgacgca gatgcatcac accgtatgaa   1680
ctgacaccag gagctaccgt ccctttcctg cttagcctaa tatgctgcat cagaacagct   1740
aaagcggcca cataccaaga ggctgcgata tacctgtgga acgagcagca acctttta      1797
```

FIGURE 12

```
atacccgtgc acatgaagtc cgacgcttcg aagttcaccc atgagaaacc ggaggggtac      60
tacaactggc accacggagc agtacagtac tcaggaggcc ggttcaccat ccctacaggt     120
gctggcaaac caggggacag cggcagaccg atcttcgaca acaagggacg cgtggtggcc     180
atagtcttag gaggagctaa tgaaggagcc cgtacagccc tctcggtggt gacctggaat     240
aaagacattg tcactaaaat caccccgag ggggccgaag agtggagtct tgccatccca      300
gttatgtgcc tgttggcaaa caccacgttc ccctgctccc agcccccttg cacgccctgc     360
tgctacgaaa aggaaccgga ggaaacccta cgcatgcttg aggacaacgt catgagacct     420
gggtactatc agctgctaca agcatcctta acatgttctc cccaccgcca gcgacgcagc     480
accaaggaca acttcaatgt ctataaagcc acaagaccat acttagctca ctgtcccgac     540
tgtggagaag ggcactcgtg ccatagtccc gtagcactag aacgcatcag aaatgaagcg     600
acagacggga cgctgaaaat ccaggtctcc ttgcaaatcg gaataaagac ggatgacagc     660
cacgattgga ccaagctgcg ttatatggac aaccacatgc cagcagacgc agagagggcg     720
gggctatttg taagaacatc agcaccgtgt acgattactg gaacaatggg acacttcatc     780
ctggcccgat gtccaaaagg ggaaactctg acggtgggat tcactgacag taggaagatt     840
agtcactcat gtacgcaccc atttcaccac gaccctcctg tgataggtcg ggaaaaattc     900
cattcccgac cgcagcacgg taaagagcta ccttgcagca cgtacgtgca gagcaccgcc     960
gcaactaccg aggagataga ggtacacatg cccccagaca cccctgatcg cacattaatg    1020
tcacaacagt ccggcaacgt aaagatcaca gtcaatggcc agacggtgcg gtacaagtgt    1080
aattgcggtg gctcaaatga aggactaaca actacagaca aagtgattaa taactgcaag    1140
gttgatcaat gtcatgccgc ggtcaccaat cacaaaaagt ggcagtataa ctcccctctg    1200
gtcccgcgta atgctgaact tggggaccga aaaggaaaaa ttcacatccc gtttccgctg    1260
gcaaatgtaa catgcagggt gcctaaagca aggaacccca ccgtgacgta cgggaaaaac    1320
caagtcatca tgctactgta tcctgaccac ccaacactcc tgtcctaccg gaatatggga    1380
gaagaaccaa actatcaaga agagtgggtg atgcataaga aggaagtcgt gctaaccgtg    1440
ccgactgaag ggctcgaggt cacgtggggc aacaacgagc cgtataagta ttggccgcag    1500
ttatctacaa acggtacagc ccatggccac ccgcacgaga taattctgta ttattatgag    1560
ctgtacccca ctatgactgt agtagttgtg tcagtggcca cgttcatact cctgtcgatg    1620
gtgggtatgg cagcggggat gtgcatgtgt gcacgacgca gatgcatcac accgtatgaa    1680
ctgacaccag gagctaccgt ccctttcctg cttagcctaa tatgctgcat cagaacagct    1740
aaagcggcca cataccaaga ggctgcgata tacctgtgga acgagcagca accttta       1797
```

FIGURE 13

```
atacccgtgc acatgaagtc cgacgcttcg aagttcaccc atgagaaacc ggaggggtac      60
tacaactggc accacggagc agtacagtac tcaggaggcc ggttcaccat ccctacaggt     120
gctggcaaac caggggacag cggcagaccg atcttcgaca acaagggacg cgtggtggcc     180
atagtcttag gaggagctaa tgaaggagcc cgtacagccc tctcggtggt gacctggaat     240
aaagacattg tcactaaaat caccccccgag gggccgaag agtggagtct tgccatccca     300
gttatgtgcc tgttggcaaa caccacgttc ccctgctccc agcccccttg cacgccctgc     360
tgctacgaaa aggaaccgga ggaaacccta cgcatgcttg aggacaacgt catgagacct     420
gggtactatc agctgctaca agcatcctta acatgttctc cccaccgcca gcgacgcagc     480
accaaggaca acttcaatgt ctataaagcc acaagaccat acttagctca ctgtcccgac     540
tgtggagaag ggcactcgtg ccatagtccc gtagcactag aacgcatcag aaatgaagcg     600
acagacggga cgctgaaaat ccaggtctcc ttgcaaatcg gaataaagac ggatgacagc     660
cacgattgga ccaagctgcg ttatatggac aaccacatgc cagcagacgc agagagggcg     720
gggctatttg taagaacatc agcaccgtgt acgattactg gaacaatggg acacttcatc     780
ctggcccgat gtccaaaagg ggaaactctg acggtgggat tcactgacag taggaagatt     840
agtcactcat gtacgcaccc atttcaccac gaccctcctg tgataggtcg ggaaaaattc     900
cattcccgac cgcagcacgg taaagagata ccttgcagca cgtacgtgca gagcaccgcc     960
gcaactaccg aggagataga ggtacacatg cccccagaca cccctgatcg cacattaatg    1020
tcacaacagt ccggcaacgt aaagatcaca gtcaatggcc agacggtgcg gtacaagtgt    1080
aattgcggtg gctcaaatga aggactaaca actacagaca aagtgattaa taactgcaag    1140
gttgatcaat gtcatgccgc ggtcaccaat cacaaaaagt ggcagtataa ctcccctctg    1200
gtcccgcgta atgctgaact tggggaccga aaaggaaaaa ttcacatccc gtttccgctg    1260
gcaaatgtaa catgcagggt gcctaaagca aggaacccca ccgtgacgta cgggaaaaac    1320
caagtcatca tgctactgta tcctgaccac ccaacactcc tgtcctaccg gaatatggga    1380
gaagaaccaa actatcaaga agagtgggtg atgcataaga aggaagtcgt gctaaccgtg    1440
ccgactgaag ggctcgaggt cacgtggggc aacaacgagc cgtataagta ttggccgcag    1500
ttatctacaa acggtacagc ccatggccac ccgcatgaga taattctgta ttattatgag    1560
ctgtacccca ctatgactgt agtagttgtg tcagtggcca cgttcatact cctgtcgatg    1620
gtgggtatgg cagcggggat gtgcatgtgt gcacgacgca gatgcatcac accgtatgaa    1680
ctgacaccag gagctaccgt ccctttcctg cttagcctaa tatgctgcat cagaacagct    1740
aaagcggcca cataccaaga ggctgcgata tacctgtgga acgagcagca accttta       1797
```

FIGURE 14

```
gacaacttca atgtctataa agccacaaga ccatacttag ctcactgtcc cgactgtgga     60
gaagggcact cgtgccatag tcccgtagca ctagaacgca tcagaaatga agcgacagac    120
gggacgctga aaatccaggt ctccttgcaa atcggaataa agacggatga cagccacgat    180
tggaccaagc tgcgttatat ggacaaccac atgccagcag acgcagagag ggcggggcta    240
tttgtaagaa catcagcacc gtgtacgatt actggaacaa tgggacactt catcctggcc    300
cgatgtccaa aaggggaaac tctgacggtg ggattcactg acagtaggaa gattagtcac    360
tcatgtacgc acccatttca ccacgaccct cctgtgatag gtcgggaaaa attccattcc    420
cgaccgcagc acggtaaaga gctaccttgc agcacgtacg tgcagagcac cgccgcaact    480
accgaggaga tagaggtaca catgccccca gacacccctg atcgcacatt aatgtcacaa    540
cagtccggca acgtaaagat cacagtcaat ggccagacgg tgcggtacaa gtgtaattgc    600
ggtggctcaa atgaaggact aacaactaca gacaaagtga ttaataactg caaggttgat    660
caatgtcatg ccgcggtcac caatcacaaa aagtggcagt ataactcccc tctggtcccg    720
cgtaatgctg aacttgggga ccgaaaagga aaaattcaca tcccgtttcc gctggcaaat    780
gtaacatgca gggtgcctaa agcaaggaac cccaccgtga cgtacgggaa aaaccaagtc    840
atcatgctac tgtatcctga ccacccaaca ctcctgtcct accggaatat gggagaagaa    900
ccaaactatc aagaagagtg ggtgatgcat aagaaggaag tcgtgctaac cgtgccgact    960
gaagggctcg aggtcacgtg ggcaacaac gagccgtata agtattggcc gcagttatct    1020
acaaacggta cagcccatgg ccacccgcat gagataattc tgtattatta tgagctgtac   1080
cccactatga ct                                                        1092
```

FIGURE 15

```
gacaacttca atgtctataa agccacaaga ccatacttag ctcactgtcc cgactgtgga     60
gaagggcact cgtgccatag tcccgtagca ctagaacgca tcagaaatga agcgacagac    120
gggacgctga aaatccaggt ctccttgcaa atcggaataa agacggatga cagccacgat    180
tggaccaagc tgcgttatat ggacaaccac atgccagcag acgcagagag ggcggggcta    240
tttgtaagaa catcagcacc gtgtacgatt actggaacaa tgggacactt catcctggcc    300
cgatgtccaa aaggggaaac tctgacggtg ggattcactg acagtaggaa gattagtcac    360
tcatgtacgc acccatttca ccacgaccct cctgtgatag gtcgggaaaa attccattcc    420
cgaccgcagc acggtaaaga gctaccttgc agcacgtacg tgcagagcac cgccgcaact    480
accgaggaga tagaggtaca catgccccca gacacccctg atcgcacatt aatgtcacaa    540
cagtccggca acgtaaagat cacagtcaat ggccagacgg tgcggtacaa gtgtaattgc    600
ggtggctcaa atgaaggact aacaactaca gacaaagtga ttaataactg caaggttgat    660
caatgtcatg ccgcggtcac caatcacaaa aagtggcagt ataactcccc tctggtcccg    720
cgtaatgctg aacttgggga ccgaaaagga aaaattcaca tcccgtttcc gctggcaaat    780
gtaacatgca gggtgcctaa agcaaggaac cccaccgtga cgtacgggaa aaaccaagtc    840
atcatgctac tgtatcctga ccacccaaca ctcctgtcct accggaatat gggagaagaa    900
ccaaactatc aagaagagtg ggtgatgcat aagaaggaag tcgtgctaac cgtgccgact    960
gaagggctcg aggtcacgtg ggcaacaac gagccgtata agtattggcc gcagttatct    1020
acaaacggta cagcccatgg ccacccgcat gagataattc tgtattatta tgagctgtac   1080
cccactatga ct                                                        1092
```

FIGURE 16

```
gacaacttca atgtctataa agccacaaga ccatacttag ctcactgtcc cgactgtgga      60
gaagggcact cgtgccatag tcccgtagca ctagaacgca tcagaaatga agcgacagac     120
gggacgctga aaatccaggt ctccttgcaa atcggaataa agacggatga cagccacgat     180
tggaccaagc tgcgttatat ggacaaccac atgccagcag acgcagagag ggcggggcta     240
tttgtaagaa catcagcacc gtgtacgatt actggaacaa tgggacactt catcctggcc     300
cgatgtccaa aaggggaaac tctgacggtg ggattcactg acagtaggaa gattagtcac     360
tcatgtacgc acccatttca ccacgaccct cctgtgatag gtcgggaaaa attccattcc     420
cgaccgcagc acggtaaaga gctaccttgc agcacgtacg tgcagagcac cgccgcaact     480
accgaggaga tagaggtaca catgccccca gacacccctg atcgcacatt aatgtcacaa     540
cagtccggca acgtaaagat cacagtcaat ggccagacgg tgcggtacaa gtgtaattgc     600
ggtggctcaa atgaaggact aacaactaca gacaaagtga ttaataactg caaggttgat     660
caatgtcatg ccgcggtcac caatcacaaa aagtggcagt ataactcccc tctggtcccg     720
cgtaatgctg aacttgggga ccgaaaagga aaaattcaca tcccgtttcc gctggcaaat     780
gtaacatgca gggtgcctaa agcaaggaac ccccaccgtga cgtacgggaa aaaccaagtc     840
atcatgctac tgtatcctga ccacccaaca ctcctgtcct accggaatat gggagaagaa     900
ccaaactatc aagaagagtg ggtgatgcat aagaaggaag tcgtgctaac cgtgccgact     960
gaagggctcg aggtcacgtg ggcaacaac gagccgtata agtattggcc gcagttatct    1020
acaaacggta cagcccatgg ccacccgcac gagataattc tgtattatta tgagctgtac    1080
cccactatga ct                                                        1092
```

FIGURE 17

```
gacaacttca atgtctataa agccacaaga ccatacttag ctcactgtcc cgactgtgga      60
gaagggcact cgtgccatag tcccgtagca ctagaacgca tcagaaatga agcgacagac     120
gggacgctga aaatccaggt ctccttgcaa atcggaataa agacggatga cagccacgat     180
tggaccaagc tgcgttatat ggacaaccac atgccagcag acgcagagag ggcggggcta     240
tttgtaagaa catcagcacc gtgtacgatt actggaacaa tgggacactt catcctggcc     300
cgatgtccaa aaggggaaac tctgacggtg ggattcactg acagtaggaa gattagtcac     360
tcatgtacgc acccatttca ccacgaccct cctgtgatag gtcgggaaaa attccattcc     420
cgaccgcagc acggtaaaga gataccttgc agcacgtacg tgcagagcac cgccgcaact     480
accgaggaga tagaggtaca catgccccca gacacccctg atcgcacatt aatgtcacaa     540
cagtccggca acgtaaagat cacagtcaat ggccagacgg tgcggtacaa gtgtaattgc     600
ggtggctcaa atgaaggact aacaactaca gacaaagtga ttaataactg caaggttgat     660
caatgtcatg ccgcggtcac caatcacaaa aagtggcagt ataactcccc tctggtcccg     720
cgtaatgctg aacttgggga ccgaaaagga aaaattcaca tcccgtttcc gctggcaaat     780
gtaacatgca gggtgcctaa agcaaggaac ccccaccgtga cgtacgggaa aaaccaagtc     840
atcatgctac tgtatcctga ccacccaaca ctcctgtcct accggaatat gggagaagaa     900
ccaaactatc aagaagagtg ggtgatgcat aagaaggaag tcgtgctaac cgtgccgact     960
gaagggctcg aggtcacgtg ggcaacaac gagccgtata agtattggcc gcagttatct    1020
acaaacggta cagcccatgg ccacccgcat gagataattc tgtattatta tgagctgtac    1080
cccactatga ct                                                        1092
```

FIGURE 18

```
IPVHMKSDAS KFTHEKPEGY YNWHHGAVQY SGGRFTIPTG AGKPGDSGRP IFDNKGRVVA    60
IVLGGANEGA RTALSVVTWN KDIVTKITPE GAEEWSLAIP VMCLLANTTF PCSQPPCTPC   120
CYEKEPEETL RMLEDNVMRP GYYQLLQASL TCSPHRQRRS TKDNFNVYKA TRPYLAHCPD   180
CGEGHSCHSP VALERIRNEA TDGTLKIQVS LQIGIKTDDS HDWTKLRYMD NHMPADAERA   240
GLFVRTSAPC TITGTMGHFI LARCPKGETL TVGFTDSRKI SHSCTHPFHH DPPVIGREKF   300
HSRPQHGKEL PCSTYVQSTA ATTEEIEVHM PPDTPDRTLM SQQSGNVKIT VNGQTVRYKC   360
NCGGSNEGLT TTDKVINNCK VDQCHAAVTN HKKWQYNSPL VPRNAELGDR KGKIHIPFPL   420
ANVTCRVPKA RNPTVTYGKN QVIMLLYPDH PTLLSYRNMG EEPNYQEEWV MHKKEVVLTV   480
PTEGLEVTWG NNEPYKYWPQ LSTNGTAHGH PHEIILYYYE LYPTMTVVVV SVATFILLSM   540
VGMAAGMCMR ARRRCITPYE LTPGATVPFL LSLICCIRTA KAATYQEAAI YLWNEQQPL    599
```

FIGURE 19

```
IPVHMKSDAS KFTHEKPEGY YNWHHGAVQY SGGRFTIPTG AGKPGDSGRP IFDNKGRVVA    60
IVLGGANEGA RTALSVVTWN KDIVTKITPE GAEEWSLAIP VMCLLANTTF PCSQPPCTPC   120
CYEKEPEETL RMLEDNVMRP GYYQLLQASL TCSPHRQRRS TKDNFNVYKA TRPYLAHCPD   180
CGEGHSCHSP VALERIRNEA TDGTLKIQVS LQIGIKTDDS HDWTKLRYMD NHMPADAERA   240
GLFVRTSAPC TITGTMGHFI LARCPKGETL TVGFTDSRKI SHSCTHPFHH DPPVIGREKF   300
HSRPQHGKEL PCSTYVQSTA ATTEEIEVHM PPDTPDRTLM SQQSGNVKIT VNGQTVRYKC   360
NCGGSNEGLT TTDKVINNCK VDQCHAAVTN HKKWQYNSPL VPRNAELGDR KGKIHIPFPL   420
ANVTCRVPKA RNPTVTYGKN QVIMLLYPDH PTLLSYRNMG EEPNYQEEWV MHKKEVVLTV   480
PTEGLEVTWG NNEPYKYWPQ LSTNGTAHGH PHEIILYYYE LYPTMTVVVV SVATFILLSM   540
VGMAAGMCMC ARRRCITPYE LTPGATVPFL LSLICCIRTA KAATYQEAAI YLWNEQQPL    599
```

FIGURE 20

```
IPVHMKSDAS KFTHEKPEGY YNWHHGAVQY SGGRFTIPTG AGKPGDSGRP IFDNKGRVVA    60
IVLGGANEGA RTALSVVTWN KDIVTKITPE GAEEWSLAIP VMCLLANTTF PCSQPPCTPC   120
CYEKEPEETL RMLEDNVMRP GYYQLLQASL TCSPHRQRRS TKDNFNVYKA TRPYLAHCPD   180
CGEGHSCHSP VALERIRNEA TDGTLKIQVS LQIGIKTDDS HDWTKLRYMD NHMPADAERA   240
GLFVRTSAPC TITGTMGHFI LARCPKGETL TVGFTDSRKI SHSCTHPFHH DPPVIGREKF   300
HSRPQHGKEL PCSTYVQSTA ATTEEIEVHM PPDTPDRTLM SQQSGNVKIT VNGQTVRYKC   360
NCGGSNEGLT TTDKVINNCK VDQCHAAVTN HKKWQYNSPL VPRNAELGDR KGKIHIPFPL   420
ANVTCRVPKA RNPTVTYGKN QVIMLLYPDH PTLLSYRNMG EEPNYQEEWV MHKKEVVLTV   480
PTEGLEVTWG NNEPYKYWPQ LSTNGTAHGH PHEIILYYYE LYPTMTVVVV SVATFILLSM   540
VGMAAGMCMC ARRRCITPYE LTPGATVPFL LSLICCIRTA KAATYQEAAI YLWNEQQPL    599
```

FIGURE 21

```
IPVHMKSDAS KFTHEKPEGY YNWHHGAVQY SGGRFTIPTG AGKPGDSGRP IFDNKGRVVA   60
IVLGGANEGA RTALSVVTWN KDIVTKITPE GAEEWSLAIP VMCLLANTTF PCSQPPCTPC  120
CYEKEPEETL RMLEDNVMRP GYYQLLQASL TCSPHRQRRS TKDNFNVYKA TRPYLAHCPD  180
CGEGHSCHSP VALERIRNEA TDGTLKIQVS LQIGIKTDDS HDWTKLRYMD NHMPADAERA  240
GLFVRTSAPC TITGTMGHFI LARCPKGETL TVGFTDSRKI SHSCTHPFHH DPPVIGREKF  300
HSRPQHGKEI PCSTYVQSTA ATTEEIEVHM PPDTPDRTLM SQQSGNVKIT VNGQTVRYKC  360
NCGGSNEGLT TTDKVINNCK VDQCHAAVTN HKKWQYNSPL VPRNAELGDR KGKIHIPFPL  420
ANVTCRVPKA RNPTVTYGKN QVIMLLYPDH PTLLSYRNMG EEPNYQEEWV MHKKEVVLTV  480
PTEGLEVTWG NNEPYKYWPQ LSTNGTAHGH PHEIILYYYE LYPTMTVVVV SVATFILLSM  540
VGMAAGMCMC ARRRCITPYE LTPGATVPFL LSLICCIRTA KAATYQEAAI YLWNEQQPL   599
```

FIGURE 22

```
DNFNVYKATR PYLAHCPDCG EGHSCHSPVA LERIRNEATD GTLKIQVSLQ IGIKTDDSHD   60
WTKLRYMDNH MPADAERAGL FVRTSAPCTI TGTMGHFILA RCPKGETLTV GFTDSRKISH  120
SCTHPFHHDP PVIGREKFHS RPQHGKELPC STYVQSTAAT TEEIEVHMPP DTPDRTLMSQ  180
QSGNVKITVN GQTVRYKCNC GGSNEGLTTT DKVINNCKVD QCHAAVTNHK KWQYNSPLVP  240
RNAELGDRKG KIHIPFPLAN VTCRVPKARN PTVTYGKNQV IMLLYPDHPT LLSYRNMGEE  300
PNYQEEWVMH KKEVVLTVPT EGLEVTWGNN EPYKYWPQLS TNGTAHGHPH EIILYYYELY  360
PTMT                                                               364
```

FIGURE 23

```
DNFNVYKATR PYLAHCPDCG EGHSCHSPVA LERIRNEATD GTLKIQVSLQ IGIKTDDSHD   60
WTKLRYMDNH MPADAERAGL FVRTSAPCTI TGTMGHFILA RCPKGETLTV GFTDSRKISH  120
SCTHPFHHDP PVIGREKFHS RPQHGKELPC STYVQSTAAT TEEIEVHMPP DTPDRTLMSQ  180
QSGNVKITVN GQTVRYKCNC GGSNEGLTTT DKVINNCKVD QCHAAVTNHK KWQYNSPLVP  240
RNAELGDRKG KIHIPFPLAN VTCRVPKARN PTVTYGKNQV IMLLYPDHPT LLSYRNMGEE  300
PNYQEEWVMH KKEVVLTVPT EGLEVTWGNN EPYKYWPQLS TNGTAHGHPH EIILYYYELY  360
PTMT                                                               364
```

FIGURE 24

```
DNFNVYKATR PYLAHCPDCG EGHSCHSPVA LERIRNEATD GTLKIQVSLQ IGIKTDDSHD    60
WTKLRYMDNH MPADAERAGL FVRTSAPCTI TGTMGHFILA RCPKGETLTV GFTDSRKISH   120
SCTHPFHHDP PVIGREKFHS RPQHGKELPC STYVQSTAAT TEEIEVHMPP DTPDRTLMSQ   180
QSGNVKITVN GQTVRYKCNC GGSNEGLTTT DKVINNCKVD QCHAAVTNHK KWQYNSPLVP   240
RNAELGDRKG KIHIPFPLAN VTCRVPKARN PTVTYGKNQV IMLLYPDHPT LLSYRNMGEE   300
PNYQEEWVMH KKEVVLTVPT EGLEVTWGNN EPYKYWPQLS TNGTAHGHPH EIILYYYELY   360
PTMT                                                                364
```

FIGURE 25

```
DNFNVYKATR PYLAHCPDCG EGHSCHSPVA LERIRNEATD GTLKIQVSLQ IGIKTDDSHD    60
WTKLRYMDNH MPADAERAGL FVRTSAPCTI TGTMGHFILA RCPKGETLTV GFTDSRKISH   120
SCTHPFHHDP PVIGREKFHS RPQHGKEIPC STYVQSTAAT TEEIEVHMPP DTPDRTLMSQ   180
QSGNVKITVN GQTVRYKCNC GGSNEGLTTT DKVINNCKVD QCHAAVTNHK KWQYNSPLVP   240
RNAELGDRKG KIHIPFPLAN VTCRVPKARN PTVTYGKNQV IMLLYPDHPT LLSYRNMGEE   300
PNYQEEWVMH KKEVVLTVPT EGLEVTWGNN EPYKYWPQLS TNGTAHGHPH EIILYYYELY   360
PTMT                                                                364
```

A

```
                                10        20        30        40        50        60
                                 |         |         |         |         |         |
Re05115_RSE1 11327 TATAGATCAAAG-GGCTACGC-AACCCCTGAATAGTAACAAAATACAAAATC-ACTAAAAAT
Re05115_RSE2 11456 ................CGAAT.........................TG...ATC.A.......
Re05115_RSE3 11542 AG...T...............TAA......................C.T.....-T.A.......
S27Afri_RSE1 11378 .G...................TAT.........................................
S27Afri_RSE2 11521 ................CGAA.........................T...ATT-A.........
S27Afri_RSE3 11607 AG...T...............TAAA.....................C.T....C-T.A.......
St37997_RSE1 11415 AT...................TA.......................C......A.C.A.......
St37997_RSE2 11544 .....................TATT.....................C......A...A......C
St37997_RSE3 11630 AG...T...............AA.......................C.T.....GT.A.......
Snagpur_RSE1  4607 AG...T...............TAAA.....................C.T....C-T.A.......
Snagpur_RSE2  4692 ..................CT.GAAT.............A...T.......T...ATA.A...G...
Snagpur_RSE3  4886 AGAT.T.......T.....TAA......-...........T....C.T......-T.A...GG..
```

CHIKV strains

```
06-27          GACAACTTCAATGTCTATAAAGCCACAAGACCATACTTAGCTCACTGTCCCG
06-49          GACAACTTCAATGTCTATAAAGCCACAAGACCATACTTAGCTCACTGTCCCG
05-115         GACAACTTCAATGTCTATAAAGCCACAAGACCATACTTAGCTCACTGTCCCG
06-21          GACAACTTCAATGTCTATAAAGCCACAAGACCATACTTAGCTCACTGTCCCG

06-27   ACTGTGGAGAAGGGCACTCGTGCCATAGTCCCGTAGCACTAGAACGCATCAGAAATGAAG
06-49   ACTGTGGAGAAGGGCACTCGTGCCATAGTCCCGTAGCACTAGAACGCATCAGAAATGAAG
05-115  ACTGTGGAGAAGGGCACTCGTGCCATAGTCCCGTAGCACTAGAACGCATCAGAAATGAAG
06-21   ACTGTGGAGAAGGGCACTCGTGCCATAGTCCCGTAGCACTAGAACGCATCAGAAATGAAG

06-27   CGACAGACGGGACGCTGAAAATCCAGGTCTCCTTGCAAATCGGAATAAAGACGGATGACA
06-49   CGACAGACGGGACGCTGAAAATCCAGGTCTCCTTGCAAATCGGAATAAAGACGGATGACA
05-115  CGACAGACGGGACGCTGAAAATCCAGGTCTCCTTGCAAATCGGAATAAAGACGGATGACA
06-21   CGACAGACGGGACGCTGAAAATCCAGGTCTCCTTGCAAATCGGAATAAAGACGGATGACA

06-27   GCCACGATTGGACCAAGCTGCGTTATATGGACAACCACATGCCAGCAGACGCAGAGAGGG
06-49   GCCACGATTGGACCAAGCTGCGTTATATGGACAACCACATGCCAGCAGACGCAGAGAGGG
05-115  GCCACGATTGGACCAAGCTGCGTTATATGGACAACCACATGCCAGCAGACGCAGAGAGGG
06-21   GCCACGATTGGACCAAGCTGCGTTATATGGACAACCACATGCCAGCAGACGCAGAGAGGG

06-27   CGGGGCTATTTGTAAGAACATCAGCACCGTGTACGATTACTGGAACAATGGGACACTTCA
06-49   CGGGGCTATTTGTAAGAACATCAGCACCGTGTACGATTACTGGAACAATGGGACACTTCA
05-115  CGGGGCTATTTGTAAGAACATCAGCACCGTGTACGATTACTGGAACAATGGGACACTTCA
06-21   CGGGGCTATTTGTAAGAACATCAGCACCGTGTACGATTACTGGAACAATGGGACACTTCA

06-27   TCCTGGCCCGATGTCCAAAAGGGGAAACTCTGACGGTGGGATTCACTGACAGTAGGAAGA
06-49   TCCTGGCCCGATGTCCAAAAGGGGAAACTCTGACGGTGGGATTCACTGACAGTAGGAAGA
05-115  TCCTGGCCCGATGTCCAAAAGGGGAAACTCTGACGGTGGGATTCACTGACAGTAGGAAGA
06-21   TCCTGGCCCGATGTCCAAAAGGGGAAACTCTGACGGTGGGATTCACTGACAGTAGGAAGA

06-27   TTAGTCACTCATGTACGCACCCATTTCACCACGACCCTCCTGTGATAGGTCGGGAAAAAT
06-49   TTAGTCACTCATGTACGCACCCATTTCACCACGACCCTCCTGTGATAGGTCGGGAAAAAT
05-115  TTAGTCACTCATGTACGCACCCATTTCACCACGACCCTCCTGTGATAGGTCGGGAAAAAT
06-21   TTAGTCACTCATGTACGCACCCATTTCACCACGACCCTCCTGTGATAGGTCGGGAAAAAT

06-27   TCCATTCCCGACCGCAGCACGGTAAAGAGCTACCTTGCAGCACGTACGTGCAGAGCACCG
06-49   TCCATTCCCGACCGCAGCACGGTAAAGAGCTACCTTGCAGCACGTACGTGCAGAGCACCG
05-115  TCCATTCCCGACGGCAGCACGGTAAAGAGCTACCTTGCAGCACGTACGTGCAGAGCACCG
06-21   TCCATTCCCGACGGCAGCACGGTAAAGAGCTACCTTGCAGCACGTACGTGCAGAGCACCG

06-27   CCGCAACTACCGAGGAGATAGAGGTACACATGCCCCCAGACACCCCTGATCGCACATTAA
06-49   CCGCAACTACCGAGGAGATAGAGGTACACATGCCCCCAGACACCCCTGATCGCACATTAA
05-115  CCGCAACTACCGAGGAGATAGAGGTACACATGCCCCCAGACACCCCTGATCGCACATTAA
06-21   CCGCAACTACCGAGGAGATAGAGGTACACATGCCCCCAGACACCCCTGATCGCACATTAA

06-27   TGTCACAACAGTCCGGCAACGTAAAGATCACAGTCAATGGCCAGACGGTGCGGTACAAGT
06-49   TGTCACAACAGTCCGGCAACGTAAAGATCACAGTCAATGGCCAGACGGTGCGGTACAAGT
05-115  TGTCACAACAGTCCGGCAACGTAAAGATCACAGTCAATGGCCAGACGGTGCGGTACAAGT
06-21   TGTCACAACAGTCCGGCAACGTAAAGATCACAGTCAATGGCCAGACGGTGCGGTACAAGT
```

FIGURE 29 (con't)

06-27 GTAATTGCGGTGGGTCAAATGAAGGACTAACAAGTACAGACAAAGTGATTAATAACTGCA
06-49 GTAATTGCGGTGGCTCAAATGAAGGACTAACAACTACAGACAAAGTGATTAATAACTGCA
05-115 GTAATTGCGGTGGCTCAAATGAAGGACTAACAACTACAGACAAAGTGATTAATAACTGCA
06-21 GTAATTGCGGTGGCTCAAATGAAGGACTAACAACTACAGACAAAGTGATTAATAACTGCA 06-27 AGGTTGATCAATGTCATGCCGCGGTCACCAATCACAAAAAGTGGCAGTATAACTCCCCTC
06-49 AGGTTGATCAATGTCATGCCGCGGTCACCAATCACAAAAAGTGGCAGTATAACTCCCCTC
05-115 AGGTTGATCAATGTCATGCCGCGGTCACCAATCACAAAAAGTGGCAGTATAACTCCCCTC
06-21 AGGTTGATCAATGTCATGCCGCGGTCACCAATCACAAAAAGTGGCAGTATAACTCCCCTC 06-27 TGGTCCCGCGTAATGCTGAACTTGGGGACCGAAAAGGAAAAATTCACATCCCGTTTCCGC
06-49 TGGTCCCGCGTAATGCTGAACTTGGGGACCGAAAAGGAAAAATTCACATCCCGTTTCCGC
05-115 TGGTCCCGCGTAATGCTGAACTTGGGGACCGAAAAGGAAAAATTCACATCCCGTTTCCGC
06-21 TGGTCCCGCGTAATGCTGAACTTGGGGACCGAAAAGGAAAAATTCACATCCCGTTTCCGC 06-27 TGGCAAATGTAACATGCAGGGTGCCTAAAGCAAGGAACCCCACCGTGACGTACGGGAAAA
06-49 TGGCAAATGTAACATGCAGGGTGCCTAAAGCAAGGAACCCGACCGTGACGTACGGGAAAA
05-115 TGGCAAATGTAACATGCAGGGTGCCTAAAGCAAGGAACCCCACCGTGACGTACGGGAAAA
06-21 TGGCAAATGTAACATGCAGGGTGCCTAAAGCAAGGAACCCCACCGTGACGTACGGGAAAA 06-27 ACCAAGTCATCATGCTACTGTATCCTGACCACCCAACACTCCTGTCCTACCGGAATATGG
06-49 ACCAAGTCATCATGCTACTGTATCCTGACCACCCAACACTCCTGTCCTACCGGAATATGG
05-115 ACCAAGTCATCATGCTACTGTATCCTGACCACCCAACACTCCTGTCCTACCGGAATATGG
06-21 ACCAAGTCATCATGCTACTGTATCCTGACCACCCAACACTCCTGTCCTACCGGAATATGG 06-27 GAGAAGAACCAAACTATCAAGAAGAGTGGGTGATGCATAAGAAGGAAGTCGTGCTAACCG
06-49 GAGAAGAACCAAACTATCAAGAAGAGTGGGTGATGCATAAGAAGGAAGTCGTGCTAACCG
05-115 GAGAAGAACCAAACTATCAAGAAGAGTGGGTGATGCATAAGAAGGAAGTCGTGCTAACCG
06-21 GAGAAGAACCAAACTATCAAGAAGAGTGGGTGATGCATAAGAAGGAAGTCGTGCTAACCG 06-27 TGCCGACTGAAGGGCTCGAGGTCACGTGGGGCAACAACGAGCCGTATAAGTATTGGCCGC
06-49 TGCCGACTGAAGGGCTCGAGGTCACGTGGGGCAACAACGAGCCGTATAAGTATTGGCCGC
05-115 TGCCGACTGAAGGGCTCGAGGTCACGTGGGGCAACAACGAGCCGTATAAGTATTGGCCGC
06-21 TGCCGACTGAAGGGCTCGAGGTCACGTGGGGCAACAACGAGCCGTATAAGTATTGGCCGC 06-27 AGTTATCTACAAACGGTACAGCCCATGGCCACCCGCATGAGATAATTCTGTATTATTATG
06-49 AGTTATCTACAAACGGTACAGCCCATGGCCACCCGCACGAGATAATTCTGTATTATTATG
05-115 AGTTATCTACAAACGGTACAGCCCATGGCCACCCGCATGAGATAATTCTGTATTATTATG
06-21 AGTTATCTACAAACGGTACAGCCCATGGCCACCCGCATGAGATAATTCTGTATTATTATG 06-27 AGCTGTACCCCACTATGACT
06-49 AGCTGTACCCCACTATGACT
05-115 AGCTGTACCCCACTATGACT
05-21 AGCTGTACCCCACTATGACT

FIGURE 30

Primer for the N-terminal sequence of CHIK E2-gp:

```
E3 furin cleavage site    D1  N   F   N   V   Y   K   A   T   R   P   Y   L   A   H   C   P
5' -cgc agc acc aag/gac aac ttc aat gtc tat aaa gcc aca aga cca tac cta gct cac tgt cca-3'

5' -aaaaaagatctgacaacttcaatgtctataaagccacaagacc-3'          primer 43-mer  A+T:27   G+C:15
         BglII
```

Primer for the C-terminal sequence of the CHIK E2 ectodomain:

```
       P   H   E   I   I   L   Y   Y   Y   E   L   Y   P   T   M   T***V   V   V   V   S
5' - ccg cat gag ata atc ttg tac tat tat gag ctg tac cct act atg act gta gta gtt gtg tca-3'

5' - ccg cat gag ata atc ttg tac tat tat gag ctg tac cct act atg acg cgg ccg caa aaa-3'
                                                                      NotI

5' -ttttgcggccgcgtcatagtagggtacagctcataatagtacaag-3'        primer 46-mer  A+T:25   G+C:21
          Not I
```

PAGE-SDS 4-12%, staining by Coomassie blue

| Purified viral antigens | Imidazole elution | date |
|---|---|---|
| • DEN-3 sE | -> fraction $E_2$ 2 | 10/07/06 |
| • DEN-4 sE | -> fraction $E_3$ 3 | 20/07/06 |
| • WN sE | -> fraction $E_3$ 2 | 25/07/06 |
| • CHIK-sE2 | -> fraction $E_3$ 3 | 03/07/06 |

Western blot-
PAGE-SDS 4-12%
16.5 µl/well

FIGURE 34

```
1/1                                          31/11                                        61/21
| BamHI            CRT signal sequence      |                                            |
GGA TCC GCC ACC ATG CTG CTG AGC GTG CCC CTG CTG CTG GGC CTG CTG GGC CTG GCC GTG GAC AAC TTC AAC GTG TAC AAG GCT ACC AGA
                M   L   L   S   V   P   L   L   L   G   L   L   G   L   A   V   D   N   F   N   V   Y   K   A   T   R

91/31                                        121/41                                       151/51
|                                            |                                            |
CCC TAC CTG GCC CAC TGC CCC GAC TGC GGC GAG GGA CAC AGC TGC CAC AGC CCC GTG GCC CTG GAG AGA ATC CGG AAC GAG GCT ACC GAC
P   Y   L   A   H   C   P   D   C   G   E   G   H   S   C   H   O   P   V   A   L   E   R   I   M   N   E   A   T   D

181/61                                       211/71                                       241/81
|                                            |                                            |
GGC ACC CTG AAG ATC CAG GTG AGC CTG CAG ATC GGC ATC AAG ACC GAC GAC AGC CAC GAC TGG ACC AAG CTG AGA TAC ATG GAC AAC CAC
G   T   L   K   I   Q   V   S   L   Q   I   G   I   K   T   D   D   S   M   D   W   T   K   L   R   Y   M   D   N   M

271/91                                       301/101                                      331/111
|                                            |                                            |
ATG CCC GCC GAC GCC GAG AGA GCC GGC CTG TTC GTG AGA ACC AGC GCC CCC TGC ACC ATC ACC GGC ACC ATG GGC CAC TTC ATC CTG GCC
M   P   A   D   A   E   R   A   G   L   F   V   R   T   S   A   P   C   T   I   T   G   T   M   G   H   F   I   L   A

361/121                                      391/131                                      421/141
|                                            |                                            |
AGA TGC CCC AAG GGC GAG ACC CTG ACC GTG GGC TTC ACC GAC AGC AGA AAG ATT AGC CAC AGC TGC ACC CAC CCC TTC CAC CAC GAT CCT
R   C   P   K   G   E   T   L   T   V   G   F   T   D   S   R   K   I   S   H   S   C   T   M   P   F   H   H   D   P

431/151                                      451/161                                      511/171
|                                            |                                            |
CCC GTG ATC GGC AGA GAG AAG TTC CAC AGC AGA CCC CAG CAC GGC AAG GAG CTG CCC TGC AGC ACC TAC GTG CAG AGC ACC GCC GCT ACA
P   V   I   G   R   E   K   F   H   S   R   P   Q   H   G   K   E   L   P   C   S   T   Y   V   Q   S   T   A   A   T

541/181                                      571/191                                      601/201
|                                            |                                            |
ACC GAG GAG ATC GAG GTG CAC ATG CCC CCC GAC ACC CCC GAC AGA ACC CTG ATG AGC CAG CAG AGC GGC AAC GTG AAG ATC ACC GTG AAC
T   E   E   I   E   V   H   M   P   P   D   T   P   D   R   T   L   M   S   Q   Q   S   G   N   V   K   I   T   V   N

631/211                                      661/221                                      691/231
|                                            |                                            |
GGC CAG ACC GTG AGA TAC AAG TGC AAC TAC GGC GGC AGC AAC GAG GGC CTG ACC ACA ACC GAC AAG GTG ATC AAC AAC TGC AAG GTG GAC
G   Q   T   V   R   Y   K   C   N   C   G   G   S   N   E   G   L   T   T   T   D   K   V   I   N   N   C   K   V   D
```

FIGURE 34 (con't)

```
721/241                       751/251                       781/261
|                             |                             |
CAG TGC CAC GCC GCC GTG ACC AAC CAC AAG AAG TGG CAG TAC AAC AGC CCC CTG GTG CCC AGA AAC GCC GAG CTG GGC GAC AGA AAG GGC
Q   C   M   A   A   V   T   N   H   K   K   W   Q   Y   N   S   P   L   V   P   R   N   A   E   L   G   D   R   K   G

811/271                       841/281                       871/291
|                             |                             |
AAG ATC CAC ATC CCC TTC CCC CTG GCC AAC GTG ACC TGC AGA GTG CCC AAG GCC AGA AAC CCC ACC GTG ACC TAC GGC AAG AAC CAG GTG
K   I   M   I   P   F   P   L   A   N   V   T   C   R   V   P   K   A   R   N   P   T   V   T   Y   G   K   N   Q   V

901/301                       931/311                       961/321
|                             |                             |
ATC ATG CTG CTG TAC CCC GAT CAC CCC ACC CTG CTG AGC TAC AGA AAC ATG GGC GAG GAG CCC AAC TAC CAG GAG GAG TGG GTG ATG CAC
I   M   L   L   Y   P   D   H   P   T   L   L   S   Y   R   N   M   G   E   E   P   N   Y   Q   E   E   W   V   M   H

991/331                       1021/341                      1051/351
|                             |                             |
AAG AAG GAG GTG GTG CTG ACC GTG CCC ACC GAG GGC CTG GAG GTG ACC TGG GGC AAC AAC GAG CCC TAC AAG TAC TGG CCC CAG CTG AGC
K   K   E   V   V   L   T   V   P   T   E   G   L   E   V   T   W   G   N   N   E   P   Y   K   Y   W   P   Q   L   S

1081/361                      1111/371                      1141/381
|                             |                             |                   XhoI
ACC AAC GGC ACC GCC CAC GGA CAC CCC CAC GAG ATC ATC CTG TAC TAC TAC GAG CTG TAC CCC ACC ATG ACC TGA CTC GAG
T   N   G   T   A   H   G   H   P   M   E   I   I   L   Y   Y   Y   E   L   Y   P   T   M   T   *
```

FIGURE 37

```
MEFIPTQTFY NRRYQPRPWT PRPTIQVIRP RPRPQRQAGQ LAQLISAVNK LTMRAVPQQK    60
PRRNRKNKKQ KQKQQAPQNN TNQKKQPPKK KPAQKKKKPG RRERMCMKIE NDCIFEVKHE   120
GKVTGYACLV GDKVMKPAHV KGTIDNADLA KLAFKRSSKY DLECAQIPVH MKSDASKFTH   180
EKPEGYYNWH HGAVQYSGGR FTIPTGAGKP GDSGRPIFDN KGRVVAIVLG GANEGARTAL   240
SVVTWNKDIV TKITPEGAEE WSLAIPVMCL LANTTFPCSQ PPCIPCCYEK EPEETLRMLE   300
DNVMRPGYYQ LLQASLTCSP HRQRRSTKDN FNVYKATRPY LAHCPDCGEG HSCHSPVALE   360
RIRNEATDGT LKIQVSLQIG IGTDDSHDWT KLRYMDNHIP ADAGRAGLFV RTSAPCTITG   420
TMGHFILARC PKGETLTVGF TDSRKISHSC THPFHHDPPV IGREKFHSRP QHGKELPCST   480
YVQSNAATAE EIEVHMPPDT PDRTLLSQQS GNVKITVNGR TVRYKCNCGG SNEGLITTDK   540
VINNCKVDQC HAAVTNHKKW QYNSPLVPRN AELGDRKGKI HIPFPLANVT CMVPKARNPT   600
VTYGKNQVIM LLYPDHPTLL SYRSMGEEPN YQEEWVTHKK EVVLTVPTEG LEVTWGNNEP   660
YKYWPQLSAN GTAHGHPHEI ILYYYELYPT MTVVVVSVAS FILLSMVGMA VGMCMCARRR   720
CITPYELTPG ATVPFLLSLI CCIRTAKAAT YQEAAVYLWN EQQPLFWLQA LIPLAALIVL   780
CNCLRLLPCC CKTLAFLAVM SIGAHTVSAY EHVTVIPNTV GVPYKTLVNR PGYSPMVLEM   840
ELLSVTLEPT LSLDYITCEY KTVIPSPYVK CCGTAECKDK NLPDYSCKVF TGVYPFMWGG   900
AYCFCDAENT QLSEAHVEKS ESCKTEFASA YRAHTASASA KLRVLYQGNN ITVTAYANGD   960
HAVTVKDAKF IVGPMSSAWT PFDNKIVVYK GDVYNMDYPP FGAGRPGQFG DIQSRTPESK  1020
DVYANTQLVL QRPAAGTVHV PYSQAPSGFK YWLKERGASL QHTAPFGCQI ATNPVRAMNC  1080
AVGNMPISID IPDAAFTRVV DAPSLTDMSC EVPACTHSSD FGGVAIIKYA VSKKGKCAVH  1140
SMTNAVTIRE AEIEVEGNSQ LQISFSTALA SAEFRVQVCS TQVHCAAECH PPKDHIVNYP  1200
ASHTTLGVQD ISATAMSWVQ KITGGVGLVV AVAALILIVV LCVSFSRH                1248
```

FIGURE 38

| | | | | | | |
|---|---|---|---|---|---|---|
| MEFIPTQTFY | NRRYQPRPWT | PRPTIQVIRP | RPRPQRQAGQ | LAQLISAVNK | LTMRAVPQQK | 60 |
| PRRNRKNKKQ | KQKQQAPQNN | TNQKKQPPKK | KPAQKKKKPG | RRERMCMKIE | NDCIFEVKHE | 120 |
| GKVTGYACLV | GDKVMKPAHV | KGTIDNADLA | KLAFKRSSKY | DLECAQIPVH | MKSDASKFTH | 180 |
| EKPEGYYNWH | HGAVQYSGGR | FTIPTGAGKP | GDSGRPIFDN | KGRVVAIVLG | GANEGARTAL | 240 |
| SVVTWNKDIV | TKITPEGAEE | WSLAIPVMCL | LANTTFPCSQ | PPCTPCCYEK | EPEETLRMLE | 300 |
| DNVMRPGYYQ | LLQASLTCSP | HRQRRSTKDN | FNVYKATRPY | LAHCPDCGEG | HSCHSPVALE | 360 |
| RIRNEATDGT | LKIQVSLQIG | IKTDDSHDWT | KLRYMDNHMP | ADAERAGLFV | RTSAPCTITG | 420 |
| TMGHFILARC | PKGETLTVGF | TDSRKISHSC | THPFHHDPPV | IGREKFHSRP | QHGKELPCST | 480 |
| YVQSTAATTE | EIEVHMPPDT | PDRTLMSQQS | GNVKITVNGQ | TVRYKCNCGG | SNEGLTTTDK | 540 |
| VINNCKVDQC | HAAVTNHKKW | QYNSPLVPRN | AELGDRKGKI | HIPFPLANVT | CRVPKARNPT | 600 |
| VTYGKNQVIM | LLYPDHPTLL | SYRNMGEEPN | YQEEWVMHKK | EVVLTVPTEG | LEVTWGNNEP | 660 |
| YKYWPQLSTN | GTAHGHPHEI | ILYYYELYPT | MTVVVVSVAT | FILLSMVGMA | AGMCMCARRR | 720 |
| CITPYELTPG | ATVPFLLSLI | CCIRTAKAAT | YQEAAIYLWN | EQQPLFWLQA | LIPLAALIVL | 780 |
| CNCLRLLPCC | CKTLAFLAVM | SVGAHTVSAY | EHVTVIPNTV | GVPYKTLVNR | PGYSPMVLEM | 840 |
| ELLSVTLEPT | LSLDYITCEY | KTVIPSPYVK | CCGTAECKDK | NLPDYSCKVF | TGVYPFMWGG | 900 |
| AYCFCDAENT | QLSEAHVEKS | ESCKTEFASA | YRAHTASASA | KLRVLYQGNN | ITVTAYANGD | 960 |
| HAVTVKDAKF | IVGPMSSAWT | PFDNKIVVYK | GDVYNMDYPP | FGAGRPGQFG | DIQSRTPESK | 1020 |
| DVYANTQLVL | QRPAAGTVHV | PYSQAPSGFK | YWLKERGASL | QHTAPFGCQI | ATNPVRAVNC | 1080 |
| AVGNMPISID | IPEAAFTRVV | DAPSLTDMSC | EVPACTHSSD | FGGVAIIKYA | ASKKGKCAVH | 1140 |
| SMTNAVTIRE | AEIEVEGNSQ | LQISFSTALA | SAEFRVQVCS | TQVHCAAECH | PPKDHIVNYP | 1200 |
| ASHTTLGVQD | ISATAMSWVQ | KITGGVGLVV | AVAALILIVV | LCVSFSRH | | 1248 |

FIGURE 39

| | | | | | | |
|---|---|---|---|---|---|---|
| MEFIPTQTFY | NRRYQPRPWT | PRPTIQVIRP | RPRPQRQAGQ | LAQLISAVNK | LTMRAVPQQK | 60 |
| PRRNRKNKKQ | KQKQQAPQNN | TNQKKQPPKK | KPAQKKKKPG | RRERMCMKIE | NDCIFEVKHE | 120 |
| GKVTGYACLV | GDKVMKPAHV | KGTIDNADLA | KLAFKRSSKY | DLECAQIPVH | MKSDASKFTH | 180 |
| EKPEGYYNWH | HGAVQYSGGR | FTIPTGAGKP | GDSGRPIFDN | KGRVVAIVLG | GANEGARTAL | 240 |
| SVVTWNKDIV | TKITPEGAEE | WSLAIPVMCL | LANTTFPCSQ | PPCTPCCYEK | EPEETLRMLE | 300 |
| DNVMRPGYYQ | LLQASLTCSP | HRQRRSTKDN | FNVYKATRPY | LAHCPDCGEG | HSCHSPVALE | 360 |
| RIRNEATDGT | LKIQVSLQIG | IKTDDSHDWT | KLRYMDNHMP | ADAERAGLFV | RTSAPCTITG | 420 |
| TMGHFILARC | PKGETLTVGF | TDSRKISHSC | THPFHHDPPV | IGREKFHSRP | RHGKELPCST | 480 |
| YVQSTAATTE | EIEVHMPPDT | PDRTLMSQQS | GNVKITVNGQ | TVRYKCNCGG | SNEGLTTTDK | 540 |
| VINNCKVDQC | HAAVTNHKKW | QYNSPLVPRN | AELGDRKGKI | HIPFPLANVT | CRVPKARNPT | 600 |
| VTYGKNQVIM | LLYPDHPTLL | SYRNMGEEPN | YQEEWVMHKK | EVVLTVPTEG | LEVTWGNNEP | 660 |
| YKYWPQLSTN | GTAHGHPHEI | ILYYYELYPT | MTVVVVSVAT | FILLSMVGMA | AGMCMCARRR | 720 |
| CITPYELTPG | ATVPFLLSLI | CCIRTAKAAT | YQEAAIYLWN | EQQPLFWLQA | LIPLAALIVL | 780 |
| CNCLRLLPCC | CKTLAFLAVM | SVGAHTVSAY | EHVTVIPNTV | GVPYKTLVNR | PGYSPMVLEM | 840 |
| ELLSVTLEPT | LSLDYITCEY | KTVIPSPYVK | CCGTAECKDK | NLPDYSCKVF | TGVYPFMWGG | 900 |
| AYCFCDAENT | QLSEAHVEKS | ESCKTEFASA | YRAHTASASA | KLRVLYQGNN | ITVTAYANGD | 960 |
| HAVTVKDAKF | IVGPMSSAWT | PFDNKIVVYK | GDVYNMDYPP | FGAGRPGQFG | DIQSRTPESK | 1020 |
| DVYANTQLVL | QRPAAGTVHV | PYSQAPSGFK | YWLKERGASL | QHTAPFGCQI | ATNPVRAVNC | 1080 |
| AVGNMPISID | IPEAAFTRVV | DAPSLTDMSC | EVPACTHSSD | FGGVAIIKYA | ASKKGKCAVH | 1140 |
| SMTNAVTIRE | AEIEVEGNSQ | LQISFSTALA | SAEFRVQVCS | TQVHCAAECH | PPKDHIVNYP | 1200 |
| ASHTTLGVQD | ISATAMSWVQ | KITGGVGLVV | AVAALILIVV | LCVSFSRH | | 1248 |

FIGURE 40

```
MEFIPTQTFY NRRYQPRPWT PRPTIQVIRP RPRPQRQAGQ LAQLISAVNK LTMRAVPQQK     60
PRRNRKNKKQ KQKQQAPQNN TNQKKQPPKK KPAQKKKKPG RRERMCMKIE NDCIFEVKHE    120
GKVTGYACLV GDKVMKPAHV KGTIDNADLA KLAFKRSSKY DLECAQIPVH MKSDASKFTH    180
EKPEGYYNWH HGAVQYSGGR FTIPTGAGKP GDSGRPIFDN KGRVVAIVLG GANEGARTAL    240
SVVTWNKDIV TKITPEGAEE WSLAIPVMCL LANTTFPCSQ PPCTPCCYEK EPEETLRMLE    300
DNVMRPGYYQ LLQASLTCSP HRQRRSTKDN FNVYKATRPY LAHCPDCGEG HSCHSPVALE    360
RIRNEATDGT LKIQVSLQIG IKTDDSHDWT KLRYMDNHMP ADAERAGLFV RTSAPCTITG    420
TMGHFILARC PKGETLTVGF TDSRKISHSC THPFHHDPPV IGREKFHSRP QHGKELPCST    480
YVQSTAATTE EIEVHMPPDT PDRTLMSQQS GNVKITVNGQ TVRYKCNCGG SNEGLTTTDK    540
VINNCKVDQC HAAVTNHKKW QYNSPLVPRN AELGDRKGKI HIPFPLANVT CRVPKARNPT    600
VTYGKNQVIM LLYPDHPTLL SYRNMGEEPN YQEEWVMHKK EVVLTVPTEG LEVTWGNNEP    660
YKYWPQLSTN GTAHGHPHEI ILYYYELYPT MTVVVVSVAT FILLSMVGMA AGMCMCARRR    720
CITPYELTPG ATVPFLLSLI CCIRTAKAAT YQEAAIYLWN EQQPLFWLQA LIPLAALIVL    780
CNCLRLLPCC CKTLAFLAVM SVGAHTVSAY EHVTVIPNTV GVPYKTLVNR PGYSPMVLEM    840
ELLSVTLEPT LSLDYITCEY KTVIPSPYVK CCGTAECKDK NLPDYSCKVF TGVYPFMWGG    900
AYCFCDAENT QLSEAHVEKS ESCKTEFASA YRAHTASASA KLRVLYQGNN ITVTAYANGD    960
HAVTVKDAKF IVGPMSSAWT PFDNKIVVYK GDVYNMDYPP FGAGRPGQFG DIQSRTPESK   1020
DVYANTQLVL QRPAAGTVHV PYSQAPSGFK YWLKERGASL QHTAPFGCQI ATNPVRAVNC   1080
AVGNMPISID IPEAAFTRVV DAPSLTDMSC EVPACTHSSD FGGVAIIKYA ASKKGKCAVH   1140
SMTNAVTIRE AEIEVEGNSQ LQISFSTALA SAEFRVQVCS TQVHCAAECH PPKDHIVNYP   1200
ASHTTLGVQD ISATAMSWVQ KITGGVGLVV AVAALILIVV LCVSFSRH                1248
```

FIGURE 41

```
MEFIPTQTFY NRRYQPRPWT PRPTIQVIRP RPRPQRQAGQ LAQLISAVNK LTMRAVPQQK     60
PRRNRKNKKQ KQKQQAPQNN TNQKKQPPKK KPAQKKKKPG RRERMCMKIE NDCIFEVKHE    120
GKVTGYACLV GDKVMKPAHV KGTIDNADLA KLAFKRSSKY DLECAQIPVH MKSDASKFTH    180
EKPEGYYNWH HGAVQYSGGR FTIPTGAGKP GDSGRPIFDN KGRVVAIVLG GANEGARTAL    240
SVVTWNKDIV TKITPEGAEE WSLAIPVMCL LANTTFPCSQ PPCTPCCYEK EPEETLRMLE    300
DNVMRPGYYQ LLQASLTCSP HRQRRSTKDN FNVYKATRPY LAHCPDCGEG HSCHSPVALE    360
RIRNEATDGT LKIQVSLQIG IKTDDSHDWT KLRYMDNHMP ADAERAGLFV RTSAPCTITG    420
TMGHFILARC PKGETLTVGF TDSRKISHSC THPFHHDPPV IGREKFHSRP QHGKELPCST    480
YVQSTAATTE EIEVHMPPDT PDRTLMSQQS GNVKITVNGQ TVRYKCNCGG SNEGLTTTDK    540
VINNCKVDQC HAAVTNHKKW QYNSPLVPRN AELGDRKGKI HIPFPLANVT CRVPKARNPT    600
VTYGKNQVIM LLYPDHPTLL SYRNMGEEPN YQEEWVMHKK EVVLTVPTEG LEVTWGNNEP    660
YKYWPQLSTN GTAHGHPHEI ILYYYELYPT MTVVVVSVAT FILLSMVGMA AGMCMCARRR    720
CITPYELTPG ATVPFLLSLI CCIRTAKAAT YQEAAIYLWN EQQPLFWLQA LIPLAALIVL    780
CNCLRLLPCC CKTLAFLAVM SVGAHTVSAY EHVTVIPNTV GVPYKTLVNR PGYSPMVLEM    840
ELLSVTLEPT LSLDYITCEY KTVIPSPYVK CCGTAECKDK NLPDYSCKVF TGVYPFMWGG    900
AYCFCDAENT QLSEAHVEKS ESCKTEFASA YRAHTASASA KLRVLYQGNN ITVTAYANGD    960
HAVTVKDAKF IVGPMSSAWT PFDNKIVVYK GDVYNMDYPP FGAGRPGQFG DIQSRTPESK   1020
DVYANTQLVL QRPAVGTVHV PYSQAPSGFK YWLKERGASL QHTAPFGCQI ATNPVRAVNC   1080
AVGNMPISID IPEAAFTRVV DAPSLTDMSC EVPACTHSSD FGGVAIIKYA ASKKGKCAVH   1140
SMTNAVTIRE AEIEVEGNSQ LQISFSTALA SAEFRVQVCS TQVHCAAECH PPKDHIVNYP   1200
ASHTTLGVQD ISATAMSWVQ KITGGVGLVV AVAALILIVV LCVSFSRH                1248
```

FIGURE 42

| | | | | | | |
|---|---|---|---|---|---|---|
| MEFIPTQTFY | NRRYQPRPWT | PRPTIQVIRP | RPRPQRQAGQ | LAQLISAVNK | LTMRAVPQQK | 60 |
| PRRNRKNKKQ | KQKQQAPQNN | TNQKKQPPKK | KPAQKKKKPG | RRERMCMKIE | NDCIFEVKHE | 120 |
| GKVTGYACLV | GDKVMKPAHV | KGTIDNADLA | KLAFKRSSKY | DLECAQIPVH | MKSDASKFTH | 180 |
| EKPEGYYNWH | HGAVQYSGGR | FTIPTGAGKP | GDSGRPIFDN | KGRVVAIVLG | GANEGARTAL | 240 |
| SVVTWNKDIV | TKITPEGAEE | WSLAIPVMCL | LANTTFPCSQ | PPCTPCCYEK | EPEETLRMLE | 300 |
| DNVMRPGYYQ | LLQASLTCSP | HRQRRSTKDN | FNVYKATRPY | LAHCPDCGEG | HSCHSPVALE | 360 |
| RIRNEATDGT | LKIQVSLQIG | IKTDDSHDWT | KLRYMDNHMP | ADAERAGLFV | RTSAPCTITG | 420 |
| TMGHFILARC | PKGETLTVGF | TDSRKISHSC | THPFHHDPPV | IGREKFHSRP | QHGKELPCST | 480 |
| YVQSTAATTE | EIEVHMPPDT | PDRTLMSQQS | GNVKITVNGQ | TVRYKCNCGG | SNEGLTTTDK | 540 |
| VINNCKVDQC | HAAVTNHKKW | QYNSPLVPRN | AELGDRKGKI | HIPFPLANVT | CRVPKARNPT | 600 |
| VTYGKNQVIM | LLYPDHPTLL | SYRNMGEEPN | YQEEWVMHKK | EVVLTVPTEG | LEVTWGNNEP | 660 |
| YKYWPQLSTN | GTAHGHPHEI | ILYYYELYPT | MTVVVVSVAT | FILLSMVGMA | AGMCMCARRR | 720 |
| CITPYELTPG | ATVPFLLSLI | CCIRTAKAAT | YQEAAIYLWN | EQQPLFWLQA | LIPLAALIVL | 780 |
| CNCLRLLPCC | CKTLAFLAVM | SVGAHTVSAY | EHVTVIPNTV | GVPYKTLVNR | PGYSPMVLEM | 840 |
| ELLSVTLEPT | LSLDYITCEY | KTVIPSPYVK | CCGTAECKDK | NLPDYSCKVF | TGVYPFMWGG | 900 |
| AYCFCDAENT | QLSEAHVEKS | ESCKTEFASA | YRAHTASASA | KLRVLYQGNN | ITVTAYANGD | 960 |
| HAVTVKDAKF | IVGPMSSAWT | PFDNKIVVYK | GDVYNMDYPP | FGAGRPGQFG | DIQSRTPESK | 1020 |
| DVYANTQLVL | QRPAVGTVHV | PYSQAPSGFK | YWLKERGASL | QHTAPFGCQI | ATNPVRAVNC | 1080 |
| AVGNMPISID | IPEAAFTRVV | DAPSLTDMSC | EVPACTHSSD | FGGVAIIKYA | ASKKGKCAVH | 1140 |
| SMTNAVTIRE | AEIEVEGNSQ | LQISFSTALA | SAEFRVQVCS | TQVHCAAECH | PPKDHIVNYP | 1200 |
| ASHTTLGVQD | ISATAMSWVQ | KITGGVGLVV | AVAALILIVV | LCVSFSRH | | 1248 |

FIGURE 43

| | | | | | | |
|---|---|---|---|---|---|---|
| MEFIPTQTFY | NRRYQPRPWT | PRPTIQVIRP | RPRPQRQAGQ | LAQLISAVNK | LTMRAVPQQK | 60 |
| PRRNRKNKKQ | KQKQQAPQNN | TNQKKQPPKK | KPAQKKKKPG | RRERMCMKIE | NDCIFEVKHE | 120 |
| GKVTGYACLV | GDKVMKPAHV | KGTIDNADLA | KLAFKRSSKY | DLECAQIPVH | MKSDASKFTH | 180 |
| EKPEGYYNWH | HGAVQYSGGR | FTIPTGAGKP | GDSGRPIFDN | KGRVVAIVLG | GANEGARTAL | 240 |
| SVVTWNKDIV | TKITPEGAEE | WSLAIPVMCL | LANTTFPCSQ | PPCTPCCYEK | EPEETLRMLE | 300 |
| DNVMRPGYYQ | LLQASLTCSP | HRQRRSTKDN | FNVYKATRPY | LAHCPDCGEG | HSCHSPVALE | 360 |
| RIRNEATDGT | LKIQVSLQIG | IKTDDSHDWT | KLRYMDNHMP | ADAERAGLFV | RTSAPCTITG | 420 |
| TMGHFILARC | PKGETLTVGF | TDSRKISHSC | THPFHHDPPV | IGREKFHSRP | QHGKELPCST | 480 |
| YVQSTAATTE | EIEVHMPPDT | PDRTLMSQQS | GNVKITVNGQ | TVRYKCNCGG | SNEGLTTTDK | 540 |
| VINNCKVDQC | HAAVTNHKKW | QYNSPLVPRN | AELGDRKGKI | HIPFPLANVT | CRVPKARNPT | 600 |
| VTYGKNQVIM | LLYPDHPTLL | SYRNMGEEPN | YQEEWVMHKK | EVVLTVPTEG | LEVTWGNNEP | 660 |
| YKYWPQLSTN | GTAHGHPHEI | ILYYYELYPT | MTVVVVSVAT | FILLSMVGMA | AGMCMCARRR | 720 |
| CITPYELTPG | ATVPFLLSLI | CCIRTAKAAT | YQEAAIYLWN | EQQPLFWLQA | LIPLAALIVL | 780 |
| CNCLRLLPCC | CKTLAFLAVM | SVGAHTVSAY | EHVTVIPNTV | GVPYKTLVNR | PGYSPMVLEM | 840 |
| ELLSVTLEPT | LSLDYITCEY | KTVIPSPYVK | CCGTAECKDK | NLPDYSCKVF | TGVYPFMWGG | 900 |
| AYCFCDAENT | QLSEAHVEKS | ESCKTEFASA | YRAHTASASA | KLRVLYQGNN | ITVTAYANGD | 960 |
| HAVTVKDAKF | IVGPMSSAWT | PFDNKIVVYK | GDVYNMDYPP | FGAGRPGQFG | DIQSRTPESK | 1020 |
| DVYANTQLVL | QRPAVGTVHV | PYSQAPSGFK | YWLKERGASL | QHTAPFGCQI | ATNPVRAVNC | 1080 |
| AVGNMPISID | IPEAAFTRVV | DAPSLTDMSC | EVPACTHSSD | FGGVAIIKYA | ASKKGKCAVH | 1140 |
| SMTNAVTIRE | AEIEVEGNSQ | LQISFSTALA | SAEFRVQVCS | TQVHCAAECH | PPKDHIVNYP | 1200 |
| ASHTTLGVQD | ISATAMSWVQ | KITGGVGLVV | AVAALILIVV | LCVSFSRH | | 1248 |

FIGURE 44

```
MDPVYVDIDA DSAFLKALQR AYPMFEVEPR QVTPNDHANA RAFSHLAIKL IEQEIDPDST     60
ILDIGSAPAR RMMSDRKYHC VCPMRSAEDP ERLANYARKL ASAAGKVLDR NISGKIGDLQ    120
AVMAVPDTET PTFCLHTDVS CRQRADVAIY QDVYAVHAPT SLYHQAIKGV RVAYWVGFDT    180
TPFMYNAMAG AYPSYSTNWA DEQVLKAKNI GLCSTDLTEG RRGKLSIMRG KKLKPCDRVL    240
FSVGSTLYPE SRKLLKSWHL PSVFHLKGKL SFTCRCDTVV SCEGYVVKRI TMSPGLYGKT    300
TGYAVTHHAD GFLMCKTTDT VDGERVSFSV CTYVPATICD QMTGILATEV TPEDAQKLLV    360
GLNQRIVVNG RTQRNTNTMK NYLLPVVAQA FSKWAKECRK DMEDEKLLGV RERTLTCCCL    420
WAFKKQKTHT VYKRPDTQSI QKVQAEFDSF VVPSLWSSGL SIPLRTRIKW LLSKVPKTDL    480
IPYSGDAREA RDAEKEAEEE REAELTREAL PPLQAAQEDV QVEIDVEQLE DRAGAGIIET    540
PRGAIKVTAQ PTDHVVGEYL VLSPQTVLRS QKLSLIHALA EQVKTCTHNG RAGRYAVEAY    600
DGRVLVPSGY AISPEDFQSL SESATMVYNE REFVNRKLHH IAMHGPALNT DEESYELVRA    660
ERTEHEYVYD VDQRRCCKKE EAAGLVLVGD LTNPPYHEFA YEGLKIRPAC PYKIAVIGVF    720
GVPGSGKSAI IKNLVTRQDL VTSGKKENCQ EITTDVMRQR GLEISARTVD SLLLNGCNRP    780
VDVLYVDEAF ACHSGTLLAL IALVRPRQKV VLCGDPKQCG FFNMMQMKVN YNHNICTQVY    840
HKSISRRCTL PVTAIVSSLH YEGKMRTTNE YNKPIVVDTT GSTKPDPGDL VLTCFRGWVK    900
QLQIDYRGYE VMTAAASQGL TRKGVYAVRQ KVNENPLYAS TSEHVNVLLT RTEGKLVWKT    960
LSGDPWIKTL QNPPKGNFKA TIKEWEVEHA SIMAGICSHQ MTFDTFQNKA NVCWAKSLVP   1020
ILETAGIKLN DRQWSQIIQA FKEDKAYSPE VALNEICTRM YGVDLDSGLF SKPLVSVYYA   1080
DNHWDNRPGG KMFGFNPEAA SILERKYPFT KGKWNINKQI CVTTRRIEDF NPTTNIIPAN   1140
RRLPHSLVAE HRPVKGERME WLVNKINGHH VLLVSGYNLA LPTKRVTWVA PLGVRGADYT   1200
YNLELGLPAT LGRYDLVVIN IHTPFRIHHY QQCVDHAMKL QMLGGDSLRL LKPGGSLLIR   1260
AYGYADRTSE RVICVLGRKF RSSRALKPPC VTSNTEMFFL FSNFDNGRRN FTTHVMNNQL   1320
NAAFVGQVTR AGCAPSYRVK RMDIAKNDEE CVVNAANPRG LPGDGVCKAV YKKWPESFKN   1380
SATPVGTAKT VMCGTYPVIH AVGPNFSNYS ESEGDRELAA AYREVAKEVT RLGVNSVAIP   1440
LLSTGVYSGG KDRLTQSLNH LFTAMDSTDA DVVIYCRDKE WEKKISEAIQ MRTQVELLDE   1500
HISIDCDIVR VHPDSSLAGR KGYSTTEGAL YSYLEGTRFH QTAVDMAEIH TMWPKQTEAN   1560
EQVCLYALGE SIESIRQKCP VDDADASSPP KTVPCLCRYA MTPERVTRLR MNHVTSIIVC   1620
SSFPLPKYKI EGVQKVKCSK VMLFDHNVPS RVSPREYRSS QESAQEASTI TSLTHSQFDL   1680
SVDGEILPVP SDLDADAPAL EPALDDGATH TLPSTTGNLA AVSDWVMSTV PVAPPRRRRG   1740
RNLTVTCDER EGNITPMASV RFFRAELCPV VQETAETRDT AMSLQAPPST ATEPNHPPIS   1800
FGASSETFPI TFGDFNEGEI ESLSSELLTF GDFLPGEVDD LTDSDWSTCS DTDDELLDRA   1860
GGYIFSSDTG PGHLQQKSVR QSVLPVNTLE EVHEEKCYPP KLDEAKEQLL LKKLQESASM   1920
ANRSRYQSRK VENMKAAIIQ RLKRGCRLYL MSETPKVPTY RTTYPAPVYS PPINVRLSNP   1980
ESAVAACNEF LARNYPTVSS YQITDEYDAY LDMVDGSESC LDRATFNPSK LRSYPKQHAY   2040
HAPSIRSAVP SPFQNTLQNV LAAATKRNCN VTQMRELPTL DSAVFNVECF KKFACNQEYW   2100
EEFAASPIRI TTENLATYVT KLKGPKAAAL FAKTHNLLPL QEVPMDRFTV DMKRDVKVTP   2160
GTKHTEERPK VQVIQAAEPL ATAYLCGIHR ELVRRLNAVL LPNVHTLFDM SAEDFDAIIA   2220
AHFKPGDTVL ETDIASFDKS QDDSLALTAL MLLEDLGVDH SLLDLIEAAF GEISSCHLPT   2280
GTRFKFGAMM KSGMFLTLFV NTLLNITIAS RVLEDRLTKS ACAAFIGDDN IIHGVVSDEL   2340
MAARCATWMN MEVKIIDAVV SLKAPYFCGG FILHDTVTGT ACRVADPLKR LFKLGKPLAA   2400
GDEQDEDRRR ALADEVIRWQ RTGLIDELEK AVYSRYEVQG ISVVVMSMAT FASSRSNFEK   2460
LRGPVITLYG GPK                                                      2473
```

FIGURE 45

MDPVYVDIDA DSAFLKALQR AYPMFEVEPR QVTPNDHANA RAFSHLAIKL IEQEIDPDST 60
ILDIGSAPAR RMMSDRKYHC VCPMRSAEDP ERLANYARKL ASAAGKVLDR NISGKIGDLQ 120
AVMAVPDTET PTFCLHTDVS CRQRADVAIY QDVYAVHAPT SLYHQAIKGV RVAYWVGFDT 180
TPFMYNAMAG AYPSYSTNWA DEQVLKAKNI GLCSTDLTEG RRGKLSIMRG KKLKPCDRVL 240
FSVGSTLYPE SRKLLKSWHL PSVFHLKGKL SFTCRCDTVV SCEGYVVKRI TMSPGLYGKT 300
TGYAVTHHAD GFLMCKTTDT VDGERVSFSV CTYVPATICD QMTGILATEV TPEDAQKLLV 360
GLNQRIVVNG RTQRNTNTMK NYLLPVVAQA FSKWAKECRK DMEDEKLLGV RERTLTCCCL 420
WAFKKQKTHT VYKRPDTQSI QKVQAEFDSF VVPSLWSSGL SIPLRTRIKW LLSKVPKTDL 480
IPYSGDAREA RDAEKEAEEE REAELTREAL PPLQAAQEDV QVEIDVEQLE DRAGAGIIET 540
PRGAIKVTAQ PTDHVVGEYL VLSPQTVLRS QKLSLIHALA EQVKTCTHNG RAGRYAVEAY 600
DGRVLVPSGY AISPEDFQSL SESATMVYNE REFVNRKLHH IAMHGPALNT DEESYELVRA 660
ERTEHEYVYD VDQRRCCKKE EAAGLVLVGD LTNPPYHEFA YEGLKIRPAC PYKIAVIGVF 720
GVPGSGKSAI IKNLVTRQDL VTSGKKENCQ EITTDVMRQR GLEISARTVD SLLLNGCNRP 780
VDVLYVDEAF ACHSGTLLAL IALVRPRQKV VLCGDPKQCG FFNMMQMKVN YNHNICTQVY 840
HKSISRRCTL PVTAIVSSLH YEGKMRTTNE YNKPIVVDTT GSTKPDPGDL VLTCFRGWVK 900
QLQIDYRGYE VMTAAASQGL TRKGVYAVRQ KVNENPLYAS TSEHVNVLLT RTEGKLVWKT 960
LSGDPWIKTL QNPPKGNFKA TIKEWEVEHA SIMAGICSHQ MTFDTFQNKA NVCWAKSLVP 1020
ILETAGIKLN DRQWSQIIQA FKEDKAYSPE VALNEICTRM YGVDLDSGLF SKPLVSVYYA 1080
DNHWDNRPGG KMFGFNPEAA SILERKYPFT KGKWNINKQI CVTTRRIEDF NPTTNIIPAN 1140
RRLPHSLVAE HRPVKGERME WLVNKINGHH VLLVSGYNLA LPTKRVTWVA PLGVRGADYT 1200
YNLELGLPAT LGRYDLVVIN IHTPFRIHHY QQCVDHAMKL QMLGGDSLRL LKPGGSLLIR 1260
AYGYADRTSE RVICVLGRKF RSSRALKPPC VTSNTEMFFL FSNFDNGRRN FTTHVMNNQL 1320
NAAFVGQVTR AGCAPSYRVK RMDIAKNDEE CVVNAANPRG LPGDGVCKAV YKKWPESFKN 1380
SATPVGTAKT VMCGTYPVIH AVGPNFSNYS ESEGDRELAA AYREVAKEVT RLGVNSVAIP 1440
LLSTGVYSGG KDRLTQSLNH LFTAMDSTDA DVVIYCRDKE WEKKISEAIQ MRTQVELLDE 1500
HISIDCDIVR VHPDSSLAGR KGYSTTEGAL YSYLEGTRFH QTAVDMAEIH TMWPKQTEAN 1560
EQVCLYALGE SIESIRQKCP VDDADASSPP KTVPCLCRYA MTPERVTRLR MNHVTSIIVC 1620
SSFPLPKYKI EGVQKVKCSK VMLFDHNVPS RVSPREYRSS QESAQEASTI TSLTHSQFDL 1680
SVDGEILPVP PDLDADAPAL EPALDDGATH TLPSTTGNLA AVSDWVMSTV PVAPPRRRRG 1740
RNLTVTCDER EGNITPMASV RFFRAELCPV VQETAETRDT AMSLQAPPST ATEPNHPPIS 1800
FGASSETFPI TFGDFNEGEI ESLSSELLTF GDFLPGEVDD LTDSDWSTCS DTDDELLDRA 1860
GGYIFSSDTG PGHLQQKSVR QSVLPVNTLE EVHEEKCYPP KLDEAKEQLL LKKLQESASM 1920
ANRSRYQSRK VENMKAAIIQ RLKRGCRLYL MSETPKVPTY RTTYPAPVYS PPINVRLSNP 1980
ESAVAACNEF LARNYPTVSS YQITDEYDAY LDMVDGSESC LDRATFNPSK LRSYPKQHAY 2040
HAPSIRSAVP SPFQNTLQNV LAAATKRNCN VTQMRELPTL DSAVFNVECF KKFACNQEYW 2100
EEFAASPIRI TTENLATYVT KLKGPKAAAL FAKTHNLLPL QEVPMDRFTV DMKRDVKVTP 2160
GTKHTEERPK VQVIQAAEPL ATAYLCGIHR ELVRRLNAVL LPNVHTLFDM SAEDFDAIIA 2220
AHFKPGDTVL ETDIASFDKS QDDSLALTAL MLLEDLGVDH SLLDLIEAAF GEISSCHLPT 2280
GTRFKFGAMM KSGMFLTLFV NTLLNITIAS RVLEDRLTKS ACAAFIGDDN IIHGVVSDEL 2340
MAARCATWMN MEVKIIDAVV SLKAPYFCGG FILHDTVTGT ACRVADPLKR LFKLGKPLAA 2400
GDEQDEDRRR ALADEVIRWQ RTGLIDELEK AVYSRYEVQG ISVVVMSMAT FASSRSNFEK 2460
LRGPVITLYG GPK 2473

FIGURE 46

```
MDPVYVDIDA DSAFLKALQR AYPMFEVEPR QVTPNDHANA RAFSHLAIKL IEQEIDPDST     60
ILDIGSAPAR RMMSDRKYHC VCPMRSAEDP ERLANYARKL ASAAGKVLDR NISGKIGDLQ    120
AVMAVPDTET PTFCLHTDVS CRQRADVAIY QDVYAVHAPT SLYHQAIKGV RVAYWVGFDT    180
TPFMYNAMAG AYPSYSTNWA DEQVLKAKNI GLCSTDLTEG RRGKLSIMRG KKLKPCDRVL    240
FSVGSTLYPE SRKLLKSWHL PSVFHLKGKL SFTCRCDTVV SCEGYVVKRI TMSPGLYGKT    300
TGYAVTHHAD GFLMCKTTDT VDGERVSFSV CTYVPATICD QMTGILATEV TPEDAQKLLV    360
GLNQRIVVNG RTQRNTNTMK NYLLPVVAQA FSKWAKECRK DMEDEKLLGV RERTLTCCCL    420
WAFKKQKTHT VYKRPDTQSI QKVQAEFDSF VVPSLWSSGL SIPLRTRIKW LLSKVPKTDL    480
IPYSGDAREA RDAEKEAEEE REAELTREAL PPLQAAQEDV QVEIDVEQLE DRAGAGIIET    540
PRGAIKVTAQ PTDHVVGEYL VLSPQTVLRS QKLSLIHALA EQVKTCTHNG RAGRYAVEAY    600
DGRVLVPSGY AISPEDFQSL SESATMVYNE REFVNRKLHH IAMHGPALNT DEESYELVRA    660
ERTEHEYVYD VDQRRCCKKE EAAGLVLVGD LTNPPYHEFA YEGLKIRPAC PYKIAVIGVF    720
GVPGSGKSAI IKNLVTRQDL VTSGKKENCQ EITTDVMRQR GLEISARTVD SLLLNGCNRP    780
VDVLYVDEAF ACHSGTLLAL IALVRPRQKV VLCGDPKQCG FFNMMQMKVN YNHNICTQVY    840
HKSISRRCTL PVTAIVSSLH YEGKMRTTNE YNKPIVVDTT GSTKPDPGDL VLTCFRGWVK    900
QLQIDYRGYE VMTAAASQGL TRKGVYAVRQ KVNENPLYAS TSEHVNVLLT RTEGKLVWKT    960
LSGDPWIKTL QNPPKGNFKA TIKEWEVEHA SIMAGICSHQ MTFDTFQNKA NVCWAKSLVP   1020
ILETAGIKLN DRQWSQIIQA FKEDKAYSPE VALNEICTRM YGVDLDSGLF SKPLVSVYYA   1080
DNHWDNRPGG KMFGFNPEAA SILERKYPFT KGKWNINKQI CVTTRRIEDF NPTTNIIPAN   1140
RRLPHSLVAE HRPVKGERME WLVNKINGHH VLLVSGYNLA LPTKRVTWVA PLGVRGADYT   1200
YNLELGLPAT LGRYDLVVIN IHTPFRIHHY QQCVDHAMKL QMLGGDSLRL LKPGGSLLIR   1260
AYGYADRTSE RVICVLGRKF RSSRALKPPC VTSNTEMFFL FSNFDNGRRN FTTHVMNNQL   1320
NAAFVGQVTR AGCAPSYRVK RMDIAKNDEE CVVNAANPRG LPGDGVCKAV YKKWPESFKN   1380
SATPVGTAKT VMCGTYPVIH AVGPNFSNYS ESEGDRELAA AYREVAKEVT RLGVNSVAIP   1440
LLSTGVYSGG KDRLTQSLNH LFTAMDSTDA DVVIYCRDKE WEKKISEAIQ MRTQVELLDE   1500
HISIDCDIVR VHPDSSLAGR KGYSTTEGAL YSYLEGTRFH QTAVDMAEIH TMWPKQTEAN   1560
EQVCLYALGE SIESIRQKCP VDDADASSPP KTVPCLCRYA MTPERVTRLR MNHVTSIIVC   1620
SSFPLPKYKI EGVQKVKCSK VMLFDHNVPS RVSPREYRSS QESAQEASTI TSLTHSQFDL   1680
SVDGEILPVP SDLDADAPAL EPALDDGATH TLPSTTGNLA AVSDWVMSTV PVAPPRRRRG   1740
RNLTVTCDER EGNITPMASV RFFRAELCPV VQETAETRDT AMSLQAPPST ATEPNHPPIS   1800
FGASSETFPI TFGDFNEGEI ESLSSELLTF GDFLPGEVDD LTDSDWSTCS DTDDELLDRA   1860
GGYIFSSDTG PGHLQQKSVR QSVLPVNTLE EVHEEKCYPP KLDEAKEQLL LKKLQESASM   1920
ANRSRYQSRK VENMKAAIIQ RLKRGCRLYL MSETPKVPTY RTTYPAPVYS PPINVRLSNP   1980
ESAVAACNEF LARNYPTVSS YQITDEYDAY LDMVDGSESC LDRATFNPSK LRSYPKQHAY   2040
HAPSIRSAVP SPFQNTLQNV LAAATKRNCN VTQMRELPTL DSAVFNVECF KKFACNQEYW   2100
EEFAASPIRI TTENLATYVT KLKGPKAAAL FAKTHNLLPL QEVPMDRFTV DMKRDVKVTP   2160
GTKHTEERPK VQVIQAAEPL ATAYLCGIHR ELVRRLNAVL LPNVHTLFDM SAEDFDAIIA   2220
AHFKPGDTVL ETDIASFDKS QDDSLALTAL MLLEDLGVDH SLLDLIEAAF GEISSCHLPT   2280
GTRFKFGAMM KSGMFLTLFV NTLLNITIAS RVLEDRLTKS ACAAFIGDDN IIHGVVSDEL   2340
MAARCATWMN MEVKIIDAVV SLKAPYFCGG FILHDTVTGT ACRVADPLKR LFKLGKPLAA   2400
GDEQDEDRRR ALADEVIRWQ RTGLIDELEK AVYSRYEVQG ISVVVMSMAT FASSRSNFEK   2460
LRGPVITLYG GPK                                                      2473
```

FIGURE 47

```
MDPVYVDIDA DSAFLKALQR AYPMFEVEPR QVTPNDHANA RAFSHLAIKL IEQEIDPDST     60
ILDIGSAPAR RMMSDRKYHC VCPMRSAEDP ERLANYARKL ASAAGKVLDR NISGKIGDLQ    120
AVMAVPDTET PTFCLHTDVS CRQRADVAIY QDVYAVHAPT SLYHQAIKGV RVAYWVGFDT    180
TPFMYNAMAG AYPSYSTNWA DEQVLKAKNI GLCSTDLTEG RRGKLSIMRG KKLKPCDRVL    240
FSVGSTLYPE SRKLLKSWHL PSVFHLKGKL SFTCRCDTVV SCEGYVVKRI TMSPGLYGKT    300
TGYAVTHHAD GFLMCKTTDT VDGERVSFSV CTYVPATICD QMTGILATEV TPEDAQKLLV    360
GLNQRIVVNG RTQRNTNTMK NYLLPVVAQA FSKWAKECRK DMEDEKLLGV RERTLTCCCL    420
WAFKKQKTHT VYKRPDTQSI QKVQAEFDSF VVPSLWSSGL SIPLRTRIKW LLSKVPKTDL    480
IPYSGDAREA RDAEKEAEEE REAELTREAL PPLQAAQEDV QVEIDVEQLE DRAGAGIIET    540
PRGAIKVTAQ PTDHVVGEYL VLSPQTVLRS QKLSLIHALA EQVKTCTHNG RAGRYAVEAY    600
DGRVLVPSGY AISPEDFQSL SESATMVYNE REFVNRKLHH IAMHGPALNT DEESYELVRA    660
ERTEHEYVYD VDQRRCCKKE EAAGLVLVGD LTNPPYHEFA YEGLKIRPAC PYKIAVIGVF    720
GVPGSGKSAI IKNLVTRQDL VTSGKKENCQ EITTDVMRQR GLEISARTVD SLLLNGCNRP    780
VDVLYVDEAF ACHSGTLLAL IALVRPRQKV VLCGDPKQCG FFNMMQMKVN YNHNICTQVY    840
HKSISRRCTL PVTAIVSSLH YEGKMRTTNE YNKPIVVDTT GSTKPDPGDL VLTCFRGWVK    900
QLQIDYRGYE VMTAAASQGL TRKGVYAVRQ KVNENPLYAS TSEHVNVLLT RTEGKLVWKT    960
LSGDPWIKTL QNPPKGNFKA TIKEWEVEHA SIMAGICSHQ MTFDTFQNKA NVCWAKSLVP   1020
ILETAGIKLN DRQWSQIIQA FKEDKAYSPE VALNEICTRM YGVDLDSGLF SKPLVSVYYA   1080
DNHWDNRPGG KMFGFNPEAA SILERKYPFT KGKWNINKQI CVTTRRIEDF NPTTNIIPAN   1140
RRLPHSLVAE HRPVKGERME WLVNKINGHH VLLVSGYNLA LPTKRVTWVA PLGVRGADYT   1200
YNLELGLPAT LGRYDLVVIN IHTPFRIHHY QQCVDHAMKL QMLGGDSLRL LKPGGSLLIR   1260
AYGYADRTSE RVICVLGRKF RSSRALKPPC VTSNTEMFFL FSNFDNGRRN FTTHVMNNQL   1320
NAAFVGQVTR AGCAPSYRVK RMDIAKNDEE CVVNAANPRG LPGDGVCKAV YKKWPESFKN   1380
SATPVGTAKT VMCGTYPVIH AVGPNFSNYS ESEGDRELAA AYREVAKEVT RLGVNSVAIP   1440
LLSTGVYSGG KDRLTQSLNH LFTAMDSTDA DVVIYCRDKE WEKKISEAIQ MRTQVELLDE   1500
HISIDCDIVR VHPDSSLAGR KGYSTTEGAL YSYLEGTRFH QTAVDMAEIH TMWPKQTEAN   1560
EQVCLYALGE SIESIRQKCP VDDADASSPP KTVPCLCRYA MTPERVTRLR MNHVTSIIVC   1620
SSFPLPKYKI EGVQKVKCSK VMLFDHNVPS RVSPREYRSS QESAQEASTI TSLTHSQFDL   1680
SVDGEILPVP SDLDADAPAL EPALDDGATH TLPSTTGNLA AVSDWVMSTV PVAPPRRRRG   1740
RNLTVTCDER EGNITPMASV RFFRAELCPV VQETAETRDT AMSLQAPPST ATEPNHPPIS   1800
FGASSETFPI TFGDFNEGEI ESLSSELLTF GDFLPGEVDD LTDSDWSTCS DTDDELLDRA   1860
GGYIFSSDTG PGHLQQKSVR QSVLPVNTLE EVHEEKCYPP KLDEAKEQLL LKKLQESASM   1920
ANRSRYQSRK VENMKAAIIQ RLKRGCRLYL MSETPKVPTY RTTYPAPVYS PPINVRLSNP   1980
ESAVAACNEF LARNYPTVSS YQITDEYDAY LDMVDGSESC LDRATFNPSK LRSYPKQHAY   2040
HAPSIRSAVP SPFQNTLQNV LAAATKRNCN VTQMRELPTL DSAVFNVECF KKFACNQEYW   2100
EEFAASPIRI TTENLATYVT KLKGPKAAAL FAKTHNLLPL QEVPMDRFTV DMKRDVKVTP   2160
GTKHTEERPK VQVIQAAEPL ATAYLCGIHR ELVRRLNAVL LPNVHTLFDM SAEDFDAIIA   2220
AHFKPGDTVL ETDIASFDKS QDDSLALTAL MLLEDLGVDH SLLDLIEAAF GEISSCHLPT   2280
GTRFKFGAMM KSGMFLTLFV NTLLNITIAS RVLEDRLTKS ACAAFIGDDN IIHGVVSDEL   2340
MAARCATWMN MEVKIIDAVV SLKAPYFCGG FILHDTVTGT ACRVADPLKR LFKLGKPLAA   2400
GDEQDEDRRR ALADEVIRWQ RTGLIDELEK AVYSRYEVQG ISVVVMSMAT FASSRSNFEK   2460
LRGPVITLYG GPK                                                      2473
```

FIGURE 48

```
MDPVYVDIDA DSAFLKALQR AYPMFEVEPR QVTPNDHANA RAFSHLAIKL IEQEIDPDST     60
ILDIGSAPAR RMMSDRKYHC VCPMRSAEDP ERLANYARKL ASAAGKVLDR NISGKIGDLQ    120
AVMAVPDTET PTFCLHTDVS CRQRADVAIY QDVYAVHAPT SLYHQAIKGV RVAYWVGFDT    180
TPFMYNAMAG AYPSYSTNWA DEQVLKAKNI GLCSTDLTEG RRGKLSIMRG KKLKPCDRVL    240
FSVGSTLYPE SRKLLKSWHL PSVFHLKGKL SFTCRCDTVV SCEGYVVKRI TMSPGLYGKT    300
IGYAVTHHAD GFLMCKTTDT VDGERVSFSV CTYVPATICD QMTGILATEV TPEDAQKLLV    360
GLNQRIVVNG RTQRNTNTMK NYLLPVVAQA FSKWAKECRK DMEDEKLLGV RERTLTCCCL    420
WAFKKQKTHT VYKRPDTQSI QKVQAEFDSF VVPSLWSSGL SIPLRTRIKW LLSKVPKTDL    480
IPYSGDAREA RDAEKEAEEE REAELTREAL PPLQAAQEDV QVEIDVEQLE DRAGAGIIET    540
PRGAIKVTAQ PTDHVVGEYL VLSPQTVLRS QKLSLIHALA EQVKTCTHNG RAGRYAVEAY    600
DGRVLVPSGY AISPEDFQSL SESATMVYNE REFVNRKLHH IAMHGPALNT DEESYELVRA    660
ERTEHEYVYD VDQRRCCKKE EAAGLVLVGD LTNPPYHEFA YEGLKIRPAC PYKIAVIGVF    720
GVPGSGKSAI IKNLVTRQDL VTSGKKENCQ EITTDVMRQR GLEISARTVD SLLLNGCNRP    780
VDVLYVDEAF ACHSGTLLAL IALVRPRQKV VLCGDPKQCG FFNMMQMKVN YNHNICTQVY    840
HKSISRRCTL PVTAIVSSLH YEGKMRTTNE YNKPIVVDTT GSTKPDPGDL VLTCFRGWVK    900
QLQIDYRGYE VMTAAASQGL TRKGVYAVRQ KVNENPLYAS TSEHVNVLLT RTEGKLVWKT    960
LSGDPWIKTL QNPPKGNFKA TIKEWEVEHA SIMAGICSHQ MTFDTFQNKA NVCWAKSLVP   1020
ILETAGIKLN DRQWSQIIQA FKEDKAYSPE VALNEICTRM YGVDLDSGLF SKPLVSVYYA   1080
DNHWDNRPGG KMFGFNPEAA SILERKYPFT KGKWNINKQI CVTTRRIEDF NPTTNIIPAN   1140
RRLPHSLVAE HRPVKGERME WLVNKINGHH VLLVSGNNLA LPTKRVTWVA PLGVRGADYT   1200
YNLELGLPAT LGRYDLVVIN IHTPFRIHHY QQCVDHAMKL QMLGGDSLRL LKPGGSLLIR   1260
AYGYADRTSE RVICVLGRKF RSSRALKPPC VTSNTEMFFL FSNFDNGRRN FTTHVMNNQL   1320
NAAFVGQVTR AGCAPSYRVK RMDIAKNDEE CVVNAANPRG LPGDGVCKAV YKKWPESFKN   1380
SATPVGTAKT VMCGTYPVIH AVGPNFSNYS ESEGDRELAA AYREVAKEVT RLGVNSVAIP   1440
LLSTGVYSGG KDRLTQSLNH LFTAMDSTDA DVVIYCRDKE WEKKISEAIQ MRTQVELLDE   1500
HISIDCDIVR VHPDSSLAGR KGYSTTEGAL YSYLEGTRFH QTAVDMAEIH TMWPKQTEAN   1560
EQVCLYALGE SIESIRQKCP VDDADASSPP KTVPCLCRYA MTPERVTRLR MNHVTSIIVC   1620
SSFPLPKYKI EGVQKVKCSK VMLFDHNVPS RVSPREYRSS QESAQEASTI TSLTHSQFDL   1680
SVDGEILPVP SDLDADAPAL EPALDDGATH TLPSTTGNLA AVSDWVMSTV PVAPPRRRRG   1740
RNLTVTCDER EGNITPMASV RFFRAELCPV VQETAETRDT AMSLQAPPST ATPNHPPISF   1800
GASSETFPIT FGDFNEGEIE SLSSELLTFG DFLPGEVDDL TDSDWSTCSD TDDELLDRAG   1860
GYIFSSDTGP GHLQQKSVRQ SVLPVNTLEE VHEEKCYPPK LDEAKEQLLL KKLQESASMA   1920
NRSRYQSRKV ENMKAAIIQR LKRGCRLYLM SETPKVPTYR TTYPAPVYSP PINVRLSNPE   1980
SAVAACNEFL ARNYPTVSSY QITDEYDAYL DMVDGSESCL DRATFNPSKL RSYPKQHAYH   2040
APSIRSAVPS PFQNTLQNVL AAATKRNCNV TQMRELPTLD SAVFNVECFK KFACNQEYWE   2100
EFAASPIRIT TENLATYVTK LKGPKAAALF AKTHNLLPLQ EVPMDRFTVD MKRDVKVTPG   2160
TKHTEERPKV QVIQAAEPLA TAYLCGIHRE LVRRLNAVLL PNVHTLFDMS AEDFDAIIAA   2220
HFKPGDTVLE TDIASFDKSQ DDSLALTALM LLEDLGVDHS LLDLIEAAFG EISSCHLPTG   2280
TRFKFGAMMK SGMFLTLFVN TLLNITIASR VLEDRLTKSA CAAFIGDDNI IHGVVSDELM   2340
AARCATWMNM EVKIIDAVVS LKAPYFCGGF ILHDTVTGTA CRVADPLKRL FKLGKPLAAG   2400
DEQDEDRRRA LADEVIRWQR TGLIDELEKA VYSRYEVQGI SVVVMSMATF ASSRSNFEKL   2460
RGPVITLYGG PK                                                       2472
```

FIGURE 49

```
MFEVEPRQVT PNDHANARAF SHLAIKLIEQ EIDPDSTILD IGSAPARRMM SDRKYHCVCP     60
MRSAEDPERL ANYARKLASA AGKVLDRNIS GKIGDLQAVM AVPDTETPTF CLHTDVSCRQ    120
RADVAIYQDV YAVHAPTSLY HQAIKGVRVA YWVGFDTTPF MYNAMAGAYP SYSTNWADEQ    180
VLKAKNIGLC STDLTEGRRG KLSIMRGKKL KPCDRVLFSV GSTLYPESRK LLKSWHLPSV    240
FHLKGKLSFT CRCDTVVSCE GYVVKRITMS PGLYGKTTGY AVTHHADGFL MCKTTDTVDG    300
ERVSFSVCTY VPATICDQMT GILATEVTPE DAQKLLVGLN QRIVVNGRTQ RNTNTMKNYL    360
LPVVAQAFSK WAKECRKDME DEKLLGVRER TLTCCCLWAF KKQKTHTVYK RPDTQSIQKV    420
QAEFDSFVVP SLWSSGLSIP LRTRIKWLLS KVPKTDLIPY SGDAREARDA EKEAEEEREA    480
ELTREALPPL QAAQEDVQVE IDVEQLEDRA GAGIIETPRG AIKVTAQPTD HVVGEYLVLS    540
PQTVLRSQKL SLIHALAEQV KTCTHNGRAG RYAVEAYDGR VLVPSGYAIS PEDFQSLSES    600
ATMVYNEREF VNRKLHHIAM HGPALNTDEE SYELVRAERT EHEYVYDVDQ RRCCKKEEAA    660
GLVLVGDLTN PPYHEFAYEG LKIRPACPYK IAVIGVFGVP GSGKSAIIKN LVTRQDLVTS    720
GKKENCQEIT TDVMRQRGLE ISARTVDSLL LNGCNRPVDV LYVDEAFACH SGTLLALIAL    780
VRPRQKVVLC GDPKQCGFFN MMQMKVNYNH NICTQVYHKS ISRRCTLPVT AIVSSLHYEG    840
KMRTTNEYNK PIVVDTTGST KPDPGDLVLT CFRGWVKQLQ IDYRGYEVMT AAASQGLTRK    900
GVYAVRQKVN ENPLYASTSE HVNVLLTRTE GKLVWKTLSG DPWIKTLQNP PKGNFKATIK    960
EWEVEHASIM AGICSHQMTF DTFQNKANVC WAKSLVPILE TAGIKLNDRQ WSQIIQAFKE   1020
DKAYSPEVAL NEICTRMYGV DLDSGLFSKP LVSVYYADNH WDNRPGGKMF GFNPEAASIL   1080
ERKYPFTKGK WNINKQICVT TRRIEDFNPT TNIIPANRRL PHSLVAEHRP VKGERMEWLV   1140
NKINGHHVLL VSGYNLALPT KRVTWVAPLG VRGADYTYNL ELGLPATLGR YDLVVINIHT   1200
PFRIHHYQQC VDHAMKLQML GGDSLRLLKP GGSLLIRAYG YADRTSERVI CVLGRKFRSS   1260
RALKPPCVTS NTEMFFLFSN FDNGRRNFTT HVMNNQLNAA FVGQVTRAGC APSYRVKRMD   1320
IAKNDEECVV NAANPRGLPG DGVCKAVYKK WPESFKNSAT PVGTAKTVMC GTYPVIHAVG   1380
PNFSNYSESE GDRELAAAYR EVAKEVTRLG VNSVAIPLLS TGVYSGGKDR LTQSLNHLFT   1440
AMDSTDADVV IYCRDKEWEK KISEAIQMRT QVELLDEHIS IDCDIVRVHP DSSLAGRKGY   1500
STTEGALYSY LEGTRFHQTA VDMAEIHTMW PKQTEANEQV CLYALGESIE SIRQKCPVDD   1560
ADASSPPKTV PCLCRYAMTP ERVTRLRMNH VTSIIVCSSF PLPKYKIEGV QKVKCSKVML   1620
FDHNVPSRVS PREYRSSQES AQEASTITSL THSQFDLSVD GEILPVPSDL DADAPALEPA   1680
LDDGATHTLP STTGNLAAVS DWVMSTVPVA PPRRRRGRNL TVTCDEREGN ITPMASVRFF   1740
RAELCPVVQE TAETRDTAMS LQAPPSTATE PNHPPISFGA SSETFPITFG DFNEGEIESL   1800
SSELLTFGDF LPGEVDDLTD SDWSTCSDTD DELLDRAGGY IFSSDTGPGH LQQKSVRQSV   1860
LPVNTLEEVH EEKCYPPKLD EAKEQLLLKK LQESASMANR SRYQSRKVEN MKAAIIQRLK   1920
RGCRLYLMSE TPKVPTYRTT YPAPVYSPPI NVRLSNPESA VAACNEFLAR NYPTVSSYQI   1980
TDEYDAYLDM VDGSESCLDR ATFNPSKLRS YPKQHAYHAP SIRSAVPSPF QNTLQNVLAA   2040
ATKRNCNVTQ MRELPTLDSA VFNVECFKKF ACNQEYWEEF AASPIRITTE NLATYVTKLK   2100
GPKAAALFAK THNLLPLQEV PMDRFTVDMK RDVKVTPGTK HTEERPKVQV IQAAEPLATA   2160
YLCGIHRELV RRLNAVLLPN VHTLFDMSAE DFDAIIAAHF KPGDTVLETD IASFDKSQDD   2220
SLALTALMLL EDLGVDHSLL DLIEAAFGEI SSCHLPTGTR FKFGAMMKSG MFLTLFVNTL   2280
LNITIASRVL EDRLTKSACA AFIGDDNIIH GVVSDELMAA RCATWMNMEV KIIDAVVSLK   2340
APYFCGGFIL HDTVTGTACR VADPLKRLFK LGKPLAAGDE QDEDRRRALA DEVIRWQRTG   2400
LIDELEKAVY SRYEVQGISV VVMSMATFAS SRSNFEKLRG PVITLYGGPK              2450
```

ISOLATED AND PURIFIED STRAINS OF CHIKUNGUNYA VIRUS AND POLYNUCLEOTIDES AND POLYPEPTIDES SEQUENCES, DIAGNOSTIC AND IMMUNOGENICAL USES THEREOF

This is a Division of application Ser. No. 12/225,111, filed Sep. 29, 2009, which is a §371 of PCT/IB2007/001716, which claims the benefit of Canadian Application No. 2,545,597, filed Apr. 4, 2006 and Canadian Application No, 2,538,898, filed Mar. 15, 2006, all of which are incorporated herein by reference.

FIELD OF THE INVENTION

The present invention concerns wild-strains of Chikungunya virus isolated from patients exhibiting severe forms of infection and stemming from a human arbovirosis epidemy. The present invention also concerns polypeptide sequences and fragment thereof derived from their genome, the polynucleotide encoding same and their use as diagnostic products, as vaccine and/or as immunogenic compositions.

BACKGROUND OF THE INVENTION

Chikungunya virus (CHIKV) is a mosquito-transmitted Alphavirus belonging to family Togaviridae [1,2]. It was isolated for the first time from a Tanzanian outbreak in 1952 [3]. It is responsible for an acute infection of abrupt onset, characterized by high fever, arthralgia, myalgia, headache and rash [4,5]. Poly-arthralgia, the pathognomonic sign of the disease, is very painful. Symptoms are generally self-limiting and last 1 to 10 days. However, arthralgia or arthritic symptoms may persist for months or years. In some patients, minor hemorrhagic signs such as epistaxis or gingivorrhagia have also been described.

CHIKV is geographically distributed in Africa, India and South East Asia. In Africa, the virus is maintained through a sylvatic transmission cycle between wild primates and mosquitoes such as *Aedes luteocephalus, Ae. furcifer* or *Ae. taylori* [4]. In Asia, CHIKV is mainly transmitted from human to human by *Ae. aegypti* and to a lesser extent by *Ae. albopictus* through an urban transmission cycle. Since the 1952 Tanzania outbreak, CHIKV has caused outbreaks in East Africa (Tanzania, Uganda), in Austral Africa (Zimbabwe, South Africa), in West Africa (Senegal, Nigeria) and in Central Africa (Central African Republic, Democratic Republic of the Congo) [4]. The most recent epidemic re-emergence was documented in 1999-2000 in Kinshasa, where an estimated 50,000 persons were infected [6]. Since the first documented Asian outbreak in 1958 in Bangkok, Thailand, outbreaks have been documented in Thailand, Cambodia, Vietnam, Laos, Myanmar, Malasia, Philippines and Indonesia [4,5]. The most recent epidemic re-emergence was documented in 2001-2003 in Java after 20 years [7]. Either in Africa or Asia, the re-emergence was unpredictable, with intervals of 7-8 years to 20 years between consecutive epidemics.

Since the end of 2004, Chikungunya virus (CHIKV) has emerged in the islands of the south-western Indian Ocean. Between January and March 2005, more than 5,000 cases were reported in Comoros. Later in 2005, the virus has circulated in the other islands, i.e Mayotte, Seychelles, Réunion and Mauritius. Starting in December 2005, the rainy season gave rise to a renewed epidemic circulation of the virus. Between January 1st and Mar. 1, 2006, 2,553, 3,471, and 4,650 cases have been reported in Mauritius, Mayotte and Seychelles (Mar. 12, 2006). The most affected island is Reunion with an estimated 212,000 cases until Mar. 12, 2006 (total population: 770,000). More recently, circulation of the virus has been documented in Madagascar.

In Reunion Island, the first documented cases were patients coming 1 ng back from Comoros in March 2005. More than 3,000 cases were reported from March to June. The transmission was limited during the winter season of the southern hemisphere and a major upsurge has been observed since mid-December, with an estimated 210,000 cases between January and March 2006 [8]. Since March 2005, 85 patients with a confirmed CHIKV infection have developed severe clinical signs (meningoencephalitis or fulminant hepatitis) which justified hospitalization in an intensive care unit. Several cases of meningo-encephalitis and major algic syndrome have been associated with vertical transmission of the virus 9.

To date, two CHIKV complete nucleotide sequences have been determined, for the strains Ross (accession no: AF490259) and S27 [9], both isolated from patients during the 1952 Tanzania outbreak. Another complete nucleotide sequence has been determined for a strain isolated in *Ae. furcifer* during the Senegal 1983 outbreak (accession no AY726732). Khan and coworkers [9] showed that the S27 genome was similar in its structure to that of other alphaviruses and that O'nyong-nyong virus (ONN) was the closest relative to CHIKV. In addition, phylogenetic analyses based on partial E1 sequences from African and Asian isolates revealed the existence of three distinct CHIKV phylogroups, one containing all isolates from West Africa, one containing isolates from Asia, and one corresponding to Eastern, Central and Southern African isolates [10]. Strains isolated in 1999-2000 in the Democratic Republic of the Congo belonged to the latter phylogroup [6].

SUMMARY OF THE INVENTION

An aspect of the invention is to provide new diagnostic and immunologic tools against CHIK virus associated diseases, such as arbovirosis.

Such an aspect is particularly achieved by providing an isolated and purified wild strain of Chikungunya virus (CHIK) capable of in vitro infecting human cells; and its use for the detection of a CHIKV associated to an arbovirus, or for the preparation of a composition that prevents and/or treats an arbovirus.

Another aspect of the invention concerns an isolated and purified strain of CHIKV comprising at least one mutation in structural protein E1 and/or structural protein E2; and its use for the detection of a CHIKV associated to an arbovirus, or for the preparation of a composition that prevents and/or treats an arbovirus.

Another aspect of the invention concerns an isolated and purified polynucleotide comprising all or part of the sequence of SEQ ID NOS: 1, 2, 3, 4, 5 or 6; and its use for the detection of a CHIKV associated to an arbovirus, or for the preparation of a composition that prevents and/or treats an arbovirus.

Another aspect of the invention concerns a fragment of the polynucleotide of the invention wherein it codes for the ectodomain of glycoprotein E2 or E1; and its use for the detection of a CHIKV associated to an arbovirus, or for the preparation of a composition that prevents and/or treats an arbovirus.

Other aspects of the invention concern a vector or plasmid comprising a polynucleotide or fragment contemplated by the present invention, and host cell comprising said vector or plasmid; and its use for the detection of a CHIKV associated to an arbovirus, or for the preparation of a composition that prevents and/or treats an arbovirus.

Yet another aspect of the invention concerns a purified polypeptide encoded by a polynucleotide or fragment of the invention; and its use for the detection of a CHIKV associated to an arbovirus, or for the preparation of a composition that prevents and/or treats an arbovirus.

A further aspect of the invention concerns a monoclonal or polyclonal antibody or fragment thereof that specifically binds to a polypeptide of the invention; and its use for the detection of a CHIKV associated to an arbovirus, or for the preparation of a composition that prevents and/or treats an arbovirus.

BRIEF DESCRIPTION OF THE FIGURES

FIG. 1: Localization of the E1 changes on the 3D structure modeled from the crystal structure of SFV E1 [43] [19].

A) Ribbon diagram of E1, with domain I colored red, domain II yellow and domain III, blue. Green tubes mark the disulfide bonds. The fusion peptide, at the tip of the molecule (in domain II) is colored orange and labeled. The N-terminus and the C-terminus observed in the crystal (which is 30 aa upstream of the transmembrane region) are also labeled. The 2 unique changes observed in the Indian Ocean isolates are indicated by stars and labeled: positions 226 (white) and 284 (magenta).

B) Partial representation (one octant, slightly extended) of the icosahedral E1 scaffold at the surface of the virion, viewed down a 5-fold symmetry axis. One E1 protomer is highlighted in colors, as in A); all the others are represented in grey. The location of some of the icosahedral symmetry axes are drawn as solid black symbols: pentagon for 5-fold axis, triangle for 3-fold axes, ellipse for 2-fold axes (which in the T=4 lattice of alphaviruses are coincident with quasi 6-fold axes). Open triangles indicate roughly the location of the E2 trimers that interact tightly with E1, covering domain II and the fusion peptide, and presenting the main antigenic sites. The open triangles mark also quasi 3-fold symmetry axes of the T=4 surface icosahedral lattice. A magenta ball marks the location of Glu 284, at an inter-E1 protomer contact site. This contact is propagated 240 times at the surface lattice (note all pink balls drawn on the grey protomers). Note that the fusion peptide, in orange, is pointing up and away from contacts with other E1 protomers. This is more easily seen at the periphery of the virion, where one of them is labeled (FP). In the virion, this region of E1 is not accessible, covered underneath the E2 molecule [19].

Figure 2:
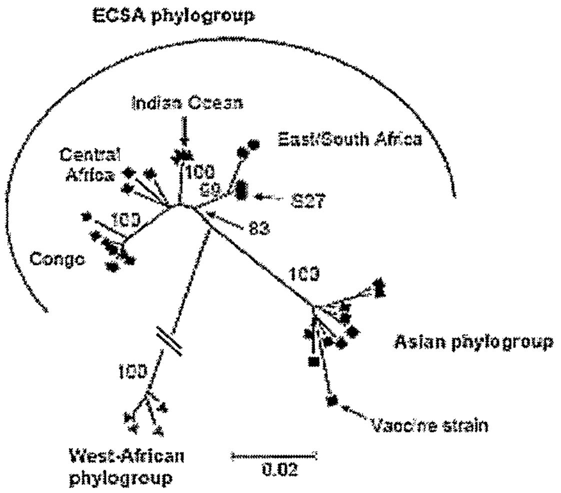

FIG. 2: Phylogenetic relationships among chikungunya isolates based on partial E1 nucleotide sequences. Isolates from the Indian Ocean outbreak (Reunion, Seychelles, Mayotte, Mauritius, Madagascar) represent a distinct Glade within a large East, Central and South African (ECSA) phylogroup. Bootstrap resampling values are indicated at major nodes. The branch leading to West-African phylogroup (of length approx. 15%) was shortened for convenience.

Figure 3:
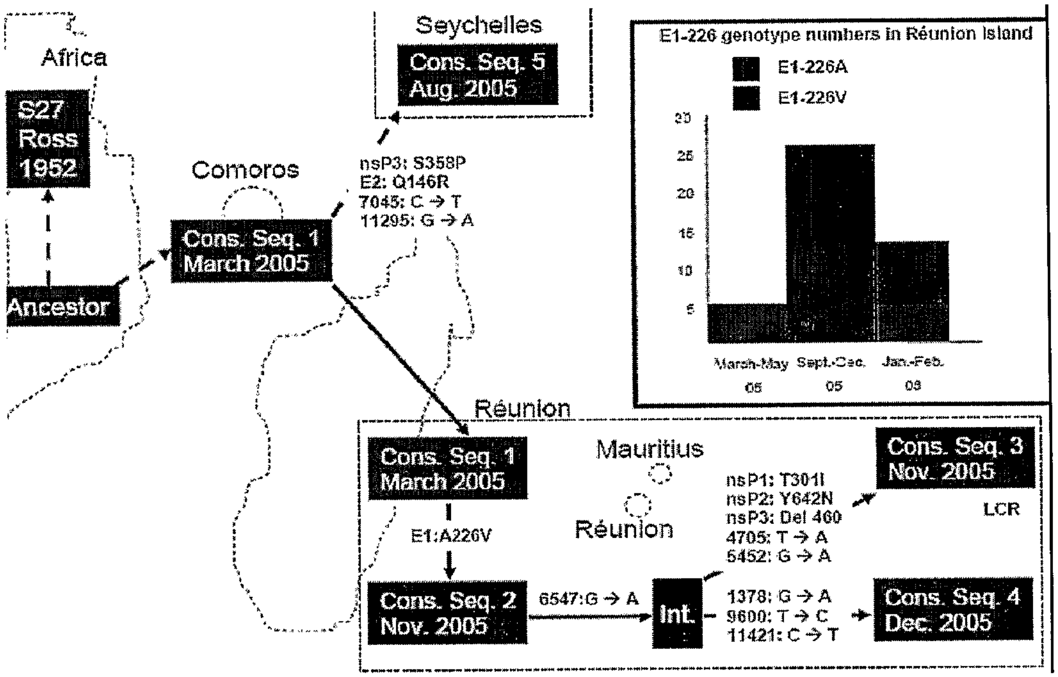

FIG. 3: Proposed evolutionary scenario of chikungunya virus isolates from 1 the Indian Ocean outbreak. The scenario is based on six genome sequences determined by direct sequencing of RT-PCR products obtained using RNA extracts as templates; the sequences thus correspond to consensus sequences (Cons. Seq.) of the possible mixture of coexisting genomes (quasispecies). Inset: number of cases of E1-226A and E1-226V at different time intervals in Reunion Island, based on partial E1 sequences. E1-226V was observed in consensus sequences 2, 3 and 4, and therefore most E1-226V isolates genotyped based on partial E1 sequences are likely related to these genotypes. However, the independent appearance of E1-226V in other genotypes cannot be excluded. Int.: intermediate sequence. The location, size and relative position of the Islands and the African border are indicative. Consensus sequence 1 was obtained from a Reunion patient who traveled back from Comoros in March 2005, and from a Reunion Island patient. Sequences 2 to 4 were sampled in Reunion Island; sequence 5 was sampled in the Seychelles.

FIG. 4 shows the nucleotide sequence of the genome of a CHIK virus strain according to a preferred embodiment of the invention and more specifically for the preferred strain named 05.115 (SEQ ID NO:1).

FIG. 5 shows the nucleotide sequence of the genome of a CHIK virus strain according to a preferred embodiment of the invention and more specifically for the preferred strain named 05.209 (SEQ ID NO:2).

FIG. 6 shows the nucleotide sequence of the genome of a CHIK virus strain according to a preferred embodiment of the invention and more specifically for the preferred strain named 06.21 (SEQ ID NO:3).

FIG. 7 shows the nucleotide sequence of the genome of a CHIK virus strain according to a preferred embodiment of the invention and more specifically for the preferred strain named 06.27 (SEQ ID NO:4).

FIG. 8 shows the nucleotide sequence of the genome of a CHIK virus strain according to a preferred embodiment of the invention and more specifically for the preferred strain named 06.49 (SEQ ID NO:5).

FIG. 9 shows the nucleotide sequence of the genome of a CHIK virus strain according to a preferred embodiment of the invention and more specifically for the preferred strain named 05.61 (SEQ ID NO:6).

FIG. 10 shows a nucleotide sequence of a fragment of a CHIK virus according to a preferred embodiment of the invention, and more specifically a fragment which codes for the ectodomain of the glycoprotein E2 of the preferred strain named 06.21 (SEQ ID NO:7).

FIG. 11 shows a nucleotide sequence of a fragment of a CHIK virus according to a preferred embodiment of the invention, and more specifically a fragment which codes for the ectodomain of the glycoprotein E2 of the preferred strain named 06.27 (SEQ ID NO:8).

FIG. 12 shows a nucleotide sequence of a fragment of a CHIK virus according to a preferred embodiment of the invention, and more specifically a fragment which codes for the ectodomain of the glycoprotein E2 of the preferred strain named 06.49 (SEQ ID NO:9).

FIG. 13 shows a nucleotide sequence of a fragment of a CHIK virus according to a preferred embodiment of the invention, and more specifically a fragment which codes for the ectodomain of the glycoprotein E2 of the preferred strain named 06.115 (SEQ ID NO:10).

FIG. 14 shows a nucleotide sequence of a fragment of a CHIK virus according to a preferred embodiment of the invention, and more specifically a fragment which codes for a soluble form of the glycoprotein E2 of the preferred strain named 06.21 (SEQ ID NO:11).

FIG. 15 shows a nucleotide sequence of a fragment of a CHIK virus according to a preferred embodiment of the invention, and more specifically a fragment which codes for a soluble form of the glycoprotein E2 of the preferred strain named 06.27 (SEQ ID NO:12).

FIG. 16 shows a nucleotide sequence of a fragment of a CHIK virus according to a preferred embodiment of the invention, and more specifically a fragment which codes for a soluble form of the glycoprotein E2 of the preferred strain named 06.49 (SEQ ID NO:13).

FIG. 17 shows a nucleotide sequence of a fragment of a CHIK virus according to a preferred embodiment of the invention, and more specifically a fragment which codes for a soluble form of the glycoprotein E2 of the preferred strain named 06.115 (SEQ ID NO:14).

FIG. 18 shows an amino acid sequence of a preferred CHIK virus polypeptide according to a preferred embodiment of the invention, and related more specifically to the ectodomain of the glycoprotein E2 of the preferred strain named 06.21 (SEQ ID NO:15).

FIG. 19 shows an amino acid sequence of a preferred CHIK virus polypeptide according to a preferred embodiment of the invention, and related more specifically to the ectodomain of the glycoprotein E2 of the preferred strain named 06.27 (SEQ ID NO:16).

FIG. 20 shows an amino acid sequence of a preferred CHIK virus polypeptide according to a preferred embodiment of the invention, and related more specifically to the ectodomain of the glycoprotein E2 of the preferred strain named 06.49 (SEQ ID NO:17).

FIG. 21 shows an amino acid sequence of a preferred CHIK virus polypeptide according to a preferred embodiment of the invention, and related more specifically to the ectodomain of the glycoprotein E2 of the preferred strain named 06.115 (SEQ ID NO:18).

FIG. 22 shows an amino acid sequence of a preferred CHIK virus polypeptide according to a preferred embodiment of the invention, and related more specifically to a soluble form of the glycoprotein E2 of the preferred strain named 06.21 (SEQ ID NO:19).

FIG. 23 shows an amino acid sequence of a preferred CHIK virus polypeptide according to a preferred embodiment of the invention, and related more specifically to a soluble form of the glycoprotein E2 of the preferred strain named 06.27 (SEQ ID NO:20).

FIG. 24 shows an amino acid sequence of a preferred CHIK virus polypeptide according to a preferred embodiment of the invention, and related more specifically to a soluble form of the glycoprotein E2 of the preferred strain named 06.49 (SEQ ID NO:21).

FIG. 25 shows an amino acid sequence of a preferred CHIK virus polypeptide according to a preferred embodiment of the invention, and related more specifically to a soluble form of the glycoprotein E2 of the preferred strain named 06.115 (SEQ ID NO:22).

Figure 26:
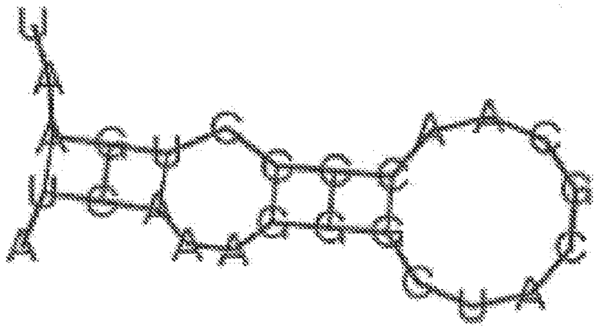

FIG. 26: Repeat Sequence Elements found in the 3'NTR region

A. Alignment of Repeat Sequence Elements found in the 3'NTR region of chikungunya virus genome. All sequences form conserved and stable stem-loop structures in which the less conserved nucleotides around position 20 constitute the loop. Three RSE are found in all chikungunya genomes. The first one (RSE1) is inserted before the internal poly-A sequence of S27 genome [9], whereas the two others are found downstream this motif.

B. Predicted secondary structure for RSE1 of isolate 05-115.

Figure 27:
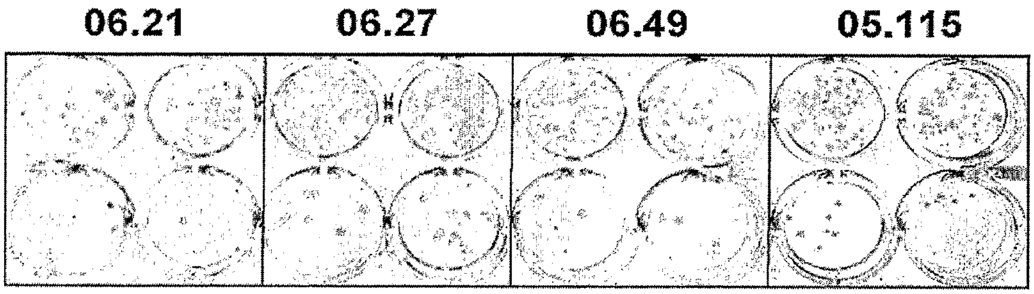

FIG. 27: Focus phenotype of chikungunya viruses on AP61 cells by Focus Immunoassay Mosquito AP61 cells in 24-well plates were infected with CHIK virus stocks grown on mosquito cells (virus titers 2–5×10%8 FFU. mL-1) at 0.0001 (top well) or 0.00001 (bottow well) multiplicity of infection. Infected cells were overlaid with CMC in Leibovitz L15 growth medium with 2% FBS for 2 days to allow focus development at 28° C. The cells were fixed with 3% PFA in PBS, permeabilized with Triton X-100 in PBS, and foci of CHIK virus replication were immunostained with mouse anti-CHIK HMAF (dilution 1:2,000) and peroxidase-conjugated goat anti-mouse Ig (dilution 1:100).

Figure 28:
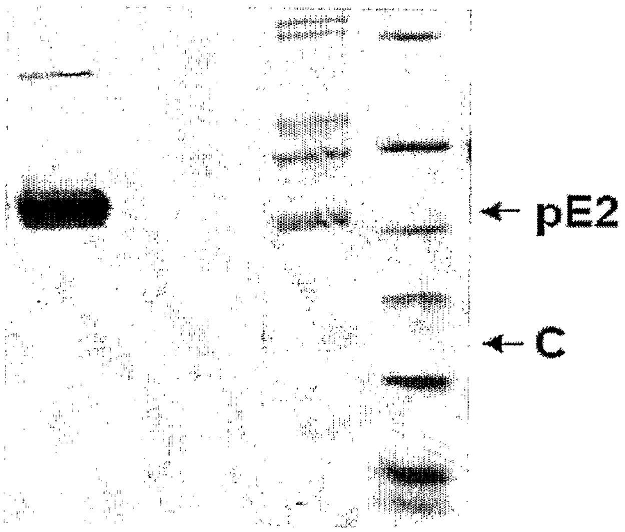

FIG. 28: Viral preparation containing pE2. pE2 proteins detected by anti-CHIK antibodies.

FIG. 29: Alignment of nucleotide sequences encoding soluble form of E2 glycoprotein (E2-1 to E2-361) from Indian Ocean CHIK virus strains -21, -27, -49 and -115.

FIG. 30: Primer sequences (SEQ ID NO:79 and 80) used for the amplification and cloning of the soluble form of the E2 (E2-1 to E2-364) (N-terminal and C-terminal nucleic acid fragment: SEQ ID NO:81 and 82; N-terminal and C-terminal protein fragment: SEQ ID NO:83 and 84) from CHIK virus into the shuttle vector pMT2/BiP/V5-HisA.

Figure 31:
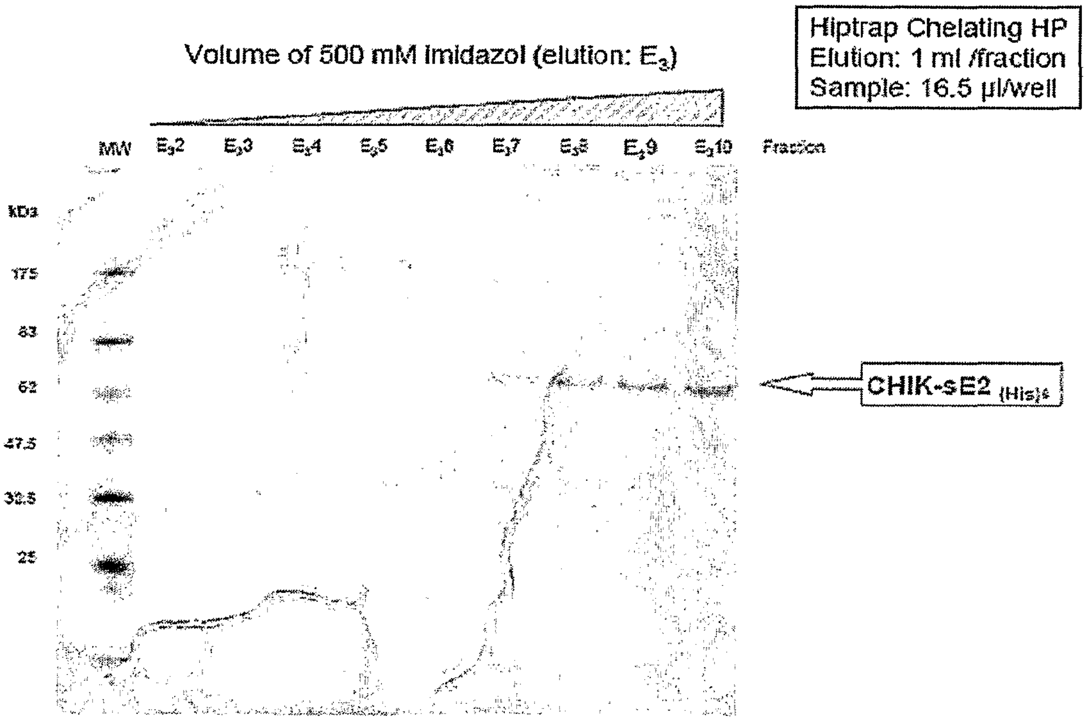

FIG. 31: SDS-PAGE showing CHIK-sE2 staining by Coomassie blue.

Figure 32:
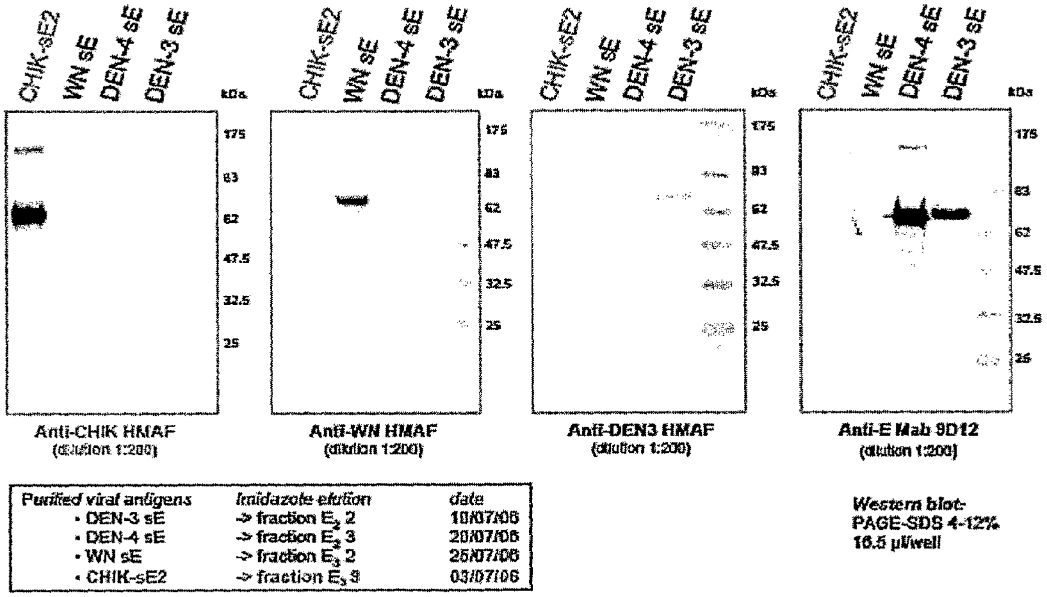

FIG. 32: Immunoblot analysis of highly purified CHIK sE2 protein.

Figure 33:
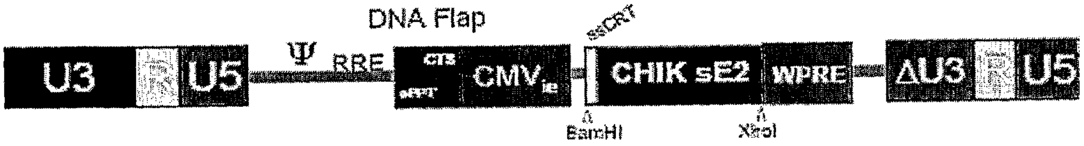

FIG. 33: Construct of the TRIP vector expressing the secreted soluble form of the E2 glycoprotein (sE2) from Chikungunya virus La Reunion 05 strains.

FIG. 34 shows the nucleotide sequence coding the secreted soluble form of the E2 glycoprotein (sE2) into the TRIP vector (SEQ ID NO:85).

Figure 35:

FIG. 35: Immunofluorescent (IF) assay using anti-CHIK antibodies on TRIP/CHIK.sE2-transduced 293 cells.

Figure 36:
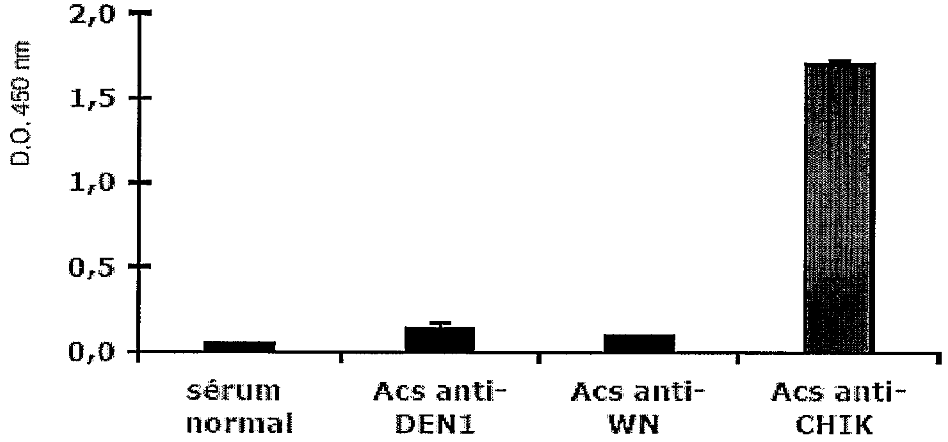

FIG. 36 shows a direct ELISA with $10^{-4}$ mL of enriched pE2 protein per well. Antigens were tested respectively with a mouse anti-DEN1 (dilution 1:1000), anti-WN (dilution 1:1000) and anti-CHIK (dilution 1:10 000).

FIG. 37 shows an amino acid sequence of the ORF 2 (structural proteins) of the CHIK S27 strain (GenBank AF339485; SEQ ID NO: 23).

FIG. 38 shows an amino acid sequence of the ORF 2 (structural proteins) of a preferred CHIK virus according to a preferred embodiment of the invention, namely the 05.61 strain (SEQ ID NO: 24).

FIG. 39 shows an amino acid sequence of the ORF 2 (structural proteins) of a preferred CHIK virus according to a preferred embodiment of the invention, namely the 05.209 strain (SEQ ID NO: 25).

FIG. 40 shows an amino acid sequence of the ORF 2 (structural proteins) of a preferred CHIK virus according to a preferred embodiment of the invention, namely the 05.115 strain (SEQ ID NO: 26).

FIG. 41 shows an amino acid sequence of the ORF 2 (structural proteins) of a preferred CHIK virus according to a preferred embodiment of the invention, namely the 06.49 strain (SEQ ID NO: 27).

FIG. 42 shows an amino acid sequence of the ORF 2 (structural proteins) of a preferred CHIK virus according to a preferred embodiment of the invention, namely the 06.27 strain (SEQ ID NO: 28).

FIG. 43 shows an amino acid sequence of the ORF 2 (structural proteins) of a preferred CHIK virus according to a preferred embodiment of the invention, namely the 06.21 strain (SEQ ID NO: 29).

FIG. 44 shows an amino acid sequence of the ORF 1 (non-structural proteins) of a preferred CHIK virus according to a preferred embodiment of the invention, namely the 05.61 strain (SEQ ID NO: 30).

FIG. 45 shows an amino acid sequence of the ORF 1 (non-structural proteins) of a preferred CHIK virus according to a preferred embodiment of the invention, namely the 05.209 strain (SEQ ID NO: 31).

FIG. 46 shows an amino acid sequence of the ORF 1 (non-structural proteins) of a preferred CHIK virus according to a preferred embodiment of the invention, namely the 05.115 strain (SEQ ID NO: 32).

FIG. 47 shows an amino acid sequence of the ORF 1 (non-structural proteins) of a preferred CHIK virus according to a preferred embodiment of the invention, namely the 06.49 strain (SEQ ID NO: 33).

FIG. 48 shows an amino acid sequence of the ORF 1 (non-structural proteins) of a preferred CHIK virus according to a preferred embodiment of the invention, namely the 06.27 strain (SEQ ID NO: 34).

FIG. 49 shows an amino acid sequence of the ORF 1 (non-structural proteins) of a preferred CHIK virus according to a preferred embodiment of the invention, namely the 06.21 strain (SEQ ID NO: 78).

Figure 50:
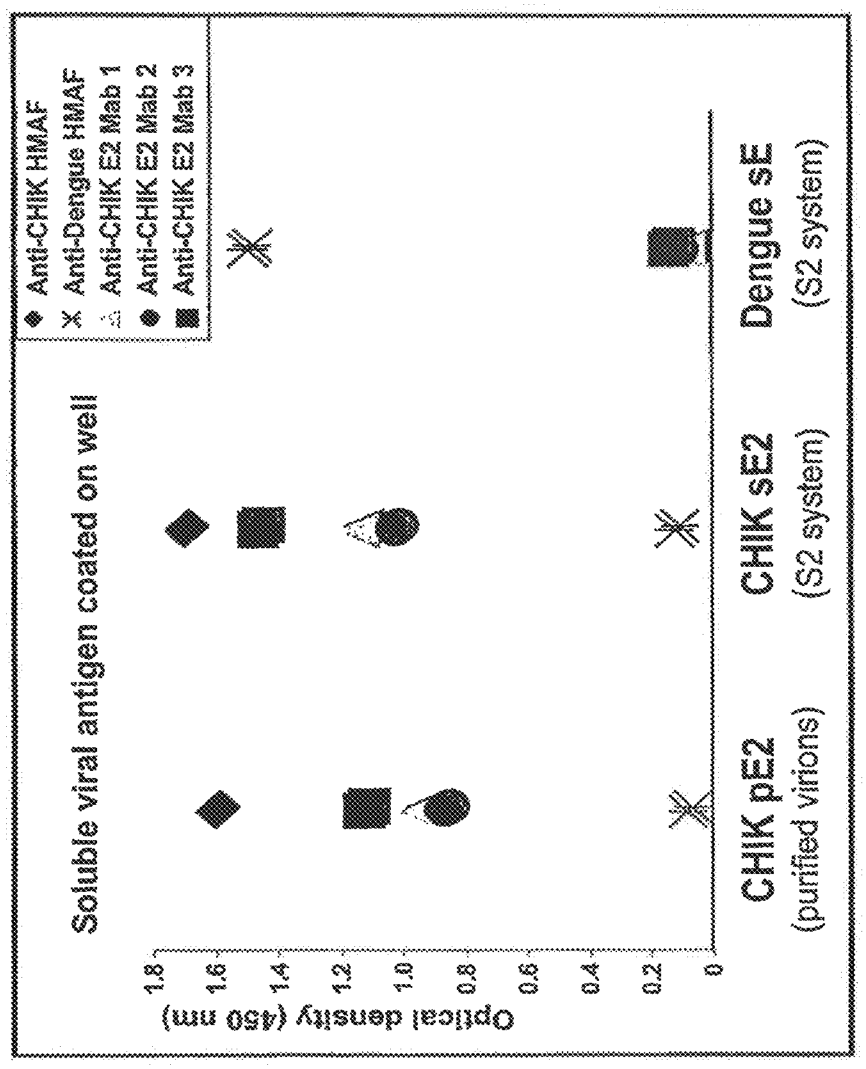

FIG. 50: Evaluation of anti-CHIK E2 Mab reactivity by ELISA.

Figure 51:
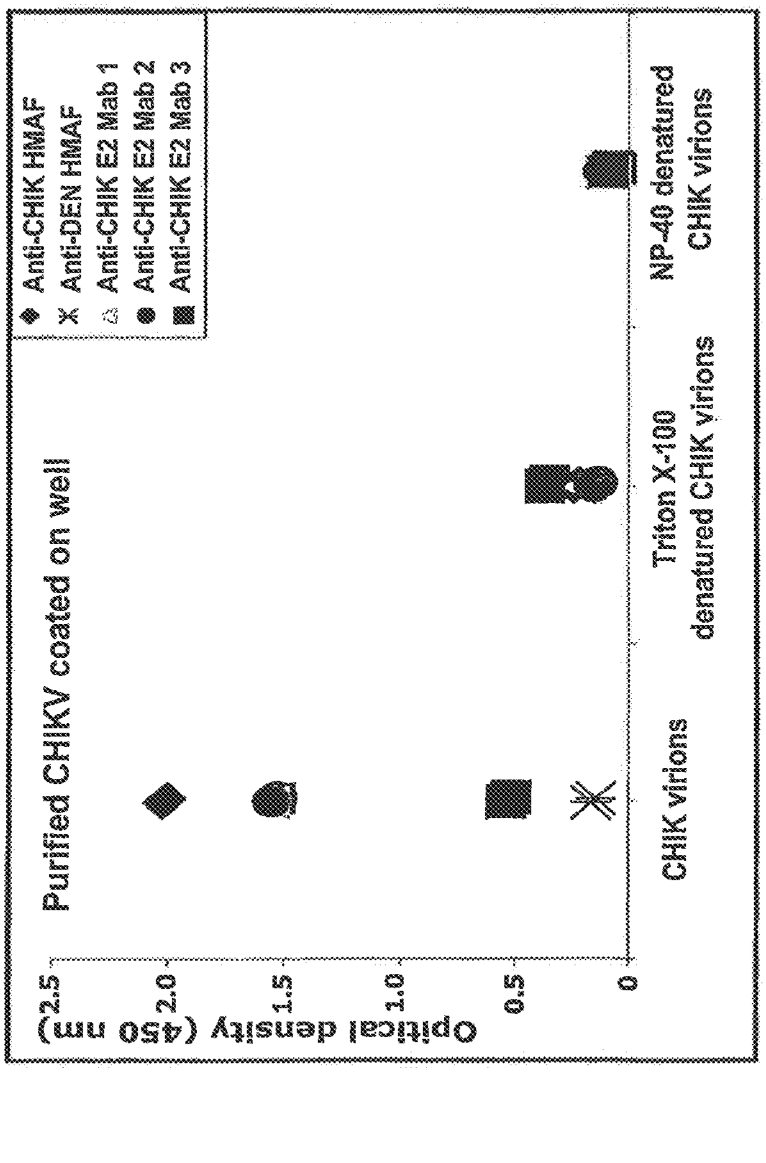

FIG. 51: Evaluation of anti-CHIK E2 MAb reactivity on CHIK virions by ELISA.

Figure 52:
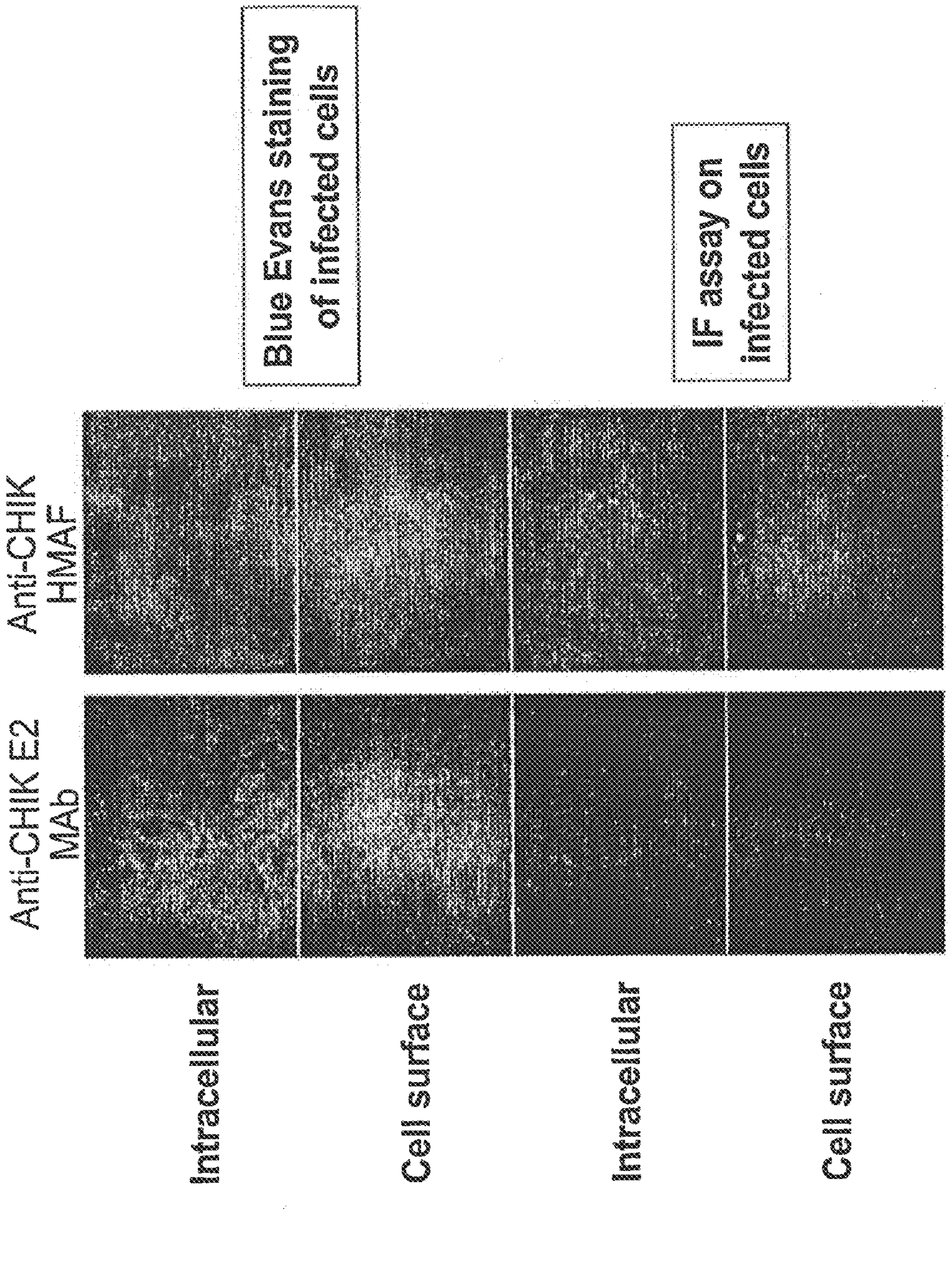

FIG. 52: Immunofluorescence (IF) analysis of anti-CHIK E2 Mab reactivity on CHIKV-infected Vero cells.

Figure 53:
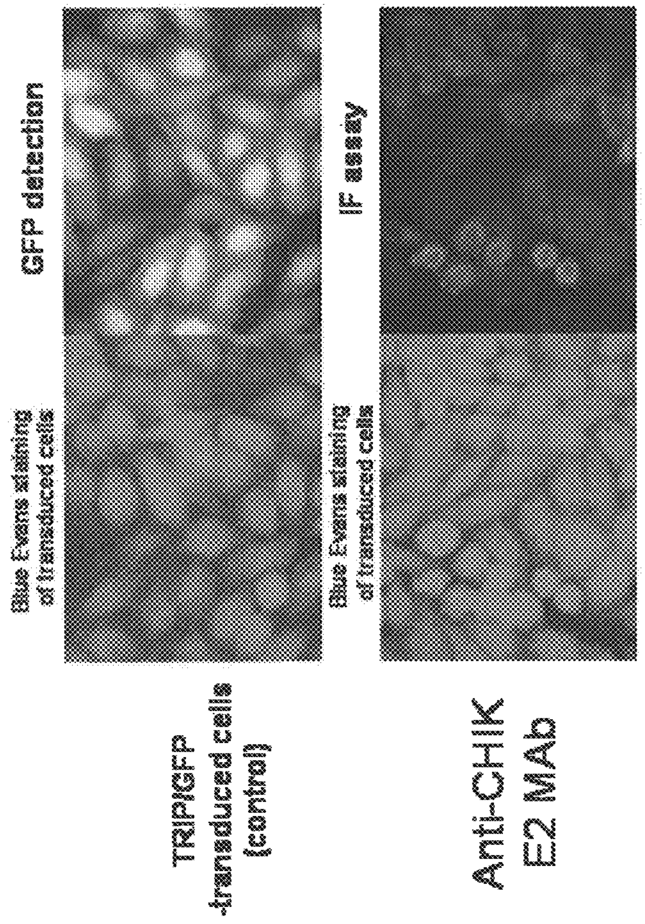

FIG. 53: Immunofluorescence (IF) analysis of anti-CHIK E2 Mab reactivity on TRIP/CHIK.sE2-transduced 293A cells.

Figure 54:
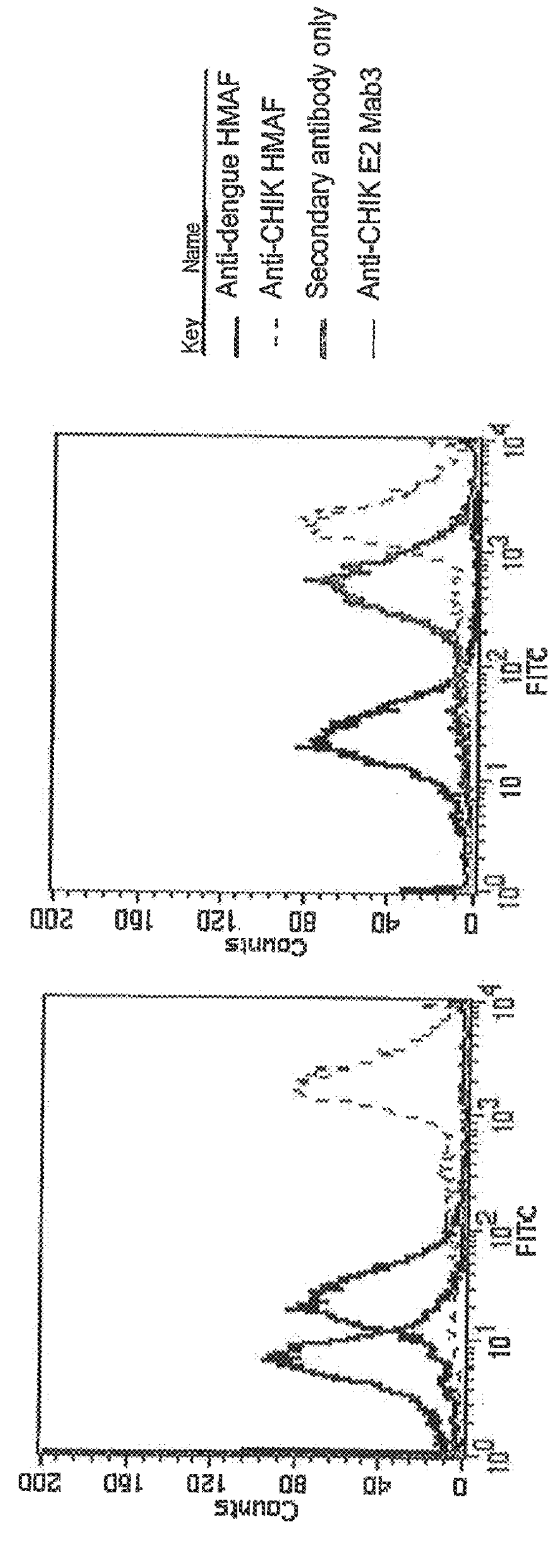

FIG. 54: Anti-CHIK E2 Mab binding on cell surface of CHIK virus-infected Vero cells by FACS analysis.

Figure 55:
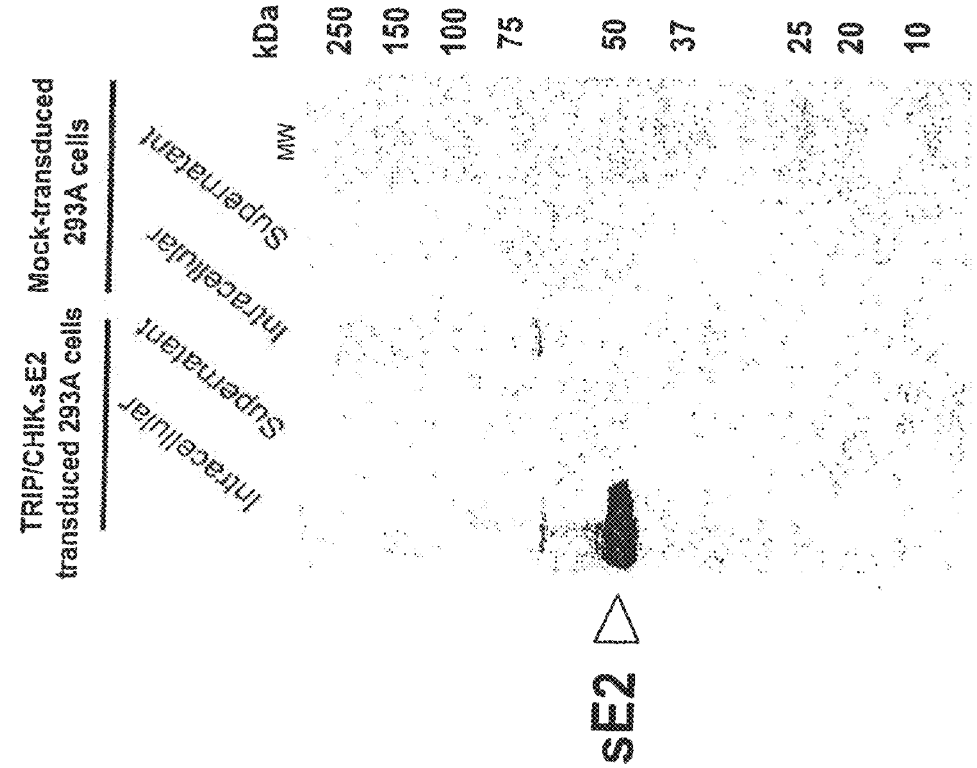

FIG. 55: Western blot analysis of CHIKsE2 expression in TRIP/CHIK.sE2-transduced 293A cells.

DETAILED DESCRIPTION OF THE INVENTION

In the present study, the inventors determined the nearly complete nucleotide sequences of viruses isolated from six patients originating from Reunion and Seychelles Islands. The present invention allows to determine the genome structure as well as the unique molecular features of the Indian Ocean outbreak isolates, which distinguish them from other reported CHIKV and alphavirus sequences.

As one in the art may appreciate, the originality of the present invention is the identification of novel strains of the Chikungunya (CHIK) virus which are distinguished from CHIK virus of the prior art, and the use of these CHIK strains and the polypeptides and the polynucleotides encoding same derived from their genome in the diagnostic, prevention and/or treatment of arbovirosis.

According to a first aspect, the present invention concerns an isolated and purified wild strain of chikungunya virus (CHIKV) capable of in vitro infecting human cells. Preferably, the present invention concerns a wild strain of CHIK virus which exhibits the same characteristics than those selected from the group consisting of the isolates 05.115, 05.61, 05.209, 06.21, 06.27 and 06.49. According to a preferred embodiment, the strains that are within the scope of the present invention are characterized in that their genome comprises at least one mutation when compared to the sequence of the genome of the CHIK virus strain S-27 (GenBank AF339485). Also within the scope of the invention, is any strain grown or obtained by cell culture from a sample of a preferred CHIK strain of the invention. The genome of the preferred strains according to the present invention comprises a sequence as shown in FIG. 4, 5, 6, 7, 8 or 9 (SEQ ID NO: 1, 2, 3, 4, 5 or 6).

According to another aspect, the present invention provides an isolated and purified strain of chikungunya virus (CHIKV) comprising at least one mutation in structural protein E1 and/or in structural protein E2, and more particularly in their ectodomain region. According to a preferred embodiment, the strain of the invention is characterized by the fact that its genome comprises at least one mutation in the E2 protein at a position homologous to amino acid position 382, 399, 404, 485, 489, 506, 536, 624, 637, 669, 700 or 711 of SEQ ID NO: 23 (FIG. 37). More particularly, the mutation is preferably selected from the group consisting of G382K, 1399M, G404E, N485T, A489T, L506M, 1536T, S624N, T637M, A669T, S700T and V711A as shown in Table 6. According to another preferred embodiment, the strain of the invention is characterized by the fact that its genome comprises at least one mutation in the E1 protein at a position homologous to amino acid position 1035, 1078, 1093 or 1131 of SEQ ID NO: 23. More particularly, the mutation is preferably selected from the group consisting of A1035V, M1078V, D1093E and V1131A as shown in Table 6. Most preferably, the mutation in the E1 protein is A1035V.

As use herein, the expression "at a position homologous to an amino acid position" of a protein, refers to amino acid positions that are determined to correspond to one another based on sequence and/or structural alignments with a specified reference protein. For instance, in a position corresponding to an amino acid position of a CHIK virus structural protein set forth as SEQ ID NO: 1 can be determined empirically by aligning the sequences of amino acids set forth in SEQ ID NO: 1 with a particular CHIK virus structural protein. Homologous or corresponding positions can be determined by such alignment by one of skill in the art using manual alignments or by using the numerous alignment programs available (for example, BLASTP). Homologous or corresponding positions also can be based on structural alignment, for example by using computers simulated alignments of protein structure. Recitation that amino acids of a polypeptide correspond to amino acids in a disclosed sequence refers to amino acids identified upon alignment of the polypeptide with the disclosed sequence to maximize identity or homology (where conserved amino acids are aligned) using a standard algorithm, such as the GAP algorithm. As used herein, "at a position homologous to" refers to a position of interest (i.e., base number or residue number) in a nucleic acid molecule or protein relative to the position in another reference nucleic acid molecule or protein. The position of interest to the position in another reference protein can be in, for example, an amino acid sequence from the same protein of another CHIK strain. Homologous positions can be determined by comparing and aligning sequences to maximize the number of matching nucleotides or residues, for instance, such that identity between the sequences is greater than 95%, preferably greater than 96%, more preferably greater than 97%, even more preferably greater than 98% and most preferably greater than 99%. The position of interest is then given the number assigned in the reference nucleic acid molecule.

Another aspect of the invention concerns an isolated and purified polynucleotide comprising all or part of the sequence as shown in FIG. 4, 5, 6, 7, 8 or 9 (SEQ ID NO: 1, 2, 3, 4, 5 or 6).

Another aspect of the invention concerns a fragment of the polynucleotide of the invention characterized by the fact that it codes for the glycoprotein E1 or E2, and more preferably for their ectodomain region. Advantageously, the fragment of the invention when coding for the E2 ectodomain, comprises, or more preferably, consists of a nucleotide sequence as shown in FIG. 10, 11, 12 or 13 (SEQ ID NO: 7, 8, 9 or 10).

Yet another aspect of the invention concerns a fragment of the polynucleotide of the invention characterized by the fact that it codes for a soluble form of glycoprotein E2. According to a preferred embodiment, the soluble fragment of glycoprotein E2 comprises or more preferably consists of a nucleotide sequence as shown in FIG. 14, 15, 16 or 17 (SEQ ID NO. 11, 12, 13 or 14).

As one skilled in the art may appreciate, a fragment as contemplated by the present invention may be obtained by:

use of restriction enzymes wherein their cleavage sites are present in the polynucleotide comprising said fragment;

amplification with specific primers for said fragment;

in vitro transcription; or chemical synthesis.

According to another aspect, the present invention is concerned with an isolated and purified polypeptide encoded by a polynucleotide or by a fragment of the invention. As used herein, the terms "polypeptide" and "protein" are used interchangeably to denote an amino acid polymer or a set of two or more interacting or bound amino acid polymers.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

Broadly defined, the terms "purified polypeptide" or "purified polynucleotide" refer to polypeptides or polynucleotides that are sufficiently free of other proteins or polynucleotides, or carbohydrates, and lipids with which they are naturally associated. The polypeptide or polynucleotide may be purified by any process by which the protein or polynucleotide is separated from other elements or compounds on the basis for instance, of charge, molecular size, or binding affinity.

The preferred peptides of the invention comprise at least one amino acid substitution compared with the amino acid sequence of strain S-27 (GenBank AF339485) and are derived from the sequence of a protein coded by a fragment of the invention. Preferably, a purified polypeptide of the invention comprises all or part of the amino acid sequence of a CHIK virus ORF 1 or 2 contemplated by the present invention such as one defined in any one of SEQ ID NOS 24 to 29 (ORF 2) or of SEQ ID NOS 30 to 34 and 78 (ORF 1). More preferably, a purified polypeptide of the invention comprises all or part of the amino acid sequence of a glycoprotein E2 contemplated by the present invention such as one defined in any one of SEQ ID NOS 15 to 18 (FIGS. 18 to 21). Even more preferably, a purified polypeptide of the invention comprises all or part of the amino acid sequence of a soluble form of glycoprotein E2 contemplated by the present invention such as one defined in any one of SEQ ID NOS 19 to 22 (FIGS. 22 to 25).

The present invention is also concerned with a vector comprising a polynucleotide of the invention or a fragment of a polynucleotide of the invention. As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector. Preferred vector are those deposited at the CNCM (Collection Nationale de Cultures de Microorganismes), 28 rue du Docteur Roux, 75724 PARIS Cedex 15, France, on Mar. 15, 2006 under accession numbers I-3587, I-3588, I-3589 and I-3590.

Another preferred vector contemplated by the present invention is the plasmid called TRIP-CHIK.sE2 which has been deposited at the CNCM (Collection Nationale de Cultures de Microorganismes), 28 rue du Docteur Roux, 75724 PARIS Cedex 15, France, on Mar. 14, 2007, under accession number I-3733. Such a vector comprises a fragment which codes for a soluble form of the glycoprotein E2 of the invention. This preferred vector has been optimised for efficient production of the recombinant E2 protein into mammalian cells. As used herein, the term "optimised" means that the vector incorporates regulation sequences, such as a signal peptide sequence, in order to provide adequate expression of the desired encoded protein.

In a related aspect, the present invention provides a host cell comprising a vector as defined above. The term "host cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A host cell can be a single eukaryotic cell, or a single prokaryotic cell, or a mammalian cell. The host cell can harbor a vector that is extragenomic. An extragenomic nucleic acid vector does not insert into the cell's genome. A host cell can further harbor a vector or a portion thereof that is intragenomic. The term intragenomic defines a nucleic acid construct incorporated within the host cell's genome. A preferred host cell of the invention *E. coli* such as the one containing a vector of the invention and deposited at the CNCM (Collection Nationale de Cultures de Microorganismes), 28 rue du Docteur Roux, 75724 PARIS Cedex 15, France, on Mar. 15, 2006 under accession numbers I-3587, I-3588, I-3589 and I-3590 and on Mar. 14, 2007 under accession number I-3733.

The present invention is further concerned with a monoclonal antibody or polyclonal antibodies, or fragments thereof, that specifically bind to a polypeptide of the invention. As used herein, the term "specifically binds to" refers to antibodies that bind with a relatively high affinity to one or more epitopes of a protein of the invention, but which do not substantially recognize and bind to molecules other than the one(s) of interest. As used herein, the term "relatively high affinity" means a binding affinity between the antibody and the protein of interest of at least $10^{-6}$ M, and preferably of at least about $10^{-7}$ M and even more preferably $10^{-8}$ M to $10^{-10}$ M. Determination of such affinity is preferably conducted under standard competitive binding immunoassay conditions which is common knowledge to one skilled in the art.

As used herein, the term "antibody" refers to a glycoprotein produced by lymphoid cells in response to a stimulation with an immunogen. Antibodies possess the ability to react in vitro and in vivo specifically and selectively with an antigenic determinant or epitope eliciting their production or with an antigenic determinant closely related to the homologous antigen. The term "antibody" is meant to encompass constructions using the binding (variable) region of such an antibody, and other antibody modifications. Thus, an antibody useful in the method of the invention may comprise a whole antibody, an antibody fragment, a polyfunctional antibody aggregate, or in general a substance comprising one or more specific binding sites from an antibody. The antibody fragment may be a fragment such as an Fv, Fab or $F(ab')_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

Another aspect of the invention is the use of an element selected from the group consisting of a strain, a polynucleotide, a fragment, a vector, a host cell, a polypeptide and an antibody of the invention for either the detection of a CHIKV associated to an arbovirosis, or for the preparation of a composition that prevents and/or treats an arbovirosis.

Another aspect of the present invention relates to a composition for treating and/or preventing an arbovirosis. The composition of the present invention advantageously comprises at least one element selected from the group consisting of a strain, a polynucleotide, a fragment, a vector, a host cell, a polypeptide and an antibody of the invention. The composition of the invention may further comprise an acceptable carrier. In a related aspect, the invention provides a method for treating and/or preventing an arbovirosis. The method comprises the step of administering to a subject in need thereof a composition of the invention.

As used herein, the term "treating" refers to a process by which the development of an infection from a CHIKV is affected or completely eliminated. As used herein, the term "preventing" refers to a process by which the CHIKV infection is obstructed or delayed.

As used herein, the expression "an acceptable carrier" means a vehicle for containing the components (or elements) of the composition of the invention that can be administered to a animal host without adverse effects. Suitable carriers known in the art include, but are not limited to, gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

The amount of components of the composition of the invention is preferably a therapeutically effective amount. A therapeutically effective amount of components of the composition of the invention is the amount necessary to allow the same to perform their preventing and/or treating role against a CHIKV infection without causing overly negative effects in the host to which the composition is administered. The exact amount of components to be used and the composition to be administered will vary according to factors such as the mode of administration, as well as the other ingredients in the composition.

The composition of the invention may be given to a host (such as a human) through various routes of administration. For instance, the composition may be administered in the form of sterile injectable preparations, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or sub-cutaneously by injection, by infusion or per os. Suitable dosages will vary, depending upon factors such as the amount of each of the components in the composition, the desired effect (short or long term), the route of administration, the age and the weight of the host to be treated. Any other methods well known in the art may be used for administering the composition of the invention.

Yet another aspect of the invention is the use of a composition as defined hereabove for the preparation of a medicament for treating and/or preventing an arbovirosis in a subject in need thereof.

Yet another aspect of the invention is to provide a kit for the detection of a CHIKV associated to an arbovirosis, comprising at least one element selected from the group consisting of a strain, a polynucleotide, a fragment, a vector, a host cell, a polypeptide and an antibody of the invention. Kits according to this embodiment of the invention may comprise packages, each containing one or more of the above mentioned elements (typically in concentrated form) which are required to perform the respective diagnostic tests.

EXAMPLES

The examples here below will highlight other characteristics and advantages of the present invention, and will serve to illustrate the scope of the use of the present invention and not to limit its scope. Modifications and variations may be made without departing from the spirit and the scope of the invention. Although it is possible to use other methods or products equivalent to those that are found here below to test or to realize the present invention, the preferred material and methods are described.

Example 1

Identification and Characterization of CHIK Viruses Causing the Indian Ocean Outbreak The inventors (as sometimes referred therein as "we") report the nearly complete genome sequence of six selected clinical isolates, along with partial sequences of glycoprotein E1 from a total of 60 patients from Reunion, Seychelles, Mauritius, Madagascar and Mayotte Islands. The present results indicate that the outbreak was initiated by a strain related to East-African isolates, from which viral variants have evolved following a traceable microevolution history. Unique molecular features of the outbreak isolates were identified. Notably, in the region coding for the non-structural proteins, ten amino acid changes were found, three of which being located in alphavirus conserved positions of nsP2 (which contains helicase, protease and RNA triphosphatase activities) and of the polymerase nsP4. The sole isolate obtained from the cerebrospinal fluid of a patient showed unique changes in nsP1 (T301I), nsP2 (Y642N) and nsP3 (E460 deletion). In the structural protein region, two noteworthy changes (A226V and D284E) were observed in the membrane fusion glycoprotein E1. Homology 3D modelling allowed mapping of these two changes to regions that are important for virion assembly and for membrane fusion. Change E1-A226V was absent in the initial strains but was observed in >85% of subsequent viral sequences from Reunion, denoting evolutionary success possibly due to adaptation to the mosquito vector.

Material and Methods

Patients.

The 60 patients for whom partial or complete CHIKV nucleotide sequences were determined originated from Reunion (N=43), Seychelles (N=3), Madagascar (N=7), Mayotte (N=4) and Mauritius (N=3). Characteristics of the patients and biological samples are listed in Table 1.

Virus Isolation and RNA Extraction.

Viruses were isolated either from serum or cerebrospinal fluid (CSF) (Table 1). Briefly, C6-36 *Aedes albopictus* cells were inoculated with 1 ml of serum or CSF diluted 1:10 in L15 medium (Gibco). The cells were grown at 28° C. in L15 supplemented with 5% foetal bovine serum and 10% tryptose-phosphate. Cells and supernatants were harvested after the first passage (5 days) and the second passage (7 days). The virus isolates were identified as CHIKV by indirect immunofluorescence, using CHIKV hyper immune ascitic fluid. In the case of isolates 05.115, 06.21, 06.27 and 06.49 whose genomes were sequenced, absence of yellow fever, dengue and West Nile viruses was confirmed by indirect immunofluorescence using specific sera. RNA was extracted using the QIAAmp Viral Minikit (Qiagen, France).

Nucleotide Sequencing.

Primers (Table 4) were designed based on the nucleotide sequence 20 of the S27 strain. RT-PCR was performed using the Titan One Tube RT-PCR kit (Roche, France). RT-PCR fragments were purified by ultrafiltration prior to sequencing (Millipore, France). Sequencing reactions were performed using the BigDye Terminator v1.1 cycle sequencing kit (Applied Biosystems, USA) and purified by ethanol precipitation. Sequence chromatograms were obtained on automated sequence analysers ABI3100 or ABI3700 (Applied Biosystems). All amplicons were sequenced on both strands.

Assembly of Genome Sequences and Sequence Analysis.

Contig assembly was performed independently by distinct operators and software, using either BioNumerics version 4.5 (Applied-Maths, Sint-Martens-Latem, Belgium) or PhredPhrap/Consed [11]. Both analyses yielded exactly the same consensus sequence for all strains. A single contig of 11,601 nt was obtained for five isolates, whereas for strain 05.61, a sequence portion was missing, between S27 positions 5,246 to 5,649 (positions 390 to 524 of nsP3). Sequence alignments and computation of substitution tables were performed using programs BioNumerics, DNASP version 4.10 [12] and DAMBE version 4.2.13 [13]. Alignments of nucleotide and amino acid sequences against selected alphavirus sequences were performed with the ClustalW1.7 software [14]. Sequence identities were computed with the Phylip package [15]. RNA secondary structure was predicted with the Vienna RNA secondary structure server [16]. Neighbor-joining trees were constructed using MEGA version 3.1 [17] with the Kimura-2 parameter corrections of multiple substitutions. Reliability of nodes was assessed by bootstrap resampling with 1,000 replicates. Amounts of synonymous substitutions per synonymous site (Ks) and of non synonymous substitutions per non synonymous site (Ka) were estimated using DNASP. RDP2 [18] was used to detect putative mosaic sequences.

3D Structure Modeling.

The crystallographic structure of the ectodomain of the glycoprotein E1 of Semliki Forest Virus (SFV) at neutral pH [19]; Protein Data Bank code 2ALA) was used as a template to model and analyze the two amino acid mutations of the Indian Ocean isolates. FIG. 2 was prepared using the program RIBBONS [20].

Detection of Viral Foci by Immunological Staining.

*Aedes pseudoscutellaris* AP61 cells were grown in a 24-well tissue culture plates in Leibovitz L-15 growth medium with 10% heat inactivated fetal calf serum (FCS) for 24 h. Mosquito cell monolayers were washed once with Leibovitz L-15 and 0.2 ml Leibovitz L-152% FCS were added. Cells were infected with CHIK virus in 0.2 ml of Leibovitz L-152% FCS and incubated at 28° C. for 1 h. Overlay medium consisting of 0.4 ml of Leibovitz L-152% FBS and carboxymethylcellulose (CMC) (1.6%) was then added and the tissue culture plates were incubated at 28° C. for 2 days. Foci of infected cells were visualized by focus immunoassay (FIA). The cells were washed with PBS, fixed with 3% paraformaldehyde (PFA) in PBS for 20 min, and permeabilized with 0.5% Triton X-100 in PBS for 4 min at room temperature. The fixed cells were incubated for 20 min at 37° C. with 1:2,000 dilution of hyperimmune mouse ascitic fluid (HMAF) directed against CHIKV. Goat anti-mouse IgG, horseradish peroxidase conjugated was used as the second antibody (1:100 dilution) at 37° C. for 20 min. Foci were visualized with DAB. Peroxidase Substrate (Sigma).

1. Genome structure and molecular signatures of the Indian Ocean outbreak chikungunya viruses Genome Organization.

We determined the nearly complete genome sequences of six CHIKV isolates (05.115, 05.61, 05.209, 06.21, 06.27 and 06.49) representing distinct geographic origins, time points and clinical forms (Table 1) of the Indian Ocean outbreak of chikungunya virus. 11,601 nucleotides were determined, corresponding to positions 52 (5'NTR) to 11,667 (3'NTR, end of third Repeat Sequence Element) in the nucleotide sequence of the 1952 Tanzanian isolate S27 (total length 11,826 nt). There were three insertion/deletion events between S27 and Réunion isolates, two of which were observed in the 3'NTR. First, the internal poly-A stretch of 14 nucleotides observed in S27 (11,440-11,443) and corresponding to a probable internal poly-A site [9] was replaced by a stretch of only 5 A in Indian Ocean isolates, similar to what was observed in other chikungunya viruses, e.g. the Ross strain (accession no.: AF490259). Second, one A was missing in Indian Ocean isolates in a 5-A stretch at S27 position 11,625. Finally, one codon was missing in isolate 06.27, corresponding to nsP3 codon 460, at which all other Indian Ocean isolates analyzed and available alphavirus sequences are GAA, coding for Glu.

The genome sequences of the six isolates presented therein was similar to those previously reported for alphaviruses [9, 21, 22]. Coding sequences consisted of two large open reading frames (ORF) of 7,422 nt and 3,744 nt encoding the non-structural polyprotein (2,474 amino-acids) and the structural polyprotein (1,248 amino-acids), respectively. The non structural polyprotein is the precursor of proteins nsP1 (535 aa), nsP2 (798 aa), nsP3 (530 aa) and nsP4 (611 aa), and the structural polyprotein is the precursor of proteins C (261 aa), p62 (487 aa, precursor to E3-64 aa- and E2-423 aa), 6K (61 aa), and E1 (439 aa). Cleavage sites characteristic of the alphavirus family in the non-structural and structural polyproteins were conserved. Glycosylation sites in E3, E2 and E1 were also conserved. A 65 nt junction sequence was identified between the stop codon (TAG, 7499-7501) of the non-structural ORF and the start codon (7567-7569) of the structural ORF. The 5' non-translated region (5'NTR) ended at position 76. The 3'NTR region started at position 11,314 and contained three repeat sequence elements (RSE) with predicted secondary structures (FIG. 26) that were consistent with previous work [9].

Differences Between Indian Ocean Outbreak Isolates and Strain S27.

Compared to strain S27, Reunion isolate 05.115 showed 28 aa changes (1.13%) in the non-structural proteins (Table 5, with the highest proportion in nsP3 (2.26%) and the lowest in nsP2 (0.6%). Ten out of 12 amino acid changes in nsP3 were concentrated between positions 326 and 524 (5.0% variation), similar to findings in ONN viruses [23]. One important difference with S27 was that the Indian Ocean isolates exhibited an opal stop codon (UGA) at nsP3 codon 524, instead of Arg (CGA) in S27. This opal codon was observed in related alphaviruses [9, 22, 23], and is believed to regulate the expression of nsP4, the putative RNA polymerase, by a read-through mechanism [21, 24].

Compared to S27, the structural proteins showed 21 (1.68%, for 05.115) to 22 (1.76%, for other isolates) amino-acid substitutions in Indian Ocean isolates (Table 6). Notably, envelope protein E2 showed the highest variation, with 14 (3.3%) aa changes, higher than envelope protein E1 (0.68%) and the capsid protein (0.38%). The ratio of rates of evolution of synonymous and non-synonymous sites (Ks/Ka) between S27 and 05.115 isolates was 11.0 for the whole polyprotein, whereas it was only 6.12 for protein E2, probably indicative of a positive selection in favor of amino-acid changes in this immunogenic protein. By comparison, Ks/Ka was 18.75 for the non-structural polyprotein.

Indian Ocean Outbreak Molecular Signatures in Non-Structural Proteins and Phenotypic Variation.

Ten positions (excluding polymorphic positions) had aa that were unique to the non-structural proteins of outbreak isolates, when compared to other CHIKV sequences (Table 2). First, nsP2-54 was Asn in Indian Ocean isolates and in SFV, but was Ser in all other sequences. Second, nsP2-374 was Tyr in Indian Ocean isolates, but was His or Asn in other alphavirus sequences (Table 2). Third, position 500 in nsP4 was Leu in the Indian Ocean sequences instead of Gln in the four other reported CHIKV sequences. Interestingly, this position, which is about 30 aa from the catalytic "GDD" motif, is a strictly conserved Glu in all other alphaviruses. The remaining seven changes took place in relatively variable regions.

Additional specific changes were observed in isolates 05.209 (S358P) and 06.27 (nsP1-T301I, nsP2-Y642N, and nsP3-460del). Notably, our phenotypic assays conducted in parallel showed differences for strain 06.27. Focus immunoassay showed that CHIKV stocks 05.115, 06.21, 06.27 and 06.49 formed mixtures of foci with different sizes on *Ae. Albopictus* C636 (data not shown) and *Ae. pseudoscuterallis* AP61 cells (FIG. 27). Interestingly, only isolate 06-27 formed medium foci, whereas others formed minutes and small foci. The particular phenotype of 06-27 could be linked to the observed aa differences in the non structural proteins, which are involved in the viral replication [21].

Indian Ocean Molecular Signatures in Structural Proteins and 3D Modelling.

When analyzing the aa sequences of the structural proteins, seven positions (four in E2, one in 6K and two in E1) were found to be unique to isolates from the Indian Ocean outbreak (Table 2). Two of these were located in the E2 ectodomain, with Thr 164 and Met 312 being identified in our isolates instead of Ala and Thr, respectively, in all other available CHIKV sequences (Table 2). The first of these two positions is variable in alphaviruses; it lies in a region defined previously as containing neutralizing epitopes [5, 25]. At position 312, Thr is present in other CHIKV, in ONNV and in SFV, but varies in other alphaviruses; it lies in a region identified as important for E1-E2 oligomerization [5, 25].

In E1, two crucial substitutions were observed, one at residue 284, specific to Indian Ocean isolates, and one at residue 284, present in 3 out of 6 Indian isolates (06.21, 06.27 and 06.49). Both mutations were mapped on the 3D structure (modeled from the crystal structure of SFV E1) in FIG. 1. Interestingly, residue 226 is Ala in all reported CHIKV sequences (Table 2), and was also Ala in the first of our Indian Ocean isolates sequenced here (05.61 and 05.115, obtained at the beginning of the outbreak). All subsequent isolates (obtained from patients collected in November and December 2005) displayed a Val residue at this position. Although position 226 is relatively variable among alphaviruses, it was observed that a single mutation at this position (Pro to Ser) allowed SFV to adapt to growth in cholesterol-depleted insect cells [26, 27].

The other unique aa observed in E1 from Indian Ocean isolates was Glu 284. This is a highly conserved position in E1, which displays an Asp in the majority of alphaviruses or an Asn in SIN (Table 2). This amino acid is located at the interface between E1 protomers at the surface of the virion, participating in contacts that make up the icosahedral E1 scaffold (FIG. 1).

2. Phylogenetic Analysis

Previous work based on E1 protein sequences showed strong phylogeographic structure of the chikungunya virus species [6, 10]. In order to determine the progenitor phylogroup from which the Indian Ocean outbreak isolates emerged, we compared a 1,044 nt region within the E1 coding sequence (positions 271 to 1314, i.e., codons 91 to 438) from 63 biological specimens from 60 patients from Reunion, Seychelles, Madagascar, Mayotte and Comoros (Table 1) with 29 other available chikungunya sequences (Table 7). Phylogenetic analysis (FIG. 2) clearly demonstrated that the current Indian Ocean isolates represent a homogeneous clade within a broad group (group ECSA) comprising isolates from East, Central and South Africa (ECSA, FIG. 2). The isolates from an outbreak in Democratic Republic of the Congo [6] also formed a homogeneous Glade within group ECSA. There was no ECSA group member showing a significantly closer relationship with the Indian Ocean isolates. Asian isolates were less related to Indian Ocean isolates and constituted the sister group of group ECSA, whereas West-African isolates were even more divergent. Inclusion of other alphaviruses, including the closest relative ONN, placed the root of the chikungunya isolates on the branch leading to the West-African phylogroup (data not shown).

Comparison of the sequences of Indian Ocean outbreak isolates to the S27 sequence revealed 316 (2.7%) nucleotide substitutions in isolate 05.115 (Table 8). The Asian Glade Nagpur strain showed 5.1% average nucleotide divergence from 05.115, whereas the West-African Glade Senegal strain 37997 displayed 15% difference (Table 8). Interestingly, the latter strain showed complete conservation of an 87 nucleotides portion (9,958-10,045, at the junction between structural proteins 6K and E1) with East-African and Indian Ocean outbreak isolates. Sequence identity in this portion may reflect a past event of genetic recombination between West-African and East/Central-African strains. Differently, we did not find statistical support (P>7E-2) for sequence mosaicism or recombination since the split between S27 and Reunion isolates, although some genomic regions differed in their density of nucleotide polymorphisms.

3. Genotypic and Phenotypic Variation Among Indian Ocean Outbreak Isolates and Microevolutionary Scenario Specific aa changes in the non-structural proteins were observed in the isolates 05209 (S358P) and 06.27 (nsP1-T3011, nsP2-Y642N, and nsP3-460del). In the structural proteins, change E1-A226V was observed in isolates 06.21, 06.27 and 06.49, and change E2-Q146R in the Seychelles isolate 05.209. In addition to these non-synonymous changes, there were 8 silent substitutions, observed in 05.209, 06.27 and 06.49 (Table 3).

A history of probable sequence evolution that occurred during the outbreak (FIG. 3) was deduced from the 14 amino-acid variations observed among the six complete genomes (Table 3). Isolate 05.61 was initially selected for genome analysis because it was isolated in March 2005, at the onset of the outbreak, from a Reunion patient returning 1 turning from Comoros Island, where the outbreak had been going on since January 2005. Remarkably, the isolates 05.61 and 05.115 (which was the second earliest isolate analyzed), the African isolate S27 and previous unrelated chikungunya isolates from Africa and Asia were identical at all 14 polymorphic sites. Therefore, the consensus sequence of isolates 05.61 and 05.115 (consensus sequence 1) likely represents the ancestral genotype of the Reunion outbreak. Distribution of the 14 polymorphisms suggested that this founder gave rise to three consensus sequences that likely evolved in four steps. First, substitution at genome position 10,670 (causing the E1 A226V change) gave rise to consensus sequence 2, represented by the late-November 2005 isolate 06.21. Second, a G to A synonymous substitution at position 6,547 (nsP4) led to an intermediate sequence, which itself gave rise to two late sequences: consensus sequence 3 (isolate 06.27), following four additional substitutions and one codon deletion (Table 3), and consensus sequence 4 (06.49), which arose after three distinct synonymous substitutions (Table 3). A fifth consensus sequence was represented by the Seychelles isolate 05.209 alone, which exhibited four substitutions (two of them causing aa changes in nsP3-S358P and in E2-Q146R) compared to consensus sequence 1 (FIG. 3).

Since Reunion isolates had E1-226A at the beginning of the outbreak and E1-266V A at the beginning of the outbreak and E1-266V later in the epidemics, we compared residue 226 in 57 additional sequences (57 sequences from 54 sera and 3 CSF) from the Indian Ocean epidemic. Remarkably, the nature of E1-226 differed totally on Reunion Island before and after the winter season. Five sequences from patients sampled from March to June 2005 (including the sequence originating from a traveller back from Comoros) had E1-226A. Between September and end December 2005, 21 sequences showed E1-226V. Among 17 Reunion sequences from 2006, E1-226V was observed 12 times and E1-226A 5 times (Table 1). On Madagascar and Seychelles sequences, for which the samples were collected when the first clinical cases were suspected (i.e probably at the beginning of the outbreaks), only the E1-226 Ala was observed. On Mayotte 2006 sequences, only the E1-226 V was observed. On Mauritius 2006 sequences, both E1-226 Ala and Val were observed.

To date, only CHIKV laboratory strains, passaged many times on mosquito or mammalian cells, had been entirely sequenced [9]. We provide for the first time nearly complete nucleotide sequences of six clinical isolates passaged in-vitro only once or twice (see M&M section). The presence in infected patients of a mixed viral population, called quasispecies [31-33], with genotypes co-existing in an equilibrium governed by a balance between mutation and natural selection. The presence in S27 of an Arg codon instead of the opal stop codon in Indian Ocean isolates is probably explained by numerous in-vitro passages of S27, as evolution of opal to Arg was observed experimentally in ONN viruses [23]. Whereas it may be advantageous for viral quasispecies to maintain the opal codon in-vivo, an Arg codon probably confers a selective advantage in-vitro, as observed for the closely related Semliki Forest virus [34]. Chikungunya virus quasispecies situation in-vivo could also explain the nsP1-T3011 polymorphism observed for the LCR isolate 06.27. Indeed, it is likely that selection for a subset of genotypes harboring this change may be associated with invasion of the LCR [33]. These results underscore that the genome sequence of laboratory "reference" strains may not accurately reflect the natural situation, as the genotypic complexity of quasispecies in-vivo is subject to erosion by in-vitro selection. Since the Indian Ocean isolates sequenced here were subjected to in-vitro selection for only a few generations, they probably correspond more closely to the in-vivo genotypes than previously sequenced chikungunya strains.

The amino acid (aa) differences detected among the outbreak 1 isolates may relate to biological or pathogenic characteristics of the virus. Although our viral culture results are preliminary, they clearly show phenotypic differences between the unique isolate from CSF (06.27), isolated from a neonatal encephalopathy case, and three other isolates, associated with either the classical form of the disease or encephalopathy. The larger foci observed in culture with 06.27 could reflect a higher replication rate of the virus and be linked to the specific amino acid changes identified in nsP1, nsP2 and nsP3. Single amino-acid changes in nsP1, including a Thr/Ile change (residue 538 of Sindbis virus) [35,36] and a 18-nt deletion in nsP3 have previously been shown to affect neurovirulence in other alphaviruses [35-37]. However, in the absence of nsP1 structural data, it is difficult to predict the structural or functional impact of the I301T change observed in 06.27 isolate. It should also be noted that all the viral sequences determined from either the serum or the isolates from three neonatal encephalopathy cases and an adult meningo-encephalitis case had E1-226 Val. However, as this genotype is observed also in classical forms of the disease, a potential link of E1-226 Val with neuropathogenesis needs further studies. Host factors have to be considered in the occurrence of neurological forms of the disease. For example, the blood-brain crossing may be favoured by young age or hypertension.

Unique molecular signatures of the Indian Ocean outbreak genomes were identified when they were compared to all other reported alphavirus sequences. These features represent interesting targets for future functional studies, as well as for epidemiological follow-up. One particularly interesting feature was the E1-226 Val residue (see above). Another interesting molecular signature of Indian Ocean outbreak genomes was E1-284 Asp. Although pseudo-atomic model of the scaffold used is of modest resolution (the resolution of the crystal structure is limited—approaching 3 Å—and the model results of fitting this structure into a 9 Å resolution cryo-electron microscopy reconstruction), it appears that the side-chain of Asp 284 interacts with the main chain of an adjacent E1 polypeptide in the virion. Indeed, it is in a position compatible with acceptance of a hydrogen bond from main chain amide 379 from the neighboring E1 protomer. Because the packing is very tight (see FIG. 1B), it is possible that the longer Glutamic acid side chain (which has an extra CH2 group compared to Asp or Asn) may introduce a slight distortion at the contact sites, an effect that is propagated by the icosahedral T=4 symmetry of the virion. Thus, a cooperative effect due to this change at position Asp 284 may play a role in either allowing a less efficient assembly of new particles in infected cells, or a more efficient particle disassembly process during invasion of a new cell, or a combination of both. This information 1 tion can guide new site-directed mutagenesis studies, using reverse genetics, to test the effect of the Asp/Glu replacement on the virus cycle.

Example 2

Identification and Characterization of a Soluble Form of E2 (sE2) of the CHIK Virus The TOPO/CHIK-21.pE2 (CNCM I-3587) plasmid containing the cDNA coding for the pE2 glycoprotein (E3+E2) from the CHIK 21 virus strain (Schuffenecker et al., *Plos Med.,* 3:1058, 2006) was used as a template for the amplification by PCR of the ectodomain sequence of the E2 envelope glycoprotein (FIG. 29). The ectodomain of gp-E2 (E2-1 to E2-364; 85% of E2) is strictly conserved among the CHIK-21, -27, 49 and 115 cell lines isolated in the Indian Ocean during the epidemic outbreak of 2005-06 (see FIG. 29). The soluble form of the sE2 corresponds to the gp-E2 ectodomain which is deleted at the carboxylic terminal of its transmembrane anchor region. It is of interest that the soluble form carries the main epitopes eliciting virus-neutralizing antibodies. The PCR primers are described in FIG. 30 (SEQ ID NO:79 and 80): they allow the cloning of the sE2 sequence between the unique sites Bg/II and NotI of the pMT/BiP/V5-HisA vector (Invitrogen), on the one hand in a phase dependent on the BiP peptide signal at the N-terminal, and on the other hand in joining successive V5 $(His)_6$ tags at its carboxylic terminal.

*Drosophila* S2 cells were transfected with the recombinant plasmid pMT/BiP/CHIK-sE2 in the presence of the plasmid coding for the blasticidin resistance gene. The S2/CHIK-sE2 stable cell line was obtained by successive passages in presence of blasticidin. The cell line was selected for its capacity to promote efficient secretion of the CHIK-sE2 virus following the activation of the metallothioneine promoter.

The S2/CHIK-sE2 cells in suspension were induced for the secretion of sE2 during 21 days in the presence of $Cu_{2+}$. The cellular supernatant is filtered at 0.22 μM and concentrated for 16 hours on an affinity column of 5 ml HiTrap Chelating HP (Amersham Biosciences) with the help of a peristaltic pump. The CHIK sE2 protein is eluded from the affinity column in the presence of increasing concentrations of imidazole (50, 100 and 500 mM, pH 8). The CHIK sE2 protein is specifically eluded at a concentration of 500 mM imidazole ($E_3$ elution) from the $E_3$7 fraction (FIG. 31). The sE2 protein is detected as being highly purified in PAGESDS following Coomassie Blue coloration. The sE2 protein eluded in the $E_3$9 fraction is specifically immunodetected by an ascite (HMAF) of a mouse hyperimmunized against the CHIK virus which was produced at the IMFH unit (FIG. 32). No cross-reactivity was observed with the anti-dengue (DEN) or anti-West Nile (WN) HMAHF and the monoclonal antibody 9D12 anti-DEN E. The soluble DEN sE proteins (DEN-3 and DEN-4) and WN sE purified from the supernatants of the S2 cellular clones induced according to the protocol described hereinabove are used as control viral antigens for the specificity of anti-CHIK murine antibodies.

Example 3

Construction of the TRIP Vector Expressing the Soluble Form of E2 (sE2) of the CHIK Virus According to the Present Invention The gene coding the CHIK sE2 protein has been optimised by the Genecust firm so as to provide a synthetic DNA with an enriched G+C content in comparison to the cDNA obtained from the viral genomic RNA. The G+C rich codons (amino acids E2-1 to E2-364, soluble gp-E2 ectodomain, sE2) were fused to the signal peptide sequence of the human calreticuline (ssCRT) MLLSVPLLLLGLLGLAA (SEQ ID NO: 77) for translocation of the viral protein into the secretion pathway. The enzyme restriction sites BamHI in 5' and XhoI in 3' have been added at their respective ends of the sequences coding for the fusion ssCRT+sE2 protein.

The synthetic gene was cloned into the TRIP vector between the BamHI and XhoI sites under the transcription of the ieCMV promoter. The non-replicative and integrative TRIP/CHIK.sE2 plasmid thus produced was validated for the expression of the sE2 protein following transduction of 293 cells.

As shown in FIG. 33, the inventors have constructed a vector expressing the CHIK sE2. As mentioned above, the original CHIK sE2 sequence cloned into the TRIP vector has been modified for improving expression in mammalian cells (FIG. 34).

FIG. 35 shows mammalian cells, such as the 293 cells, transduced with the TRIP-CHIK.sE2 vector. The expressed sE2 protein has been revealed by IF with anti-CHIK antibodies.

Example 4

Production of Recombinant Protein sE2 and Specific Monoclonal Antibodies

The inventors have generated the stable inducible S2/CHIK.sE2 cell line which releases the soluble form of the envelope E2-glycoprotein (sE2) from Reunion CHIK virus strains. The inventors have also generated a stable cell line 293A/CHIK.sE2 which was transducted by the recombinant lentiviral vector TRIP/CHIK.sE2. A synthetic sE2 gene that was modified for optimal codon usage in mammalian cells had to be used in order to obtain efficient expression of CHIK virus sE2 in human fibroblastic 293A cells. The TRIP/CHIK.sE2 vector is currently assessed for its capability to induce protective immunity in a murine model of experimental infection. Viral suspension mainly enriched in CHIK pE2 (E2 precursor or E3E2) was obtained by solubilizing CHIK virions grown in mosquito cells with Triton X-100. Adult mice were hyperimmunized with CHIK pE2 in the presence of adjuvant in order to generate hybridoma directed against CHIK structural proteins. Anti-CHIK E2 monoclonal antibodies produced by mouse hybridoma were characterized by ELISA assay on highly purified CHIK virion and Western blot on secreted sE2 from stable cell line S2/CHIK.sE2. (FIGS. 50, 51 and Table 9). Fluorescent immunodetection assays of intracellular or surface viral antigens were also established on CHIK virus-infected VERO cells and stable 293A/CHIK.sE2 transduced cell line (FIGS. 52-55). Anti-CHIK.sE2 MAbs of the inventors find a potential use in developing early viral diagnosis of CHIK disease based on immunocapture of CHIK virions in viremic blood of patients, and as tools for immunological as well as virological studies.

TABLE 1

| Characteristics of the patients | | | | | | | | |
|---|---|---|---|---|---|---|---|---|
| Patients No. | Island | Region or Island | Town or Locality | Sample (b) | Sampling Date | Clinical signs (c) | Virus Isolate No. (d) | E1-226 (e) |
| 1 | Réunion (Comoros) (a) | — | — | S | 16-Mar-05 | Classical | 05.61 (G) | A (*) |
| 2 | Réunion | West | St Gilles Les Bains | S | 11-Apr-05 | Classical | 05.55 | A (*) |
| 3 | Réunion | South | Saint Pierre | S | 2-May-05 | Classical | 05.107 | A (*) |
| 4 | Réunion | West | Mare Sèche Cilaos | S | 4-May-05 | Classical | 05.111 | A (*) |
| 5 | Réunion | South | La Rivièνe St Louis | S | 6-May-05 | Classical | 05.115 (G) | A (*) |
| 6 | Réunion | South | St Louis | CSF | 7-Sep-05 | Neonatal encephalopathy | 05.223 | V (**) |
| 7 | Réunion | South | La Rivièνe St Louis | S | 11-Oct-05 | Classical | 06.55 | V (**) |
| 8 | Réunion | South | St Louis | S | 21-Oct-05 | Classical | 06.59 | V (**) |
| 9 | Réunion | South | La Rivièνe St Louis | S | 21-Oct-05 | Classical | 06.53 | V (**) |
| 10 | Réunion | South | La Rivièνe St Louis | P | 26-Oct-05 | Classical | n.i. | V (**) |
| 11 | Réunion | South | St Joseph | P | 9-Nov-05 | Classical | n.i. | V (**) |
| 12 | Réunion | South | La Rivièνe St Louis | P | 10-Nov-05 | Classical | n.i. | V (**) |
| 13 | Réunion | South | St Louis | P | 20-Nov-05 | Classical | n.i. | V (**) |
| 14 | Réunion | South | La Rivièνe St Louis | P | 21-Nov-05 | Classical | n.i. | V (**) |
| 15 | Réunion | South | La Rivieve St Louis | S | 23-Nov-05 | Classical | 06.45 | V (**) |
| 16 | Réunion | South | La Rivièνe St Louis (parents) | S | 28-Nov-05 | Neonatal ME | 06.21 (G) | V (***) |
| 17 | Réunion | South | St Joseph | S | 23-Nov-05 | Classical | 06.47 | V (**) |
| 18 | Réunion | South | La Rivièνe St Louis | P | 24-Nov-05 | Classical | n.i. | V (**) |
| 19 | Réunion | South | Le Tampon | P | 26-Nov-05 | Classical | n.i. | V (**) |
| 20 | Réunion | South | Ravine des Cabris | P | 25-Nov-05 | Classical | n.i. | V (**) |
| 21 | Réunion | South | St Joseph (parents) | S | 29-Nov-05 | Neonatal ME | 06.25 | V (**) |
| 21 | Réunion | South | St Joseph (parents) | CSF | 29-Nov-05 | Neonatal ME | 06.27 (G) | V (***) |
| 22 | Réunion | South | St Louis | S | 2-Dec-05 | Classical | 06.49 (G) | V (***) |
| 23 | Réunion | South | St Louis | P | 8-Dec-05 | Classical | n.i. | V (**) |
| 24 | Réunion | South | Ravine des Cabris | S | 9-Dec-05 | ME | 06.17 | V (**) |
| 25 | Réunion | South | St Louis | P | 13-Dec-05 | Classical | n.i. | V (**) |
| 26 | Réunion | South | St Pierre | P | 2-Jan-06 | Classical | n.i. | A (**) |
| 27 | Réunion | South | St Pierre | P | 4-Jan-06 | Algic symdrome | n.i. | A (**) |
| 28 | Réunion | East | St André | S | 4-Jan-06 | Classical | n.i. | A (**) |
| 29 | Réunion | South | St Louis | P | 29-Dec-05 | Algic syndrome | n.i. | V (**) |
| 29 | Réunion | South | St Louis | CSF | 29-Dec-05 | Algic syndrome | n.i. | V (**) |
| 30 | Réunion | South | La Rivièνe St Louis | P | 29-Dec-05 | Classical | n.i. | V (**) |
| 31 | Réunion | South | La Rivièνe St Louis | P | 27-Dec-05 | Classical | n.i. | V (**) |
| 32 | Réunion | South | St Pierre | P | 27-Dec-05 | Severe vesicular rash lower limbs | n.i. | V (**) |
| 32 | Réunion | South | St Pierre | L | 28-Dec-05 | Severe vesicular rash lower limbs | n.i. | V (**) |
| 33 | Réunion | South | Ravine des Cabris | P | 4-Jan-06 | n.d. | n.i. | A (**) |
| 34 | Réunion | South | St Joseph | P | 3-Jan-06 | Algic syndrome | n.i. | V (**) |
| 35 | Réunion | South | St Louis | P | 2-Jan-06 | Algic syndrome | n.i. | V (**) |
| 36 | Réunion | South | St Joseph | P | 5-Jan-06 | Algic syndrome | n.i. | To be determined |
| 37 | Réunion | South | Ravine des Cabris | P | 6-Jan-06 | Classical | n.i. | V (**) |
| 38 | Réunion | South | St Louis | P | 6-Jan-06 | Algic syndrome | n.i. | V (**) |
| 39 | Réunion | West | Saint-Paul hospital | S | 5-Jan-06 | n.d. | n.i. | A (**) |
| 40 | Réunion | West | St Leu | S | 19-Jan-06 | Classical | n.i. | V (**) |
| 41 | Réunion | South | Les Avirons | S | 30-Jan-06 | Classical | 06.97 | V (**) |
| 42 | Réunion | East | St Benoit | S | 3-Feb-06 | Hepatitis | n.i. | V (**) |
| 43 | Réunion | n.d. | n.d. | S | 22-Feb-06 | Classical | n.i. | V (**) |
| 44 | Seychelles | Mahe island | Anse aux Pins | S | 9-Aug-05 | Classical | 05.209 (G) | A (*) |
| 45 | Seychelles | Mahe island | Anse aux Pins | S | 10-Aug-05 | Classical | negative | A (**) |
| 46 | Seychelles | Mahe island | Anse aux Pins | S | 10-Aug-05 | Classical | negative | A (**) |
| 47 | Madagascar | East | Toamasina | S | 1-Feb-06 | Classical | 06.103 | A (**) |
| 48 | Madagascar | East | Toamasina | S | 8-Feb-06 | Classical | 06.99 | A (**) |
| 49 | Madagascar | East | Toamasina | S | 9-Feb-06 | Classical | 06.101 | A (**) |
| 50 | Madagascar | East | Toamasina | S | 15-Feb-06 | Classical | n.i. | A (**) |
| 51 | Madagascar | North | Ampany | S | 14-Feb-06 | Classical | n.i. | A (**) |
| 52 | Madagascar | North | Djamandjary | S | 14-Feb-06 | Classical | n.i. | A (**) |
| 53 | Madagascar | North | Djamandjary | S | 15-Feb-06 | Classical | n.i. | A (**) |
| 54 | Mayotte | n.d. | n.d. | S | 7-Feb-06 | Classical | 06.111 | To be determined |
| 55 | Mayotte | n.d. | n.d. | S | 11-Feb-06 | Classical | n.i. | V (**) |
| 56 | Mayotte | n.d. | n.d. | S | 13-Feb-06 | Classical | n.i. | V (**) |
| 57 | Mayotte | n.d. | n.d. | S | 13-Feb-06 | Classical | n.i. | V (**) |
| 58 | Mauritius | n.d. | n.d. | S | 12-Feb-06 | Classical | 06.93 | V (*) |

TABLE 1-continued

| Characteristics of the patients | | | | | | | | |
|---|---|---|---|---|---|---|---|---|
| Patients No. | Island | Region or Island | Town or Locality | Sample (b) | Sampling Date | Clinical signs (c) | Virus Isolate No. (d) | E1-226 (e) |
| 59 | Mauritius | n.d. | n.d. | S | 27-Feb-06 | Classical | n.i. | A (**) |
| 60 | Mauritius | n.d. | n.d. | S | 1-Mar-06 | Classical | n.i. | A (**) |

(a) This patent traveled back from Comoros and is believed to have been infected there.

(b) S: serum; P: plasma; CSF: cerebrospinal fluid (c) ME: meningo-encephalitis (d) Isolates labeled with (G) correspond to those for which the nearly complete genome sequence was established (e) A: Alanine; V: Valine; (*): Sequence determined from virus isolates; (): Sequence determined from biological samples; (*): Sequence determined from both virus isolates and biological samples n.i.: isolation of virus not intended;

n.d.: not determined

TABLE 2

Relevant amino acid changes identified between Indian Ocean isolates versus a selection of Alphavirus sequences.

| | Non-structural proteins | | | | | | | | | | | | | |
|---|---|---|---|---|---|---|---|---|---|---|---|---|---|---|
| Protein | nsP1 | nsP1 | nsP2 | nsP2 | nsP2 | nsP2 | nsP3 | nsP3 | nsP3 | nsP3 | nsP3 | nsP4 | nsP4 | nsP4 |
| Polypeptide position (a) | 301 | 488 | 589 | 909 | 1177 | 1328 | 1550 | 1670 | 1691 | 1793 | 1804 | 1938 | 2117 | 2363 |
| Protein position (a) | 301 | 488 | 54 | 374 | 642 | 793 | 217 | 337 | 358 | 460 | 471 | 75 | 254 | 500 |
| 05.115 (Genotype 1) | T | R | N | Y | Y | V | H | I | S | E | S | A | A | L |
| 06.21 (Genotype 2) | T | R | N | Y | Y | V | H | I | S | Nd | nd | A | A | L |
| 06.27 (Genotype 3) | I | R | N | Y | N | V | H | I | S | Del | S | A | A | L |
| 06.49 (Genotype 4) | T | R | N | Y | Y | V | H | I | S | E | S | A | A | L |
| 05.209 (Genotype 5) | T | R | N | Y | Y | V | H | I | P | E | S | A | A | L |
| S27 | T | Q | S | H | C | A | Y | T | S | L | P | T | T | Q |
| Ross | T | Q | S | H | C | A | Y | T | S | L | P | T | T | Q |
| 37997 (West-African phylogroup) | T | K | S | H | Y | A | Y | T | S | P | P | T | T | Q |
| Nagpur (Asian phylogroup) | nd | nd | nd | nd | nd | nd | nd | nd | nd | Nd | nd | nd | nd | nd |
| ONNV | S | Q | S | N | H | A | Y | ** | S | ** | ** | T | T | E |
| EEV | S | Q | S | N | E | R | N | ** | ** | ** | ** | I | V | E |
| SFV | V | S | N | H | Y | A | L | ** | S | ** | ** | T | T | E |
| RRV | V | N | S | H | Y | G | S | ** | ** | ** | ** | V | T | E |
| SINV | V | M | S | H | E | R | K | ** | ** | ** | ** | I | T | E |

| | Structural proteins | | | | | | | | |
|---|---|---|---|---|---|---|---|---|---|
| Protein | E2 | E2 | E2 | E2 | E2 | 6K | E1 | E1 | E1 |
| Polypeptide position (a) | 471 | 489 | 637 | 700 | 711 | 756 | 1035 | 1078 | 1093 |
| Protein position (a) | 146 | 164 | 312 | 375 | 386 | 8 | 226 | 269 | 284 |
| 05.115 (Genotype 1) | Q | T | M | T | A | I | A | V | E |
| 06.21 (Genotype 2) | Q | T | M | T | A | I | V | V | E |
| 06.27 (Genotype 3) | Q | T | M | T | A | I | V | V | E |
| 06.49 (Genotype 4) | Q | T | M | T | A | I | V | V | E |
| 05.209 (Genotype 5) | R | T | M | T | A | I | A | V | E |
| S27 | Q | A | T | S | V | I | A | M | D |
| Ross | Q | A | T | S | V | V | A | M | D |
| 37997 (West-African phylogroup) | Q | A | T | S | V | A | A | V | D |
| Nagpur (Asian phylogroup) | Q | A | T | S | G | V | A | M | D |
| ONNV | H | A* | T | S | L* | T* | A | V | D |
| EEV | E | G* | S | A | T* | D* | A | E | D |

TABLE 2-continued

Relevant amino acid changes identified between Indian Ocean isolates versus a selection of Alphavirus sequences.

| | | | | | | | | | |
|---|---|---|---|---|---|---|---|---|---|
| SFV | H | V* | T | S | C* | A* | P | M | D |
| RRV | H | D* | D | S | C* | A* | P | M | D |
| SINV | V | A* | V | T | V* | S* | A | V | N |

(a) S27 reference numbering
*Variable position,
**Hypervariable position
ONV: o'nyong-nyong virus;
SFV: Semliki Forest virus;
RRV: Ross River virus;
SINV: Sindbis virus;
EEV: Eastern-Equine Encephalitis virus.
nd: not determined.
Note that the opal stop codon observed in nsP3-524 of Indian Ocean outbreak isolates, but not in S27, is not represented in the Table.

TABLE 3

Polymorphisms observed among Indian Ocean isolates

| | Genome position (b) | | | | | | | |
|---|---|---|---|---|---|---|---|---|
| | 978 | 1378 | 3605 | 4705 | 5147 | 5452 | 5453-5455 | 6547 |
| Protein | nsP1 | nsP1 | nsP2 | nsP3 | nsP3 | nsP3 | nsP3 | nsP4 |
| Protein position (for aa change) | 301 | — | 642 | — | 358 | — | 460 | — |
| 05.115 (Genotype 1) | C | G | T | T | T | G | GAA (Glu) | G |
| 05.61 (Genotype 1) | C | G | T | T | T | n.d. | n.d. | G |
| 06.21 (Genotype 2) | C | G | T | T | T | G | GAA (Glu) | G |
| 06.27 (Genotype 3) | T (Thr→Ile) | G | A (Tyr→Asn) | A | T | A | Deleted | A |
| 06.49 (Genotype 4) | C | A | T | T | T | G | GAA (Glu) | A |
| 05.209 (Genotype 5) | C | G | T | T | C (Ser→Pro) | G | GAA (Glu) | G |
| S27 (a) | C | G | T | T | T | G | GAA (Glu) | G |

| | Genome position (b) | | | | | |
|---|---|---|---|---|---|---|
| | 7045 | 8978 | 9600 | 10670 | 11295 | 11421 |
| Protein | nsP4 | E2 | E2 | E1 | E1 | 3'NTR |
| Protein position (for aa change) | — | 146 | — | 226 | — | — |
| 05.115 (Genotype 1) | C | A | T | C | G | C |
| 05.61 (Genotype 1) | C | A | T | C | G | C |
| 06.21 (Genotype 2) | C | A | T | T (Ala→Val) | G | C |
| 06.27 (Genotype 3) | C | A | T | T (Ala→Val) | G | C |
| 06.49 (Genotype 4) | C | A | C | T (Ala→Val) | G | T |
| 05.209 (Genotype 5) | T | G (Gln→Arg) | T | C | A | C |
| S27 (a) | C | A | T | C | G | C |

(a) Only sites that are variable among Indian Ocean outbreak isolates are represented; those sites that were distinct between Indian Ocean outbreak isolates and other viruses are given as Supplementary Information
(b) S27 numbering

TABLE 4

Primers used for RT-PCR and sequencing

| Fragment | Gene | Primer (a) | Sequence (5' to 3') | SEQ ID NO. |
|---|---|---|---|---|
| FG1 | 5'NC | 18F | CACGTAGCCTACCAGTTTCTTA | 35 |
| | nsP1 | 871R | ATGGAACACCGATGGTAGGTG | 36 |
| FG2 | nsP1 | 616F | AACCCCGTTCATGTACAATGC | 37 |
| | nsP1 | 1435R | CGGTACCACAAAGCTGTCAAAC | 38 |
| FG3 | nsP1 | 1317F | CACTGACCTGCTGCTGTCTATG | 39 |
| | nsP2 | 2130R | AGTCCTGCAGCTTCTTCCTTC | 40 |
| FG4 | nsP1 | 1412F | CGAGTTTGACAGCTTTGTGGTA | 41 |
| | nsP2 | 2227R | ATGACTGCAATTTTGTATGGGC | 42 |
| FG5 | nsP2 | 1908F | CAATCTCGCCTGAAGACTTCC | 43 |
| | nsP2 | 2709R | TCCACTACAATCGGCTTGTTG | 44 |
| FG6 | nsP2 | 2530F | GTGCGGCTTCTTCAATATGATG | 45 |
| | nsP2 | 3343R | TCCAGGCCTATTATCCCAGTG | 46 |

TABLE 4-continued

| Primers used for RT-PCR and sequencing | | | | |
|---|---|---|---|---|
| Fragment | Gene | Primer (a) | Sequence (5' to 3') | SEQ ID NO. |
| FG7 | nsP2 | 2577F | AACATCTGCACCCAAGTGTACC | 47 |
| | nsP2 | 3504R | GTCTCCTGTTGGCCGGTATAAT | 48 |
| FG8 | nsP2 | 3332F | TAATAGGCCTGGAGGGAAGATG | 49 |
| | nsP3 | 4134R | CTACGCACTCTTCATCGTTCTT | 50 |
| FG9 | nsP2 | 3885F | GAACGAGTCATCTGCGTATTGG | 51 |
| | nsP3 | 4725R | ATATCTCTGCCATATCCACTGC | 52 |
| FG10 | nsP3 | 4458F | TCTTTACAGCCATGGACTCGAC | 53 |
| | nsP3 | 5273R | CGACAGGTACGGTGCTCATTAC | 54 |
| FG11 | nsP3 | 5065F | TGTACAGGAAGCGAGTACGACC | 55 |
| | nsP4 | 5874R | TCTACTTTGCGCGACTGATACC | 56 |
| FG12 | nsP4 | 5630F | ACGGACGACGAGTTACGACTAG | 57 |
| | nsP4 | 6380R | CCCAGTATTCTTGGTTGCATG | 58 |
| FG13 | nsP4 | 6184F | AAAACAGCACGCTTACCACG | 59 |
| | nsP4 | 6936R | AACTTGAAGCGCGTACCTGTC | 60 |
| FG14 | nsP4 | 6732F | TCATAGCCGCACACTTTAAGC | 61 |
| | nsP4 | 7495R | AGGACCGCCGTACAAAGTTAC | 62 |
| FG15 | nsP4 | 7278F | GCAGGTGACGAACAAGATGAG | 63 |
| | C | 8034R | CCGCTTAAAGGCCAATTTG | 64 |
| FG16 | C | 7910F | TCGAAGTCAAGCACGAAGG | 65 |
| | E2 | 8670R | GTCTGTCGCTTCATTTCTGATG | 66 |
| FG17 | E3 | 8459F | TGCTTGAGGACAACGTCATGAG | 67 |
| | E2 | 9240R | TTTGTGATTGGTGACCGCG | 68 |
| FG18 | E2 | 9093F | AGTCCGGCAACGTAAAGATCAC | 69 |
| | 6K | 9861R | AAAGGTTGCTGCTCGTTCCAC | 70 |
| FG19 | E2 | 9648F | AGTTGTGTCAGTGGCCTCGTTC | 71 |
| | E1 | 10403R | TAAAGGACGCGGAGCTTAGCTG | 72 |
| FG20 | E1 | 10145F | ACAAAACCGTCATCCCGTCTC | 73 |
| | E1 | 11158R | TGACTATGTGGTCCTTCGGAGG | 74 |
| FG21 | E1 | 10959F | CAGCAAGAAAGGCAAGTGTGC | 75 |
| | 3'NC | 11770R | TTTGCCAATTATGGTATTCA | 76 |

(a) The primer name indicates their position and direction on the nucleotide sequence of the S27 genome.

TABLE 5

| Amino-acid changes observed between strain S27 and Indian Ocean outbreak strains in the non-structural proteins | | | | | | | | | | | | | |
|---|---|---|---|---|---|---|---|---|---|---|---|---|---|
| nsP1 and nsP2 | | | | | | | | | | | | | |
| Protein | nsP1 | nsP1 | nsP1 | nsP1 | nsP1 | nsP1 | nsP1 | nsP1 | nsP2 | nsP2 | nsP2 | nsP2 | nsP2 |
| Protein position | 172 | 234 | 301 | 383 | 384 | 481 | 488 | 507 | 54 | 374 | 642 | 643 | 793 |
| Poly-peptide position | 172 | 234 | 301 | 383 | 384 | 481 | 488 | 507 | 589 | 909 | 1177 | 1178 | 1328 |
| S27 | L | E | T | M | I | T | Q | L | S | H | C | S | A |
| 05.115 | V | K | T | L | L | I | R | R | N | Y | Y | N | V |
| 05.61 | V | K | T | L | L | I | R | R | N | Y | Y | N | V |
| 06.21 | V | K | T | L | L | I | R | R | N | Y | Y | N | V |
| 06.27 | V | K | I | L | L | I | R | R | N | Y | N | N | V |

TABLE 5-continued

Amino-acid changes observed between strain S27 and Indian Ocean outbreak strains in the non-structural proteins

| | | | | | | | | | | | | |
|---|---|---|---|---|---|---|---|---|---|---|---|---|
| 06.49 | V | K | T | L | L | I | R | R | N | Y | Y | N | V |
| 05.209 | V | K | T | L | L | I | R | R | N | Y | Y | N | V |

nsP3 and nsP4

| Protein | nsP3 | nsP3 | nsP3 | nsP3 | nsP3 | nsP3 | nsP3 | nsP3 | nsP3 | nsP3 | nsP3 |
|---|---|---|---|---|---|---|---|---|---|---|---|
| Protein position | 175 | 217 | 326 | 331 | 337 | 352 | 358 | 376 | 382 | 460 | 461 |
| Poly-peptide position | 1508 | 1550 | 1659 | 1664 | 1670 | 1685 | 1691 | 1709 | 1715 | 1793 | 1794 |
| S27 | V | Y | P | V | T | K | S | I | A | L | L |
| 05.115 | I | H | S | A | I | E | S | T | T | E | P |
| 05.61 | I | H | S | A | I | E | S | T | T | nd | nd |
| 06.21 | I | H | S | A | I | E | S | T | T | E | P |
| 06.27 | I | H | S | A | I | E | S | T | T | del | P |
| 06.49 | I | H | S | A | I | E | S | T | T | E | P |
| 05.209 | I | H | S | A | I | E | P | T | T | E | P |

nsP3 and nsP4

| Protein | nsP3 | nsP3 | nsP3 | nsP4 | nsP4 | nsP4 | nsP4 | nsP4 | nsP4 |
|---|---|---|---|---|---|---|---|---|---|
| Protein position | 462 | 471 | 524 | 75 | 254 | 500 | 514 | 555 | 604 |
| Polypeptide position | 1795 | 1804 | 1857 | 1938 | 2117 | 2363 | 2377 | 2418 | 2467 |
| S27 | S | P | R | T | T | Q | I | V | V |
| 05.115 | N | S | STOP | A | A | L | T | I | I |
| 05.61 | nd | nd | nd | A | A | L | T | I | I |
| 06.21 | N | S | STOP | A | A | L | T | I | I |
| 06.27 | N | S | STOP | A | A | L | T | I | I |
| 06.49 | N | S | STOP | A | A | L | T | I | I |
| 05.209 | N | S | STOP | A | A | L | T | I | I |

Grayed cells correspond to aa that were variable among Indian Ocean outbreak isolates

TABLE 6

Amino-acid changes observed in the structural genes among S27, Ross and Indian Ocean outbreak strains.

| Protein | C | E3 | E2 | E2 | E2 | E2 | E2 | E2 | E2 | E2 | E2 | E2 | E2 | E2 | E2 | E2 | E2 | E2 | E2 |
|---|---|---|---|---|---|---|---|---|---|---|---|---|---|---|---|---|---|---|---|
| Cleaved protein AA position | 63 | 23 | 57 | 74 | 79 | 1446 | 160 | 164 | 181 | 194 | 195 | 211 | 251 | 267 | 299 | 312 | 344 | 375 | 386 |
| Polyprotein AA position | 63 | 284 | 382 | 399 | 404 | 471 | 485 | 489 | 506 | 519 | 520 | 536 | 576 | 592 | 624 | 637 | 669 | 700 | 711 |
| Genome nt position (a) | 7754 | 8417 | 8710 | 8763 | 8777 | 8978 | 9020 | 9031 | 9082 | 9121 | 9125 | 9173 | 9293 | 9341 | 9437 | 9476 | 9571 | 9664 | 9698 |
| S27 | K | I | G | I | G | Q | N | A | L | S | Q | I | R | M | S | T | A | S | V |
| Ross | R | I | G | I | G | Q | N | A | L | G | R | I | P | R | S | T | A | S | V |
| 05.115 | R | T | K | M | E | Q | T | T | M | G | Q | T | R | R | N | M | T | T | A |
| 05.61 | R | T | K | M | E | Q | T | T | M | G | Q | T | R | R | N | M | T | T | A |
| 06.21 | R | T | K | M | E | Q | T | T | M | G | Q | T | R | R | N | M | T | T | A |
| 06.27 | R | T | K | M | E | Q | T | T | M | G | Q | T | R | R | N | M | T | T | A |
| 06.49 | R | T | K | M | E | Q | T | T | M | G | Q | T | R | R | N | M | T | T | A |
| 05.209 | R | T | K | M | E | R | T | T | M | G | Q | T | R | R | N | M | T | T | A |

TABLE 6-continued

Amino-acid changes observed in the structural genes among S27, Ross and Indian Ocean outbreak strains.

| Protein | 6K | 6K | E1 | E1 | E1 | E1 |
|---|---|---|---|---|---|---|
| Cleaved protein AA position | 8 | 54 | 226 | 269 | 284 | 322 |
| Polyprotein AA position | 756 | 802 | 1035 | 1078 | 1093 | 1131 |
| Genome nt position (a) | 9832 | 9970 | 10670 | 10798 | 10845 | 10958 |
| S27 | V | I | A | M | D | V |
| Ross | V | I | A | M | D | V |
| 05.115 | I | V | A | V | E | A |
| 05.61 | I | V | A | V | E | A |
| 06.21 | I | V | V | V | E | A |
| 06.27 | I | V | V | V | E | A |
| 06.49 | I | V | V | V | E | A |
| 05.209 | I | V | A | V | E | A |

(a) When two nt positions were variable in the same codon, only the position of the upstream nt is given
Grayed cells correspond to amino acid changes among Indian Ocean outbreak isolates.

TABLE 7

Sequence used for the phylogenetic analysis of partial E1 sequences

| Accession No. | Strain | Genomic domain | Strain Origin | Isolation Date | Phylogroup | Reference |
|---|---|---|---|---|---|---|
| AF192906 | CAR 256 | E1 partial | Central African Region | Unknown | Central Africa | 1 |
| AF192907 | Ag41855 | E1 partial | Uganda | 1982 | Central Africa | 1 |
| AY549583 | ChikRCA | E1 partial | DRC (b) | 1996 | Central Africa | 2 |
| AF192903 | AR 18211 | E1 partial | South African Republic | 1976 | Central-East/South Africa | 1 |
| AF192904 | SA H2123 | E1 partial | South African Republic | 1976 | Central-East/South Africa | 1 |
| AF192905 | Ross | E1 partial | Tanzanie | 1953 | Central-East/South Africa | 1 |
| AF490259 | Ross | Complete genome | Tanzanie | 1953 | Central-East/South Africa | na |
| AF369024 | S27 | Complete genome | Tanzanie | 1952 | Central-East/South Africa | 3 |
| AY549576 | DRC010 | E1 partial | DRC (b) | 2000 | Central Africa | 2 |
| AY549577 | DRC027 | E1 partial | DRC (b) | 2000 | Central Africa | 2 |
| AY549579 | DRC1719 | E1 partial | DRC (b) | 2000 | Central Africa | 2 |
| AY549575 | DRC007 | E1 partial | DRC (b) | 2000 | Central Africa | 2 |
| AY549578 | DRC1718 | E1 partial | DRC (b) | 2000 | Central Africa | 2 |
| AY549581 | DRC1725 | E1 partial | DRC (b) | 2000 | Central Africa | 2 |
| AY549582 | DRC1728 | E1 partial | DRC (b) | 2000 | Central Africa | 2 |
| AY549580 | DRC1720 | E1 partial | DRC (b) | 2000 | Central Africa | 2 |
| AY549584 | DRC1730 | E1 partial | DRC (b) | 2000 | Central Africa | 2 |
| AF192896 | 644188 | E1 partial | Thailand | 1988 | Asian | 1 |
| AF192899 | 3412/78 | E1 partial | Thailand | 1978 | Asian | 1 |
| AF192894 | RSU1 | E1 partial | Indonesia | 1985 | Asian | 1 |
| AF192895 | H15483 | E1 partial | Philippines | 1985 | Asian | 1 |
| AF192898 | 1455/75 | E1 partial | Thailand | 1975 | Asian | 1 |
| AF192901 | Gibbs 63-263 | E1 partial | India | 1963 | Asian | 1 |
| AF192902 | PO731460 | E1 partial | India | 1973 | Asian | 1 |
| AF192897 | C-03295 | E1 partial | Thailand | 1995 | Asian | 1 |
| AF192900 | SV045196 | E1 partial | Thailand | 1996 | Asian | 1 |
| L37661 | Vaccine strain | polyprotein gene | Na | na | Asian | na |
| AF192892 | 37997 | E1 partial | Na | na | West African | 1 |
| AY726732 | 37997 | Complete genome | Senegal | 1983 | West African | 4 |
| AF192891 | PM2951 | E1 partial | Senegal | 1966 | West African | 1 |
| AF192893 | IbH35 E1 | E1 partial | Nigeria | 1964 | West African | 1 |

References: (1) Powers et al., Pastorino et al., 2004; (3) Khan et al., 2002; (4) Vanlandingham et al., 2005.
(b) Democratic Republic of the Congo

TABLE 8

Sequence percent similarity based on amino acids and nucleotides (in parentheses) for the structural (SP) and non-structural (NSP) proteins of selected Alphaviruses.

| Virus | Strain | Accession No. | 05.115/06.49 NSP | 05.115 SP | 06.49 SP |
|---|---|---|---|---|---|
| CHIKV | 05.115 | To be submitted | 100 (100) | 100 (100) | — |
| | 06.49 | To be submitted | 100 (99.97) | 99.91 (99.95) | 100 (100) |
| | S27 | AF369024 | 98.79 (97.3) | 98.47 (97.34) | 98.38 (97.33) |
| | 37997 | AY726732 | 95.88 (85.5) | 95.82 (84.87) | 95.74 (84.81) |
| | Nagpur | AY424803 | NA | 97.18 (94.85) | 97.10 (94.79) |
| | Vaccine | L37661 | NA | 96.92 (94.24) | 96.83 (94.19) |
| ONNV | Gulu | M20303 | 85.90 | 87.30 | 87.22 |
| SFV | 42S RNA genome | X04129 | 70.55 | 65.20 | 65.20 |
| RRV | NB5092 | M20162 | 69.66 | 64.40 | 64.40 |
| SINV | HRSP | J02363 | 59.25 | 47.40 | 47.31 |

CHIKV: chikungunya virus;
ONNV: o'nyong-nyong virus;
SFV: Semliki Forest virus;
RRV: Ross River virus;
SINV: Sindbis virus
NA: Not Available.

TABLE 9

| List of biological assays performed to validate the reactivity of anti-CHIK E2 MAbs BIOLOGICAL ASSAYS |
|---|
| ELISA on solubilized antigens from CHIK virions |
| ELISA on purified CHIK virions (La Réunion Isl.) |
| ELISA on purified CHIK virions (+ TX-100) |
| ELISA on purified CHIK virions (+ NP-40) |
| IF assay on CHIKV-infected VERO cells |
| FACS analysis on cell surface of CHIKV-infected VERO cells |
| Western blot on recombinant CHIK sE2 from S2 cells |
| IF assay on stable TRIP/CHIK.sE2-transduced 293A cell clone |
| Western blot on recombinant CHIK sE2 from TRIP/CHIK.sE2-transduced 293A cell clone |

REFERENCES

1. Strauss E G, Strauss J H (1986) Structure and replication of the alphavirus genome. In Schlesinger S, Schlesinger M J, editors. The Togaviridae and Flaviviridae. New York: Plenum Press. pp. 35-90.
2. Porterfield J H (1980) Antigenic characteristics and classification of the Togaviridae. In: Schlesinger R, editor. The Togaviruses. New York: Academic Press. pp. 13-46.
3. Ross R W (1956) The Newala epidemic. III. The virus: isolation, pathogenic properties and relationship to the epidemic. J Hyg 54: 177-191.
4. Jupp P G, McIntosh B M (1988) Chikungunya disease. In: editors MTP, editor. The Arboviruses: epidemiology and ecology. Boca Raton, Fla.: CRC Press. pp. 137-13 157.
5. Johnston R E, Peters C J (1996) Alphaviruses associated primarily with fever and polyarthritis. In: Fields B N, Knipe D M, Howley P M, editors. Fields Virology. pp. 16 843-898.
6. Pastorino B, Muyembe-Tamfum J J, Bessaud M, Tock F, Tolou H, et al. (2004) Epidemic resurgence of Chikungunya virus in democratic Republic of the Congo: identification of a new central African strain. J Med Virol 74: 277-282.
7. Laras K, Sukri N C, Larasati R P, Bangs M J, Kosim R, et al. (2005) Tracking the re-emergence of epidemic chikungunya virus in Indonesia. Trans R Soc Trop Med Hyg 99: 128-141.
8. Paquet C, Quatresous I, Solet J L, Sissoko D, Renault P (2006) Chikungunya outbreak in Reunion: epidemiology and surveillance, 2005 to early January 2006. Eurosurveillance weekly 11: 2.
9. Khan A H, Morita K, Parquet Md Mdel C, Hasebe F, Mathenge E G, et al. (2002) Complete nucleotide sequence of chikungunya virus and evidence for an internal polyadenylation site. J Gen Virol 83: 3075-3084.
10. Powers A M, Brault A C, Tesh R B, Weaver S C (2000) Re-emergence of Chikungunya and O'nyong-nyong viruses: evidence for distinct geographical lineages and distant evolutionary relationships. J Gen Virol 81: 471-479.
11. Gordon D A C, Green P. (1998) Consed: a graphical tool for sequence finishing. Genome Res 8: 195-202.
12. Rozas J, Sanchez-DelBarrio J C, Messeguer X, Rozas R (2003) DnaSP, DNA 2 polymorphism analyses by the coalescent and other methods. Bioinformatics 19: 2496-2497.
13. Xia X, Xie Z (2001) DAMBE: software package for data analysis in molecular biology and evolution. J Hered 92: 371-373.
14. Thompson J D, Higgins D G, Gibson T J (1994) CLUSTAL W: improving the sensitivity of progressive multiple sequence alignment through sequence weighting, positions-specific gap penalties and weight matrix choice. Nucleic Acids Research 22: 4673-4680.
15. Felsenstein J (1989) PHYLIP—Phylogeny Interferne Package (version 3.2). Cladistics 5: 164-166.
16. Hofacker I L (2003) Vienna RNA secondary structure server. Nucleic Acids Res 31: 3429-3431.
17. Kumar S, Tamura K, Nei M (2004) MEGA3: Integrated software for Molecular Evolutionary Genetics Analysis and sequence alignment. Brief Bioinform 5: 150-163.
18. Martin D P, Williamson C, Posada D (2005) RDP2: recombination detection and analysis from sequence alignments. Bioinformatics 21: 260-262.
19. Roussel A, Lescar J, Vaney M C, Wengler G, Wengler G, et al. (2006) Structure and interactions at the viral surface of the envelope protein E1 of semliki forest virus. Structure 14: 75-86.
20. Carson M (1987) Ribbon models of macromolecules. J Mol Graph 5: 103-106.
21. Strauss J H, Strauss E G (1994) The alphaviruses: gene expression, replication, and evolution. Microbiol. Rev 58: 491-562.

22. Layergne A, Thoisy B D, Lacoste V, Pascal's H, Pouliquen J F, et al. (2005) Mayaro virus: Complete nucleotide sequence and phylogenetic relationships with other alphaviruses. Virus Res in press.
23. Lanciotti R S, Ludwig M L, Rwaguma E B, Lutwama J J, Kram T M, et al. (1998) Emergence of epidemic O' nyong-nyong fever in Uganda after a 35-year absence: genetic characterization of the virus. Virology 252: 258-268.
24. Strauss E G, Levinson R, Rice C M, Dalrymple J, Strauss J H (1988) Nonstructural proteins nsP3 and nsP4 of Ross River and O'Nyong-nyong viruses: sequence and comparison with those of other alphaviruses. Virology 164: 265-274.
25. Griffin D E (2001) Alphaviruses. In: Knipe D M, Howley P M, editors. Fields Virology. Philadelphia: Lippincott Williams & Wilkins. pp. 917-962.
26. Vashishtha M, Phalen T, Marquardt M T, Ryu J S, Ng A C, et al. (1998) A single point mutation controls the cholesterol dependence of Semliki Forest virus entry and exit. J Cell Biol 140: 91-99.
27. Ahn A, Schoepp R J, Sternberg D, Kielian M (1999) Growth and stability of a cholesterol-independent Semliki Forest virus mutant in mosquitoes. Virology 262: 452-456.
28. Williams M C, Woodall J P, Corbet P S, Gillett J D (1965) O'nyong-Nyong Fever: An Epidemic Virus Disease In East Africa. 8. Virus Isolations From *Anopheles* Mosquitoes. Trans R Soc Trop Med Hyg 59: 300-306.
29. Weaver S C, Barrett A D (2004) Transmission cycles, host range, evolution and emergence of arboviral disease. Nat Rev Microbiol 2: 789-801.
30. Lu Y E, Cassese T, Kielian M (1999) The cholesterol requirement for sindbis virus entry and exit and characterization of a spike protein region involved in cholesterol dependence. J Viroi 73: 4272-4278.
31. Holland J, Spindler K, Horodyski F, Grabau E, Nichol S, et al. (1982) Rapid evolution of RNA genomes. Science 215: 1577-1585.
32. Domingo E, Holland J J (1997) RNA virus mutations and fitness for survival. Annu Rev Microbiol 51: 151-178.
33. Vignuzzi M, Stone J K, Arnold J J, Cameron C E, Andino R (2006) Quasispecies diversity determines pathogenesis through cooperative interactions in a viral population. Nature 439: 344-348.
34. Kim K H, Rumenapf T, Strauss E G, Strauss J H (2004) Regulation of Semliki Forest virus RNA replication: a model for the control of alphavirus pathogenesis in invertebrate hosts. Virology 323: 153-163.
35. Heise C, Kirn D H (2000) Replication-selective adenoviruses as oncolytic agents. J Clin Invest 105: 847-851.
36. Heise M T, White L J, Simpson D A, Leonard C, Bernard K A, et al. (2003) An attenuating mutation in nsP1 of the Sindbis-group virus S.A.AR86 accelerates non-structural protein processing and up-regulates viral 26S RNA synthesis. J Virol 77: 1149-1156.
37. Suthar M S, Shabman R, Madric K, Lambeth C, Heise M T (2005) Identification of adult mouse neurovirulence determinants of the Sindbis virus strain AR86. J Virol 79: 4219-4228.
38. Condon R J, Rouse I L (1995) Acute symptoms and sequelae of Ross River virus infection in South-Western Australia: a follow-up study. Clin Diagn Virol 3: 273-284.
39. Selden S M, Cameron 1 ron A S (1996) Changing epidemiology of Ross River virus disease in South Australia. Med. J Aust 165: 313-317.
40. Mazaud R, Salaün J J, Montabone H, Goube P, Bazillio R (1971) Troubles neurologiques et sensoriels aigus dans la dengue et Ia fièvre á Chikungunya. Bull Soc Pathol Exot 64: 22-30.
41. Nimmannitya S, Halstead S B, Cohen S N, Margiotta M R (1969) Dengue and chikungunya virus infection in man in Thailand, 1962-1964.1. Observations on hospitalized patients with hemorrhagic fever. Am J Trop Med Hyg 18: 954-971.
42. Gratz N G (2004) Critical review of the vector status of *Aedes albopictus*. Med Vet Entomol 18: 215-227.
43. Lescar J, Roussel A, Wien M W, Navaza J, Fuller S D, et al. (2001) The Fusion glycoprotein shell of Semliki Forest virus: an icosahedral assembly primed for fusogenic activation at endosomal pH. Cell 105: 137-148.

The invention claimed is:

1. A vector comprising a nucleotide sequence encoding a Chikungunya virus E2 protein and a heterologous nucleotide sequence regulating expression of the E2 protein, wherein the E2 protein comprises a threonine at amino acid position 489 of the Chikungunya virus E2 protein and a methionine at amino acid position 637 of the Chikungunya virus E2 protein.

2. The vector of claim 1, further comprising a nucleotide sequence encoding a Chikungunya E1 protein and a heterologous nucleotide sequence regulating expression of the E1 protein, wherein the E1 protein comprises a valine at amino acid position 1078 of the Chikungunya virus E1 protein, a glutamic acid at position 1093 of the Chikungunya virus E1 protein and an alanine at position 1131 of the Chikungunya virus E1 protein.

3. The vector of claim 1, further comprising a nucleotide sequence encoding a Chikungunya 6K protein and a heterologous nucleotide sequence regulating expression of the 6K protein, wherein the 6K protein comprises an isoleucine at amino acid position 756 of the Chikungunya virus 6K protein and a valine at position 802 of the Chikungunya virus 6K protein.

4. The vector of claim 1, wherein the E2 protein further comprises a lysine at amino acid position 382, a methionine at amino acid position 399, a glutamic acid at amino acid position 404, a threonine at amino acid position 485, a methionine at amino acid position 506, a threonine at amino acid position 536, an asparagine at amino acid position 624, a threonine at amino acid position 669, a threonine at amino acid position 700, and an alanine at amino acid position 711 of the Chikungunya virus E2 protein.

5. The vector of claim 4, wherein the vector encodes the amino acid sequence of SEQ ID NO:21.

6. The vector of claim 5, wherein the vector is a viral vector.

7. The vector of claim 6, wherein the vector is a recombinant lentiviral vector.

8. The vector of claim 5, wherein the vector is plasmid.

9. The vector of claim 5, wherein the vector comprises a synthetic soluble E2 gene that has been modified for optimal codon usage in mammalian cells.

10. A method for producing a Chikungunya virus E2 protein comprising introducing the vector of claim 5 into a host cell.

11. The vector of claim 1, wherein the vector encodes the amino acid sequence of SEQ ID NO:27.

12. A method for producing a Chikungunya virus E2 protein comprising introducing the vector of claim 11 into a host cell.

13. The vector of claim 1, wherein the vector is a viral vector.

14. The vector of claim 13, wherein the vector is a recombinant lentiviral vector.

15. The vector of claim 1, wherein the vector is plasmid.

16. The vector of claim 1, wherein the vector comprises a synthetic soluble E2 gene that has been modified for optimal codon usage in mammalian cells.

17. A method for producing a Chikungunya virus E2 protein comprising introducing the vector of claim 1 into a host cell.

* * * * *

UNITED STATES PATENT AND TRADEMARK OFFICE

CERTIFICATE OF CORRECTION

PATENT NO. : 9,442,114 B2
APPLICATION NO. : 14/335065
DATED : September 13, 2016
INVENTOR(S) : Despres et al.

It is certified that error appears in the above-identified patent and that said Letters Patent is hereby corrected as shown below:

On the Title Page

Item (66): replace "filed on Sep. 29, 2009, now abandoned. Substitute for application No. PCT/IB2007/001716, filed on Mar. 15, 2007" with -- filed as application No. PCT/IB2007/001716 on Mar. 15, 2007, now abandoned --.

Signed and Sealed this
Fifteenth Day of August, 2017

Joseph Matal

*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 103

<210> SEQ ID NO 1
<211> LENGTH: 11601
<212> TYPE: DNA
<213> ORGANISM: Chikungunya virus

<400> SEQUENCE: 1

caaagcaaga gattaataac ccatcatgga tcctgtgtac gtggacatag acgctgacag      60

cgcctttttg aaggccctgc aacgtgcgta ccccatgttt gaggtggaac caaggcaggt     120

cacaccgaat gaccatgcta atgctagagc gttctcgcat ctagctataa aactaataga     180

gcaggaaatt gaccccgact caaccatcct ggatatcggc agtgcgccag caaggaggat     240

gatgtcggac aggaagtacc actgcgtctg cccgatgcgc agtgcggaag atcccgagag     300

actcgccaat tatgcgagaa agctagcatc tgccgcagga aaagtcctgg acagaaacat     360

ctctggaaag atcggggact tacaagcagt aatggccgtg ccagacacgg agacgccaac     420

attctgctta cacacagacg tctcatgtag acagagagca gacgtcgcta tataccaaga     480

cgtctatgct gtacacgcac ccacgtcgct ataccaccag gcgattaaag ggtccgagt      540
```

-continued

```
ggcgtactgg gttgggttcg acacaacccc gttcatgtac aatgccatgg cgggtgccta    600
cccctcatac tcgacaaact gggcagatga gcaggtactg aaggctaaga acataggatt    660
atgttcaaca gacctgacgg aaggtagacg aggcaagttg tctattatga gagggaaaaa    720
gctaaaaccg tgcgaccgtg tgctgttctc agtagggtca acgctctacc cggaaagccg    780
caagctactt aagagctggc acctgccatc ggtgttccat ttaaagggca aactcagctt    840
cacatgccgc tgtgatacag tggtttcgtg tgagggctac gtcgttaaga gaataacgat    900
gagcccaggc ctttatggaa aaaccacagg gtatgcggta acccaccacg cagacggatt    960
cctgatgtgc aagactaccg acacggttga cggcgaaaga gtgtcattct cggtgtgcac   1020
atacgtgccg gcgaccattt gtgatcaaat gaccggcatc cttgctacag aagtcacgcc   1080
ggaggatgca cagaagctgt tggtggggct gaaccagaga atagtggtta acggcagaac   1140
gcaacggaat acgaacacca tgaaaaatta tctgcttccc gtggtcgccc aagccttcag   1200
taagtgggca aaggagtgcc ggaaagacat ggaagatgaa aaactcctgg gggtcagaga   1260
aagaacactg acctgctgct gtctatgggc attcaagaag cagaaaacac acacggtcta   1320
caagaggcct gatacccagt caattcagaa ggttcaggcc gagtttgaca gctttgtggt   1380
accgagtctg tggtcgtccg ggttgtcaat ccctttgagg actagaatca aatggttgtt   1440
aagcaaggtg ccaaaaaccg acctgatccc atacagcgga gacgcccgag aagcccggga   1500
cgcagaaaaa gaagcagagg aagaacgaga agcagaactg actcgcgaag ccctaccacc   1560
tctacaggca gcacaggaag atgttcaggt cgaaatcgac gtggaacagc ttgaggacag   1620
agcgggcgca ggaataatag agactccgag aggagctatc aaagttactg cccaaccaac   1680
agaccacgtc gtgggagagt acctggtact ctccccgcag accgtactac gtagccagaa   1740
gctcagtctg attcacgctt tggcggagca agtgaagacg tgcacgcaca acggacgagc   1800
agggaggtat gcggtcgaag cgtacgacgg ccgagtccta gtgccctcag gctatgcaat   1860
ctcgcctgaa gacttccaga gtctaagcga aagcgcaacg atggtgtata acgaaagaga   1920
gttcgtaaac agaaagctac accatattgc gatgcacgga ccagccctga acaccgacga   1980
agagtcgtat gagctggtga gggcagagag gacagaacac gagtacgtct acgacgtgga   2040
tcagagaaga tgctgtaaga aggaagaagc cgcaggactg gtactggtgg gcgacttgac   2100
taatccgccc taccacgaat tcgcatatga agggctaaaa atccgccctg cctgcccata   2160
caaaattgca gtcataggag tcttcggagt accgggatct ggcaagtcag ctattatcaa   2220
gaacctagtt accaggcagg acctggtgac tagcggaaag aaagaaaact gccaagaaat   2280
caccaccgac gtgatgagac agagaggtct agagatatct gcacgtacgg ttgactcgct   2340
gctcttgaat ggatgcaaca gaccagtcga cgtgttgtac gtagacgagg cgtttgcgtg   2400
ccactctgga acgctacttg ctttgatcgc cttggtgaga ccaaggcaga aagttgtact   2460
ttgtggtgac ccgaagcagt gcggcttctt caatatgatg cagatgaaag tcaactataa   2520
tcacaacatc tgcacccaag tgtaccacaa aagtatctcc aggcggtgta cactgcctgt   2580
gaccgccatt gtgtcatcgt tgcattacga aggcaaaatg cgcactacga atgagtacaa   2640
caagccgatt gtagtggaca ctacaggctc aacaaaacct gaccctggag acctcgtgtt   2700
aacgtgcttc agagggtggg ttaaacaact gcaaattgac tatcgtggat acgaggtcat   2760
gacagcagcc gcatcccaag ggttaaccag aaaaggagtt tacgcagtta gacaaaaagt   2820
taatgaaaac ccgctctatg catcaacgtc agagcacgtc aacgtactcc taacgcgtac   2880
```

-continued

```
ggaaggtaaa ctggtatgga agacactttc cggcgacccg tggataaaga cgctgcagaa   2940
cccaccgaaa ggaaacttca aagcaactat taaggagtgg gaggtggagc atgcatcaat   3000
aatggcgggc atctgcagtc accaaatgac cttcgataca ttccaaaata aagccaacgt   3060
ttgttgggct aagagcttgg tccctatcct cgaaacagcg gggataaaac taaatgatag   3120
gcagtggtct cagataattc aagccttcaa agaagacaaa gcatactcac ctgaagtagc   3180
cctgaatgaa atatgtacgc gcatgtatgg ggtggatcta gacagcgggc tattttctaa   3240
accgttggtg tctgtgtatt acgcggataa ccactgggat aataggcctg gagggaaaat   3300
gttcggattt aaccccgagg cagcatccat tctagaaaga aagtatccat tcacaaaagg   3360
gaagtggaac atcaacaagc agatctgcgt gactaccagg aggatagaag actttaaccc   3420
taccaccaac atcataccgg ccaacaggag actaccacac tcattagtgg ccgaacaccg   3480
cccagtaaaa ggggaaagaa tggaatggct ggttaacaag ataaacggcc accacgtgct   3540
cctggtcagt ggctataacc ttgcactgcc tactaagaga gtcacttggg tagcgccgtt   3600
aggtgtccgc ggagcggact acacatacaa cctagagttg ggtctgccag caacgcttgg   3660
taggtatgac ctagtggtca taaacatcca cacacctttt cgcatacacc attaccaaca   3720
gtgcgtcgac cacgcaatga aactgcaaat gctcgggggt gactcattga gactgctcaa   3780
accgggcggc tctctattga tcagagcata tggttacgca gatagaacca gtgaacgagt   3840
catctgcgta ttgggacgca agtttagatc gtctagagcg ttgaaaccac catgtgtcac   3900
cagcaacact gagatgtttt tcctattcag caactttgac aatggcagaa ggaatttcac   3960
aactcatgtc atgaacaatc aactgaatgc agccttcgta ggacaggtca cccgagcagg   4020
atgtgcaccg tcgtaccggg taaaacgcat ggacatcgcg aagaacgatg aagagtgcgt   4080
agtcaacgcc gctaaccctc gcgggttacc gggtgacggt gtttgcaagg cagtatacaa   4140
aaaatggccg gagtccttta agaacagtgc aacaccagtg ggaaccgcaa aaacagttat   4200
gtgcggtacg tatccagtaa tccacgctgt tggaccaaac ttctctaatt attcggagtc   4260
tgaaggggac cgggaattgg cagctgccta tcgagaagtc gcaaaggaag taactaggct   4320
gggagtaaat agtgtagcta tacctctcct ctccacaggt gtatactcag gagggaaaga   4380
caggctgacc cagtcactga accacctctt tacagccatg gactcgacgg atgcagacgt   4440
ggtcatctac tgccgcgaca aagaatggga gaagaaaata tctgaggcca tacagatgcg   4500
gacccaagta gagctgctgg atgagcacat ctccatagac tgcgatattg ttcgcgtgca   4560
ccctgacagc agcttggcag gcagaaaagg atacagcacc acggaaggcg cactgtactc   4620
atatctagaa gggacccgtt ttcatcagac ggctgtggat atggcggaga tacatactat   4680
gtggccaaag caaacagagg ccaatgagca agtctgccta tatgccctgg gggaaagtat   4740
tgaatcgatc aggcagaaat gcccggtgga tgatgcagac gcatcatctc cccccaaaac   4800
tgtcccgtgc ctttgccgtt acgctatgac tccagaacgc gtcacccggc ttcgcatgaa   4860
ccacgtcaca agcataattg tgtgttcttc gtttcccctc ccaaagtaca aaatagaagg   4920
agtgcaaaaa gtcaaatgct ctaaggtaat gctatttgac cacaacgtgc catcgcgcgt   4980
aagtccaagg gaatatagat cttcccagga gtctgcacag gaggcgagta caatcacgtc   5040
actgacgcat agtcaattcg acctaagcgt tgatggcgag atactgcccg tcccgtcaga   5100
cctggatgct gacgccccag ccctagaacc agcactagac gacggggcga cacacacgct   5160
gccatccaca accggaaacc ttgcggccgt gtctgattgg gtaatgagca ccgtacctgt   5220
cgcgccgccc agaagaaggc gagggagaaa cctgactgtg acatgtgacg agagagaagg   5280
```

-continued

```
gaatataaca cccatggcta gcgtccgatt ctttagggca gagctgtgtc cggtcgtaca   5340
agaaacagcg gagacgcgtg acacagcaat gtctcttcag gcaccaccga gtaccgccac   5400
ggaaccgaat catccgccga tctccttcgg agcatcaagc gagacgttcc ccattacatt   5460
tggggacttc aacgaaggag aaatcgaaag cttgtcttct gagctactaa ctttcggaga   5520
cttcttacca ggagaagtgg atgacttgac agacagcgac tggtccacgt gctcagacac   5580
ggacgacgag ttatgactag acagggcagg tgggtatata ttctcgtcgg acaccggtcc   5640
aggtcattta caacagaagt cagtacgcca gtcagtgctg ccggtgaaca ccctggagga   5700
agtccacgag gagaagtgtt acccacctaa gctggatgaa gcaaaggagc aactattact   5760
taagaaactc caggagagtg catccatggc caacagaagc aggtatcagt cgcgcaaagt   5820
agaaaacatg aaagcagcaa tcatccagag actaaagaga ggctgtagac tatacttaat   5880
gtcagagacc ccaaaagtcc ctacttaccg gactacatat ccggcgcctg tgtactcgcc   5940
tccgatcaac gtccgattgt ccaatcccga gtccgcagtg gcagcatgca atgagttctt   6000
agctagaaac tatccaactg tctcatcata ccaaattacc gacgagtatg atgcatatct   6060
agacatggtg gacgggtcgg agagttgcct ggaccgagcg acattcaatc cgtcaaaact   6120
caggagctac ccgaaacagc acgcttacca cgcgccctcc atcagaagcg ctgtaccgtc   6180
cccattccag aacacactac agaatgtact ggcagcagcc acgaaaagaa actgcaacgt   6240
cacacagatg agggaattac ccactttgga ctcagcagta ttcaacgtgg agtgtttcaa   6300
aaaattcgca tgcaaccaag aatactggga agaatttgct gccagcccta ttaggataac   6360
aactgagaat ttagcaacct atgttactaa actaaaaggg ccaaaagcag cagcgctatt   6420
cgcaaaaacc cataatctac tgccactaca ggaagtacca atggataggt tcacagtaga   6480
tatgaaaagg gacgtgaagg tgactcctgg tacaaagcat acagaggaaa gacctaaggt   6540
gcaggttata caggcggctg aacccttggc gacagcatac ctatgtggga ttcacagaga   6600
gctggttagg aggctgaacg ccgtcctcct acccaatgta catacactat ttgacatgtc   6660
tgccgaggat ttcgatgcca tcatagccgc acactttaag ccaggagaca ctgttttgga   6720
aacggacata gcctcctttg ataagagcca agatgattca cttgcgctta ctgctttgat   6780
gctgttagag gatttagggg tggatcactc cctgctggac ttgatagagg ctgctttcgg   6840
agagatttcc agctgtcacc taccgacagg tacgcgcttc aagttcggcg ccatgatgaa   6900
atcaggtatg ttcctaactc tgttcgtcaa cacattgtta aacatcacca tcgccagccg   6960
agtgctggaa gatcgtctga caaaatccgc gtgcgcggcc ttcatcggcg acgacaacat   7020
aatacatgga gtcgtctccg atgaattgat ggcagccaga tgtgccactt ggatgaacat   7080
ggaagtgaag atcatagatg cagttgtatc cttgaaagcc ccttactttt gtggagggtt   7140
tatactgcac gatactgtga caggaacagc ttgcagagtg gcagacccgc taaaaaggct   7200
ttttaaactg ggcaaaccgc tagcggcagg tgacgaacaa gatgaagata gaagacgagc   7260
gctggctgac gaagtgatca gatggcaacg aacagggcta attgatgagc tggagaaagc   7320
ggtatactct aggtacgaag tgcagggtat atcagttgtg gtaatgtcca tggccacctt   7380
tgcaagctcc agatccaact tcgagaagct cagaggaccc gtcataactt tgtacggcgg   7440
tcctaaatag gtacgcacta cagctaccta ttttgcagaa gccgacagca agtatctaaa   7500
cactaatcag ctacaatgga gttcatccca acccaaactt tttacaatag gaggtaccag   7560
cctcgaccct ggactccgcg ccctactatc caagtcatca ggcccagacc gcgccctcag   7620
```

-continued

```
aggcaagctg ggcaacttgc ccagctgatc tcagcagtta ataaactgac aatgcgcgcg   7680
gtaccccaac agaagccacg caggaatcgg aagaataaga agcaaaagca aaaacaacag   7740
gcgccacaaa acaacacaaa tcaaaagaag cagccaccta aaaagaaacc ggctcaaaag   7800
aaaaagaagc cgggccgcag agagaggatg tgcatgaaaa tcgaaaatga ttgtattttc   7860
gaagtcaagc acgaaggtaa ggtaacaggt tacgcgtgcc tggtggggga caaagtaatg   7920
aaaccagcac acgtaaaggg gaccatcgat aacgcggacc tggccaaact ggcctttaag   7980
cggtcatcta agtatgacct tgaatgcgcg cagatacccg tgcacatgaa gtccgacgct   8040
tcgaagttca cccatgagaa accggagggg tactacaact ggcaccacgg agcagtacag   8100
tactcaggag gccggttcac catccctaca ggtgctggca aaccagggga cagcggcaga   8160
ccgatcttcg acaacaaggg acgcgtggtg gccatagtct taggaggagc taatgaagga   8220
gcccgtacag ccctctcggt ggtgacctgg aataaagaca ttgtcactaa aatcaccccc   8280
gagggggccg aagagtggag tcttgccatc ccagttatgt gcctgttggc aaacaccacg   8340
ttcccctgct cccagccccc ttgcacgccc tgctgctacg aaaaggaacc ggaggaaacc   8400
ctacgcatgc ttgaggacaa cgtcatgaga cctgggtact atcagctgct acaagcatcc   8460
ttaacatgtt ctccccaccg ccagcgacgc agcaccaagg acaacttcaa tgtctataaa   8520
gccacaagac catacttagc tcactgtccc gactgtggag aagggcactc gtgccatagt   8580
cccgtagcac tagaacgcat cagaaatgaa gcgacagacg ggacgctgaa aatccaggtc   8640
tccttgcaaa tcggaataaa gacggatgac agccacgatt ggaccaagct gcgttatatg   8700
gacaaccaca tgccagcaga cgcagagagg gcggggctat ttgtaagaac atcagcaccg   8760
tgtacgatta ctggaacaat gggacacttc atcctggccc gatgtccaaa aggggaaact   8820
ctgacggtgg gattcactga cagtaggaag attagtcact catgtacgca cccatttcac   8880
cacgaccctc ctgtgatagg tcgggaaaaa ttccattccc gaccgcagca cggtaaagag   8940
ctaccttgca gcacgtacgt gcagagcacc gccgcaacta ccgaggagat agaggtacac   9000
atgcccccag acacccctga tcgcacatta atgtcacaac agtccggcaa cgtaaagatc   9060
acagtcaatg gccagacggt gcggtacaag tgtaattgcg gtggctcaaa tgaaggacta   9120
acaactacag acaaagtgat taataactgc aaggttgatc aatgtcatgc cgcggtcacc   9180
aatcacaaaa agtggcagta taactcccct ctggtcccgc gtaatgctga acttggggac   9240
cgaaaaggaa aaattcacat cccgtttccg ctggcaaatg taacatgcag ggtgcctaaa   9300
gcaaggaacc ccaccgtgac gtacgggaaa aaccaagtca tcatgctact gtatcctgac   9360
cacccaacac tcctgtccta ccggaatatg ggagaagaac caaactatca agaagagtgg   9420
gtgatgcata agaaggaagt cgtgctaacc gtgccgactg aagggctcga ggtcacgtgg   9480
ggcaacaacg agccgtataa gtattggccg cagttatcta caaacggtac agcccatggc   9540
cacccgcatg agataattct gtattattat gagctgtacc ccactatgac tgtagtagtt   9600
gtgtcagtgg ccacgttcat actcctgtcg atggtgggta tggcagcggg gatgtgcatg   9660
tgtgcacgac gcagatgcat cacaccgtat gaactgacac caggagctac cgtccctttc   9720
ctgcttagcc taatatgctg catcagaaca gctaaagcgg ccacatacca agaggctgcg   9780
atatacctgt ggaacgagca gcaacctttg ttttggctac aagcccttat tccgctggca   9840
gccctgattg ttctatgcaa ctgtctgaga ctcttaccat gctgctgtaa aacgttggct   9900
tttttagccg taatgagcgt cggtgcccac actgtgagcg cgtacgaaca cgtaacagtg   9960
atcccgaaca cggtgggagt accgtataag actctagtca atagacctgg ctacagcccc  10020
```

```
atggtattgg agatggaact actgtcagtc actttggagc caacactatc gcttgattac  10080
atcacgtgcg agtacaaaac cgtcatcccg tctccgtacg tgaagtgctg cggtacagca  10140
gagtgcaagg acaaaaacct acctgactac agctgtaagg tcttcaccgg cgtctaccca  10200
tttatgtggg gcggcgccta ctgcttctgc gacgctgaaa acacgcagtt gagcgaagca  10260
cacgtggaga agtccgaatc atgcaaaaca gaatttgcat cagcatacag ggctcatacc  10320
gcatctgcat cagctaagct ccgcgtcctt taccaaggaa ataacatcac tgtaactgcc  10380
tatgcaaacg gcgaccatgc cgtcacagtt aaggacgcca aattcattgt ggggccaatg  10440
tcttcagcct ggacaccttt cgacaacaaa attgtggtgt acaaaggtga cgtctataac  10500
atggactacc cgccctttgg cgcaggaaga ccaggacaat ttggcgatat ccaaagtcgc  10560
acacctgaga gtaaagacgt ctatgctaat acacaactgg tactgcagag accggctgcg  10620
ggtacggtac acgtgccata ctctcaggca ccatctggct ttaagtattg gctaaaagaa  10680
cgcggggcgt cgctgcagca cacagcacca tttggctgcc aaatagcaac aaacccggta  10740
agagcggtga actgcgccgt agggaacatg cccatctcca tcgacatacc ggaagcggcc  10800
ttcactaggg tcgtcgacgc gccctcttta acggacatgt cgtgcgaggt accagcctgc  10860
acccattcct cagactttgg gggcgtcgcc attattaaat atgcagccag caagaaaggc  10920
aagtgtgcgg tgcattcgat gactaacgcc gtcactattc gggaagctga gatagaagtt  10980
gaagggaatt ctcagctgca aatctctttc tcgacggcct tagccagcgc cgaattccgc  11040
gtacaagtct gttctacaca agtacactgt gcagccgagt gccacccccc gaaggaccac  11100
atagtcaact acccggcgtc acataccacc ctcggggtcc aggacatctc cgctacggcg  11160
atgtcatggg tgcagaagat cacgggaggt gtgggactgg ttgttgctgt tgccgcactg  11220
attctaatcg tggtgctatg cgtgtcgttc agcaggcact aacttgacaa ttaagtatga  11280
aggtatatgt gtcccctaag agacacactg tacatagcaa ataatctata gatcaaaggg  11340
ctacgcaacc cctgaatagt aacaaaatac aaaatcacta aaaattataa aaacagaaaa  11400
atacataaat aggtatacgt gtcccctaag agacacattg tatgtaggtg ataagtatag  11460
atcaaagggc cgaataaccc ctgaatagta acaaaatatg aaaatcaata aaaatcataa  11520
aatagaaaaa ccataaacag aagtagttca aagggctata aaacccctga atagtaacaa  11580
aacataaaat taataaaaat c                                            11601
```

<210> SEQ ID NO 2
<211> LENGTH: 11601
<212> TYPE: DNA
<213> ORGANISM: Chikungunya virus

<400> SEQUENCE: 2

```
caaagcaaga gattaataac ccatcatgga tcctgtgtac gtggacatag acgctgacag     60
cgcctttttg aaggccctgc aacgtgcgta ccccatgttt gaggtggaac caaggcaggt    120
cacaccgaat gaccatgcta atgctagagc gttctcgcat ctagctataa aactaataga    180
gcaggaaatt gaccccgact caaccatcct ggatatcggc agtgcgccag caaggaggat    240
gatgtcggac aggaagtacc actgcgtctg cccgatgcgc agtgcggaag atcccgagag    300
actcgccaat tatgcgagaa agctagcatc tgccgcagga aaagtcctgg acagaaacat    360
ctctggaaag atcggggact tacaagcagt aatggccgtg ccagacacgg agacgccaac    420
attctgctta cacacagacg tctcatgtag acagagagca gacgtcgcta tataccaaga    480
```

-continued

```
cgtctatgct gtacacgcac ccacgtcgct ataccaccag gcgattaaag gggtccgagt    540
ggcgtactgg gttgggttcg acacaacccc gttcatgtac aatgccatgg cgggtgccta    600
cccctcatac tcgacaaact gggcagatga gcaggtactg aaggctaaga acataggatt    660
atgttcaaca gacctgacgg aaggtagacg aggcaagttg tctattatga gagggaaaaa    720
gctaaaaccg tgcgaccgtg tgctgttctc agtagggtca acgctctacc cggaaagccg    780
caagctactt aagagctggc acctgccatc ggtgttccat ttaaagggca aactcagctt    840
cacatgccgc tgtgatacag tggtttcgtg tgagggctac gtcgttaaga gaataacgat    900
gagcccaggc ctttatggaa aaaccacagg gtatgcggta acccaccacg cagacggatt    960
cctgatgtgc aagactaccg acacggttga cggcgaaaga gtgtcattct cggtgtgcac   1020
atacgtgccg gcgaccattt gtgatcaaat gaccggcatc cttgctacag aagtcacgcc   1080
ggaggatgca cagaagctgt tggtggggct gaaccagaga atagtggtta acggcagaac   1140
gcaacggaat acgaacacca tgaaaaatta tctgcttccc gtggtcgccc aagccttcag   1200
taagtgggca aaggagtgcc ggaaagacat ggaagatgaa aaactcctgg gggtcagaga   1260
aagaacactg acctgctgct gtctatgggc attcaagaag cagaaaacac acacggtcta   1320
caagaggcct gatacccagt caattcagaa ggttcaggcc gagtttgaca gctttgtggt   1380
accgagtctg tggtcgtccg ggttgtcaat ccctttgagg actagaatca aatggttgtt   1440
aagcaaggtg ccaaaaaccg acctgatccc atacagcgga gacgcccgag aagcccggga   1500
cgcagaaaaa gaagcagagg aagaacgaga agcagaactg actcgcgaag ccctaccacc   1560
tctacaggca gcacaggaag atgttcaggt cgaaatcgac gtggaacagc ttgaggacag   1620
agcgggcgca ggaataatag agactccgag aggagctatc aaagttactg cccaaccaac   1680
agaccacgtc gtgggagagt acctggtact ctccccgcag accgtactac gtagccagaa   1740
gctcagtctg attcacgctt tggcggagca agtgaagacg tgcacgcaca acggacgagc   1800
agggaggtat gcggtcgaag cgtacgacgg ccgagtccta gtgccctcag gctatgcaat   1860
ctcgcctgaa gacttccaga gtctaagcga aagcgcaacg atggtgtata acgaaagaga   1920
gttcgtaaac agaaagctac accatattgc gatgcacgga ccagccctga acaccgacga   1980
agagtcgtat gagctggtga gggcagagag gacagaacac gagtacgtct acgacgtgga   2040
tcagagaaga tgctgtaaga aggaagaagc cgcaggactg gtactggtgg gcgacttgac   2100
taatccgccc taccacgaat tcgcatatga agggctaaaa atccgccctg cctgcccata   2160
caaaattgca gtcataggag tcttcggagt accgggatct ggcaagtcag ctattatcaa   2220
gaacctagtt accaggcagg acctggtgac tagcggaaag aaagaaaact gccaagaaat   2280
caccaccgac gtgatgagac agagaggtct agagatatct gcacgtacgg ttgactcgct   2340
gctcttgaat ggatgcaaca gaccagtcga cgtgttgtac gtagacgagg cgtttgcgtg   2400
ccactctgga acgctacttg ctttgatcgc cttggtgaga ccaaggcaga aagttgtact   2460
ttgtggtgac ccgaagcagt gcggcttctt caatatgatg cagatgaaag tcaactataa   2520
tcacaacatc tgcacccaag tgtaccacaa aagtatctcc aggcggtgta cactgcctgt   2580
gaccgccatt gtgtcatcgt tgcattacga aggcaaaatg cgcactacga atgagtacaa   2640
caagccgatt gtagtggaca ctacaggctc aacaaaacct gaccctggag acctcgtgtt   2700
aacgtgcttc agagggtggg ttaaacaact gcaaattgac tatcgtggat acgaggtcat   2760
gacagcagcc gcatcccaag ggttaaccag aaaaggagtt tacgcagtta gacaaaaagt   2820
taatgaaaac ccgctctatg catcaacgtc agagcacgtc aacgtactcc taacgcgtac   2880
```

-continued ggaaggtaaa ctggtatgga agacactttc cggcgacccg tggataaaga cgctgcagaa 2940
cccaccgaaa ggaaacttca aagcaactat taaggagtgg gaggtggagc atgcatcaat 3000
aatggcgggc atctgcagtc accaaatgac cttcgataca ttccaaaata aagccaacgt 3060
ttgttgggct aagagcttgg tccctatcct cgaaacagcg gggataaaac taaatgatag 3120
gcagtggtct cagataattc aagccttcaa agaagacaaa gcatactcac ctgaagtagc 3180
cctgaatgaa atatgtacgc gcatgtatgg ggtggatcta gacagcgggc tattttctaa 3240
accgttggtg tctgtgtatt acgcggataa ccactgggat aataggcctg gagggaaaat 3300
gttcggattt aaccccgagg cagcatccat tctagaaaga aagtatccat tcacaaaagg 3360
gaagtggaac atcaacaagc agatctgcgt gactaccagg aggatagaag actttaaccc 3420
taccaccaac atcataccgg ccaacaggag actaccacac tcattagtgg ccgaacaccg 3480
cccagtaaaa ggggaaagaa tggaatggct ggttaacaag ataaacggcc accacgtgct 3540
cctggtcagt ggctataacc ttgcactgcc tactaagaga gtcacttggg tagcgccgtt 3600
aggtgtccgc ggagcggact acacatacaa cctagagttg ggtctgccag caacgcttgg 3660
taggtatgac ctagtggtca taaacatcca cacacctttt cgcatacacc attaccaaca 3720
gtgcgtcgac cacgcaatga aactgcaaat gctcgggggt gactcattga gactgctcaa 3780
accgggcggc tctctattga tcagagcata tggttacgca gatagaacca gtgaacgagt 3840
catctgcgta ttgggacgca agtttagatc gtctagagcg ttgaaaccac catgtgtcac 3900
cagcaacact gagatgtttt tcctattcag caactttgac aatggcagaa ggaatttcac 3960
aactcatgtc atgaacaatc aactgaatgc agccttcgta ggacaggtca cccgagcagg 4020
atgtgcaccg tcgtaccggg taaaacgcat ggacatcgcg aagaacgatg aagagtgcgt 4080
agtcaacgcc gctaaccctc gcgggttacc gggtgacggt gtttgcaagg cagtatacaa 4140
aaaatggccg gagtccttta agaacagtgc aacaccagtg ggaaccgcaa aaacagttat 4200
gtgcggtacg tatccagtaa tccacgctgt tggaccaaac ttctctaatt attcggagtc 4260
tgaaggggac cgggaattgg cagctgccta tcgagaagtc gcaaaggaag taactaggct 4320
gggagtaaat agtgtagcta tacctctcct ctccacaggt gtatactcag gagggaaaga 4380
caggctgacc cagtcactga accacctctt tacagccatg gactcgacgg atgcagacgt 4440
ggtcatctac tgccgcgaca aagaatggga gaagaaaata tctgaggcca tacagatgcg 4500
gacccaagta gagctgctgg atgagcacat ctccatagac tgcgatattg ttcgcgtgca 4560
ccctgacagc agcttggcag gcagaaaagg atacagcacc acggaaggcg cactgtactc 4620
atatctagaa gggacccgtt ttcatcagac ggctgtggat atggcggaga tacatactat 4680
gtggccaaag caaacagagg ccaatgagca agtctgccta tatgccctgg gggaaagtat 4740
tgaatcgatc aggcagaaat gcccggtgga tgatgcagac gcatcatctc cccccaaaac 4800
tgtcccgtgc ctttgccgtt acgctatgac tccagaacgc gtcacccggc ttcgcatgaa 4860
ccacgtcaca agcataattg tgtgttcttc gtttcccctc ccaaagtaca aaatagaagg 4920
agtgcaaaaa gtcaaatgct ctaaggtaat gctatttgac cacaacgtgc catcgcgcgt 4980
aagtccaagg gaatatagat cttcccagga gtctgcacag gaggcgagta caatcacgtc 5040
actgacgcat agtcaattcg acctaagcgt tgatggcgag atactgcccg tcccgccaga 5100
cctggatgct gacgccccag ccctagaacc agcactagac gacggggcga cacacacgct 5160
gccatccaca accggaaacc ttgcggccgt gtctgattgg gtaatgagca ccgtacctgt 5220

-continued

```
cgcgccgccc agaagaaggc gagggagaaa cctgactgtg acatgtgacg agagagaagg   5280
gaatataaca cccatggcta gcgtccgatt ctttagggca gagctgtgtc cggtcgtaca   5340
agaaacagcg gagacgcgtg acacagcaat gtctcttcag gcaccaccga gtaccgccac   5400
ggaaccgaat catccgccga tctccttcgg agcatcaagc gagacgttcc ccattacatt   5460
tggggacttc aacgaaggag aaatcgaaag cttgtcttct gagctactaa ctttcggaga   5520
cttcttacca ggagaagtgg atgacttgac agacagcgac tggtccacgt gctcagacac   5580
ggacgacgag ttatgactag acagggcagg tgggtatata ttctcgtcgg acaccggtcc   5640
aggtcattta caacagaagt cagtacgcca gtcagtgctg ccggtgaaca ccctggagga   5700
agtccacgag gagaagtgtt acccacctaa gctggatgaa gcaaaggagc aactattact   5760
taagaaactc caggagagtg catccatggc caacagaagc aggtatcagt cgcgcaaagt   5820
agaaaacatg aaagcagcaa tcatccagag actaaagaga ggctgtagac tatacttaat   5880
gtcagagacc ccaaaagtcc ctacttaccg gactacatat ccggcgcctg tgtactcgcc   5940
tccgatcaac gtccgattgt ccaatcccga gtccgcagtg gcagcatgca atgagttctt   6000
agctagaaac tatccaactg tctcatcata ccaaattacc gacgagtatg atgcatatct   6060
agacatggtg gacgggtcgg agagttgcct ggaccgagcg acattcaatc cgtcaaaact   6120
caggagctac ccgaaacagc acgcttacca cgcgccctcc atcagaagcg ctgtaccgtc   6180
cccattccag aacacactac agaatgtact ggcagcagcc acgaaaagaa actgcaacgt   6240
cacacagatg agggaattac ccactttgga ctcagcagta ttcaacgtgg agtgtttcaa   6300
aaaattcgca tgcaaccaag aatactggga agaatttgct gccagcccta ttaggataac   6360
aactgagaat ttagcaacct atgttactaa actaaaaggg ccaaaagcag cagcgctatt   6420
cgcaaaaacc cataatctac tgccactaca ggaagtacca atggataggt tcacagtaga   6480
tatgaaaagg gacgtgaagg tgactcctgg tacaaagcat acagaggaaa gacctaaggt   6540
gcaggttata caggcggctg aacccttggc gacagcatac ctatgtggga ttcacagaga   6600
gctggttagg aggctgaacg ccgtcctcct acccaatgta catacactat ttgacatgtc   6660
tgccgaggat ttcgatgcca tcatagccgc acactttaag ccaggagaca ctgttttgga   6720
aacggacata gcctcctttg ataagagcca agatgattca cttgcgctta ctgctttgat   6780
gctgttagag gatttagggg tggatcactc cctgctggac ttgatagagg ctgctttcgg   6840
agagatttcc agctgtcacc taccgacagg tacgcgcttc aagttcggcg ccatgatgaa   6900
atcaggtatg ttcctaactc tgttcgtcaa cacattgtta aacatcacca tcgccagccg   6960
agtgctggaa gatcgtctga caaaatccgc gtgtgcggcc ttcatcggcg acgacaacat   7020
aatacatgga gtcgtctccg atgaattgat ggcagccaga tgtgccactt ggatgaacat   7080
ggaagtgaag atcatagatg cagttgtatc cttgaaagcc ccttactttt gtggagggtt   7140
tatactgcac gatactgtga caggaacagc ttgcagagtg gcagacccgc taaaaaggct   7200
ttttaaactg ggcaaaccgc tagcggcagg tgacgaacaa gatgaagata gaagacgagc   7260
gctggctgac gaagtgatca gatggcaacg aacagggcta attgatgagc tggagaaagc   7320
ggtatactct aggtacgaag tgcagggtat atcagttgtg gtaatgtcca tggccacctt   7380
tgcaagctcc agatccaact tcgagaagct cagaggaccc gtcataactt tgtacggcgg   7440
tcctaaatag gtacgcacta cagctaccta ttttgcagaa gccgacagca agtatctaaa   7500
cactaatcag ctacaatgga gttcatccca acccaaactt tttacaatag gaggtaccag   7560
cctcgaccct ggactccgcg ccctactatc caagtcatca ggcccagacc gcgccctcag   7620
```

-continued

```
aggcaagctg ggcaacttgc ccagctgatc tcagcagtta ataaactgac aatgcgcgcg   7680
gtaccccaac agaagccacg caggaatcgg aagaataaga agcaaaagca aaaacaacag   7740
gcgccacaaa acaacacaaa tcaaaagaag cagccaccta aaaagaaacc ggctcaaaag   7800
aaaaagaagc cgggccgcag agagaggatg tgcatgaaaa tcgaaaatga ttgtattttc   7860
gaagtcaagc acgaaggtaa ggtaacaggt tacgcgtgcc tggtggggga caaagtaatg   7920
aaaccagcac acgtaaaggg gaccatcgat aacgcggacc tggccaaact ggcctttaag   7980
cggtcatcta agtatgacct tgaatgcgcg cagatacccg tgcacatgaa gtccgacgct   8040
tcgaagttca cccatgagaa accggagggg tactacaact ggcaccacgg agcagtacag   8100
tactcaggag gccggttcac catccctaca ggtgctggca aaccagggga cagcggcaga   8160
ccgatcttcg acaacaaggg acgcgtggtg gccatagtct taggaggagc taatgaagga   8220
gcccgtacag ccctctcggt ggtgacctgg aataaagaca ttgtcactaa aatcaccccc   8280
gagggggccg aagagtggag tcttgccatc ccagttatgt gcctgttggc aaacaccacg   8340
ttcccctgct cccagccccc ttgcacgccc tgctgctacg aaaaggaacc ggaggaaacc   8400
ctacgcatgc ttgaggacaa cgtcatgaga cctgggtact atcagctgct acaagcatcc   8460
ttaacatgtt ctccccaccg ccagcgacgc agcaccaagg acaacttcaa tgtctataaa   8520
gccacaagac catacttagc tcactgtccc gactgtggag aagggcactc gtgccatagt   8580
cccgtagcac tagaacgcat cagaaatgaa gcgacagacg ggacgctgaa aatccaggtc   8640
tccttgcaaa tcggaataaa gacggatgac agccacgatt ggaccaagct gcgttatatg   8700
gacaaccaca tgccagcaga cgcagagagg gcggggctat ttgtaagaac atcagcaccg   8760
tgtacgatta ctggaacaat gggacacttc atcctggccc gatgtccaaa aggggaaact   8820
ctgacggtgg gattcactga cagtaggaag attagtcact catgtacgca cccatttcac   8880
cacgaccctc ctgtgatagg tcgggaaaaa ttccattccc gaccgcggca cggtaaagag   8940
ctaccttgca gcacgtacgt gcagagcacc gccgcaacta ccgaggagat agaggtacac   9000
atgcccccag acacccctga tcgcacatta atgtcacaac agtccggcaa cgtaaagatc   9060
acagtcaatg gccagacggt gcggtacaag tgtaattgcg gtggctcaaa tgaaggacta   9120
acaactacag acaaagtgat taataactgc aaggttgatc aatgtcatgc cgcggtcacc   9180
aatcacaaaa agtggcagta taactcccct ctggtcccgc gtaatgctga acttggggac   9240
cgaaaaggaa aaattcacat cccgtttccg ctggcaaatg taacatgcag ggtgcctaaa   9300
gcaaggaacc ccaccgtgac gtacgggaaa aaccaagtca tcatgctact gtatcctgac   9360
cacccaacac tcctgtccta ccggaatatg ggagaagaac caaactatca agaagagtgg   9420
gtgatgcata agaaggaagt cgtgctaacc gtgccgactg aagggctcga ggtcacgtgg   9480
ggcaacaacg agccgtataa gtattggccg cagttatcta caaacggtac agcccatggc   9540
cacccgcatg agataattct gtattattat gagctgtacc ccactatgac tgtagtagtt   9600
gtgtcagtgg ccacgttcat actcctgtcg atggtgggta tggcagcggg gatgtgcatg   9660
tgtgcacgac gcagatgcat cacaccgtat gaactgacac caggagctac cgtccctttc   9720
ctgcttagcc taatatgctg catcagaaca gctaaagcgg ccacatacca agaggctgcg   9780
atatacctgt ggaacgagca gcaacctttg ttttggctac aagcccttat tccgctggca   9840
gccctgattg ttctatgcaa ctgtctgaga ctcttaccat gctgctgtaa aacgttggct   9900
tttttagccg taatgagcgt cggtgcccac actgtgagcg cgtacgaaca cgtaacagtg   9960
```

-continued atcccgaaca cggtgggagt accgtataag actctagtca atagacctgg ctacagcccc 10020
atggtattgg agatggaact actgtcagtc actttggagc caacactatc gcttgattac 10080
atcacgtgcg agtacaaaac cgtcatcccg tctccgtacg tgaagtgctg cggtacagca 10140
gagtgcaagg acaaaaacct acctgactac agctgtaagg tcttcaccgg cgtctaccca 10200
tttatgtggg gcggcgccta ctgcttctgc gacgctgaaa acacgcagtt gagcgaagca 10260
cacgtggaga agtccgaatc atgcaaaaca gaatttgcat cagcatacag ggctcatacc 10320
gcatctgcat cagctaagct ccgcgtcctt taccaaggaa ataacatcac tgtaactgcc 10380
tatgcaaacg gcgaccatgc cgtcacagtt aaggacgcca aattcattgt ggggccaatg 10440
tcttcagcct ggacaccttt cgacaacaaa attgtggtgt acaaaggtga cgtctataac 10500
atggactacc cgccctttgg cgcaggaaga ccaggacaat ttggcgatat ccaaagtcgc 10560
acacctgaga gtaaagacgt ctatgctaat acacaactgg tactgcagag accggctgcg 10620
ggtacggtac acgtgccata ctctcaggca ccatctggct ttaagtattg gctaaaagaa 10680
cgcggggcgt cgctgcagca cacagcacca tttggctgcc aaatagcaac aaacccggta 10740
agagcggtga actgcgccgt agggaacatg cccatctcca tcgacatacc ggaagcggcc 10800
ttcactaggg tcgtcgacgc gccctcttta acggacatgt cgtgcgaggt accagcctgc 10860
acccattcct cagactttgg gggcgtcgcc attattaaat atgcagccag caagaaaggc 10920
aagtgtgcgg tgcattcgat gactaacgcc gtcactattc gggaagctga gatagaagtt 10980
gaagggaatt ctcagctgca aatctctttc tcgacggcct tagccagcgc cgaattccgc 11040
gtacaagtct gttctacaca agtacactgt gcagccgagt gccacccccc gaaggaccac 11100
atagtcaact acccggcgtc acataccacc ctcggggtcc aggacatctc cgctacggcg 11160
atgtcatggg tgcagaagat cacgggaggt gtgggactgg ttgttgctgt tgccgcactg 11220
attctaatcg tggtgctatg cgtatcgttc agcaggcact aacttgacaa ttaagtatga 11280
aggtatatgt gtcccctaag agacacactg tacatagcaa ataatctata gatcaaaggg 11340
ctacgcaacc cctgaatagt aacaaaatac aaaatcacta aaaattataa aaacagaaaa 11400
atacataaat aggtatacgt gtcccctaag agacacattg tatgtaggtg ataagtatag 11460
atcaaagggc cgaataaccc ctgaatagta acaaaatatg aaaatcaata aaaatcataa 11520
aatagaaaaa ccataaacag aagtagttca aagggctata aaacccctga atagtaacaa 11580
aacataaaat taataaaaat c 11601

<210> SEQ ID NO 3
<211> LENGTH: 11601
<212> TYPE: DNA
<213> ORGANISM: Chikungunya virus

<400> SEQUENCE: 3
caaagcaaga gattaataac ccatcatgga tcctgtgtac gtggacatag acgctgacag 60
cgcctttttg aaggccctgc aacgtgcgta ccccatgttt gaggtggaac caaggcaggt 120
cacaccgaat gaccatgcta atgctagagc gttctcgcat ctagctataa aactaataga 180
gcaggaaatt gaccccgact caaccatcct ggatatcggc agtgcgccag caaggaggat 240
gatgtcggac aggaagtacc actgcgtctg cccgatgcgc agtgcggaag atcccgagag 300
actcgccaat tatgcgagaa agctagcatc tgccgcagga aaagtcctgg acagaaacat 360
ctctggaaag atcggggact tacaagcagt aatggccgtg ccagacacgg agacgccaac 420
attctgctta cacacagacg tctcatgtag acagagagca gacgtcgcta tataccaaga 480

```
cgtctatgct gtacacgcac ccacgtcgct ataccaccag gcgattaaag gggtccgagt    540
ggcgtactgg gttgggttcg acacaacccc gttcatgtac aatgccatgg cgggtgccta    600
cccctcatac tcgacaaact gggcagatga gcaggtactg aaggctaaga acataggatt    660
atgttcaaca gacctgacgg aaggtagacg aggcaagttg tctattatga gagggaaaaa    720
gctaaaaccg tgcgaccgtg tgctgttctc agtagggtca acgctctacc cggaaagccg    780
caagctactt aagagctggc acctgccatc ggtgttccat ttaaagggca aactcagctt    840
cacatgccgc tgtgatacag tggtttcgtg tgagggctac gtcgttaaga gaataacgat    900
gagcccaggc ctttatggaa aaaccacagg gtatgcggta acccaccacg cagacggatt    960
cctgatgtgc aagactaccg acacggttga cggcgaaaga gtgtcattct cggtgtgcac   1020
atacgtgccg gcgaccattt gtgatcaaat gaccggcatc cttgctacag aagtcacgcc   1080
ggaggatgca cagaagctgt tggtggggct gaaccagaga atagtggtta acggcagaac   1140
gcaacggaat acgaacacca tgaaaaatta tctgcttccc gtggtcgccc aagccttcag   1200
taagtgggca aaggagtgcc ggaaagacat ggaagatgaa aaactcctgg gggtcagaga   1260
aagaacactg acctgctgct gtctatgggc attcaagaag cagaaaacac acacggtcta   1320
caagaggcct gatacccagt caattcagaa ggttcaggcc gagtttgaca gctttgtggt   1380
accgagtctg tggtcgtccg ggttgtcaat ccctttgagg actagaatca aatggttgtt   1440
aagcaaggtg ccaaaaaccg acctgatccc atacagcgga gacgcccgag aagcccggga   1500
cgcagaaaaa gaagcagagg aagaacgaga agcagaactg actcgcgaag ccctaccacc   1560
tctacaggca gcacaggaag atgttcaggt cgaaatcgac gtggaacagc ttgaggacag   1620
agcgggcgca ggaataatag agactccgag aggagctatc aaagttactg cccaaccaac   1680
agaccacgtc gtgggagagt acctggtact ctccccgcag accgtactac gtagccagaa   1740
gctcagtctg attcacgctt tggcggagca agtgaagacg tgcacgcaca acggacgagc   1800
agggaggtat gcggtcgaag cgtacgacgg ccgagtccta gtgccctcag gctatgcaat   1860
ctcgcctgaa gacttccaga gtctaagcga aagcgcaacg atggtgtata acgaaagaga   1920
gttcgtaaac agaaagctac accatattgc gatgcacgga ccagccctga acaccgacga   1980
agagtcgtat gagctggtga gggcagagag gacagaacac gagtacgtct acgacgtgga   2040
tcagagaaga tgctgtaaga aggaagaagc cgcaggactg gtactggtgg gcgacttgac   2100
taatccgccc taccacgaat tcgcatatga agggctaaaa atccgccctg cctgcccata   2160
caaaattgca gtcataggag tcttcggagt accgggatct ggcaagtcag ctattatcaa   2220
gaacctagtt accaggcagg acctggtgac tagcggaaag aaagaaaact gccaagaaat   2280
caccaccgac gtgatgagac agagaggtct agagatatct gcacgtacgg ttgactcgct   2340
gctcttgaat ggatgcaaca gaccagtcga cgtgttgtac gtagacgagg cgtttgcgtg   2400
ccactctgga acgctacttg ctttgatcgc cttggtgaga ccaaggcaga aagttgtact   2460
ttgtggtgac ccgaagcagt gcggcttctt caatatgatg cagatgaaag tcaactataa   2520
tcacaacatc tgcacccaag tgtaccacaa aagtatctcc aggcggtgta cactgcctgt   2580
gaccgccatt gtgtcatcgt tgcattacga aggcaaaatg cgcactacga atgagtacaa   2640
caagccgatt gtagtggaca ctacaggctc aacaaaacct gaccctggag acctcgtgtt   2700
aacgtgcttc agagggtggg ttaaacaact gcaaattgac tatcgtggat acgaggtcat   2760
gacagcagcc gcatcccaag ggttaaccag aaaaggagtt tacgcagtta gacaaaaagt   2820
```

```
taatgaaaac ccgctctatg catcaacgtc agagcacgtc aacgtactcc taacgcgtac   2880
ggaaggtaaa ctggtatgga agacactttc cggcgacccg tggataaaga cgctgcagaa   2940
cccaccgaaa ggaaacttca aagcaactat taaggagtgg gaggtggagc atgcatcaat   3000
aatggcgggc atctgcagtc accaaatgac cttcgataca ttccaaaata aagccaacgt   3060
ttgttgggct aagagcttgg tccctatcct cgaaacagcg gggataaaac taaatgatag   3120
gcagtggtct cagataattc aagccttcaa agaagacaaa gcatactcac ctgaagtagc   3180
cctgaatgaa atatgtacgc gcatgtatgg ggtggatcta gacagcgggc tattttctaa   3240
accgttggtg tctgtgtatt acgcggataa ccactgggat aataggcctg gagggaaaat   3300
gttcggattt aaccccgagg cagcatccat tctagaaaga aagtatccat tcacaaaagg   3360
gaagtggaac atcaacaagc agatctgcgt gactaccagg aggatagaag actttaaccc   3420
taccaccaac atcataccgg ccaacaggag actaccacac tcattagtgg ccgaacaccg   3480
cccagtaaaa ggggaaagaa tggaatggct ggttaacaag ataaacggcc accacgtgct   3540
cctggtcagt ggctataacc ttgcactgcc tactaagaga gtcacttggg tagcgccgtt   3600
aggtgtccgc ggagcggact acacatacaa cctagagttg ggtctgccag caacgcttgg   3660
taggtatgac ctagtggtca taaacatcca cacacctttt cgcatacacc attaccaaca   3720
gtgcgtcgac cacgcaatga aactgcaaat gctcgggggt gactcattga gactgctcaa   3780
accgggcggc tctctattga tcagagcata tggttacgca gatagaacca gtgaacgagt   3840
catctgcgta ttgggacgca agtttagatc gtctagagcg ttgaaaccac catgtgtcac   3900
cagcaacact gagatgtttt tcctattcag caactttgac aatggcagaa ggaatttcac   3960
aactcatgtc atgaacaatc aactgaatgc agccttcgta ggacaggtca cccgagcagg   4020
atgtgcaccg tcgtaccggg taaaacgcat ggacatcgcg aagaacgatg aagagtgcgt   4080
agtcaacgcc gctaaccctc gcgggttacc gggtgacggt gtttgcaagg cagtatacaa   4140
aaaatggccg gagtccttta agaacagtgc aacaccagtg ggaaccgcaa aaacagttat   4200
gtgcggtacg tatccagtaa tccacgctgt tggaccaaac ttctctaatt attcggagtc   4260
tgaaggggac cgggaattgg cagctgccta tcgagaagtc gcaaaggaag taactaggct   4320
gggagtaaat agtgtagcta tacctctcct ctccacaggt gtatactcag gagggaaaga   4380
caggctgacc cagtcactga accacctctt tacagccatg gactcgacgg atgcagacgt   4440
ggtcatctac tgccgcgaca aagaatggga gaagaaaata tctgaggcca tacagatgcg   4500
gacccaagta gagctgctgg atgagcacat ctccatagac tgcgatattg ttcgcgtgca   4560
ccctgacagc agcttggcag gcagaaaagg atacagcacc acggaaggcg cactgtactc   4620
atatctagaa gggacccgtt ttcatcagac ggctgtggat atggcggaga tacatactat   4680
gtggccaaag caaacagagg ccaatgagca agtctgccta tatgccctgg gggaaagtat   4740
tgaatcgatc aggcagaaat gcccggtgga tgatgcagac gcatcatctc cccccaaaac   4800
tgtcccgtgc ctttgccgtt acgctatgac tccagaacgc gtcacccggc ttcgcatgaa   4860
ccacgtcaca agcataattg tgtgttcttc gtttcccctc ccaaagtaca aaatagaagg   4920
agtgcaaaaa gtcaaatgct ctaaggtaat gctatttgac cacaacgtgc catcgcgcgt   4980
aagtccaagg gaatatagat cttcccagga gtctgcacag gaggcgagta caatcacgtc   5040
actgacgcat agtcaattcg acctaagcgt tgatggcgag atactgcccg tcccgtcaga   5100
cctggatgct gacgccccag ccctagaacc agcactagac gacggggcga cacacacgct   5160
gccatccaca accggaaacc ttgcggccgt gtctgattgg gtaatgagca ccgtacctgt   5220
```

-continued

```
cgcgccgccc agaagaaggc gagggagaaa cctgactgtg acatgtgacg agagagaagg   5280
gaatataaca cccatggcta gcgtccgatt ctttagggca gagctgtgtc cggtcgtaca   5340
agaaacagcg gagacgcgtg acacagcaat gtctcttcag gcaccaccga gtaccgccac   5400
ggaaccgaat catccgccga tctccttcgg agcatcaagc gagacgttcc ccattacatt   5460
tggggacttc aacgaaggag aaatcgaaag cttgtcttct gagctactaa ctttcggaga   5520
cttcttacca ggagaagtgg atgacttgac agacagcgac tggtccacgt gctcagacac   5580
ggacgacgag ttatgactag acagggcagg tgggtatata ttctcgtcgg acaccggtcc   5640
aggtcattta caacagaagt cagtacgcca gtcagtgctg ccggtgaaca ccctggagga   5700
agtccacgag gagaagtgtt acccacctaa gctggatgaa gcaaaggagc aactattact   5760
taagaaactc caggagagtg catccatggc caacagaagc aggtatcagt cgcgcaaagt   5820
agaaaacatg aaagcagcaa tcatccagag actaaagaga ggctgtagac tatacttaat   5880
gtcagagacc ccaaaagtcc ctacttaccg gactacatat ccggcgcctg tgtactcgcc   5940
tccgatcaac gtccgattgt ccaatcccga gtccgcagtg gcagcatgca atgagttctt   6000
agctagaaac tatccaactg tctcatcata ccaaattacc gacgagtatg atgcatatct   6060
agacatggtg gacgggtcgg agagttgcct ggaccgagcg acattcaatc cgtcaaaact   6120
caggagctac ccgaaacagc acgcttacca cgcgccctcc atcagaagcg ctgtaccgtc   6180
cccattccag aacacactac agaatgtact ggcagcagcc acgaaaagaa actgcaacgt   6240
cacacagatg agggaattac ccactttgga ctcagcagta ttcaacgtgg agtgtttcaa   6300
aaaattcgca tgcaaccaag aatactggga agaatttgct gccagcccta ttaggataac   6360
aactgagaat ttagcaacct atgttactaa actaaaaggg ccaaaagcag cagcgctatt   6420
cgcaaaaacc cataatctac tgccactaca ggaagtacca atggataggt tcacagtaga   6480
tatgaaaagg gacgtgaagg tgactcctgg tacaaagcat acagaggaaa gacctaaggt   6540
gcaggttata caggcggctg aacccttggc gacagcatac ctatgtggga ttcacagaga   6600
gctggttagg aggctgaacg ccgtcctcct acccaatgta catacactat ttgacatgtc   6660
tgccgaggat ttcgatgcca tcatagccgc acactttaag ccaggagaca ctgttttgga   6720
aacggacata gcctcctttg ataagagcca agatgattca cttgcgctta ctgctttgat   6780
gctgttagag gatttagggg tggatcactc cctgctggac ttgatagagg ctgctttcgg   6840
agagatttcc agctgtcacc taccgacagg tacgcgcttc aagttcggcg ccatgatgaa   6900
atcaggtatg ttcctaactc tgttcgtcaa cacattgtta aacatcacca tcgccagccg   6960
agtgctggaa gatcgtctga caaaatccgc gtgcgcggcc ttcatcggcg acgacaacat   7020
aatacatgga gtcgtctccg atgaattgat ggcagccaga tgtgccactt ggatgaacat   7080
ggaagtgaag atcatagatg cagttgtatc cttgaaagcc ccttactttt gtggagggtt   7140
tatactgcac gatactgtga caggaacagc ttgcagagtg gcagacccgc taaaaaggct   7200
ttttaaactg ggcaaaccgc tagcggcagg tgacgaacaa gatgaagata gaagacgagc   7260
gctggctgac gaagtgatca gatggcaacg aacagggcta attgatgagc tggagaaagc   7320
ggtatactct aggtacgaag tgcagggtat atcagttgtg gtaatgtcca tggccacctt   7380
tgcaagctcc agatccaact tcgagaagct cagaggaccc gtcataactt tgtacggcgg   7440
tcctaaatag gtacgcacta cagctaccta ttttgcagaa gccgacagca agtatctaaa   7500
cactaatcag ctacaatgga gttcatccca acccaaactt tttacaatag gaggtaccag   7560
```

-continued

```
cctcgaccct ggactccgcg ccctactatc caagtcatca ggcccagacc gcgccctcag   7620
aggcaagctg ggcaacttgc ccagctgatc tcagcagtta ataaactgac aatgcgcgcg   7680
gtaccccaac agaagccacg caggaatcgg aagaataaga agcaaaagca aaaacaacag   7740
gcgccacaaa acaacacaaa tcaaaagaag cagccaccta aaaagaaacc ggctcaaaag   7800
aaaaagaagc cgggccgcag agagaggatg tgcatgaaaa tcgaaaatga ttgtattttc   7860
gaagtcaagc acgaaggtaa ggtaacaggt tacgcgtgcc tggtggggga caaagtaatg   7920
aaaccagcac acgtaaaggg gaccatcgat aacgcggacc tggccaaact ggcctttaag   7980
cggtcatcta agtatgacct tgaatgcgcg cagataccccg tgcacatgaa gtccgacgct   8040
tcgaagttca cccatgagaa accggagggg tactacaact ggcaccacgg agcagtacag   8100
tactcaggag gccggttcac catccctaca ggtgctggca aaccagggga cagcggcaga   8160
ccgatcttcg acaacaaggg acgcgtggtg gccatagtct taggaggagc taatgaagga   8220
gcccgtacag ccctctcggt ggtgacctgg aataaagaca ttgtcactaa aatcaccccc   8280
gaggggggccg aagagtggag tcttgccatc ccagttatgt gcctgttggc aaacaccacg   8340
ttcccctgct cccagccccc ttgcacgccc tgctgctacg aaaaggaacc ggaggaaacc   8400
ctacgcatgc ttgaggacaa cgtcatgaga cctgggtact atcagctgct acaagcatcc   8460
ttaacatgtt ctccccaccg ccagcgacgc agcaccaagg acaacttcaa tgtctataaa   8520
gccacaagac catacttagc tcactgtccc gactgtggag aagggcactc gtgccatagt   8580
cccgtagcac tagaacgcat cagaaatgaa gcgacagacg ggacgctgaa aatccaggtc   8640
tccttgcaaa tcggaataaa gacggatgac agccacgatt ggaccaagct gcgttatatg   8700
gacaaccaca tgccagcaga cgcagagagg gcggggctat ttgtaagaac atcagcaccg   8760
tgtacgatta ctggaacaat gggacacttc atcctggccc gatgtccaaa aggggaaact   8820
ctgacggtgg gattcactga cagtaggaag attagtcact catgtacgca cccatttcac   8880
cacgaccctc ctgtgatagg tcgggaaaaa ttccattccc gaccgcagca cggtaaagag   8940
ctaccttgca gcacgtacgt gcagagcacc gccgcaacta ccgaggagat agaggtacac   9000
atgcccccag acacccctga tcgcacatta atgtcacaac agtccggcaa cgtaaagatc   9060
acagtcaatg gccagacggt gcggtacaag tgtaattgcg gtggctcaaa tgaaggacta   9120
acaactacag acaaagtgat taataactgc aaggttgatc aatgtcatgc cgcggtcacc   9180
aatcacaaaa agtggcagta taactcccct ctggtcccgc gtaatgctga acttggggac   9240
cgaaaaggaa aaattcacat cccgtttccg ctggcaaatg taacatgcag ggtgcctaaa   9300
gcaaggaacc ccaccgtgac gtacgggaaa aaccaagtca tcatgctact gtatcctgac   9360
cacccaacac tcctgtccta ccggaatatg ggagaagaac caaactatca agaagagtgg   9420
gtgatgcata agaaggaagt cgtgctaacc gtgccgactg aagggctcga ggtcacgtgg   9480
ggcaacaacg agccgtataa gtattggccg cagttatcta caaacggtac agcccatggc   9540
cacccgcatg agataattct gtattattat gagctgtacc ccactatgac tgtagtagtt   9600
gtgtcagtgg ccacgttcat actcctgtcg atggtgggta tggcagcggg gatgtgcatg   9660
tgtgcacgac gcagatgcat cacaccgtat gaactgacac caggagctac cgtccctttc   9720
ctgcttagcc taatatgctg catcagaaca gctaaagcgg ccacatacca agaggctgcg   9780
atatacctgt ggaacgagca gcaacctttg ttttggctac aagcccttat tccgctggca   9840
gccctgattg ttctatgcaa ctgtctgaga ctcttaccat gctgctgtaa aacgttggct   9900
tttttagccg taatgagcgt cggtgcccac actgtgagcg cgtacgaaca cgtaacagtg   9960
```

-continued

```
atcccgaaca cggtgggagt accgtataag actctagtca atagacctgg ctacagcccc  10020
atggtattgg agatggaact actgtcagtc actttggagc caacactatc gcttgattac  10080
atcacgtgcg agtacaaaac cgtcatcccg tctccgtacg tgaagtgctg cggtacagca  10140
gagtgcaagg acaaaaacct acctgactac agctgtaagg tcttcaccgg cgtctaccca  10200
tttatgtggg gcggcgccta ctgcttctgc gacgctgaaa acacgcagtt gagcgaagca  10260
cacgtggaga agtccgaatc atgcaaaaca gaatttgcat cagcatacag ggctcatacc  10320
gcatctgcat cagctaagct ccgcgtcctt taccaaggaa ataacatcac tgtaactgcc  10380
tatgcaaacg gcgaccatgc cgtcacagtt aaggacgcca aattcattgt ggggccaatg  10440
tcttcagcct ggacaccttt cgacaacaaa attgtggtgt acaaaggtga cgtctataac  10500
atggactacc cgccctttgg cgcaggaaga ccaggacaat ttggcgatat ccaaagtcgc  10560
acacctgaga gtaaagacgt ctatgctaat acacaactgg tactgcagag accggctgtg  10620
ggtacggtac acgtgccata ctctcaggca ccatctggct ttaagtattg gctaaaagaa  10680
cgcggggcgt cgctgcagca cacagcacca tttggctgcc aaatagcaac aaacccggta  10740
agagcggtga actgcgccgt agggaacatg cccatctcca tcgacatacc ggaagcggcc  10800
ttcactaggg tcgtcgacgc gccctcttta acggacatgt cgtgcgaggt accagcctgc  10860
acccattcct cagactttgg gggcgtcgcc attattaaat atgcagccag caagaaaggc  10920
aagtgtgcgg tgcattcgat gactaacgcc gtcactattc gggaagctga gatagaagtt  10980
gaagggaatt ctcagctgca aatctctttc tcgacggcct tagccagcgc cgaattccgc  11040
gtacaagtct gttctacaca agtacactgt gcagccgagt gccacccccc gaaggaccac  11100
atagtcaact acccggcgtc acataccacc ctcggggtcc aggacatctc cgctacggcg  11160
atgtcatggg tgcagaagat cacgggaggt gtgggactgg ttgttgctgt tgccgcactg  11220
attctaatcg tggtgctatg cgtgtcgttc agcaggcact aacttgacaa ttaagtatga  11280
aggtatatgt gtcccctaag agacacactg tacatagcaa ataatctata gatcaaaggg  11340
ctacgcaacc cctgaatagt aacaaaatac aaaatcacta aaaattataa aaacagaaaa  11400
atacataaat aggtatacgt gtcccctaag agacacattg tatgtaggtg ataagtatag  11460
atcaaagggc cgaataaccc ctgaatagta acaaaatatg aaaatcaata aaaatcataa  11520
aatagaaaaa ccataaacag aagtagttca aagggctata aaacccctga atagtaacaa  11580
aacataaaat taataaaaat c                                            11601
```

<210> SEQ ID NO 4
<211> LENGTH: 11598
<212> TYPE: DNA
<213> ORGANISM: Chikungunya virus

<400> SEQUENCE: 4

```
caaagcaaga gattaataac ccatcatgga tcctgtgtac gtggacatag acgctgacag     60
cgcctttttg aaggccctgc aacgtgcgta ccccatgttt gaggtggaac caaggcaggt    120
cacaccgaat gaccatgcta atgctagagc gttctcgcat ctagctataa aactaataga    180
gcaggaaatt gaccccgact caaccatcct ggatatcggc agtgcgccag caaggaggat    240
gatgtcggac aggaagtacc actgcgtctg cccgatgcgc agtgcggaag atcccgagag    300
actcgccaat tatgcgagaa agctagcatc tgccgcagga aaagtcctgg acagaaacat    360
ctctggaaag atcggggact tacaagcagt aatggccgtg ccagacacgg agacgccaac    420
```

```
attctgctta cacacagacg tctcatgtag acagagagca gacgtcgcta tataccaaga    480
cgtctatgct gtacacgcac ccacgtcgct ataccaccag gcgattaaag gggtccgagt    540
ggcgtactgg gttgggttcg acacaacccc gttcatgtac aatgccatgg cgggtgccta    600
cccctcatac tcgacaaact gggcagatga gcaggtactg aaggctaaga acataggatt    660
atgttcaaca gacctgacgg aaggtagacg aggcaagttg tctattatga gagggaaaaa    720
gctaaaaccg tgcgaccgtg tgctgttctc agtagggtca acgctctacc cggaaagccg    780
caagctactt aagagctggc acctgccatc ggtgttccat ttaaagggca aactcagctt    840
cacatgccgc tgtgatacag tggtttcgtg tgagggctac gtcgttaaga gaataacgat    900
gagcccaggc ctttatggaa aaaccatagg gtatgcggta acccaccacg cagacggatt    960
cctgatgtgc aagactaccg acacggttga cggcgaaaga gtgtcattct cggtgtgcac   1020
atacgtgccg gcgaccattt gtgatcaaat gaccggcatc cttgctacag aagtcacgcc   1080
ggaggatgca cagaagctgt tggtggggct gaaccagaga atagtggtta acggcagaac   1140
gcaacggaat acgaacacca tgaaaaatta tctgcttccc gtggtcgccc aagccttcag   1200
taagtgggca aaggagtgcc ggaaagacat ggaagatgaa aaactcctgg gggtcagaga   1260
aagaacactg acctgctgct gtctatgggc attcaagaag cagaaaacac acacggtcta   1320
caagaggcct gatacccagt caattcagaa ggttcaggcc gagtttgaca gctttgtggt   1380
accgagtctg tggtcgtccg ggttgtcaat ccctttgagg actagaatca aatggttgtt   1440
aagcaaggtg ccaaaaaccg acctgatccc atacagcgga gacgcccgag aagcccggga   1500
cgcagaaaaa gaagcagagg aagaacgaga agcagaactg actcgcgaag ccctaccacc   1560
tctacaggca gcacaggaag atgttcaggt cgaaatcgac gtggaacagc ttgaggacag   1620
agcgggcgca ggaataatag agactccgag aggagctatc aaagttactg cccaaccaac   1680
agaccacgtc gtgggagagt acctggtact ctccccgcag accgtactac gtagccagaa   1740
gctcagtctg attcacgctt tggcggagca agtgaagacg tgcacgcaca acggacgagc   1800
agggaggtat gcggtcgaag cgtacgacgg ccgagtccta gtgccctcag gctatgcaat   1860
ctcgcctgaa gacttccaga gtctaagcga aagcgcaacg atggtgtata acgaaagaga   1920
gttcgtaaac agaaagctac accatattgc gatgcacgga ccagccctga acaccgacga   1980
agagtcgtat gagctggtga gggcagagag gacagaacac gagtacgtct acgacgtgga   2040
tcagagaaga tgctgtaaga aggaagaagc cgcaggactg gtactggtgg gcgacttgac   2100
taatccgccc taccacgaat tcgcatatga agggctaaaa atccgccctg cctgcccata   2160
caaaattgca gtcataggag tcttcggagt accgggatct ggcaagtcag ctattatcaa   2220
gaacctagtt accaggcagg acctggtgac tagcggaaag aaagaaaact gccaagaaat   2280
caccaccgac gtgatgagac agagaggtct agagatatct gcacgtacgg ttgactcgct   2340
gctcttgaat ggatgcaaca gaccagtcga cgtgttgtac gtagacgagg cgtttgcgtg   2400
ccactctgga acgctacttg ctttgatcgc cttggtgaga ccaaggcaga aagttgtact   2460
ttgtggtgac ccgaagcagt gcggcttctt caatatgatg cagatgaaag tcaactataa   2520
tcacaacatc tgcacccaag tgtaccacaa aagtatctcc aggcggtgta cactgcctgt   2580
gaccgccatt gtgtcatcgt tgcattacga aggcaaaatg cgcactacga atgagtacaa   2640
caagccgatt gtagtggaca ctacaggctc aacaaaacct gaccctggag acctcgtgtt   2700
aacgtgcttc agagggtggg ttaaacaact gcaaattgac tatcgtggat acgaggtcat   2760
gacagcagcc gcatcccaag ggttaaccag aaaaggagtt tacgcagtta gacaaaaagt   2820
```

-continued

```
taatgaaaac ccgctctatg catcaacgtc agagcacgtc aacgtactcc taacgcgtac   2880
ggaaggtaaa ctggtatgga agacactttc cggcgacccg tggataaaga cgctgcagaa   2940
cccaccgaaa ggaaacttca aagcaactat taaggagtgg gaggtggagc atgcatcaat   3000
aatggcgggc atctgcagtc accaaatgac cttcgataca ttccaaaata aagccaacgt   3060
ttgttgggct aagagcttgg tccctatcct cgaaacagcg gggataaaac taaatgatag   3120
gcagtggtct cagataattc aagccttcaa agaagacaaa gcatactcac ctgaagtagc   3180
cctgaatgaa atatgtacgc gcatgtatgg ggtggatcta gacagcgggc tattttctaa   3240
accgttggtg tctgtgtatt acgcggataa ccactgggat aataggcctg gagggaaaat   3300
gttcggattt aaccccgagg cagcatccat tctagaaaga aagtatccat tcacaaaagg   3360
gaagtggaac atcaacaagc agatctgcgt gactaccagg aggatagaag actttaaccc   3420
taccaccaac atcataccgg ccaacaggag actaccacac tcattagtgg ccgaacaccg   3480
cccagtaaaa ggggaaagaa tggaatggct ggttaacaag ataaacggcc accacgtgct   3540
cctggtcagt ggcaataacc ttgcactgcc tactaagaga gtcacttggg tagcgccgtt   3600
aggtgtccgc ggagcggact acacatacaa cctagagttg ggtctgccag caacgcttgg   3660
taggtatgac ctagtggtca taaacatcca cacacctttt cgcatacacc attaccaaca   3720
gtgcgtcgac cacgcaatga aactgcaaat gctcgggggt gactcattga gactgctcaa   3780
accgggcggc tctctattga tcagagcata tggttacgca gatagaacca gtgaacgagt   3840
catctgcgta ttgggacgca agtttagatc gtctagagcg ttgaaaccac catgtgtcac   3900
cagcaacact gagatgtttt tcctattcag caactttgac aatggcagaa ggaatttcac   3960
aactcatgtc atgaacaatc aactgaatgc agccttcgta ggacaggtca cccgagcagg   4020
atgtgcaccg tcgtaccggg taaaacgcat ggacatcgcg aagaacgatg aagagtgcgt   4080
agtcaacgcc gctaaccctc gcgggttacc gggtgacggt gtttgcaagg cagtatacaa   4140
aaaatggccg gagtccttta agaacagtgc aacaccagtg ggaaccgcaa aaacagttat   4200
gtgcggtacg tatccagtaa tccacgctgt tggaccaaac ttctctaatt attcggagtc   4260
tgaaggggac cgggaattgg cagctgccta tcgagaagtc gcaaaggaag taactaggct   4320
gggagtaaat agtgtagcta tacctctcct ctccacaggt gtatactcag gagggaaaga   4380
caggctgacc cagtcactga accacctctt tacagccatg gactcgacgg atgcagacgt   4440
ggtcatctac tgccgcgaca aagaatggga gaagaaaata tctgaggcca tacagatgcg   4500
gacccaagta gagctgctgg atgagcacat ctccatagac tgcgatattg ttcgcgtgca   4560
ccctgacagc agcttggcag gcagaaaagg atacagcacc acggaaggcg cactgtactc   4620
atatctagaa gggacccgtt ttcatcagac ggcagtggat atggcggaga tacatactat   4680
gtggccaaag caaacagagg ccaatgagca agtctgccta tatgccctgg gggaaagtat   4740
tgaatcgatc aggcagaaat gcccggtgga tgatgcagac gcatcatctc cccccaaaac   4800
tgtcccgtgc ctttgccgtt acgctatgac tccagaacgc gtcacccggc ttcgcatgaa   4860
ccacgtcaca agcataattg tgtgttcttc gtttcccctc ccaaagtaca aaatagaagg   4920
agtgcaaaaa gtcaaatgct ctaaggtaat gctatttgac cacaacgtgc catcgcgcgt   4980
aagtccaagg gaatatagat cttcccagga gtctgcacag gaggcgagta caatcacgtc   5040
actgacgcat agtcaattcg acctaagcgt tgatggcgag atactgcccg tcccgtcaga   5100
cctggatgct gacgccccag ccctagaacc agcactagac gacggggcga cacacacgct   5160
```

-continued

```
gccatccaca accggaaacc ttgcggccgt gtctgattgg gtaatgagca ccgtacctgt   5220
cgcgccgccc agaagaaggc gagggagaaa cctgactgtg acatgtgacg agagagaagg   5280
gaatataaca cccatggcta gcgtccgatt ctttagggca gagctgtgtc cggtcgtaca   5340
agaaacagcg gagacgcgtg acacagcaat gtctcttcag gcaccaccga gtaccgccac   5400
accgaatcat ccgccgatct ccttcggagc atcaagcgag acgttcccca ttacatttgg   5460
ggacttcaac gaaggagaaa tcgaaagctt gtcttctgag ctactaactt tcggagactt   5520
cttaccagga gaagtggatg acttgacaga cagcgactgg tccacgtgct cagacacgga   5580
cgacgagtta tgactagaca gggcaggtgg gtatatattc tcgtcggaca ccggtccagg   5640
tcatttacaa cagaagtcag tacgccagtc agtgctgccg gtgaacaccc tggaggaagt   5700
ccacgaggag aagtgttacc cacctaagct ggatgaagca aaggagcaac tattacttaa   5760
gaaactccag gagagtgcat ccatggccaa cagaagcagg tatcagtcgc gcaaagtaga   5820
aaacatgaaa gcagcaatca tccagagact aaagagaggc tgtagactat acttaatgtc   5880
agagacccca aaagtcccta cttaccggac tacatatccg gcgcctgtgt actcgcctcc   5940
gatcaacgtc cgattgtcca atcccgagtc cgcagtggca gcatgcaatg agttcttagc   6000
tagaaactat ccaactgtct catcatacca aattaccgac gagtatgatg catatctaga   6060
catggtggac gggtcggaga gttgcctgga ccgagcgaca ttcaatccgt caaaactcag   6120
gagctacccg aaacagcacg cttaccacgc gccctccatc agaagcgctg taccgtcccc   6180
attccagaac acactacaga atgtactggc agcagccacg aaaagaaact gcaacgtcac   6240
acagatgagg gaattaccca ctttggactc agcagtattc aacgtggagt gtttcaaaaa   6300
attcgcatgc aaccaagaat actgggaaga atttgctgcc agccctatta ggataacaac   6360
tgagaattta gcaacctatg ttactaaact aaaagggcca aaagcagcag cgctattcgc   6420
aaaaacccat aatctactgc cactacagga agtaccaatg gataggttca cagtagatat   6480
gaaaagggac gtaaaggtga ctcctggtac aaagcataca gaggaaagac ctaaggtgca   6540
ggttatacag gcggctgaac ccttggcgac agcataccta tgtgggattc acagagagct   6600
ggttaggagg ctgaacgccg tcctcctacc caatgtacat acactatttg acatgtctgc   6660
cgaggatttc gatgccatca tagccgcaca ctttaagcca ggagacactg ttttggaaac   6720
ggacatagcc tcctttgata agagccaaga tgattcactt gcgcttactg ctttgatgct   6780
gttagaggat ttaggggtgg atcactccct gctggacttg atagaggctg ctttcggaga   6840
gatttccagc tgtcacctac cgacaggtac gcgcttcaag ttcggcgcca tgatgaaatc   6900
aggtatgttc ctaactctgt tcgtcaacac attgttaaac atcaccatcg ccagccgagt   6960
gctggaagat cgtctgacaa aatccgcgtg cgcggccttc atcggcgacg acaacataat   7020
acatggagtc gtctccgatg aattgatggc agccagatgt gccacttgga tgaacatgga   7080
agtgaagatc atagatgcag ttgtatcctt gaaagcccct tacttttgtg gagggtttat   7140
actgcacgat actgtgacag gaacagcttg cagagtggca gacccgctaa aaaggctttt   7200
taaactgggc aaaccgctag cggcaggtga cgaacaagat gaagatagaa gacgagcgct   7260
ggctgacgaa gtgatcagat ggcaacgaac agggctaatt gatgagctgg agaaagcggt   7320
atactctagg tacgaagtgc agggtatatc agttgtggta atgtccatgg ccacctttgc   7380
aagctccaga tccaacttcg agaagctcag aggacccgtc ataactttgt acggcggtcc   7440
taaataggta cgcactacag ctacctattt tgcagaagcc gacagcaagt atctaaacac   7500
taatcagcta caatggagtt catcccaacc caaacttttt acaataggag gtaccagcct   7560
```

-continued

```
cgaccctgga ctccgcgccc tactatccaa gtcatcaggc ccagaccgcg ccctcagagg   7620
caagctgggc aacttgccca gctgatctca gcagttaata aactgacaat gcgcgcggta   7680
ccccaacaga agccacgcag gaatcggaag aataagaagc aaaagcaaaa acaacaggcg   7740
ccacaaaaca acacaaatca aaagaagcag ccacctaaaa agaaaccggc tcaaaagaaa   7800
aagaagccgg gccgcagaga gaggatgtgc atgaaaatcg aaaatgattg tattttcgaa   7860
gtcaagcacg aaggtaaggt aacaggttac gcgtgcctgg tgggggacaa agtaatgaaa   7920
ccagcacacg taaaggggac catcgataac gcggacctgg ccaaactggc ctttaagcgg   7980
tcatctaagt atgaccttga atgcgcgcag atacccgtgc acatgaagtc cgacgcttcg   8040
aagttcaccc atgagaaacc ggagggggtac tacaactggc accacggagc agtacagtac   8100
tcaggaggcc ggttcaccat ccctacaggt gctggcaaac caggggacag cggcagaccg   8160
atcttcgaca acaagggacg cgtggtggcc atagtcttag gaggagctaa tgaaggagcc   8220
cgtacagccc tctcggtggt gacctggaat aaagacattg tcactaaaat caccccccgag   8280
ggggccgaag agtggagtct tgccatccca gttatgtgcc tgttggcaaa caccacgttc   8340
ccctgctccc agcccccttg cacgccctgc tgctacgaaa aggaaccgga ggaaacccta   8400
cgcatgcttg aggacaacgt catgagacct gggtactatc agctgctaca agcatcctta   8460
acatgttctc cccaccgcca gcgacgcagc accaaggaca acttcaatgt ctataaagcc   8520
acaagaccat acttagctca ctgtcccgac tgtggagaag ggcactcgtg ccatagtccc   8580
gtagcactag aacgcatcag aaatgaagcg acagacggga cgctgaaaat ccaggtctcc   8640
ttgcaaatcg gaataaagac ggatgacagc cacgattgga ccaagctgcg ttatatggac   8700
aaccacatgc cagcagacgc agagagggcg gggctatttg taagaacatc agcaccgtgt   8760
acgattactg gaacaatggg acacttcatc ctggcccgat gtccaaaagg ggaaactctg   8820
acggtgggat tcactgacag taggaagatt agtcactcat gtacgcaccc atttcaccac   8880
gaccctcctg tgataggtcg ggaaaaattc cattcccgac cgcagcacgg taaagagcta   8940
ccttgcagca cgtacgtgca gagcaccgcc gcaactaccg aggagataga ggtacacatg   9000
cccccagaca cccctgatcg cacattaatg tcacaacagt ccggcaacgt aaagatcaca   9060
gtcaatggcc agacggtgcg gtacaagtgt aattgcggtg gctcaaatga aggactaaca   9120
actacagaca aagtgattaa taactgcaag gttgatcaat gtcatgccgc ggtcaccaat   9180
cacaaaaagt ggcagtataa ctcccctctg gtcccgcgta atgctgaact tggggaccga   9240
aaaggaaaaa ttcacatccc gtttccgctg gcaaatgtaa catgcagggt gcctaaagca   9300
aggaacccca ccgtgacgta cgggaaaaac caagtcatca tgctactgta tcctgaccac   9360
ccaacactcc tgtcctaccg gaatatggga gaagaaccaa actatcaaga agagtgggtg   9420
atgcataaga aggaagtcgt gctaaccgtg ccgactgaag ggctcgaggt cacgtggggc   9480
aacaacgagc cgtataagta ttggccgcag ttatctacaa acggtacagc ccatggccac   9540
ccgcatgaga taattctgta ttattatgag ctgtacccca ctatgactgt agtagttgtg   9600
tcagtggcca cgttcatact cctgtcgatg gtgggtatgg cagcggggat gtgcatgtgt   9660
gcacgacgca gatgcatcac accgtatgaa ctgacaccag gagctaccgt ccctttcctg   9720
cttagcctaa tatgctgcat cagaacagct aaagcggcca cataccaaga ggctgcgata   9780
tacctgtgga acgagcagca acctttgttt tggctacaag cccttattcc gctggcagcc   9840
ctgattgttc tatgcaactg tctgagactc ttaccatgct gctgtaaaac gttggctttt   9900
```

-continued

```
ttagccgtaa tgagcgtcgg tgcccacact gtgagcgcgt acgaacacgt aacagtgatc    9960

ccgaacacgg tgggagtacc gtataagact ctagtcaata gacctggcta cagccccatg   10020

gtattggaga tggaactact gtcagtcact ttggagccaa cactatcgct tgattacatc   10080

acgtgcgagt acaaaaccgt catcccgtct ccgtacgtga agtgctgcgg tacagcagag   10140

tgcaaggaca aaaacctacc tgactacagc tgtaaggtct tcaccggcgt ctacccattt   10200

atgtggggcg gcgcctactg cttctgcgac gctgaaaaca cgcagttgag cgaagcacac   10260

gtggagaagt ccgaatcatg caaaacagaa tttgcatcag catacagggc tcataccgca   10320

tctgcatcag ctaagctccg cgtcctttac caaggaaata acatcactgt aactgcctat   10380

gcaaacggcg accatgccgt cacagttaag gacgccaaat tcattgtggg gccaatgtct   10440

tcagcctgga cacctttcga caacaaaatt gtggtgtaca aaggtgacgt ctataacatg   10500

gactacccgc cctttggcgc aggaagacca ggacaatttg gcgatatcca aagtcgcaca   10560

cctgagagta aagacgtcta tgctaataca caactggtac tgcagagacc ggctgtgggt   10620

acggtacacg tgccatactc tcaggcacca tctggcttta agtattggct aaaagaacgc   10680

ggggcgtcgc tgcagcacac agcaccattt ggctgccaaa tagcaacaaa cccggtaaga   10740

gcggtgaact gcgccgtagg gaacatgccc atctccatcg acataccgga agcggccttc   10800

actagggtcg tcgacgcgcc ctctttaacg gacatgtcgt gcgaggtacc agcctgcacc   10860

cattcctcag actttggggg cgtcgccatt attaaatatg cagccagcaa gaaaggcaag   10920

tgtgcggtgc attcgatgac taacgccgtc actattcggg aagctgagat agaagttgaa   10980

gggaattctc agctgcaaat ctctttctcg acggccttag ccagcgccga attccgcgta   11040

caagtctgtt ctacacaagt acactgtgca gccgagtgcc accccccgaa ggaccacata   11100

gtcaactacc cggcgtcaca taccaccctc ggggtccagg acatctccgc tacggcgatg   11160

tcatgggtgc agaagatcac gggaggtgtg ggactggttg ttgctgttgc cgcactgatt   11220

ctaatcgtgg tgctatgcgt gtcgttcagc aggcactaac ttgacaatta agtatgaagg   11280

tatatgtgtc ccctaagaga cacactgtac atagcaaata atctatagat caaagggcta   11340

cgcaacccct gaatagtaac aaaatacaaa atcactaaaa attataaaaa cagaaaaata   11400

cataaatagg tatacgtgtc ccctaagaga cacattgtat gtaggtgata agtatagatc   11460

aaagggccga ataacccctg aatagtaaca aaatatgaaa atcaataaaa atcataaaat   11520

agaaaaacca taaacagaag tagttcaaag ggctataaaa cccctgaata gtaacaaaac   11580

ataaaattaa taaaaatc                                                 11598
```

<210> SEQ ID NO 5
<211> LENGTH: 11601
<212> TYPE: DNA
<213> ORGANISM: Chikungunya virus

<400> SEQUENCE: 5

```
caaagcaaga gattaataac ccatcatgga tcctgtgtac gtggacatag acgctgacag      60

cgcctttttg aaggccctgc aacgtgcgta ccccatgttt gaggtggaac caaggcaggt     120

cacaccgaat gaccatgcta atgctagagc gttctcgcat ctagctataa aactaataga     180

gcaggaaatt gaccccgact caaccatcct ggatatcggc agtgcgccag caaggaggat     240

gatgtcggac aggaagtacc actgcgtctg cccgatgcgc agtgcggaag atcccgagag     300

actcgccaat tatgcgagaa agctagcatc tgccgcagga aaagtcctgg acagaaacat     360

ctctggaaag atcggggact tacaagcagt aatggccgtg ccagacacgg agacgccaac     420
```

-continued

```
attctgctta cacacagacg tctcatgtag acagagagca gacgtcgcta tataccaaga    480
cgtctatgct gtacacgcac ccacgtcgct ataccaccag gcgattaaag gggtccgagt    540
ggcgtactgg gttgggttcg acacaacccc gttcatgtac aatgccatgg cgggtgccta    600
cccctcatac tcgacaaact gggcagatga gcaggtactg aaggctaaga acataggatt    660
atgttcaaca gacctgacgg aaggtagacg aggcaagttg tctattatga gagggaaaaa    720
gctaaaaccg tgcgaccgtg tgctgttctc agtagggtca acgctctacc cggaaagccg    780
caagctactt aagagctggc acctgccatc ggtgttccat ttaaagggca aactcagctt    840
cacatgccgc tgtgatacag tggtttcgtg tgagggctac gtcgttaaga gaataacgat    900
gagcccaggc ctttatggaa aaaccacagg gtatgcggta acccaccacg cagacggatt    960
cctgatgtgc aagactaccg acacggttga cggcgaaaga gtgtcattct cggtgtgcac   1020
atacgtgccg gcgaccattt gtgatcaaat gaccggcatc cttgctacag aagtcacgcc   1080
ggaggatgca cagaagctgt tggtggggct gaaccagaga atagtggtta acggcagaac   1140
gcaacggaat acgaacacca tgaaaaatta tctgcttccc gtggtcgccc aagccttcag   1200
taagtgggca aaggagtgcc ggaaagacat ggaagatgaa aaactcctgg gggtcagaga   1260
aagaacactg acctgctgct gtctatgggc attcaagaag cagaaaacac acacggtcta   1320
caagagacct gatacccagt caattcagaa ggttcaggcc gagtttgaca gctttgtggt   1380
accgagtctg tggtcgtccg ggttgtcaat ccctttgagg actagaatca aatggttgtt   1440
aagcaaggtg ccaaaaaccg acctgatccc atacagcgga gacgcccgag aagcccggga   1500
cgcagaaaaa gaagcagagg aagaacgaga agcagaactg actcgcgaag ccctaccacc   1560
tctacaggca gcacaggaag atgttcaggt cgaaatcgac gtggaacagc ttgaggacag   1620
agcgggcgca ggaataatag agactccgag aggagctatc aaagttactg cccaaccaac   1680
agaccacgtc gtgggagagt acctggtact ctccccgcag accgtactac gtagccagaa   1740
gctcagtctg attcacgctt tggcggagca agtgaagacg tgcacgcaca acggacgagc   1800
agggaggtat gcggtcgaag cgtacgacgg ccgagtccta gtgccctcag gctatgcaat   1860
ctcgcctgaa gacttccaga gtctaagcga aagcgcaacg atggtgtata acgaaagaga   1920
gttcgtaaac agaaagctac accatattgc gatgcacgga ccagccctga acaccgacga   1980
agagtcgtat gagctggtga gggcagagag gacagaacac gagtacgtct acgacgtgga   2040
tcagagaaga tgctgtaaga aggaagaagc cgcaggactg gtactggtgg gcgacttgac   2100
taatccgccc taccacgaat tcgcatatga agggctaaaa atccgccctg cctgcccata   2160
caaaattgca gtcataggag tcttcggagt accgggatct ggcaagtcag ctattatcaa   2220
gaacctagtt accaggcagg acctggtgac tagcggaaag aaagaaaact gccaagaaat   2280
caccaccgac gtgatgagac agagaggtct agagatatct gcacgtacgg ttgactcgct   2340
gctcttgaat ggatgcaaca gaccagtcga cgtgttgtac gtagacgagg cgtttgcgtg   2400
ccactctgga acgctacttg ctttgatcgc cttggtgaga ccaaggcaga aagttgtact   2460
ttgtggtgac ccgaagcagt gcggcttctt caatatgatg cagatgaaag tcaactataa   2520
tcacaacatc tgcacccaag tgtaccacaa aagtatctcc aggcggtgta cactgcctgt   2580
gaccgccatt gtgtcatcgt tgcattacga aggcaaaatg cgcactacga atgagtacaa   2640
caagccgatt gtagtggaca ctacaggctc aacaaaacct gaccctggag acctcgtgtt   2700
aacgtgcttc agagggtggg ttaaacaact gcaaattgac tatcgtggat acgaggtcat   2760
```

-continued

```
gacagcagcc gcatcccaag ggttaaccag aaaaggagtt tacgcagtta gacaaaaagt   2820
taatgaaaac ccgctctatg catcaacgtc agagcacgtc aacgtactcc taacgcgtac   2880
ggaaggtaaa ctggtatgga agacactttc cggcgacccg tggataaaga cgctgcagaa   2940
cccaccgaaa ggaaacttca aagcaactat taaggagtgg gaggtggagc atgcatcaat   3000
aatggcgggc atctgcagtc accaaatgac cttcgataca ttccaaaata aagccaacgt   3060
ttgttgggct aagagcttgg tccctatcct cgaaacagcg ggataaaac taaatgatag    3120
gcagtggtct cagataattc aagccttcaa agaagacaaa gcatactcac ctgaagtagc   3180
cctgaatgaa atatgtacgc gcatgtatgg ggtggatcta gacagcgggc tattttctaa   3240
accgttggtg tctgtgtatt acgcggataa ccactgggat aataggcctg gagggaaaat   3300
gttcggattt aaccccgagg cagcatccat tctagaaaga aagtatccat tcacaaaagg   3360
gaagtggaac atcaacaagc agatctgcgt gactaccagg aggatagaag actttaaccc   3420
taccaccaac atcataccgg ccaacaggag actaccacac tcattagtgg ccgaacaccg   3480
cccagtaaaa ggggaaagaa tggaatggct ggttaacaag ataaacggcc accacgtgct   3540
cctggtcagt ggctataacc ttgcactgcc tactaagaga gtcacttggg tagcgccgtt   3600
aggtgtccgc ggagcggact acacatacaa cctagagttg ggtctgccag caacgcttgg   3660
taggtatgac ctagtggtca taaacatcca cacacctttt cgcatacacc attaccaaca   3720
gtgcgtcgac cacgcaatga aactgcaaat gctcgggggt gactcattga gactgctcaa   3780
accgggcggc tctctattga tcagagcata tggttacgca gatagaacca gtgaacgagt   3840
catctgcgta ttgggacgca agtttagatc gtctagagcg ttgaaaccac catgtgtcac   3900
cagcaacact gagatgtttt tcctattcag caactttgac aatggcagaa ggaatttcac   3960
aactcatgtc atgaacaatc aactgaatgc agccttcgta ggacaggtca cccgagcagg   4020
atgtgcaccg tcgtaccggg taaaacgcat ggacatcgcg aagaacgatg aagagtgcgt   4080
agtcaacgcc gctaaccctc gcgggttacc gggtgacggt gtttgcaagg cagtatacaa   4140
aaaatggccg gagtccttta agaacagtgc aacaccagtg ggaaccgcaa aaacagttat   4200
gtgcggtacg tatccagtaa tccacgctgt tggaccaaac ttctctaatt attcggagtc   4260
tgaaggggac cgggaattgg cagctgccta tcgagaagtc gcaaaggaag taactaggct   4320
gggagtaaat agtgtagcta tacctctcct ctccacaggt gtatactcag gagggaaaga   4380
caggctgacc cagtcactga accacctctt tacagccatg gactcgacgg atgcagacgt   4440
ggtcatctac tgccgcgaca aagaatggga gaagaaaata tctgaggcca tacagatgcg   4500
gacccaagta gagctgctgg atgagcacat ctccatagac tgcgatattg ttcgcgtgca   4560
ccctgacagc agcttggcag gcagaaaagg atacagcacc acggaaggcg cactgtactc   4620
atatctagaa gggacccgtt ttcatcagac ggctgtggat atggcggaga tacatactat   4680
gtggccaaag caaacagagg ccaatgagca agtctgccta tatgccctgg gggaaagtat   4740
tgaatcgatc aggcagaaat gcccggtgga tgatgcagac gcatcatctc cccccaaaac   4800
tgtcccgtgc ctttgccgtt acgctatgac tccagaacgc gtcacccggc ttcgcatgaa   4860
ccacgtcaca agcataattg tgtgttcttc gtttcccctc ccaaagtaca aaatagaagg   4920
agtgcaaaaa gtcaaatgct ctaaggtaat gctatttgac cacaacgtgc catcgcgcgt   4980
aagtccaagg gaatatagat cttcccagga gtctgcacag gaggcgagta caatcacgtc   5040
actgacgcat agtcaattcg acctaagcgt tgatggcgag atactgcccg tcccgtcaga   5100
cctggatgct gacgccccag ccctagaacc agcactagac gacggggcga cacacacgct   5160
```

-continued

```
gccatccaca accggaaacc ttgcggccgt gtctgattgg gtaatgagca ccgtacctgt   5220
cgcgccgccc agaagaaggc gagggagaaa cctgactgtg acatgtgacg agagagaagg   5280
gaatataaca cccatggcta gcgtccgatt ctttagggca gagctgtgtc cggtcgtaca   5340
agaaacagcg gagacgcgtg acacagcaat gtctcttcag gcaccaccga gtaccgccac   5400
ggaaccgaat catccgccga tctccttcgg agcatcaagc gagacgttcc ccattacatt   5460
tggggacttc aacgaaggag aaatcgaaag cttgtcttct gagctactaa ctttcggaga   5520
cttcttacca ggagaagtgg atgacttgac agacagcgac tggtccacgt gctcagacac   5580
ggacgacgag ttatgactag acagggcagg tgggtatata ttctcgtcgg acaccggtcc   5640
aggtcattta caacagaagt cagtacgcca gtcagtgctg ccggtgaaca ccctggagga   5700
agtccacgag gagaagtgtt acccacctaa gctggatgaa gcaaaggagc aactattact   5760
taagaaactc caggagagtg catccatggc caacagaagc aggtatcagt cgcgcaaagt   5820
agaaaacatg aaagcagcaa tcatccagag actaaagaga ggctgtagac tatacttaat   5880
gtcagagacc ccaaaagtcc ctacttaccg gactacatat ccggcgcctg tgtactcgcc   5940
tccgatcaac gtccgattgt ccaatcccga gtccgcagtg gcagcatgca atgagttctt   6000
agctagaaac tatccaactg tctcatcata ccaaattacc gacgagtatg atgcatatct   6060
agacatggtg gacgggtcgg agagttgcct ggaccgagcg acattcaatc cgtcaaaact   6120
caggagctac ccgaaacagc acgcttacca cgcgccctcc atcagaagcg ctgtaccgtc   6180
cccattccag aacacactac agaatgtact ggcagcagcc acgaaaagaa actgcaacgt   6240
cacacagatg agggaattac ccactttgga ctcagcagta ttcaacgtgg agtgtttcaa   6300
aaaattcgca tgcaaccaag aatactggga agaatttgct gccagcccta ttaggataac   6360
aactgagaat ttagcaacct atgttactaa actaaaaggg ccaaaagcag cagcgctatt   6420
cgcaaaaacc cataatctac tgccactaca ggaagtacca atggatagct tcacagtaga   6480
tatgaaaagg gacgtaaagg tgactcctgg tacaaagcat acagaggaaa gacctaaggt   6540
gcaggttata caggcggctg aacccttggc gacagcatac ctatgtggga ttcacagaga   6600
gctggttagg aggctgaacg ccgtcctcct acccaatgta catacactat ttgacatgtc   6660
tgccgaggat ttcgatgcca tcatagccgc acactttaag ccaggagaca ctgttttgga   6720
aacggacata gcctcctttg ataagagcca agatgattca cttgcgctta ctgctttgat   6780
gctgttagag gatttagggg tggatcactc cctgctggac ttgatagagg ctgctttcgg   6840
agagatttcc agctgtcacc taccgacagg tacgcgcttc aagttcggcg ccatgatgaa   6900
atcaggtatg ttcctaactc tgttcgtcaa cacattgtta aacatcacca tcgccagccg   6960
agtgctggaa gatcgtctga caaaatccgc gtgcgcggcc ttcatcggcg acgacaacat   7020
aatacatgga gtcgtctccg atgaattgat ggcagccaga tgtgccactt ggatgaacat   7080
ggaagtgaag atcatagatg cagttgtatc cttgaaagcc ccttactttt gtggagggtt   7140
tatactgcac gatactgtga caggaacagc ttgcagagtg gcagacccgc taaaaaggct   7200
ttttaaactg ggcaaaccgc tagcggcagg tgacgaacaa gatgaagata gaagacgagc   7260
gctggctgac gaagtgatca gatggcaacg aacagggcta attgatgagc tggagaaagc   7320
ggtatactct aggtacgaag tgcagggtat atcagttgtg gtaatgtcca tggccacctt   7380
tgcaagctcc agatccaact tcgagaagct cagaggaccc gtcataactt tgtacggcgg   7440
tcctaaatag gtacgcacta cagctaccta ttttgcagaa gccgacagca agtatctaaa   7500
```

-continued

```
cactaatcag ctacaatgga gttcatccca acccaaactt tttacaatag gaggtaccag   7560
cctcgaccct ggactccgcg ccctactatc caagtcatca ggcccagacc gcgccctcag   7620
aggcaagctg ggcaacttgc ccagctgatc tcagcagtta ataaactgac aatgcgcgcg   7680
gtaccccaac agaagccacg caggaatcgg aagaataaga agcaaaagca aaaacaacag   7740
gcgccacaaa acaacacaaa tcaaaagaag cagccaccta aaaagaaacc ggctcaaaag   7800
aaaaagaagc cgggccgcag agagaggatg tgcatgaaaa tcgaaaatga ttgtattttc   7860
gaagtcaagc acgaaggtaa ggtaacaggt tacgcgtgcc tggtggggga caaagtaatg   7920
aaaccagcac acgtaaaggg gaccatcgat aacgcggacc tggccaaact ggcctttaag   7980
cggtcatcta agtatgacct tgaatgcgcg cagatacccg tgcacatgaa gtccgacgct   8040
tcgaagttca cccatgagaa accggagggg tactacaact ggcaccacgg agcagtacag   8100
tactcaggag gccggttcac catccctaca ggtgctggca aaccagggga cagcggcaga   8160
ccgatcttcg acaacaaggg acgcgtggtg gccatagtct taggaggagc taatgaagga   8220
gcccgtacag ccctctcggt ggtgacctgg aataaagaca ttgtcactaa aatcaccccc   8280
gagggggccg aagagtggag tcttgccatc ccagttatgt gcctgttggc aaacaccacg   8340
ttcccctgct cccagccccc ttgcacgccc tgctgctacg aaaaggaacc ggaggaaacc   8400
ctacgcatgc ttgaggacaa cgtcatgaga cctgggtact atcagctgct acaagcatcc   8460
ttaacatgtt ctccccaccg ccagcgacgc agcaccaagg acaacttcaa tgtctataaa   8520
gccacaagac catacttagc tcactgtccc gactgtggag aagggcactc gtgccatagt   8580
cccgtagcac tagaacgcat cagaaatgaa gcgacagacg ggacgctgaa aatccaggtc   8640
tccttgcaaa tcggaataaa gacggatgac agccacgatt ggaccaagct gcgttatatg   8700
gacaaccaca tgccagcaga cgcagagagg gcggggctat ttgtaagaac atcagcaccg   8760
tgtacgatta ctggaacaat gggacacttc atcctggccc gatgtccaaa aggggaaact   8820
ctgacggtgg gattcactga cagtaggaag attagtcact catgtacgca cccatttcac   8880
cacgaccctc ctgtgatagg tcgggaaaaa ttccattccc gaccgcagca cggtaaagag   8940
ctaccttgca gcacgtacgt gcagagcacc gccgcaacta ccgaggagat agaggtacac   9000
atgcccccag acacccctga tcgcacatta atgtcacaac agtccggcaa cgtaaagatc   9060
acagtcaatg gccagacggt gcggtacaag tgtaattgcg gtggctcaaa tgaaggacta   9120
acaactacag acaaagtgat taataactgc aaggttgatc aatgtcatgc cgcggtcacc   9180
aatcacaaaa agtggcagta taactcccct ctggtcccgc gtaatgctga acttggggac   9240
cgaaaaggaa aaattcacat cccgtttccg ctggcaaatg taacatgcag ggtgcctaaa   9300
gcaaggaacc ccaccgtgac gtacgggaaa aaccaagtca tcatgctact gtatcctgac   9360
cacccaacac tcctgtccta ccggaatatg ggagaagaac caaactatca agaagagtgg   9420
gtgatgcata agaaggaagt cgtgctaacc gtgccgactg aagggctcga ggtcacgtgg   9480
ggcaacaacg agccgtataa gtattggccg cagttatcta caaacggtac agcccatggc   9540
cacccgcacg agataattct gtattattat gagctgtacc ccactatgac tgtagtagtt   9600
gtgtcagtgg ccacgttcat actcctgtcg atggtgggta tggcagcggg gatgtgcatg   9660
tgtgcacgac gcagatgcat cacaccgtat gaactgacac caggagctac cgtccctttc   9720
ctgcttagcc taatatgctg catcagaaca gctaaagcgg ccacatacca agaggctgcg   9780
atatacctgt ggaacgagca gcaacctttg ttttggctac aagcccttat tccgctggca   9840
gccctgattg ttctatgcaa ctgtctgaga ctcttaccat gctgctgtaa aacgttggct   9900
```

```
tttttagccg taatgagcgt cggtgcccac actgtgagcg cgtacgaaca cgtaacagtg   9960
atcccgaaca cggtgggagt accgtataag actctagtca atagacctgg ctacagcccc  10020
atggtattgg agatggaact actgtcagtc actttggagc caacactatc gcttgattac  10080
atcacgtgcg agtacaaaac cgtcatcccg tctccgtacg tgaagtgctg cggtacagca  10140
gagtgcaagg acaaaaacct acctgactac agctgtaagg tcttcaccgg cgtctaccca  10200
tttatgtggg gcggcgccta ctgcttctgc gacgctgaaa acacgcagtt gagcgaagca  10260
cacgtggaga agtccgaatc atgcaaaaca gaatttgcat cagcatacag ggctcatacc  10320
gcatctgcat cagctaagct ccgcgtcctt taccaaggaa ataacatcac tgtaactgcc  10380
tatgcaaacg gcgaccatgc cgtcacagtt aaggacgcca aattcattgt ggggccaatg  10440
tcttcagcct ggacaccttt cgacaacaaa attgtggtgt acaaaggtga cgtctataac  10500
atggactacc cgccctttgg cgcaggaaga ccaggacaat ttggcgatat ccaaagtcgc  10560
acacctgaga gtaaagacgt ctatgctaat acacaactgg tactgcagag accggctgtg  10620
ggtacggtac acgtgccata ctctcaggca ccatctggct ttaagtattg gctaaaagaa  10680
cgcggggcgt cgctgcagca cacagcacca tttggctgcc aaatagcaac aaacccggta  10740
agagcggtga actgcgccgt agggaacatg cccatctcca tcgacatacc ggaagcggcc  10800
ttcactaggg tcgtcgacgc gccctcttta acggacatgt cgtgcgaggt accagcctgc  10860
acccattcct cagactttgg gggcgtcgcc attattaaat atgcagccag caagaaaggc  10920
aagtgtgcgg tgcattcgat gactaacgcc gtcactattc gggaagctga gatagaagtt  10980
gaagggaatt ctcagctgca aatctctttc tcgacggcct tagccagcgc cgaattccgc  11040
gtacaagtct gttctacaca agtacactgt gcagccgagt gccacccccc gaaggaccac  11100
atagtcaact acccggcgtc acataccacc ctcggggtcc aggacatctc cgctacggcg  11160
atgtcatggg tgcagaagat cacgggaggt gtgggactgg ttgttgctgt tgccgcactg  11220
attctaatcg tggtgctatg cgtgtcgttc agcaggcact aacttgacaa ttaagtatga  11280
aggtatatgt gtcccctaag agacacactg tacatagcaa ataatctata gatcaaaggg  11340
ctacgcaacc cctgaatagt aacaaaatat aaaatcacta aaaattataa aaacagaaaa  11400
atacataaat aggtatacgt gtcccctaag agacacattg tatgtaggtg ataagtatag  11460
atcaaagggc cgaataaccc ctgaatagta acaaaatatg aaaatcaata aaaatcataa  11520
aatagaaaaa ccataaacag aagtagttca aagggctata aaacccctga atagtaacaa  11580
aacataaaat taataaaaat c                                            11601
```

<210> SEQ ID NO 6
<211> LENGTH: 11237
<212> TYPE: DNA
<213> ORGANISM: Chikungunya virus

<400> SEQUENCE: 6

```
cagtttctta ctgctctact ctgcaaagca agagattaat aacccatcat ggatcctgtg     60
tacgtggaca tagacgctga cagcgccttt ttgaaggccc tgcaacgtgc gtaccccatg    120
tttgaggtgg aaccaaggca ggtcacaccg aatgaccatg ctaatgctag agcgttctcg    180
catctagcta taaaactaat agagcaggaa attgaccccg actcaaccat cctggatatc    240
ggcagtgcgc cagcaaggag gatgatgtcg gacaggaagt accactgcgt ctgcccgatg    300
cgcagtgcgg aagatcccga gagactcgcc aattatgcga gaaagctagc atctgccgca    360
```

-continued

```
ggaaaagtcc tggacagaaa catctctgga aagatcgggg acttacaagc agtaatggcc    420
gtgccagaca cggagacgcc aacattctgc ttacacacag acgtctcatg tagacagaga    480
gcagacgtcg ctatatacca agacgtctat gctgtacacg cacccacgtc gctataccac    540
caggcgatta aaggggtccg agtggcgtac tgggttgggt tcgacacaac cccgttcatg    600
tacaatgcca tggcgggtgc ctacccctca tactcgacaa actgggcaga tgagcaggta    660
ctgaaggcta agaacatagg attatgttca acagacctga cggaaggtag acgaggcaag    720
ttgtctatta tgagagggaa aaagctaaaa ccgtgcgacc gtgtgctgtt ctcagtaggg    780
tcaacgctct acccggaaag ccgcaagcta cttaagagct ggcacctgcc atcggtgttc    840
catttaaagg gcaaactcag cttcacatgc cgctgtgata cagtggtttc gtgtgagggc    900
tacgtcgtta agagaataac gatgagccca ggcctttatg gaaaaaccac agggtatgcg    960
gtaacccacc acgcagacgg attcctgatg tgcaagacta ccgacacggt tgacggcgaa   1020
agagtgtcat tctcggtgtg cacatacgtg ccggcgacca tttgtgatca aatgaccggc   1080
atccttgcta cagaagtcac gccggaggat gcacagaagc tgttggtggg gctgaaccag   1140
agaatagtgg ttaacggcag aacgcaacgg aatacgaaca ccatgaaaaa ttatctgctt   1200
cccgtggtcg cccaagcctt cagtaagtgg gcaaaggagt gccggaaaga catggaagat   1260
gaaaaactcc tgggggtcag agaaagaaca ctgacctgct gctgtctatg ggcattcaag   1320
aagcagaaaa cacacacggt ctacaagagg cctgataccc agtcaattca gaaggttcag   1380
gccgagtttg acagctttgt ggtaccgagt ctgtggtcgt ccgggttgtc aatccctttg   1440
aggactagaa tcaaatggtt gttaagcaag gtgccaaaaa ccgacctgat cccatacagc   1500
ggagacgccc gagaagcccg ggacgcagaa aaagaagcag aggaagaacg agaagcagaa   1560
ctgactcgcg aagccctacc acctctacag gcagcacagg aagatgttca ggtcgaaatc   1620
gacgtggaac agcttgagga cagagcgggc gcaggaataa tagagactcc gagaggagct   1680
atcaaagtta ctgcccaacc aacagaccac gtcgtgggag agtacctggt actctccccg   1740
cagaccgtac tacgtagcca gaagctcagt ctgattcacg ctttggcgga gcaagtgaag   1800
acgtgcacgc acaacggacg agcagggagg tatgcggtcg aagcgtacga cggccgagtc   1860
ctagtgccct caggctatgc aatctcgcct gaagacttcc agagtctaag cgaaagcgca   1920
acgatggtgt ataacgaaag agagttcgta aacagaaagc tacaccatat tgcgatgcac   1980
ggaccagccc tgaacaccga cgaagagtcg tatgagctgg tgagggcaga gaggacagaa   2040
cacgagtacg tctacgacgt ggatcagaga agatgctgta agaaggaaga agccgcagga   2100
ctggtactgg tgggcgactt gactaatccg ccctaccacg aattcgcata tgaagggcta   2160
aaaatccgcc ctgcctgccc atacaaaatt gcagtcatag gagtcttcgg agtaccggga   2220
tctggcaagt cagctattat caagaaccta gttaccaggc aggacctggt gactagcgga   2280
aagaaagaaa actgccaaga aatcaccacc gacgtgatga gacagagagg tctagagata   2340
tctgcacgta cggttgactc gctgctcttg aatggatgca acagaccagt cgacgtgttg   2400
tacgtagacg aggcgtttgc gtgccactct ggaacgctac ttgctttgat cgccttggtg   2460
agaccaaggc agaaagttgt actttgtggt gacccgaagc agtgcggctt cttcaatatg   2520
atgcagatga aagtcaacta taatcacaac atctgcaccc aagtgtacca caaaagtatc   2580
tccaggcggt gtacactgcc tgtgaccgcc attgtgtcat cgttgcatta cgaaggcaaa   2640
atgcgcacta cgaatgagta caacaagccg attgtagtgg acactacagg ctcaacaaaa   2700
cctgaccctg gagacctcgt gttaacgtgc ttcagagggt gggttaaaca actgcaaatt   2760
```

-continued

```
gactatcgtg gatacgaggt catgacagca gccgcatccc aagggttaac cagaaaagga   2820
gtttacgcag ttagacaaaa agttaatgaa aacccgctct atgcatcaac gtcagagcac   2880
gtcaacgtac tcctaacgcg tacggaaggt aaactggtat ggaagacact ttccggcgac   2940
ccgtggataa agacgctgca gaacccaccg aaaggaaact tcaaagcaac tattaaggag   3000
tgggaggtgg agcatgcatc aataatggcg ggcatctgca gtcaccaaat gaccttcgat   3060
acattccaaa ataaagccaa cgtttgttgg gctaagagct tggtccctat cctcgaaaca   3120
gcggggataa aactaaatga taggcagtgg tctcagataa ttcaagcctt caaagaagac   3180
aaagcatact cacctgaagt agccctgaat gaaatatgta cgcgcatgta tggggtggat   3240
ctagacagcg ggctattttc taaaccgttg gtgtctgtgt attacgcgga taaccactgg   3300
gataataggc ctggagggaa aatgttcgga tttaaccccg aggcagcatc cattctagaa   3360
agaaagtatc cattcacaaa agggaagtgg aacatcaaca agcagatctg cgtgactacc   3420
aggaggatag aagactttaa ccctaccacc aacatcatac cggccaacag gagactacca   3480
cactcattag tggccgaaca ccgcccagta aaaggggaaa gaatggaatg gctggttaac   3540
aagataaacg gccaccacgt gctcctggtc agtggctata accttgcact gcctactaag   3600
agagtcactt gggtagcgcc gttaggtgtc cgcggagcgg actacacata caacctagag   3660
ttgggtctgc cagcaacgct tggtaggtat gacctagtgg tcataaacat ccacacacct   3720
tttcgcatac accattacca acagtgcgtc gaccacgcaa tgaaactgca aatgctcggg   3780
ggtgactcat tgagactgct caaaccgggc ggctctctat tgatcagagc atatggttac   3840
gcagatagaa ccagtgaacg agtcatctgc gtattgggac gcaagtttag atcgtctaga   3900
gcgttgaaac caccatgtgt caccagcaac actgagatgt tttcctattt cagcaacttt   3960
gacaatggca gaaggaattt cacaactcat gtcatgaaca atcaactgaa tgcagccttc   4020
gtaggacagg tcacccgagc aggatgtgca ccgtcgtacc gggtaaaacg catggacatc   4080
gcgaagaacg atgaagagtg cgtagtcaac gccgctaacc ctcgcgggtt accgggtgac   4140
ggtgtttgca aggcagtata caaaaaatgg ccggagtcct ttaagaacag tgcaacacca   4200
gtgggaaccg caaaaacagt tatgtgcggt acgtatccag taatccacgc tgttggacca   4260
aacttctcta attattcgga gtctgaaggg gaccgggaat tggcagctgc ctatcgagaa   4320
gtcgcaaagg aagtaactag gctgggagta aatagtgtag ctatacctct cctctccaca   4380
ggtgtatact caggagggaa agacaggctg acccagtcac tgaaccacct ctttacagcc   4440
atggactcga cggatgcaga cgtggtcatc tactgccgcg acaaagaatg ggagaagaaa   4500
atatctgagg ccatacagat gcggacccaa gtagagctgc tggatgagca catctccata   4560
gactgcgata ttgttcgcgt gcaccctgac agcagcttgg caggcagaaa aggatacagc   4620
accacggaag gcgcactgta ctcatatcta gaagggaccc gttttcatca gacggctgtg   4680
gatatggcgg agatacatac tatgtggcca aagcaaacag aggccaatga gcaagtctgc   4740
ctatatgccc tgggggaaag tattgaatcg atcaggcaga aatgcccggt ggatgatgca   4800
gacgcatcat ctcccccaa aactgtcccg tgcctttgcc gttacgctat gactccagaa   4860
cgcgtcaccc ggcttcgcat gaaccacgtc acaagcataa ttgtgtgttc ttcgtttccc   4920
ctcccaaagt acaaaataga aggagtgcaa aaagtcaaat gctctaaggt aatgctattt   4980
gaccacaacg tgccatcgcg cgtaagtcca agggaatata gatcttccca ggagtctgca   5040
caggaggcga gtacaatcac gtcactgacg catagtcaat tcgacctaag cgttgatggc   5100
```

```
gagatactgc ccgtcccgtc agacctggat gctgacgccc cagccctaga accagcacta   5160
gacgacgggg cgacacacac gctgccatcc acaaccggaa accttgcggc cgtgtctaga   5220
cagggcaggt gggtatatat tctcgtcgga caccggtcca ggtcatttac aacagaagtc   5280
agtacgccag tcagtgctgc cggtgaacac cctggaggaa gtccacgagg agaagtgtta   5340
cccacctaag ctggatgaag caaaggagca actattactt aagaaactcc aggagagtgc   5400
atccatggcc aacagaagca ggtatcagtc gcgcaaagta gaaaacatga aagcagcaat   5460
catccagaga ctaaagagag gctgtagact atacttaatg tcagagaccc caaaagtccc   5520
tacttaccgg actacatatc cggcgcctgt gtactcgcct ccgatcaacg tccgattgtc   5580
caatcccgag tccgcagtgg cagcatgcaa tgagttctta gctagaaact atccaactgt   5640
ctcatcatac caaattaccg acgagtatga tgcatatcta gacatggtgg acgggtcgga   5700
gagttgcctg gaccgagcga cattcaatcc gtcaaaactc aggagctacc cgaaacagca   5760
cgcttaccac gcgccctcca tcagaagcgc tgtaccgtcc ccattccaga acacactaca   5820
gaatgtactg gcagcagcca cgaaaagaaa ctgcaacgtc acacagatga gggaattacc   5880
cactttggac tcagcagtat tcaacgtgga gtgtttcaaa aaattcgcat gcaaccaaga   5940
atactgggaa gaatttgctg ccagccctat taggataaca actgagaatt tagcaaccta   6000
tgttactaaa ctaaaagggc caaaagcagc agcgctattc gcaaaaaccc ataatctact   6060
gccactacag gaagtaccaa tggataggtt cacagtagat atgaaaaggg acgtgaaggt   6120
gactcctggt acaaagcata cagaggaaag acctaaggtg caggttatac aggcggctga   6180
acccttggcg acagcatacc tatgtgggat tcacagagag ctggttagga ggctgaacgc   6240
cgtcctccta cccaatgtac atacactatt tgacatgtct gccgaggatt tcgatgccat   6300
catagccgca cactttaagc caggagacac tgttttggaa acggacatag cctcctttga   6360
taagagccaa gatgattcac ttgcgcttac tgctttgatg ctgttagagg atttaggggt   6420
ggatcactcc ctgctggact tgatagaggc tgctttcgga gagatttcca gctgtcacct   6480
accgacaggt acgcgcttca agttcggcgc catgatgaaa tcaggtatgt tcctaactct   6540
gttcgtcaac acattgttaa acatcaccat cgccagccga gtgctggaag atcgtctgac   6600
aaaatccgcg tgcgcggcct tcatcggcga cgacaacata atacatggag tcgtctccga   6660
tgaattgatg gcagccagat gtgccacttg gatgaacatg gaagtgaaga tcatagatgc   6720
agttgtatcc ttgaaagccc cttacttttg tggagggttt atactgcacg atactgtgac   6780
aggaacagct tgcagagtgg cagacccgct aaaaaggctt tttaaactgg gcaaaccgct   6840
agcggcaggt gacgaacaag atgaagatag aagacgagcg ctggctgacg aagtgatcag   6900
atggcaacga acagggctaa ttgatgagct ggagaaagcg gtatactcta ggtacgaagt   6960
gcagggtata tcagttgtgg taatgtccat ggccaccttt gcaagctcca gatccaactt   7020
cgagaagctc agaggacccg tcataacttt gtacggcggt cctaaatagg tacgcactac   7080
agctacctat tttgcagaag ccgacagcaa gtatctaaac actaatcagc tacaatggag   7140
ttcatcccaa cccaaacttt ttacaatagg aggtaccagc ctcgaccctg gactccgcgc   7200
cctactatcc aagtcatcag gcccagaccg cgccctcaga ggcaagctgg gcaacttgcc   7260
cagctgatct cagcagttaa taaactgaca atgcgcgcgg taccccaaca gaagccacgc   7320
aggaatcgga agaataagaa gcaaaagcaa aaacaacagg cgccacaaaa caacacaaat   7380
caaaagaagc agccacctaa aaagaaaccg gctcaaaaga aaaagaagcc gggccgcaga   7440
gagaggatgt gcatgaaaat cgaaaatgat tgtattttcg aagtcaagca cgaaggtaag   7500
```

-continued

```
gtaacaggtt acgcgtgcct ggtgggggac aaagtaatga aaccagcaca cgtaaagggg   7560
accatcgata acgcggacct ggccaaactg gcctttaagc ggtcatctaa gtatgacctt   7620
gaatgcgcgc agatacccgt gcacatgaag tccgacgctt cgaagttcac ccatgagaaa   7680
ccggaggggt actacaactg gcaccacgga gcagtacagt actcaggagg ccggttcacc   7740
atccctacag gtgctggcaa accaggggac agcggcagac cgatcttcga caacaaggga   7800
cgcgtggtgg ccatagtctt aggaggagct aatgaaggag cccgtacagc cctctcggtg   7860
gtgacctgga ataaagacat tgtcactaaa atcacccccg agggggccga agagtggagt   7920
cttgccatcc cagttatgtg cctgttggca aacaccacgt tcccctgctc ccagcccccct   7980
tgcacgccct gctgctacga aaaggaaccg gaggaaaccc tacgcatgct tgaggacaac   8040
gtcatgagac ctgggtacta tcagctgcta caagcatcct taacatgttc tccccaccgc   8100
cagcgacgca gcaccaagga caacttcaat gtctataaag ccacaagacc atacttagct   8160
cactgtcccg actgtggaga agggcactcg tgccatagtc ccgtagcact agaacgcatc   8220
agaaatgaag cgacagacgg gacgctgaaa atccaggtct ccttgcaaat cggaataaag   8280
acggatgaca gccacgattg gaccaagctg cgttatatgg acaaccacat gccagcagac   8340
gcagagaggg cggggctatt tgtaagaaca tcagcaccgt gtacgattac tggaacaatg   8400
ggacacttca tcctggcccg atgtccaaaa ggggaaactc tgacggtggg attcactgac   8460
agtaggaaga ttagtcactc atgtacgcac ccatttcacc acgaccctcc tgtgataggt   8520
cgggaaaaat tccattcccg accgcagcac ggtaaagagc taccttgcag cacgtacgtg   8580
cagagcaccg ccgcaactac cgaggagata gaggtacaca tgcccccaga cacccctgat   8640
cgcacattaa tgtcacaaca gtccggcaac gtaaagatca cagtcaatgg ccagacggtg   8700
cggtacaagt gtaattgcgg tggctcaaat gaaggactaa caactacaga caaagtgatt   8760
aataactgca aggttgatca atgtcatgcc gcggtcacca atcacaaaaa gtggcagtat   8820
aactcccctc tggtcccgcg taatgctgaa cttggggacc gaaaaggaaa aattcacatc   8880
ccgtttccgc tggcaaatgt aacatgcagg gtgcctaaag caaggaaccc caccgtgacg   8940
tacgggaaaa accaagtcat catgctactg tatcctgacc acccaacact cctgtcctac   9000
cggaatatgg gagaagaacc aaactatcaa gaagagtggg tgatgcataa gaaggaagtc   9060
gtgctaaccg tgccgactga agggctcgag gtcacgtggg gcaacaacga gccgtataag   9120
tattggccgc agttatctac aaacggtaca gcccatggcc acccgcatga gataattctg   9180
tattattatg agctgtaccc cactatgact gtagtagttg tgtcagtggc cacgttcata   9240
ctcctgtcga tggtgggtat ggcagcgggg atgtgcatgt gtgcacgacg cagatgcatc   9300
acaccgtatg aactgacacc aggagctacc gtccctttcc tgcttagcct aatatgctgc   9360
atcagaacag ctaaagcggc cacataccaa gaggctgcga tatacctgtg gaacgagcag   9420
caacctttgt tttggctaca agcccttatt ccgctggcag ccctgattgt tctatgcaac   9480
tgtctgagac tcttaccatg ctgctgtaaa acgttggctt ttttagccgt aatgagcgtc   9540
ggtgcccaca ctgtgagcgc gtacgaacac gtaacagtga tcccgaacac ggtgggagta   9600
ccgtataaga ctctagtcaa tagacctggc tacagcccca tggtattgga gatggaacta   9660
ctgtcagtca ctttggagcc aacactatcg cttgattaca tcacgtgcga gtacaaaacc   9720
gtcatcccgt ctccgtacgt gaagtgctgc ggtacagcag agtgcaagga caaaaaccta   9780
cctgactaca gctgtaaggt cttcaccggc gtctacccat ttatgtgggg cggcgcctac   9840
```

```
tgcttctgcg acgctgaaaa cacgcagttg agcgaagcac acgtggagaa gtccgaatca   9900

tgcaaaacag aatttgcatc agcatacagg gctcataccg catctgcatc agctaagctc   9960

cgcgtccttt accaaggaaa taacatcact gtaactgcct atgcaaacgg cgaccatgcc  10020

gtcacagtta aggacgccaa attcattgtg gggccaatgt cttcagcctg gacacctttc  10080

gacaacaaaa ttgtggtgta caaaggtgac gtctataaca tggactaccc gccctttggc  10140

gcaggaagac caggacaatt tggcgatatc caaagtcgca cacctgagag taaagacgtc  10200

tatgctaata cacaactggt actgcagaga ccggctgcgg gtacggtaca cgtgccatac  10260

tctcaggcac catctggctt taagtattgg ctaaaagaac gcggggcgtc gctgcagcac  10320

acagcaccat ttggctgcca aatagcaaca aacccggtaa gagcggtgaa ctgcgccgta  10380

gggaacatgc ccatctccat cgacataccg gaagcggcct tcactagggt cgtcgacgcg  10440

ccctctttaa cggacatgtc gtgcgaggta ccagcctgca cccattcctc agactttggg  10500

ggcgtcgcca ttattaaata tgcagccagc aagaaaggca agtgtgcggt gcattcgatg  10560

actaacgccg tcactattcg ggaagctgag atagaagttg aagggaattc tcagctgcaa  10620

atctctttct cgacggcctt agccagcgcc gaattccgcg tacaagtctg ttctacacaa  10680

gtacactgtg cagccgagtg ccaccccccg aaggaccaca tagtcaacta cccggcgtca  10740

cataccaccc tcggggtcca ggacatctcc gctacggcga tgtcatgggt gcagaagatc  10800

acgggaggtg tgggactggt tgttgctgtt gccgcactga ttctaatcgt ggtgctatgc  10860

gtgtcgttca gcaggcacta acttgacaat taagtatgaa ggtatatgtg tcccctaaga  10920

gacacactgt acatagcaaa taatctatag atcaaagggc tacgcaaccc ctgaatagta  10980

acaaaataca aaatcactaa aaattataaa aacagaaaaa tacataaata ggtatacgtg  11040

tcccctaaga gacacattgt atgtaggtga taagtataga tcaaagggcc gaataacccc  11100

tgaatagtaa caaaatatga aaatcaataa aaatcataaa atagaaaaac cataaacaga  11160

agtagttcaa agggctataa aacccctgaa tagtaacaaa acataaaatt aataaaaatc  11220

aaatgaatac catatgg                                                 11237
```

```
<210> SEQ ID NO 7
<211> LENGTH: 1797
<212> TYPE: DNA
<213> ORGANISM: Chikungunya virus

<400> SEQUENCE: 7

atacccgtgc acatgaagtc cgacgcttcg aagttcaccc atgagaaacc ggaggggtac     60

tacaactggc accacggagc agtacagtac tcaggaggcc ggttcaccat ccctacaggt    120

gctggcaaac caggggacag cggcagaccg atcttcgaca acaagggacg cgtggtggcc    180

atagtcttag gaggagctaa tgaaggagcc cgtacagccc tctcggtggt gacctggaat    240

aaagacattg tcactaaaat cacccccgag gggccgaag agtggagtct tgccatccca    300

gttatgtgcc tgttggcaaa caccacgttc ccctgctccc agccccccttg cacgccctgc    360

tgctacgaaa aggaaccgga ggaaaccta cgcatgcttg aggacaacgt catgagacct    420

gggtactatc agctgctaca agcatcctta acatgttctc cccaccgcca gcgacgcagc    480

accaaggaca acttcaatgt ctataaagcc acaagaccat acttagctca ctgtcccgac    540

tgtggagaag ggcactcgtg ccatagtccc gtagcactag aacgcatcag aaatgaagcg    600

acagacggga cgctgaaaat ccaggtctcc ttgcaaatcg gaataaagac ggatgacagc    660

cacgattgga ccaagctgcg ttatatggac aaccacatgc cagcagacgc agagagggcg    720
```

-continued

```
gggctatttg taagaacatc agcaccgtgt acgattactg gaacaatggg acacttcatc    780
ctggcccgat gtccaaaagg ggaaactctg acggtgggat tcactgacag taggaagatt    840
agtcactcat gtacgcaccc atttcaccac gaccctcctg tgataggtcg ggaaaaattc    900
cattcccgac cgcagcacgg taaagagcta ccttgcagca cgtacgtgca gagcaccgcc    960
gcaactaccg aggagataga ggtacacatg cccccagaca cccctgatcg cacattaatg   1020
tcacaacagt ccggcaacgt aaagatcaca gtcaatggcc agacggtgcg gtacaagtgt   1080
aattgcggtg gctcaaatga aggactaaca actacagaca aagtgattaa taactgcaag   1140
gttgatcaat gtcatgccgc ggtcaccaat cacaaaaagt ggcagtataa ctcccctctg   1200
gtcccgcgta atgctgaact tggggaccga aaaggaaaaa ttcacatccc gtttccgctg   1260
gcaaatgtaa catgcagggt gcctaaagca aggaacccca ccgtgacgta cgggaaaaac   1320
caagtcatca tgctactgta tcctgaccac ccaacactcc tgtcctaccg gaatatggga   1380
gaagaaccaa actatcaaga agagtgggtg atgcataaga aggaagtcgt gctaaccgtg   1440
ccgactgaag ggctcgaggt cacgtggggc aacaacgagc cgtataagta ttggccgcag   1500
ttatctacaa acggtacagc ccatggccac ccgcatgaga taattctgta ttattatgag   1560
ctgtacccca ctatgactgt agtagttgtg tcagtggcca cgttcatact cctgtcgatg   1620
gtgggtatgg cagcggggat gtgcatgcgt gcacgacgca gatgcatcac accgtatgaa   1680
ctgacaccag gagctaccgt ccctttcctg cttagcctaa tatgctgcat cagaacagct   1740
aaagcggcca cataccaaga ggctgcgata tacctgtgga acgagcagca acctttta     1797
```

<210> SEQ ID NO 8
<211> LENGTH: 1797
<212> TYPE: DNA
<213> ORGANISM: Chikungunya virus

<400> SEQUENCE: 8

```
atacccgtgc acatgaagtc cgacgcttcg aagttcaccc atgagaaacc ggaggggtac     60
tacaactggc accacggagc agtacagtac tcaggaggcc ggttcaccat ccctacaggt    120
gctggcaaac caggggacag cggcagaccg atcttcgaca acaagggacg cgtggtggcc    180
atagtcttag gaggagctaa tgaaggagcc cgtacagccc tctcggtggt gacctggaat    240
aaagacattg tcactaaaat cacccccgag gggggccgaag agtggagtct tgccatccca    300
gttatgtgcc tgttggcaaa caccacgttc ccctgctccc agccccctg cacgccctgc    360
tgctacgaaa aggaaccgga ggaaacccta cgcatgcttg aggacaacgt catgagacct    420
gggtactatc agctgctaca agcatcctta acatgttctc cccaccgcca gcgacgcagc    480
accaaggaca acttcaatgt ctataaagcc acaagaccat acttagctca ctgtcccgac    540
tgtggagaag ggcactcgtg ccatagtccc gtagcactag aacgcatcag aaatgaagcg    600
acagacggga cgctgaaaat ccaggtctcc ttgcaaatcg gaataaagac ggatgacagc    660
cacgattgga ccaagctgcg ttatatggac aaccacatgc cagcagacgc agagagggcg    720
gggctatttg taagaacatc agcaccgtgt acgattactg gaacaatggg acacttcatc    780
ctggcccgat gtccaaaagg ggaaactctg acggtgggat tcactgacag taggaagatt    840
agtcactcat gtacgcaccc atttcaccac gaccctcctg tgataggtcg ggaaaaattc    900
cattcccgac cgcagcacgg taaagagcta ccttgcagca cgtacgtgca gagcaccgcc    960
gcaactaccg aggagataga ggtacacatg cccccagaca cccctgatcg cacattaatg   1020
```

-continued

```
tcacaacagt ccggcaacgt aaagatcaca gtcaatggcc agacggtgcg gtacaagtgt   1080

aattgcggtg gctcaaatga aggactaaca actacagaca aagtgattaa taactgcaag   1140

gttgatcaat gtcatgccgc ggtcaccaat cacaaaaagt ggcagtataa ctcccctctg   1200

gtcccgcgta atgctgaact tggggaccga aaaggaaaaa ttcacatccc gtttccgctg   1260

gcaaatgtaa catgcagggt gcctaaagca aggaacccca ccgtgacgta cgggaaaaac   1320

caagtcatca tgctactgta tcctgaccac ccaacactcc tgtcctaccg gaatatggga   1380

gaagaaccaa actatcaaga agagtgggtg atgcataaga aggaagtcgt gctaaccgtg   1440

ccgactgaag ggctcgaggt cacgtggggc aacaacgagc cgtataagta ttggccgcag   1500

ttatctacaa acggtacagc ccatggccac ccgcatgaga taattctgta ttattatgag   1560

ctgtacccca ctatgactgt agtagttgtg tcagtggcca cgttcatact cctgtcgatg   1620

gtgggtatgg cagcggggat gtgcatgtgt gcacgacgca gatgcatcac accgtatgaa   1680

ctgacaccag gagctaccgt ccctttcctg cttagcctaa tatgctgcat cagaacagct   1740

aaagcggcca cataccaaga ggctgcgata tacctgtgga acgagcagca accttta      1797
```

```
<210> SEQ ID NO 9
<211> LENGTH: 1797
<212> TYPE: DNA
<213> ORGANISM: Chikungunya virus

<400> SEQUENCE: 9

atacccgtgc acatgaagtc cgacgcttcg aagttcaccc atgagaaacc ggaggggtac     60

tacaactggc accacggagc agtacagtac tcaggaggcc ggttcaccat ccctacaggt    120

gctggcaaac caggggacag cggcagaccg atcttcgaca acaagggacg cgtggtggcc    180

atagtcttag gaggagctaa tgaaggagcc cgtacagccc tctcggtggt gacctggaat    240

aaagacattg tcactaaaat cacccccgag gggggccgaag agtggagtct tgccatccca    300

gttatgtgcc tgttggcaaa caccacgttc ccctgctccc agccccccttg cacgccctgc    360

tgctacgaaa aggaaccgga ggaaacccta cgcatgcttg aggacaacgt catgagacct    420

gggtactatc agctgctaca agcatcctta acatgttctc cccaccgcca gcgacgcagc    480

accaaggaca acttcaatgt ctataaagcc acaagaccat acttagctca ctgtcccgac    540

tgtggagaag ggcactcgtg ccatagtccc gtagcactag aacgcatcag aaatgaagcg    600

acagacggga cgctgaaaat ccaggtctcc ttgcaaatcg gaataaagac ggatgacagc    660

cacgattgga ccaagctgcg ttatatggac aaccacatgc cagcagacgc agagagggcg    720

gggctatttg taagaacatc agcaccgtgt acgattactg gaacaatggg acacttcatc    780

ctggcccgat gtccaaaagg ggaaactctg acggtgggat tcactgacag taggaagatt    840

agtcactcat gtacgcaccc atttcaccac gaccctcctg tgataggtcg ggaaaaattc    900

cattcccgac cgcagcacgg taaagagcta ccttgcagca cgtacgtgca gagcaccgcc    960

gcaactaccg aggagataga ggtacacatg cccccagaca cccctgatcg cacattaatg   1020

tcacaacagt ccggcaacgt aaagatcaca gtcaatggcc agacggtgcg gtacaagtgt   1080

aattgcggtg gctcaaatga aggactaaca actacagaca aagtgattaa taactgcaag   1140

gttgatcaat gtcatgccgc ggtcaccaat cacaaaaagt ggcagtataa ctcccctctg   1200

gtcccgcgta atgctgaact tggggaccga aaaggaaaaa ttcacatccc gtttccgctg   1260

gcaaatgtaa catgcagggt gcctaaagca aggaacccca ccgtgacgta cgggaaaaac   1320

caagtcatca tgctactgta tcctgaccac ccaacactcc tgtcctaccg gaatatggga   1380
```

-continued

```
gaagaaccaa actatcaaga agagtgggtg atgcataaga aggaagtcgt gctaaccgtg   1440

ccgactgaag ggctcgaggt cacgtggggc aacaacgagc cgtataagta ttggccgcag   1500

ttatctacaa acggtacagc ccatggccac ccgcacgaga taattctgta ttattatgag   1560

ctgtacccca ctatgactgt agtagttgtg tcagtggcca cgttcatact cctgtcgatg   1620

gtgggtatgg cagcggggat gtgcatgtgt gcacgacgca gatgcatcac accgtatgaa   1680

ctgacaccag gagctaccgt ccctttcctg cttagcctaa tatgctgcat cagaacagct   1740

aaagcggcca cataccaaga ggctgcgata tacctgtgga acgagcagca acctttta     1797


<210> SEQ ID NO 10
<211> LENGTH: 1797
<212> TYPE: DNA
<213> ORGANISM: Chikungunya virus

<400> SEQUENCE: 10

atacccgtgc acatgaagtc cgacgcttcg aagttcaccc atgagaaacc ggaggggtac     60

tacaactggc accacggagc agtacagtac tcaggaggcc ggttcaccat ccctacaggt    120

gctggcaaac caggggacag cggcagaccg atcttcgaca acaagggacg cgtggtggcc    180

atagtcttag gaggagctaa tgaaggagcc cgtacagccc tctcggtggt gacctggaat    240

aaagacattg tcactaaaat cacccccgag gggccgaag agtggagtct tgccatccca    300

gttatgtgcc tgttggcaaa caccacgttc ccctgctccc agccccccttg cacgccctgc    360

tgctacgaaa aggaaccgga ggaaacccta cgcatgcttg aggacaacgt catgagacct    420

gggtactatc agctgctaca agcatcctta acatgttctc cccaccgcca gcgacgcagc    480

accaaggaca acttcaatgt ctataaagcc acaagaccat acttagctca ctgtcccgac    540

tgtggagaag ggcactcgtg ccatagtccc gtagcactag aacgcatcag aaatgaagcg    600

acagacggga cgctgaaaat ccaggtctcc ttgcaaatcg gaataaagac ggatgacagc    660

cacgattgga ccaagctgcg ttatatggac aaccacatgc cagcagacgc agagagggcg    720

gggctatttg taagaacatc agcaccgtgt acgattactg gaacaatggg acacttcatc    780

ctggcccgat gtccaaaagg ggaaactctg acggtgggat tcactgacag taggaagatt    840

agtcactcat gtacgcaccc atttcaccac gaccctcctg tgataggtcg ggaaaaattc    900

cattcccgac cgcagcacgg taaagagata ccttgcagca cgtacgtgca gagcaccgcc    960

gcaactaccg aggagataga ggtacacatg cccccagaca cccctgatcg cacattaatg   1020

tcacaacagt ccggcaacgt aaagatcaca gtcaatggcc agacggtgcg gtacaagtgt   1080

aattgcggtg gctcaaatga aggactaaca actacagaca aagtgattaa taactgcaag   1140

gttgatcaat gtcatgccgc ggtcaccaat cacaaaaagt ggcagtataa ctcccctctg   1200

gtcccgcgta atgctgaact tggggaccga aaaggaaaaa ttcacatccc gtttccgctg   1260

gcaaatgtaa catgcagggt gcctaaagca aggaaccccca ccgtgacgta cgggaaaaac   1320

caagtcatca tgctactgta tcctgaccac ccaacactcc tgtcctaccg gaatatggga   1380

gaagaaccaa actatcaaga agagtgggtg atgcataaga aggaagtcgt gctaaccgtg   1440

ccgactgaag ggctcgaggt cacgtggggc aacaacgagc cgtataagta ttggccgcag   1500

ttatctacaa acggtacagc ccatggccac ccgcatgaga taattctgta ttattatgag   1560

ctgtacccca ctatgactgt agtagttgtg tcagtggcca cgttcatact cctgtcgatg   1620

gtgggtatgg cagcggggat gtgcatgtgt gcacgacgca gatgcatcac accgtatgaa   1680
```

-continued

```
ctgacaccag gagctaccgt ccctttcctg cttagcctaa tatgctgcat cagaacagct   1740

aaagcggcca cataccaaga ggctgcgata tacctgtgga acgagcagca accttta      1797
```

<210> SEQ ID NO 11
<211> LENGTH: 1092
<212> TYPE: DNA
<213> ORGANISM: Chikungunya virus

<400> SEQUENCE: 11

```
gacaacttca atgtctataa agccacaaga ccatacttag ctcactgtcc cgactgtgga     60

gaagggcact cgtgccatag tcccgtagca ctagaacgca tcagaaatga agcgacagac    120

gggacgctga aaatccaggt ctccttgcaa atcggaataa agacggatga cagccacgat    180

tggaccaagc tgcgttatat ggacaaccac atgccagcag acgcagagag ggcggggcta    240

tttgtaagaa catcagcacc gtgtacgatt actggaacaa tgggacactt catcctggcc    300

cgatgtccaa aaggggaaac tctgacggtg ggattcactg acagtaggaa gattagtcac    360

tcatgtacgc acccatttca ccacgaccct cctgtgatag gtcgggaaaa attccattcc    420

cgaccgcagc acggtaaaga gctaccttgc agcacgtacg tgcagagcac cgccgcaact    480

accgaggaga tagaggtaca catgccccca gacacccctg atcgcacatt aatgtcacaa    540

cagtccggca acgtaaagat cacagtcaat ggccagacgg tgcggtacaa gtgtaattgc    600

ggtggctcaa atgaaggact aacaactaca gacaaagtga ttaataactg caaggttgat    660

caatgtcatg ccgcggtcac caatcacaaa aagtggcagt ataactcccc tctggtcccg    720

cgtaatgctg aacttgggga ccgaaaagga aaaattcaca tcccgtttcc gctggcaaat    780

gtaacatgca gggtgcctaa agcaaggaac cccaccgtga cgtacgggaa aaaccaagtc    840

atcatgctac tgtatcctga ccacccaaca ctcctgtcct accggaatat gggagaagaa    900

ccaaactatc aagaagagtg ggtgatgcat aagaaggaag tcgtgctaac cgtgccgact    960

gaagggctcg aggtcacgtg ggcaacaac gagccgtata agtattggcc gcagttatct   1020

acaaacggta cagcccatgg ccacccgcat gagataattc tgtattatta tgagctgtac   1080

cccactatga ct                                                       1092
```

<210> SEQ ID NO 12
<211> LENGTH: 1092
<212> TYPE: DNA
<213> ORGANISM: Chikungunya virus

<400> SEQUENCE: 12

```
gacaacttca atgtctataa agccacaaga ccatacttag ctcactgtcc cgactgtgga     60

gaagggcact cgtgccatag tcccgtagca ctagaacgca tcagaaatga agcgacagac    120

gggacgctga aaatccaggt ctccttgcaa atcggaataa agacggatga cagccacgat    180

tggaccaagc tgcgttatat ggacaaccac atgccagcag acgcagagag ggcggggcta    240

tttgtaagaa catcagcacc gtgtacgatt actggaacaa tgggacactt catcctggcc    300

cgatgtccaa aaggggaaac tctgacggtg ggattcactg acagtaggaa gattagtcac    360

tcatgtacgc acccatttca ccacgaccct cctgtgatag gtcgggaaaa attccattcc    420

cgaccgcagc acggtaaaga gctaccttgc agcacgtacg tgcagagcac cgccgcaact    480

accgaggaga tagaggtaca catgccccca gacacccctg atcgcacatt aatgtcacaa    540

cagtccggca acgtaaagat cacagtcaat ggccagacgg tgcggtacaa gtgtaattgc    600

ggtggctcaa atgaaggact aacaactaca gacaaagtga ttaataactg caaggttgat    660
```

caatgtcatg ccgcggtcac caatcacaaa aagtggcagt ataactcccc tctggtcccg 720
cgtaatgctg aacttgggga ccgaaaagga aaaattcaca tcccgtttcc gctggcaaat 780
gtaacatgca gggtgcctaa agcaaggaac ccccaccgtga cgtacgggaa aaaccaagtc 840
atcatgctac tgtatcctga ccacccaaca ctcctgtcct accggaatat gggagaagaa 900
ccaaactatc aagaagagtg ggtgatgcat aagaaggaag tcgtgctaac cgtgccgact 960
gaagggctcg aggtcacgtg gggcaacaac gagccgtata agtattggcc gcagttatct 1020
acaaacggta cagcccatgg ccacccgcat gagataattc tgtattatta tgagctgtac 1080
cccactatga ct 1092

<210> SEQ ID NO 13
<211> LENGTH: 1092
<212> TYPE: DNA
<213> ORGANISM: Chikungunya virus

<400> SEQUENCE: 13
gacaacttca atgtctataa agccacaaga ccatacttag ctcactgtcc cgactgtgga 60
gaagggcact cgtgccatag tcccgtagca ctagaacgca tcagaaatga agcgacagac 120
gggacgctga aaatccaggt ctccttgcaa atcggaataa agacggatga cagccacgat 180
tggaccaagc tgcgttatat ggacaaccac atgccagcag acgcagagag ggcggggcta 240
tttgtaagaa catcagcacc gtgtacgatt actggaacaa tgggacactt catcctggcc 300
cgatgtccaa aaggggaaac tctgacggtg ggattcactg acagtaggaa gattagtcac 360
tcatgtacgc acccatttca ccacgaccct cctgtgatag gtcgggaaaa attccattcc 420
cgaccgcagc acggtaaaga gctaccttgc agcacgtacg tgcagagcac cgccgcaact 480
accgaggaga tagaggtaca catgcccccca gacacccctg atcgcacatt aatgtcacaa 540
cagtccggca acgtaaagat cacagtcaat ggccagacgg tgcggtacaa gtgtaattgc 600
ggtggctcaa atgaaggact aacaactaca gacaaagtga ttaataactg caaggttgat 660
caatgtcatg ccgcggtcac caatcacaaa aagtggcagt ataactcccc tctggtcccg 720
cgtaatgctg aacttgggga ccgaaaagga aaaattcaca tcccgtttcc gctggcaaat 780
gtaacatgca gggtgcctaa agcaaggaac cccaccgtga cgtacgggaa aaaccaagtc 840
atcatgctac tgtatcctga ccacccaaca ctcctgtcct accggaatat gggagaagaa 900
ccaaactatc aagaagagtg ggtgatgcat aagaaggaag tcgtgctaac cgtgccgact 960
gaagggctcg aggtcacgtg gggcaacaac gagccgtata agtattggcc gcagttatct 1020
acaaacggta cagcccatgg ccacccgcac gagataattc tgtattatta tgagctgtac 1080
cccactatga ct 1092

<210> SEQ ID NO 14
<211> LENGTH: 1092
<212> TYPE: DNA
<213> ORGANISM: Chikungunya virus

<400> SEQUENCE: 14
gacaacttca atgtctataa agccacaaga ccatacttag ctcactgtcc cgactgtgga 60
gaagggcact cgtgccatag tcccgtagca ctagaacgca tcagaaatga agcgacagac 120
gggacgctga aaatccaggt ctccttgcaa atcggaataa agacggatga cagccacgat 180
tggaccaagc tgcgttatat ggacaaccac atgccagcag acgcagagag ggcggggcta 240

-continued

```
tttgtaagaa catcagcacc gtgtacgatt actggaacaa tgggacactt catcctggcc    300

cgatgtccaa aaggggaaac tctgacggtg ggattcactg acagtaggaa gattagtcac    360

tcatgtacgc acccatttca ccacgaccct cctgtgatag gtcgggaaaa attccattcc    420

cgaccgcagc acggtaaaga gataccttgc agcacgtacg tgcagagcac cgccgcaact    480

accgaggaga tagaggtaca catgccccca gacacccctg atcgcacatt aatgtcacaa    540

cagtccggca acgtaaagat cacagtcaat ggccagacgg tgcggtacaa gtgtaattgc    600

ggtggctcaa atgaaggact aacaactaca gacaaagtga ttaataactg caaggttgat    660

caatgtcatg ccgcggtcac caatcacaaa aagtggcagt ataactcccc tctggtcccg    720

cgtaatgctg aacttgggga ccgaaaagga aaaattcaca tcccgtttcc gctggcaaat    780

gtaacatgca gggtgcctaa agcaaggaac cccaccgtga cgtacgggaa aaaccaagtc    840

atcatgctac tgtatcctga ccacccaaca ctcctgtcct accggaatat gggagaagaa    900

ccaaactatc aagaagagtg ggtgatgcat aagaaggaag tcgtgctaac cgtgccgact    960

gaagggctcg aggtcacgtg ggcaacaac gagccgtata agtattggcc gcagttatct   1020

acaaacggta cagcccatgg ccacccgcat gagataattc tgtattatta tgagctgtac   1080

cccactatga ct                                                       1092
```

```
<210> SEQ ID NO 15
<211> LENGTH: 599
<212> TYPE: PRT
<213> ORGANISM: Chikungunya virus

<400> SEQUENCE: 15

Ile Pro Val His Met Lys Ser Asp Ala Ser Lys Phe Thr His Glu Lys
1               5                   10                  15

Pro Glu Gly Tyr Tyr Asn Trp His His Gly Ala Val Gln Tyr Ser Gly
            20                  25                  30

Gly Arg Phe Thr Ile Pro Thr Gly Ala Gly Lys Pro Gly Asp Ser Gly
        35                  40                  45

Arg Pro Ile Phe Asp Asn Lys Gly Arg Val Val Ala Ile Val Leu Gly
    50                  55                  60

Gly Ala Asn Glu Gly Ala Arg Thr Ala Leu Ser Val Val Thr Trp Asn
65                  70                  75                  80

Lys Asp Ile Val Thr Lys Ile Thr Pro Glu Gly Ala Glu Glu Trp Ser
                85                  90                  95

Leu Ala Ile Pro Val Met Cys Leu Leu Ala Asn Thr Thr Phe Pro Cys
            100                 105                 110

Ser Gln Pro Pro Cys Thr Pro Cys Cys Tyr Glu Lys Glu Pro Glu Glu
        115                 120                 125

Thr Leu Arg Met Leu Glu Asp Asn Val Met Arg Pro Gly Tyr Tyr Gln
    130                 135                 140

Leu Leu Gln Ala Ser Leu Thr Cys Ser Pro His Arg Gln Arg Arg Ser
145                 150                 155                 160

Thr Lys Asp Asn Phe Asn Val Tyr Lys Ala Thr Arg Pro Tyr Leu Ala
                165                 170                 175

His Cys Pro Asp Cys Gly Glu Gly His Ser Cys His Ser Pro Val Ala
            180                 185                 190

Leu Glu Arg Ile Arg Asn Glu Ala Thr Asp Gly Thr Leu Lys Ile Gln
        195                 200                 205

Val Ser Leu Gln Ile Gly Ile Lys Thr Asp Asp Ser His Asp Trp Thr
    210                 215                 220
```

```
Lys Leu Arg Tyr Met Asp Asn His Met Pro Ala Asp Ala Glu Arg Ala
225                 230                 235                 240

Gly Leu Phe Val Arg Thr Ser Ala Pro Cys Thr Ile Thr Gly Thr Met
                245                 250                 255

Gly His Phe Ile Leu Ala Arg Cys Pro Lys Gly Glu Thr Leu Thr Val
            260                 265                 270

Gly Phe Thr Asp Ser Arg Lys Ile Ser His Ser Cys Thr His Pro Phe
        275                 280                 285

His His Asp Pro Pro Val Ile Gly Arg Glu Lys Phe His Ser Arg Pro
    290                 295                 300

Gln His Gly Lys Glu Leu Pro Cys Ser Thr Tyr Val Gln Ser Thr Ala
305                 310                 315                 320

Ala Thr Thr Glu Glu Ile Glu Val His Met Pro Pro Asp Thr Pro Asp
                325                 330                 335

Arg Thr Leu Met Ser Gln Gln Ser Gly Asn Val Lys Ile Thr Val Asn
            340                 345                 350

Gly Gln Thr Val Arg Tyr Lys Cys Asn Cys Gly Gly Ser Asn Glu Gly
        355                 360                 365

Leu Thr Thr Thr Asp Lys Val Ile Asn Asn Cys Lys Val Asp Gln Cys
    370                 375                 380

His Ala Ala Val Thr Asn His Lys Lys Trp Gln Tyr Asn Ser Pro Leu
385                 390                 395                 400

Val Pro Arg Asn Ala Glu Leu Gly Asp Arg Lys Gly Lys Ile His Ile
                405                 410                 415

Pro Phe Pro Leu Ala Asn Val Thr Cys Arg Val Pro Lys Ala Arg Asn
            420                 425                 430

Pro Thr Val Thr Tyr Gly Lys Asn Gln Val Ile Met Leu Leu Tyr Pro
        435                 440                 445

Asp His Pro Thr Leu Leu Ser Tyr Arg Asn Met Gly Glu Glu Pro Asn
    450                 455                 460

Tyr Gln Glu Glu Trp Val Met His Lys Lys Glu Val Val Leu Thr Val
465                 470                 475                 480

Pro Thr Glu Gly Leu Glu Val Thr Trp Gly Asn Asn Glu Pro Tyr Lys
                485                 490                 495

Tyr Trp Pro Gln Leu Ser Thr Asn Gly Thr Ala His Gly His Pro His
            500                 505                 510

Glu Ile Ile Leu Tyr Tyr Tyr Glu Leu Tyr Pro Thr Met Thr Val Val
        515                 520                 525

Val Val Ser Val Ala Thr Phe Ile Leu Leu Ser Met Val Gly Met Ala
    530                 535                 540

Ala Gly Met Cys Met Arg Ala Arg Arg Arg Cys Ile Thr Pro Tyr Glu
545                 550                 555                 560

Leu Thr Pro Gly Ala Thr Val Pro Phe Leu Leu Ser Leu Ile Cys Cys
                565                 570                 575

Ile Arg Thr Ala Lys Ala Ala Thr Tyr Gln Glu Ala Ala Ile Tyr Leu
            580                 585                 590

Trp Asn Glu Gln Gln Pro Leu
        595
```

<210> SEQ ID NO 16
<211> LENGTH: 599
<212> TYPE: PRT
<213> ORGANISM: Chikungunya virus

<400> SEQUENCE: 16

```
Ile Pro Val His Met Lys Ser Asp Ala Ser Lys Phe Thr His Glu Lys
1               5                   10                  15

Pro Glu Gly Tyr Tyr Asn Trp His His Gly Ala Val Gln Tyr Ser Gly
            20                  25                  30

Gly Arg Phe Thr Ile Pro Thr Gly Ala Gly Lys Pro Gly Asp Ser Gly
        35                  40                  45

Arg Pro Ile Phe Asp Asn Lys Gly Arg Val Val Ala Ile Val Leu Gly
    50                  55                  60

Gly Ala Asn Glu Gly Ala Arg Thr Ala Leu Ser Val Val Thr Trp Asn
65                  70                  75                  80

Lys Asp Ile Val Thr Lys Ile Thr Pro Glu Gly Ala Glu Glu Trp Ser
                85                  90                  95

Leu Ala Ile Pro Val Met Cys Leu Leu Ala Asn Thr Thr Phe Pro Cys
            100                 105                 110

Ser Gln Pro Pro Cys Thr Pro Cys Cys Tyr Glu Lys Glu Pro Glu Glu
        115                 120                 125

Thr Leu Arg Met Leu Glu Asp Asn Val Met Arg Pro Gly Tyr Tyr Gln
    130                 135                 140

Leu Leu Gln Ala Ser Leu Thr Cys Ser Pro His Arg Gln Arg Arg Ser
145                 150                 155                 160

Thr Lys Asp Asn Phe Asn Val Tyr Lys Ala Thr Arg Pro Tyr Leu Ala
                165                 170                 175

His Cys Pro Asp Cys Gly Glu Gly His Ser Cys His Ser Pro Val Ala
            180                 185                 190

Leu Glu Arg Ile Arg Asn Glu Ala Thr Asp Gly Thr Leu Lys Ile Gln
        195                 200                 205

Val Ser Leu Gln Ile Gly Ile Lys Thr Asp Asp Ser His Asp Trp Thr
    210                 215                 220

Lys Leu Arg Tyr Met Asp Asn His Met Pro Ala Asp Ala Glu Arg Ala
225                 230                 235                 240

Gly Leu Phe Val Arg Thr Ser Ala Pro Cys Thr Ile Thr Gly Thr Met
                245                 250                 255

Gly His Phe Ile Leu Ala Arg Cys Pro Lys Gly Glu Thr Leu Thr Val
            260                 265                 270

Gly Phe Thr Asp Ser Arg Lys Ile Ser His Ser Cys Thr His Pro Phe
        275                 280                 285

His His Asp Pro Pro Val Ile Gly Arg Glu Lys Phe His Ser Arg Pro
    290                 295                 300

Gln His Gly Lys Glu Leu Pro Cys Ser Thr Tyr Val Gln Ser Thr Ala
305                 310                 315                 320

Ala Thr Thr Glu Glu Ile Glu Val His Met Pro Pro Asp Thr Pro Asp
                325                 330                 335

Arg Thr Leu Met Ser Gln Gln Ser Gly Asn Val Lys Ile Thr Val Asn
            340                 345                 350

Gly Gln Thr Val Arg Tyr Lys Cys Asn Cys Gly Gly Ser Asn Glu Gly
        355                 360                 365

Leu Thr Thr Thr Asp Lys Val Ile Asn Asn Cys Lys Val Asp Gln Cys
    370                 375                 380

His Ala Ala Val Thr Asn His Lys Lys Trp Gln Tyr Asn Ser Pro Leu
385                 390                 395                 400

Val Pro Arg Asn Ala Glu Leu Gly Asp Arg Lys Gly Lys Ile His Ile
                405                 410                 415
```

```
Pro Phe Pro Leu Ala Asn Val Thr Cys Arg Val Pro Lys Ala Arg Asn
            420                 425                 430

Pro Thr Val Thr Tyr Gly Lys Asn Gln Val Ile Met Leu Leu Tyr Pro
        435                 440                 445

Asp His Pro Thr Leu Leu Ser Tyr Arg Asn Met Gly Glu Glu Pro Asn
    450                 455                 460

Tyr Gln Glu Glu Trp Val Met His Lys Lys Glu Val Val Leu Thr Val
465                 470                 475                 480

Pro Thr Glu Gly Leu Glu Val Thr Trp Gly Asn Asn Glu Pro Tyr Lys
                485                 490                 495

Tyr Trp Pro Gln Leu Ser Thr Asn Gly Thr Ala His Gly His Pro His
            500                 505                 510

Glu Ile Ile Leu Tyr Tyr Tyr Glu Leu Tyr Pro Thr Met Thr Val Val
        515                 520                 525

Val Val Ser Val Ala Thr Phe Ile Leu Leu Ser Met Val Gly Met Ala
    530                 535                 540

Ala Gly Met Cys Met Cys Ala Arg Arg Arg Cys Ile Thr Pro Tyr Glu
545                 550                 555                 560

Leu Thr Pro Gly Ala Thr Val Pro Phe Leu Leu Ser Leu Ile Cys Cys
                565                 570                 575

Ile Arg Thr Ala Lys Ala Ala Thr Tyr Gln Glu Ala Ala Ile Tyr Leu
            580                 585                 590

Trp Asn Glu Gln Gln Pro Leu
        595


<210> SEQ ID NO 17
<211> LENGTH: 599
<212> TYPE: PRT
<213> ORGANISM: Chikungunya virus

<400> SEQUENCE: 17

Ile Pro Val His Met Lys Ser Asp Ala Ser Lys Phe Thr His Glu Lys
1               5                   10                  15

Pro Glu Gly Tyr Tyr Asn Trp His His Gly Ala Val Gln Tyr Ser Gly
            20                  25                  30

Gly Arg Phe Thr Ile Pro Thr Gly Ala Gly Lys Pro Gly Asp Ser Gly
        35                  40                  45

Arg Pro Ile Phe Asp Asn Lys Gly Arg Val Val Ala Ile Val Leu Gly
    50                  55                  60

Gly Ala Asn Glu Gly Ala Arg Thr Ala Leu Ser Val Val Thr Trp Asn
65                  70                  75                  80

Lys Asp Ile Val Thr Lys Ile Thr Pro Glu Gly Ala Glu Glu Trp Ser
                85                  90                  95

Leu Ala Ile Pro Val Met Cys Leu Leu Ala Asn Thr Thr Phe Pro Cys
            100                 105                 110

Ser Gln Pro Pro Cys Thr Pro Cys Cys Tyr Glu Lys Glu Pro Glu Glu
        115                 120                 125

Thr Leu Arg Met Leu Glu Asp Asn Val Met Arg Pro Gly Tyr Tyr Gln
    130                 135                 140

Leu Leu Gln Ala Ser Leu Thr Cys Ser Pro His Arg Gln Arg Arg Ser
145                 150                 155                 160

Thr Lys Asp Asn Phe Asn Val Tyr Lys Ala Thr Arg Pro Tyr Leu Ala
                165                 170                 175

His Cys Pro Asp Cys Gly Glu Gly His Ser Cys His Ser Pro Val Ala
```

-continued

```
            180                 185                 190

Leu Glu Arg Ile Arg Asn Glu Ala Thr Asp Gly Thr Leu Lys Ile Gln
        195                 200                 205

Val Ser Leu Gln Ile Gly Ile Lys Thr Asp Asp Ser His Asp Trp Thr
    210                 215                 220

Lys Leu Arg Tyr Met Asp Asn His Met Pro Ala Asp Ala Glu Arg Ala
225                 230                 235                 240

Gly Leu Phe Val Arg Thr Ser Ala Pro Cys Thr Ile Thr Gly Thr Met
                245                 250                 255

Gly His Phe Ile Leu Ala Arg Cys Pro Lys Gly Glu Thr Leu Thr Val
            260                 265                 270

Gly Phe Thr Asp Ser Arg Lys Ile Ser His Ser Cys Thr His Pro Phe
        275                 280                 285

His His Asp Pro Pro Val Ile Gly Arg Glu Lys Phe His Ser Arg Pro
    290                 295                 300

Gln His Gly Lys Glu Leu Pro Cys Ser Thr Tyr Val Gln Ser Thr Ala
305                 310                 315                 320

Ala Thr Thr Glu Glu Ile Glu Val His Met Pro Pro Asp Thr Pro Asp
                325                 330                 335

Arg Thr Leu Met Ser Gln Gln Ser Gly Asn Val Lys Ile Thr Val Asn
            340                 345                 350

Gly Gln Thr Val Arg Tyr Lys Cys Asn Cys Gly Gly Ser Asn Glu Gly
        355                 360                 365

Leu Thr Thr Thr Asp Lys Val Ile Asn Asn Cys Lys Val Asp Gln Cys
    370                 375                 380

His Ala Ala Val Thr Asn His Lys Lys Trp Gln Tyr Asn Ser Pro Leu
385                 390                 395                 400

Val Pro Arg Asn Ala Glu Leu Gly Asp Arg Lys Gly Lys Ile His Ile
                405                 410                 415

Pro Phe Pro Leu Ala Asn Val Thr Cys Arg Val Pro Lys Ala Arg Asn
            420                 425                 430

Pro Thr Val Thr Tyr Gly Lys Asn Gln Val Ile Met Leu Leu Tyr Pro
        435                 440                 445

Asp His Pro Thr Leu Leu Ser Tyr Arg Asn Met Gly Glu Glu Pro Asn
    450                 455                 460

Tyr Gln Glu Glu Trp Val Met His Lys Lys Glu Val Val Leu Thr Val
465                 470                 475                 480

Pro Thr Glu Gly Leu Glu Val Thr Trp Gly Asn Asn Glu Pro Tyr Lys
                485                 490                 495

Tyr Trp Pro Gln Leu Ser Thr Asn Gly Thr Ala His Gly His Pro His
            500                 505                 510

Glu Ile Ile Leu Tyr Tyr Tyr Glu Leu Tyr Pro Thr Met Thr Val Val
        515                 520                 525

Val Val Ser Val Ala Thr Phe Ile Leu Leu Ser Met Val Gly Met Ala
    530                 535                 540

Ala Gly Met Cys Met Cys Ala Arg Arg Arg Cys Ile Thr Pro Tyr Glu
545                 550                 555                 560

Leu Thr Pro Gly Ala Thr Val Pro Phe Leu Leu Ser Leu Ile Cys Cys
                565                 570                 575

Ile Arg Thr Ala Lys Ala Ala Thr Tyr Gln Glu Ala Ala Ile Tyr Leu
            580                 585                 590

Trp Asn Glu Gln Gln Pro Leu
        595
```

<210> SEQ ID NO 18
<211> LENGTH: 599
<212> TYPE: PRT
<213> ORGANISM: Chikungunya virus

<400> SEQUENCE: 18

```
Ile Pro Val His Met Lys Ser Asp Ala Ser Lys Phe Thr His Glu Lys
1               5                   10                  15

Pro Glu Gly Tyr Tyr Asn Trp His His Gly Ala Val Gln Tyr Ser Gly
            20                  25                  30

Gly Arg Phe Thr Ile Pro Thr Gly Ala Gly Lys Pro Gly Asp Ser Gly
        35                  40                  45

Arg Pro Ile Phe Asp Asn Lys Gly Arg Val Val Ala Ile Val Leu Gly
    50                  55                  60

Gly Ala Asn Glu Gly Ala Arg Thr Ala Leu Ser Val Val Thr Trp Asn
65                  70                  75                  80

Lys Asp Ile Val Thr Lys Ile Thr Pro Glu Gly Ala Glu Glu Trp Ser
                85                  90                  95

Leu Ala Ile Pro Val Met Cys Leu Leu Ala Asn Thr Thr Phe Pro Cys
            100                 105                 110

Ser Gln Pro Pro Cys Thr Pro Cys Cys Tyr Glu Lys Glu Pro Glu Glu
        115                 120                 125

Thr Leu Arg Met Leu Glu Asp Asn Val Met Arg Pro Gly Tyr Tyr Gln
    130                 135                 140

Leu Leu Gln Ala Ser Leu Thr Cys Ser Pro His Arg Gln Arg Arg Ser
145                 150                 155                 160

Thr Lys Asp Asn Phe Asn Val Tyr Lys Ala Thr Arg Pro Tyr Leu Ala
                165                 170                 175

His Cys Pro Asp Cys Gly Glu Gly His Ser Cys His Ser Pro Val Ala
            180                 185                 190

Leu Glu Arg Ile Arg Asn Glu Ala Thr Asp Gly Thr Leu Lys Ile Gln
        195                 200                 205

Val Ser Leu Gln Ile Gly Ile Lys Thr Asp Asp Ser His Asp Trp Thr
    210                 215                 220

Lys Leu Arg Tyr Met Asp Asn His Met Pro Ala Asp Ala Glu Arg Ala
225                 230                 235                 240

Gly Leu Phe Val Arg Thr Ser Ala Pro Cys Thr Ile Thr Gly Thr Met
                245                 250                 255

Gly His Phe Ile Leu Ala Arg Cys Pro Lys Gly Glu Thr Leu Thr Val
            260                 265                 270

Gly Phe Thr Asp Ser Arg Lys Ile Ser His Ser Cys Thr His Pro Phe
        275                 280                 285

His His Asp Pro Pro Val Ile Gly Arg Glu Lys Phe His Ser Arg Pro
    290                 295                 300

Gln His Gly Lys Glu Ile Pro Cys Ser Thr Tyr Val Gln Ser Thr Ala
305                 310                 315                 320

Ala Thr Thr Glu Glu Ile Glu Val His Met Pro Pro Asp Thr Pro Asp
                325                 330                 335

Arg Thr Leu Met Ser Gln Gln Ser Gly Asn Val Lys Ile Thr Val Asn
            340                 345                 350

Gly Gln Thr Val Arg Tyr Lys Cys Asn Cys Gly Gly Ser Asn Glu Gly
        355                 360                 365

Leu Thr Thr Thr Asp Lys Val Ile Asn Asn Cys Lys Val Asp Gln Cys
```

```
    370                 375                 380

His Ala Ala Val Thr Asn His Lys Lys Trp Gln Tyr Asn Ser Pro Leu
385                 390                 395                 400

Val Pro Arg Asn Ala Glu Leu Gly Asp Arg Lys Gly Lys Ile His Ile
                405                 410                 415

Pro Phe Pro Leu Ala Asn Val Thr Cys Arg Val Pro Lys Ala Arg Asn
            420                 425                 430

Pro Thr Val Thr Tyr Gly Lys Asn Gln Val Ile Met Leu Leu Tyr Pro
        435                 440                 445

Asp His Pro Thr Leu Leu Ser Tyr Arg Asn Met Gly Glu Glu Pro Asn
    450                 455                 460

Tyr Gln Glu Glu Trp Val Met His Lys Lys Glu Val Val Leu Thr Val
465                 470                 475                 480

Pro Thr Glu Gly Leu Glu Val Thr Trp Gly Asn Asn Glu Pro Tyr Lys
                485                 490                 495

Tyr Trp Pro Gln Leu Ser Thr Asn Gly Thr Ala His Gly His Pro His
            500                 505                 510

Glu Ile Ile Leu Tyr Tyr Tyr Glu Leu Tyr Pro Thr Met Thr Val Val
        515                 520                 525

Val Val Ser Val Ala Thr Phe Ile Leu Leu Ser Met Val Gly Met Ala
    530                 535                 540

Ala Gly Met Cys Met Cys Ala Arg Arg Arg Cys Ile Thr Pro Tyr Glu
545                 550                 555                 560

Leu Thr Pro Gly Ala Thr Val Pro Phe Leu Leu Ser Leu Ile Cys Cys
                565                 570                 575

Ile Arg Thr Ala Lys Ala Ala Thr Tyr Gln Glu Ala Ala Ile Tyr Leu
            580                 585                 590

Trp Asn Glu Gln Gln Pro Leu
        595


<210> SEQ ID NO 19
<211> LENGTH: 364
<212> TYPE: PRT
<213> ORGANISM: Chikungunya virus

<400> SEQUENCE: 19

Asp Asn Phe Asn Val Tyr Lys Ala Thr Arg Pro Tyr Leu Ala His Cys
1               5                   10                  15

Pro Asp Cys Gly Glu Gly His Ser Cys His Ser Pro Val Ala Leu Glu
            20                  25                  30

Arg Ile Arg Asn Glu Ala Thr Asp Gly Thr Leu Lys Ile Gln Val Ser
        35                  40                  45

Leu Gln Ile Gly Ile Lys Thr Asp Asp Ser His Asp Trp Thr Lys Leu
    50                  55                  60

Arg Tyr Met Asp Asn His Met Pro Ala Asp Ala Glu Arg Ala Gly Leu
65                  70                  75                  80

Phe Val Arg Thr Ser Ala Pro Cys Thr Ile Thr Gly Thr Met Gly His
                85                  90                  95

Phe Ile Leu Ala Arg Cys Pro Lys Gly Glu Thr Leu Thr Val Gly Phe
            100                 105                 110

Thr Asp Ser Arg Lys Ile Ser His Ser Cys Thr His Pro Phe His His
        115                 120                 125

Asp Pro Pro Val Ile Gly Arg Glu Lys Phe His Ser Arg Pro Gln His
    130                 135                 140
```

Gly Lys Glu Leu Pro Cys Ser Thr Tyr Val Gln Ser Thr Ala Ala Thr
145 150 155 160

Thr Glu Glu Ile Glu Val His Met Pro Pro Asp Thr Pro Asp Arg Thr
165 170 175

Leu Met Ser Gln Gln Ser Gly Asn Val Lys Ile Thr Val Asn Gly Gln
180 185 190

Thr Val Arg Tyr Lys Cys Asn Cys Gly Gly Ser Asn Glu Gly Leu Thr
195 200 205

Thr Thr Asp Lys Val Ile Asn Asn Cys Lys Val Asp Gln Cys His Ala
210 215 220

Ala Val Thr Asn His Lys Lys Trp Gln Tyr Asn Ser Pro Leu Val Pro
225 230 235 240

Arg Asn Ala Glu Leu Gly Asp Arg Lys Gly Lys Ile His Ile Pro Phe
245 250 255

Pro Leu Ala Asn Val Thr Cys Arg Val Pro Lys Ala Arg Asn Pro Thr
260 265 270

Val Thr Tyr Gly Lys Asn Gln Val Ile Met Leu Leu Tyr Pro Asp His
275 280 285

Pro Thr Leu Leu Ser Tyr Arg Asn Met Gly Glu Glu Pro Asn Tyr Gln
290 295 300

Glu Glu Trp Val Met His Lys Lys Glu Val Val Leu Thr Val Pro Thr
305 310 315 320

Glu Gly Leu Glu Val Thr Trp Gly Asn Asn Glu Pro Tyr Lys Tyr Trp
325 330 335

Pro Gln Leu Ser Thr Asn Gly Thr Ala His Gly His Pro His Glu Ile
340 345 350

Ile Leu Tyr Tyr Tyr Glu Leu Tyr Pro Thr Met Thr
355 360

<210> SEQ ID NO 20
<211> LENGTH: 364
<212> TYPE: PRT
<213> ORGANISM: Chikungunya virus

<400> SEQUENCE: 20

Asp Asn Phe Asn Val Tyr Lys Ala Thr Arg Pro Tyr Leu Ala His Cys
1 5 10 15

Pro Asp Cys Gly Glu Gly His Ser Cys His Ser Pro Val Ala Leu Glu
20 25 30

Arg Ile Arg Asn Glu Ala Thr Asp Gly Thr Leu Lys Ile Gln Val Ser
35 40 45

Leu Gln Ile Gly Ile Lys Thr Asp Asp Ser His Asp Trp Thr Lys Leu
50 55 60

Arg Tyr Met Asp Asn His Met Pro Ala Asp Ala Glu Arg Ala Gly Leu
65 70 75 80

Phe Val Arg Thr Ser Ala Pro Cys Thr Ile Thr Gly Thr Met Gly His
85 90 95

Phe Ile Leu Ala Arg Cys Pro Lys Gly Glu Thr Leu Thr Val Gly Phe
100 105 110

Thr Asp Ser Arg Lys Ile Ser His Ser Cys Thr His Pro Phe His His
115 120 125

Asp Pro Pro Val Ile Gly Arg Glu Lys Phe His Ser Arg Pro Gln His
130 135 140

Gly Lys Glu Leu Pro Cys Ser Thr Tyr Val Gln Ser Thr Ala Ala Thr
145 150 155 160

```
Thr Glu Glu Ile Glu Val His Met Pro Pro Asp Thr Pro Asp Arg Thr
                165                 170                 175

Leu Met Ser Gln Gln Ser Gly Asn Val Lys Ile Thr Val Asn Gly Gln
            180                 185                 190

Thr Val Arg Tyr Lys Cys Asn Cys Gly Gly Ser Asn Glu Gly Leu Thr
        195                 200                 205

Thr Thr Asp Lys Val Ile Asn Asn Cys Lys Val Asp Gln Cys His Ala
    210                 215                 220

Ala Val Thr Asn His Lys Lys Trp Gln Tyr Asn Ser Pro Leu Val Pro
225                 230                 235                 240

Arg Asn Ala Glu Leu Gly Asp Arg Lys Gly Lys Ile His Ile Pro Phe
                245                 250                 255

Pro Leu Ala Asn Val Thr Cys Arg Val Pro Lys Ala Arg Asn Pro Thr
            260                 265                 270

Val Thr Tyr Gly Lys Asn Gln Val Ile Met Leu Leu Tyr Pro Asp His
        275                 280                 285

Pro Thr Leu Leu Ser Tyr Arg Asn Met Gly Glu Glu Pro Asn Tyr Gln
    290                 295                 300

Glu Glu Trp Val Met His Lys Lys Glu Val Val Leu Thr Val Pro Thr
305                 310                 315                 320

Glu Gly Leu Glu Val Thr Trp Gly Asn Asn Glu Pro Tyr Lys Tyr Trp
                325                 330                 335

Pro Gln Leu Ser Thr Asn Gly Thr Ala His Gly His Pro His Glu Ile
            340                 345                 350

Ile Leu Tyr Tyr Tyr Glu Leu Tyr Pro Thr Met Thr
        355                 360


<210> SEQ ID NO 21
<211> LENGTH: 364
<212> TYPE: PRT
<213> ORGANISM: Chikungunya virus

<400> SEQUENCE: 21

Asp Asn Phe Asn Val Tyr Lys Ala Thr Arg Pro Tyr Leu Ala His Cys
1               5                   10                  15

Pro Asp Cys Gly Glu Gly His Ser Cys His Ser Pro Val Ala Leu Glu
            20                  25                  30

Arg Ile Arg Asn Glu Ala Thr Asp Gly Thr Leu Lys Ile Gln Val Ser
        35                  40                  45

Leu Gln Ile Gly Ile Lys Thr Asp Asp Ser His Asp Trp Thr Lys Leu
    50                  55                  60

Arg Tyr Met Asp Asn His Met Pro Ala Asp Ala Glu Arg Ala Gly Leu
65                  70                  75                  80

Phe Val Arg Thr Ser Ala Pro Cys Thr Ile Thr Gly Thr Met Gly His
                85                  90                  95

Phe Ile Leu Ala Arg Cys Pro Lys Gly Glu Thr Leu Thr Val Gly Phe
            100                 105                 110

Thr Asp Ser Arg Lys Ile Ser His Ser Cys Thr His Pro Phe His His
        115                 120                 125

Asp Pro Pro Val Ile Gly Arg Glu Lys Phe His Ser Arg Pro Gln His
    130                 135                 140

Gly Lys Glu Leu Pro Cys Ser Thr Tyr Val Gln Ser Thr Ala Ala Thr
145                 150                 155                 160

Thr Glu Glu Ile Glu Val His Met Pro Pro Asp Thr Pro Asp Arg Thr
```

```
                165                 170                 175

Leu Met Ser Gln Gln Ser Gly Asn Val Lys Ile Thr Val Asn Gly Gln
            180                 185                 190

Thr Val Arg Tyr Lys Cys Asn Cys Gly Gly Ser Asn Glu Gly Leu Thr
        195                 200                 205

Thr Thr Asp Lys Val Ile Asn Asn Cys Lys Val Asp Gln Cys His Ala
    210                 215                 220

Ala Val Thr Asn His Lys Lys Trp Gln Tyr Asn Ser Pro Leu Val Pro
225                 230                 235                 240

Arg Asn Ala Glu Leu Gly Asp Arg Lys Gly Lys Ile His Ile Pro Phe
                245                 250                 255

Pro Leu Ala Asn Val Thr Cys Arg Val Pro Lys Ala Arg Asn Pro Thr
            260                 265                 270

Val Thr Tyr Gly Lys Asn Gln Val Ile Met Leu Leu Tyr Pro Asp His
        275                 280                 285

Pro Thr Leu Leu Ser Tyr Arg Asn Met Gly Glu Glu Pro Asn Tyr Gln
    290                 295                 300

Glu Glu Trp Val Met His Lys Lys Glu Val Val Leu Thr Val Pro Thr
305                 310                 315                 320

Glu Gly Leu Glu Val Thr Trp Gly Asn Asn Glu Pro Tyr Lys Tyr Trp
                325                 330                 335

Pro Gln Leu Ser Thr Asn Gly Thr Ala His Gly His Pro His Glu Ile
            340                 345                 350

Ile Leu Tyr Tyr Tyr Glu Leu Tyr Pro Thr Met Thr
        355                 360


<210> SEQ ID NO 22
<211> LENGTH: 364
<212> TYPE: PRT
<213> ORGANISM: Chikungunya virus

<400> SEQUENCE: 22

Asp Asn Phe Asn Val Tyr Lys Ala Thr Arg Pro Tyr Leu Ala His Cys
1               5                   10                  15

Pro Asp Cys Gly Glu Gly His Ser Cys His Ser Pro Val Ala Leu Glu
            20                  25                  30

Arg Ile Arg Asn Glu Ala Thr Asp Gly Thr Leu Lys Ile Gln Val Ser
        35                  40                  45

Leu Gln Ile Gly Ile Lys Thr Asp Asp Ser His Asp Trp Thr Lys Leu
    50                  55                  60

Arg Tyr Met Asp Asn His Met Pro Ala Asp Ala Glu Arg Ala Gly Leu
65                  70                  75                  80

Phe Val Arg Thr Ser Ala Pro Cys Thr Ile Thr Gly Thr Met Gly His
                85                  90                  95

Phe Ile Leu Ala Arg Cys Pro Lys Gly Glu Thr Leu Thr Val Gly Phe
            100                 105                 110

Thr Asp Ser Arg Lys Ile Ser His Ser Cys Thr His Pro Phe His His
        115                 120                 125

Asp Pro Pro Val Ile Gly Arg Glu Lys Phe His Ser Arg Pro Gln His
    130                 135                 140

Gly Lys Glu Ile Pro Cys Ser Thr Tyr Val Gln Ser Thr Ala Ala Thr
145                 150                 155                 160

Thr Glu Glu Ile Glu Val His Met Pro Pro Asp Thr Pro Asp Arg Thr
                165                 170                 175
```

```
Leu Met Ser Gln Gln Ser Gly Asn Val Lys Ile Thr Val Asn Gly Gln
            180                 185                 190

Thr Val Arg Tyr Lys Cys Asn Cys Gly Gly Ser Asn Glu Gly Leu Thr
        195                 200                 205

Thr Thr Asp Lys Val Ile Asn Asn Cys Lys Val Asp Gln Cys His Ala
    210                 215                 220

Ala Val Thr Asn His Lys Lys Trp Gln Tyr Asn Ser Pro Leu Val Pro
225                 230                 235                 240

Arg Asn Ala Glu Leu Gly Asp Arg Lys Gly Lys Ile His Ile Pro Phe
                245                 250                 255

Pro Leu Ala Asn Val Thr Cys Arg Val Pro Lys Ala Arg Asn Pro Thr
            260                 265                 270

Val Thr Tyr Gly Lys Asn Gln Val Ile Met Leu Leu Tyr Pro Asp His
        275                 280                 285

Pro Thr Leu Leu Ser Tyr Arg Asn Met Gly Glu Glu Pro Asn Tyr Gln
    290                 295                 300

Glu Glu Trp Val Met His Lys Lys Glu Val Val Leu Thr Val Pro Thr
305                 310                 315                 320

Glu Gly Leu Glu Val Thr Trp Gly Asn Asn Glu Pro Tyr Lys Tyr Trp
                325                 330                 335

Pro Gln Leu Ser Thr Asn Gly Thr Ala His Gly His Pro His Glu Ile
            340                 345                 350

Ile Leu Tyr Tyr Tyr Glu Leu Tyr Pro Thr Met Thr
        355                 360
```

<210> SEQ ID NO 23
<211> LENGTH: 1248
<212> TYPE: PRT
<213> ORGANISM: Chikungunya virus

<400> SEQUENCE: 23

```
Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190
```

-continued

```
Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Ile Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Gly Thr Asp
    370                 375                 380

Asp Ser His Asp Trp Thr Lys Leu Arg Tyr Met Asp Asn His Ile Pro
385                 390                 395                 400

Ala Asp Ala Gly Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Asn Ala Ala Thr Ala Glu Glu Ile Glu Val His Met
                485                 490                 495

Pro Pro Asp Thr Pro Asp Arg Thr Leu Leu Ser Gln Gln Ser Gly Asn
            500                 505                 510

Val Lys Ile Thr Val Asn Gly Arg Thr Val Arg Tyr Lys Cys Asn Cys
        515                 520                 525

Gly Gly Ser Asn Glu Gly Leu Ile Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Met
            580                 585                 590

Val Pro Lys Ala Arg Asn Pro Thr Val Thr Tyr Gly Lys Asn Gln Val
        595                 600                 605
```

```
Ile Met Leu Leu Tyr Pro Asp His Pro Thr Leu Leu Ser Tyr Arg Ser
    610                 615                 620

Met Gly Glu Glu Pro Asn Tyr Gln Glu Glu Trp Val Thr His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Ala Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Ser Phe Ile Leu Leu
    690                 695                 700

Ser Met Val Gly Met Ala Val Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Val Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                1005

Phe Gly  Asp Ile Gln Ser Arg  Thr Pro Glu Ser Lys  Asp Val Tyr
    1010                1015                1020

Ala Asn  Thr Gln Leu Val Leu  Gln Arg Pro Ala Ala  Gly Thr Val
```

```
    1025                1030                1035

His Val  Pro Tyr Ser Gln Ala  Pro Ser Gly Phe Lys  Tyr Trp Leu
    1040                1045                1050

Lys Glu  Arg Gly Ala Ser Leu  Gln His Thr Ala Pro  Phe Gly Cys
    1055                1060                1065

Gln Ile  Ala Thr Asn Pro Val  Arg Ala Met Asn Cys  Ala Val Gly
    1070                1075                1080

Asn Met  Pro Ile Ser Ile Asp  Ile Pro Asp Ala Ala  Phe Thr Arg
    1085                1090                1095

Val Val  Asp Ala Pro Ser Leu  Thr Asp Met Ser Cys  Glu Val Pro
    1100                1105                1110

Ala Cys  Thr His Ser Ser Asp  Phe Gly Gly Val Ala  Ile Ile Lys
    1115                1120                1125

Tyr Ala  Val Ser Lys Lys Gly  Lys Cys Ala Val His  Ser Met Thr
    1130                1135                1140

Asn Ala  Val Thr Ile Arg Glu  Ala Glu Ile Glu Val  Glu Gly Asn
    1145                1150                1155

Ser Gln  Leu Gln Ile Ser Phe  Ser Thr Ala Leu Ala  Ser Ala Glu
    1160                1165                1170

Phe Arg  Val Gln Val Cys Ser  Thr Gln Val His Cys  Ala Ala Glu
    1175                1180                1185

Cys His  Pro Pro Lys Asp His  Ile Val Asn Tyr Pro  Ala Ser His
    1190                1195                1200

Thr Thr  Leu Gly Val Gln Asp  Ile Ser Ala Thr Ala  Met Ser Trp
    1205                1210                1215

Val Gln  Lys Ile Thr Gly Gly  Val Gly Leu Val Val  Ala Val Ala
    1220                1225                1230

Ala Leu  Ile Leu Ile Val Val  Leu Cys Val Ser Phe  Ser Arg His
    1235                1240                1245


<210> SEQ ID NO 24
<211> LENGTH: 1248
<212> TYPE: PRT
<213> ORGANISM: Chikungunya virus

<400> SEQUENCE: 24

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140
```

-continued

```
Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
```

```
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990
```

```
Val Tyr Asn Met Asp Tyr Pro Pro  Phe Gly Ala Gly Arg  Pro Gly Gln
        995                 1000                 1005

Phe Gly  Asp Ile Gln Ser Arg  Thr Pro Glu Ser Lys  Asp Val Tyr
    1010                 1015                 1020

Ala Asn  Thr Gln Leu Val Leu  Gln Arg Pro Ala Ala  Gly Thr Val
    1025                 1030                 1035

His Val  Pro Tyr Ser Gln Ala  Pro Ser Gly Phe Lys  Tyr Trp Leu
    1040                 1045                 1050

Lys Glu  Arg Gly Ala Ser Leu  Gln His Thr Ala Pro  Phe Gly Cys
    1055                 1060                 1065

Gln Ile  Ala Thr Asn Pro Val  Arg Ala Val Asn Cys  Ala Val Gly
    1070                 1075                 1080

Asn Met  Pro Ile Ser Ile Asp  Ile Pro Glu Ala Ala  Phe Thr Arg
    1085                 1090                 1095

Val Val  Asp Ala Pro Ser Leu  Thr Asp Met Ser Cys  Glu Val Pro
    1100                 1105                 1110

Ala Cys  Thr His Ser Ser Asp  Phe Gly Gly Val Ala  Ile Ile Lys
    1115                 1120                 1125

Tyr Ala  Ala Ser Lys Lys Gly  Lys Cys Ala Val His  Ser Met Thr
    1130                 1135                 1140

Asn Ala  Val Thr Ile Arg Glu  Ala Glu Ile Glu Val  Glu Gly Asn
    1145                 1150                 1155

Ser Gln  Leu Gln Ile Ser Phe  Ser Thr Ala Leu Ala  Ser Ala Glu
    1160                 1165                 1170

Phe Arg  Val Gln Val Cys Ser  Thr Gln Val His Cys  Ala Ala Glu
    1175                 1180                 1185

Cys His  Pro Pro Lys Asp His  Ile Val Asn Tyr Pro  Ala Ser His
    1190                 1195                 1200

Thr Thr  Leu Gly Val Gln Asp  Ile Ser Ala Thr Ala  Met Ser Trp
    1205                 1210                 1215

Val Gln  Lys Ile Thr Gly Gly  Val Gly Leu Val Val  Ala Val Ala
    1220                 1225                 1230

Ala Leu  Ile Leu Ile Val Val  Leu Cys Val Ser Phe  Ser Arg His
    1235                 1240                 1245


<210> SEQ ID NO 25
<211> LENGTH: 1248
<212> TYPE: PRT
<213> ORGANISM: Chikungunya virus

<400> SEQUENCE: 25

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
```

```
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Arg His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525
```

-continued

```
Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940
```

```
Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                 1005

Phe Gly  Asp Ile Gln Ser Arg  Thr Pro Glu Ser Lys  Asp Val Tyr
    1010                 1015                 1020

Ala Asn  Thr Gln Leu Val Leu  Gln Arg Pro Ala Ala  Gly Thr Val
    1025                 1030                 1035

His Val  Pro Tyr Ser Gln Ala  Pro Ser Gly Phe Lys  Tyr Trp Leu
    1040                 1045                 1050

Lys Glu  Arg Gly Ala Ser Leu  Gln His Thr Ala Pro  Phe Gly Cys
    1055                 1060                 1065

Gln Ile  Ala Thr Asn Pro Val  Arg Ala Val Asn Cys  Ala Val Gly
    1070                 1075                 1080

Asn Met  Pro Ile Ser Ile Asp  Ile Pro Glu Ala Ala  Phe Thr Arg
    1085                 1090                 1095

Val Val  Asp Ala Pro Ser Leu  Thr Asp Met Ser Cys  Glu Val Pro
    1100                 1105                 1110

Ala Cys  Thr His Ser Ser Asp  Phe Gly Gly Val Ala  Ile Ile Lys
    1115                 1120                 1125

Tyr Ala  Ala Ser Lys Lys Gly  Lys Cys Ala Val His  Ser Met Thr
    1130                 1135                 1140

Asn Ala  Val Thr Ile Arg Glu  Ala Glu Ile Glu Val  Glu Gly Asn
    1145                 1150                 1155

Ser Gln  Leu Gln Ile Ser Phe  Ser Thr Ala Leu Ala  Ser Ala Glu
    1160                 1165                 1170

Phe Arg  Val Gln Val Cys Ser  Thr Gln Val His Cys  Ala Ala Glu
    1175                 1180                 1185

Cys His  Pro Pro Lys Asp His  Ile Val Asn Tyr Pro  Ala Ser His
    1190                 1195                 1200

Thr Thr  Leu Gly Val Gln Asp  Ile Ser Ala Thr Ala  Met Ser Trp
    1205                 1210                 1215

Val Gln  Lys Ile Thr Gly Gly  Val Gly Leu Val Val  Ala Val Ala
    1220                 1225                 1230

Ala Leu  Ile Leu Ile Val Val  Leu Cys Val Ser Phe  Ser Arg His
    1235                 1240                 1245


<210> SEQ ID NO 26
<211> LENGTH: 1248
<212> TYPE: PRT
<213> ORGANISM: Chikungunya virus

<400> SEQUENCE: 26

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60
```

```
Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480
```

-continued

```
Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
```

```
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                1005

Phe Gly  Asp Ile Gln Ser Arg  Thr Pro Glu Ser Lys  Asp Val Tyr
    1010                 1015                 1020

Ala Asn  Thr Gln Leu Val Leu  Gln Arg Pro Ala Ala  Gly Thr Val
    1025                 1030                 1035

His Val  Pro Tyr Ser Gln Ala  Pro Ser Gly Phe Lys  Tyr Trp Leu
    1040                 1045                 1050

Lys Glu  Arg Gly Ala Ser Leu  Gln His Thr Ala Pro  Phe Gly Cys
    1055                 1060                 1065

Gln Ile  Ala Thr Asn Pro Val  Arg Ala Val Asn Cys  Ala Val Gly
    1070                 1075                 1080

Asn Met  Pro Ile Ser Ile Asp  Ile Pro Glu Ala Ala  Phe Thr Arg
    1085                 1090                 1095

Val Val  Asp Ala Pro Ser Leu  Thr Asp Met Ser Cys  Glu Val Pro
    1100                 1105                 1110

Ala Cys  Thr His Ser Ser Asp  Phe Gly Gly Val Ala  Ile Ile Lys
    1115                 1120                 1125

Tyr Ala  Ala Ser Lys Lys Gly  Lys Cys Ala Val His  Ser Met Thr
    1130                 1135                 1140

Asn Ala  Val Thr Ile Arg Glu  Ala Glu Ile Glu Val  Glu Gly Asn
    1145                 1150                 1155

Ser Gln  Leu Gln Ile Ser Phe  Ser Thr Ala Leu Ala  Ser Ala Glu
    1160                 1165                 1170

Phe Arg  Val Gln Val Cys Ser  Thr Gln Val His Cys  Ala Ala Glu
    1175                 1180                 1185

Cys His  Pro Pro Lys Asp His  Ile Val Asn Tyr Pro  Ala Ser His
    1190                 1195                 1200

Thr Thr  Leu Gly Val Gln Asp  Ile Ser Ala Thr Ala  Met Ser Trp
    1205                 1210                 1215

Val Gln  Lys Ile Thr Gly Gly  Val Gly Leu Val Val  Ala Val Ala
    1220                 1225                 1230

Ala Leu  Ile Leu Ile Val Val  Leu Cys Val Ser Phe  Ser Arg His
    1235                 1240                 1245


<210> SEQ ID NO 27
<211> LENGTH: 1248
<212> TYPE: PRT
<213> ORGANISM: Chikungunya virus

<400> SEQUENCE: 27

Met Glu Phe Ile Pro Thr Gln Thr Phe Tyr Asn Arg Arg Tyr Gln Pro
1               5                   10                  15
```

-continued

```
Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
```

-continued

```
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860
```

```
Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                1005

Phe Gly  Asp Ile Gln Ser Arg  Thr Pro Glu Ser Lys  Asp Val Tyr
    1010                1015                1020

Ala Asn  Thr Gln Leu Val Leu  Gln Arg Pro Ala Val  Gly Thr Val
    1025                1030                1035

His Val  Pro Tyr Ser Gln Ala  Pro Ser Gly Phe Lys  Tyr Trp Leu
    1040                1045                1050

Lys Glu  Arg Gly Ala Ser Leu  Gln His Thr Ala Pro  Phe Gly Cys
    1055                1060                1065

Gln Ile  Ala Thr Asn Pro Val  Arg Ala Val Asn Cys  Ala Val Gly
    1070                1075                1080

Asn Met  Pro Ile Ser Ile Asp  Ile Pro Glu Ala Ala  Phe Thr Arg
    1085                1090                1095

Val Val  Asp Ala Pro Ser Leu  Thr Asp Met Ser Cys  Glu Val Pro
    1100                1105                1110

Ala Cys  Thr His Ser Ser Asp  Phe Gly Gly Val Ala  Ile Ile Lys
    1115                1120                1125

Tyr Ala  Ala Ser Lys Lys Gly  Lys Cys Ala Val His  Ser Met Thr
    1130                1135                1140

Asn Ala  Val Thr Ile Arg Glu  Ala Glu Ile Glu Val  Glu Gly Asn
    1145                1150                1155

Ser Gln  Leu Gln Ile Ser Phe  Ser Thr Ala Leu Ala  Ser Ala Glu
    1160                1165                1170

Phe Arg  Val Gln Val Cys Ser  Thr Gln Val His Cys  Ala Ala Glu
    1175                1180                1185

Cys His  Pro Pro Lys Asp His  Ile Val Asn Tyr Pro  Ala Ser His
    1190                1195                1200

Thr Thr  Leu Gly Val Gln Asp  Ile Ser Ala Thr Ala  Met Ser Trp
    1205                1210                1215

Val Gln  Lys Ile Thr Gly Gly  Val Gly Leu Val Val  Ala Val Ala
    1220                1225                1230

Ala Leu  Ile Leu Ile Val Val  Leu Cys Val Ser Phe  Ser Arg His
    1235                1240                1245

<210> SEQ ID NO 28
<211> LENGTH: 1248
```

-continued

```
<212> TYPE: PRT
<213> ORGANISM: Chikungunya virus

<400> SEQUENCE: 28

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400
```

-continued

```
Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815
```

```
Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                1005

Phe Gly  Asp Ile Gln Ser Arg  Thr Pro Glu Ser Lys  Asp Val Tyr
    1010                 1015                1020

Ala Asn  Thr Gln Leu Val Leu  Gln Arg Pro Ala Val  Gly Thr Val
    1025                 1030                1035

His Val  Pro Tyr Ser Gln Ala  Pro Ser Gly Phe Lys  Tyr Trp Leu
    1040                 1045                1050

Lys Glu  Arg Gly Ala Ser Leu  Gln His Thr Ala Pro  Phe Gly Cys
    1055                 1060                1065

Gln Ile  Ala Thr Asn Pro Val  Arg Ala Val Asn Cys  Ala Val Gly
    1070                 1075                1080

Asn Met  Pro Ile Ser Ile Asp  Ile Pro Glu Ala Ala  Phe Thr Arg
    1085                 1090                1095

Val Val  Asp Ala Pro Ser Leu  Thr Asp Met Ser Cys  Glu Val Pro
    1100                 1105                1110

Ala Cys  Thr His Ser Ser Asp  Phe Gly Gly Val Ala  Ile Ile Lys
    1115                 1120                1125

Tyr Ala  Ala Ser Lys Lys Gly  Lys Cys Ala Val His  Ser Met Thr
    1130                 1135                1140

Asn Ala  Val Thr Ile Arg Glu  Ala Glu Ile Glu Val  Glu Gly Asn
    1145                 1150                1155

Ser Gln  Leu Gln Ile Ser Phe  Ser Thr Ala Leu Ala  Ser Ala Glu
    1160                 1165                1170

Phe Arg  Val Gln Val Cys Ser  Thr Gln Val His Cys  Ala Ala Glu
    1175                 1180                1185

Cys His  Pro Pro Lys Asp His  Ile Val Asn Tyr Pro  Ala Ser His
    1190                 1195                1200

Thr Thr  Leu Gly Val Gln Asp  Ile Ser Ala Thr Ala  Met Ser Trp
    1205                 1210                1215

Val Gln  Lys Ile Thr Gly Gly  Val Gly Leu Val Val  Ala Val Ala
```

```
    1220                1225                1230

Ala Leu  Ile Leu Ile Val Val  Leu Cys Val Ser Phe  Ser Arg His
    1235                1240                1245


<210> SEQ ID NO 29
<211> LENGTH: 1248
<212> TYPE: PRT
<213> ORGANISM: Chikungunya virus

<400> SEQUENCE: 29

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350
```

```
Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
```

```
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                1005

Phe Gly  Asp Ile Gln Ser Arg  Thr Pro Glu Ser Lys  Asp Val Tyr
    1010                1015                1020

Ala Asn  Thr Gln Leu Val Leu  Gln Arg Pro Ala Val  Gly Thr Val
    1025                1030                1035

His Val  Pro Tyr Ser Gln Ala  Pro Ser Gly Phe Lys  Tyr Trp Leu
    1040                1045                1050

Lys Glu  Arg Gly Ala Ser Leu  Gln His Thr Ala Pro  Phe Gly Cys
    1055                1060                1065

Gln Ile  Ala Thr Asn Pro Val  Arg Ala Val Asn Cys  Ala Val Gly
    1070                1075                1080

Asn Met  Pro Ile Ser Ile Asp  Ile Pro Glu Ala Ala  Phe Thr Arg
    1085                1090                1095

Val Val  Asp Ala Pro Ser Leu  Thr Asp Met Ser Cys  Glu Val Pro
    1100                1105                1110

Ala Cys  Thr His Ser Ser Asp  Phe Gly Gly Val Ala  Ile Ile Lys
    1115                1120                1125

Tyr Ala  Ala Ser Lys Lys Gly  Lys Cys Ala Val His  Ser Met Thr
    1130                1135                1140

Asn Ala  Val Thr Ile Arg Glu  Ala Glu Ile Glu Val  Glu Gly Asn
    1145                1150                1155

Ser Gln  Leu Gln Ile Ser Phe  Ser Thr Ala Leu Ala  Ser Ala Glu
    1160                1165                1170

Phe Arg  Val Gln Val Cys Ser  Thr Gln Val His Cys  Ala Ala Glu
    1175                1180                1185
```

```
Cys His  Pro Pro Lys Asp His  Ile Val Asn Tyr Pro  Ala Ser His
    1190                 1195                 1200

Thr Thr  Leu Gly Val Gln Asp  Ile Ser Ala Thr Ala  Met Ser Trp
    1205                 1210                 1215

Val Gln  Lys Ile Thr Gly Gly  Val Gly Leu Val Val  Ala Val Ala
    1220                 1225                 1230

Ala Leu  Ile Leu Ile Val Val  Leu Cys Val Ser Phe  Ser Arg His
    1235                 1240                 1245


<210> SEQ ID NO 30
<211> LENGTH: 2473
<212> TYPE: PRT
<213> ORGANISM: Chikungunya virus

<400> SEQUENCE: 30

Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Gly Lys Ile Gly Asp Leu Gln Ala Val Met Ala Val Pro Asp Thr
        115                 120                 125

Glu Thr Pro Thr Phe Cys Leu His Thr Asp Val Ser Cys Arg Gln Arg
    130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
        195                 200                 205

Asn Ile Gly Leu Cys Ser Thr Asp Leu Thr Glu Gly Arg Arg Gly Lys
    210                 215                 220

Leu Ser Ile Met Arg Gly Lys Lys Leu Lys Pro Cys Asp Arg Val Leu
225                 230                 235                 240

Phe Ser Val Gly Ser Thr Leu Tyr Pro Glu Ser Arg Lys Leu Leu Lys
                245                 250                 255

Ser Trp His Leu Pro Ser Val Phe His Leu Lys Gly Lys Leu Ser Phe
            260                 265                 270

Thr Cys Arg Cys Asp Thr Val Val Ser Cys Glu Gly Tyr Val Val Lys
        275                 280                 285

Arg Ile Thr Met Ser Pro Gly Leu Tyr Gly Lys Thr Thr Gly Tyr Ala
    290                 295                 300

Val Thr His His Ala Asp Gly Phe Leu Met Cys Lys Thr Thr Asp Thr
```

-continued

```
305                 310                 315                 320

Val Asp Gly Glu Arg Val Ser Phe Ser Val Cys Thr Tyr Val Pro Ala
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Lys Gln Lys Thr His Thr Val Tyr
            420                 425                 430

Lys Arg Pro Asp Thr Gln Ser Ile Gln Lys Val Gln Ala Glu Phe Asp
        435                 440                 445

Ser Phe Val Val Pro Ser Leu Trp Ser Ser Gly Leu Ser Ile Pro Leu
    450                 455                 460

Arg Thr Arg Ile Lys Trp Leu Leu Ser Lys Val Pro Lys Thr Asp Leu
465                 470                 475                 480

Ile Pro Tyr Ser Gly Asp Ala Arg Glu Ala Arg Asp Ala Glu Lys Glu
                485                 490                 495

Ala Glu Glu Glu Arg Glu Ala Glu Leu Thr Arg Glu Ala Leu Pro Pro
            500                 505                 510

Leu Gln Ala Ala Gln Glu Asp Val Gln Val Glu Ile Asp Val Glu Gln
        515                 520                 525

Leu Glu Asp Arg Ala Gly Ala Gly Ile Ile Glu Thr Pro Arg Gly Ala
    530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Asn Gly Arg Ala
            580                 585                 590

Gly Arg Tyr Ala Val Glu Ala Tyr Asp Gly Arg Val Leu Val Pro Ser
        595                 600                 605

Gly Tyr Ala Ile Ser Pro Glu Asp Phe Gln Ser Leu Ser Glu Ser Ala
    610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
            660                 665                 670

Gln Arg Arg Cys Cys Lys Lys Glu Glu Ala Ala Gly Leu Val Leu Val
        675                 680                 685

Gly Asp Leu Thr Asn Pro Pro Tyr His Glu Phe Ala Tyr Glu Gly Leu
    690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735
```

-continued

```
Arg Gln Asp Leu Val Thr Ser Gly Lys Lys Glu Asn Cys Gln Glu Ile
            740                 745                 750

Thr Thr Asp Val Met Arg Gln Arg Gly Leu Glu Ile Ser Ala Arg Thr
        755                 760                 765

Val Asp Ser Leu Leu Leu Asn Gly Cys Asn Arg Pro Val Asp Val Leu
    770                 775                 780

Tyr Val Asp Glu Ala Phe Ala Cys His Ser Gly Thr Leu Leu Ala Leu
785                 790                 795                 800

Ile Ala Leu Val Arg Pro Arg Gln Lys Val Val Leu Cys Gly Asp Pro
                805                 810                 815

Lys Gln Cys Gly Phe Phe Asn Met Met Gln Met Lys Val Asn Tyr Asn
            820                 825                 830

His Asn Ile Cys Thr Gln Val Tyr His Lys Ser Ile Ser Arg Arg Cys
        835                 840                 845

Thr Leu Pro Val Thr Ala Ile Val Ser Ser Leu His Tyr Glu Gly Lys
    850                 855                 860

Met Arg Thr Thr Asn Glu Tyr Asn Lys Pro Ile Val Val Asp Thr Thr
865                 870                 875                 880

Gly Ser Thr Lys Pro Asp Pro Gly Asp Leu Val Leu Thr Cys Phe Arg
                885                 890                 895

Gly Trp Val Lys Gln Leu Gln Ile Asp Tyr Arg Gly Tyr Glu Val Met
            900                 905                 910

Thr Ala Ala Ala Ser Gln Gly Leu Thr Arg Lys Gly Val Tyr Ala Val
        915                 920                 925

Arg Gln Lys Val Asn Glu Asn Pro Leu Tyr Ala Ser Thr Ser Glu His
    930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975

Asn Phe Lys Ala Thr Ile Lys Glu Trp Glu Val Glu His Ala Ser Ile
            980                 985                 990

Met Ala Gly Ile Cys Ser His Gln  Met Thr Phe Asp Thr  Phe Gln Asn
        995                 1000                1005

Lys Ala  Asn Val Cys Trp Ala  Lys Ser Leu Val Pro  Ile Leu Glu
    1010                1015                1020

Thr Ala  Gly Ile Lys Leu Asn  Asp Arg Gln Trp Ser  Gln Ile Ile
    1025                1030                1035

Gln Ala  Phe Lys Glu Asp Lys  Ala Tyr Ser Pro Glu  Val Ala Leu
    1040                1045                1050

Asn Glu  Ile Cys Thr Arg Met  Tyr Gly Val Asp Leu  Asp Ser Gly
    1055                1060                1065

Leu Phe  Ser Lys Pro Leu Val  Ser Val Tyr Tyr Ala  Asp Asn His
    1070                1075                1080

Trp Asp  Asn Arg Pro Gly Gly  Lys Met Phe Gly Phe  Asn Pro Glu
    1085                1090                1095

Ala Ala  Ser Ile Leu Glu Arg  Lys Tyr Pro Phe Thr  Lys Gly Lys
    1100                1105                1110

Trp Asn  Ile Asn Lys Gln Ile  Cys Val Thr Thr Arg  Arg Ile Glu
    1115                1120                1125

Asp Phe  Asn Pro Thr Thr Asn  Ile Ile Pro Ala Asn  Arg Arg Leu
    1130                1135                1140
```

```
Pro His  Ser Leu Val Ala Glu  His Arg Pro Val Lys  Gly Glu Arg
    1145                 1150                 1155

Met Glu  Trp Leu Val Asn Lys  Ile Asn Gly His His  Val Leu Leu
    1160                 1165                 1170

Val Ser  Gly Tyr Asn Leu Ala  Leu Pro Thr Lys Arg  Val Thr Trp
    1175                 1180                 1185

Val Ala  Pro Leu Gly Val Arg  Gly Ala Asp Tyr Thr  Tyr Asn Leu
    1190                 1195                 1200

Glu Leu  Gly Leu Pro Ala Thr  Leu Gly Arg Tyr Asp  Leu Val Val
    1205                 1210                 1215

Ile Asn  Ile His Thr Pro Phe  Arg Ile His His Tyr  Gln Gln Cys
    1220                 1225                 1230

Val Asp  His Ala Met Lys Leu  Gln Met Leu Gly Gly  Asp Ser Leu
    1235                 1240                 1245

Arg Leu  Leu Lys Pro Gly Gly  Ser Leu Leu Ile Arg  Ala Tyr Gly
    1250                 1255                 1260

Tyr Ala  Asp Arg Thr Ser Glu  Arg Val Ile Cys Val  Leu Gly Arg
    1265                 1270                 1275

Lys Phe  Arg Ser Ser Arg Ala  Leu Lys Pro Pro Cys  Val Thr Ser
    1280                 1285                 1290

Asn Thr  Glu Met Phe Phe Leu  Phe Ser Asn Phe Asp  Asn Gly Arg
    1295                 1300                 1305

Arg Asn  Phe Thr Thr His Val  Met Asn Asn Gln Leu  Asn Ala Ala
    1310                 1315                 1320

Phe Val  Gly Gln Val Thr Arg  Ala Gly Cys Ala Pro  Ser Tyr Arg
    1325                 1330                 1335

Val Lys  Arg Met Asp Ile Ala  Lys Asn Asp Glu Glu  Cys Val Val
    1340                 1345                 1350

Asn Ala  Ala Asn Pro Arg Gly  Leu Pro Gly Asp Gly  Val Cys Lys
    1355                 1360                 1365

Ala Val  Tyr Lys Lys Trp Pro  Glu Ser Phe Lys Asn  Ser Ala Thr
    1370                 1375                 1380

Pro Val  Gly Thr Ala Lys Thr  Val Met Cys Gly Thr  Tyr Pro Val
    1385                 1390                 1395

Ile His  Ala Val Gly Pro Asn  Phe Ser Asn Tyr Ser  Glu Ser Glu
    1400                 1405                 1410

Gly Asp  Arg Glu Leu Ala Ala  Ala Tyr Arg Glu Val  Ala Lys Glu
    1415                 1420                 1425

Val Thr  Arg Leu Gly Val Asn  Ser Val Ala Ile Pro  Leu Leu Ser
    1430                 1435                 1440

Thr Gly  Val Tyr Ser Gly Gly  Lys Asp Arg Leu Thr  Gln Ser Leu
    1445                 1450                 1455

Asn His  Leu Phe Thr Ala Met  Asp Ser Thr Asp Ala  Asp Val Val
    1460                 1465                 1470

Ile Tyr  Cys Arg Asp Lys Glu  Trp Glu Lys Lys Ile  Ser Glu Ala
    1475                 1480                 1485

Ile Gln  Met Arg Thr Gln Val  Glu Leu Leu Asp Glu  His Ile Ser
    1490                 1495                 1500

Ile Asp  Cys Asp Ile Val Arg  Val His Pro Asp Ser  Ser Leu Ala
    1505                 1510                 1515

Gly Arg  Lys Gly Tyr Ser Thr  Thr Glu Gly Ala Leu  Tyr Ser Tyr
    1520                 1525                 1530

Leu Glu  Gly Thr Arg Phe His  Gln Thr Ala Val Asp  Met Ala Glu
```

```
    1535                1540                1545

Ile His  Thr Met Trp Pro Lys  Gln Thr Glu Ala Asn  Glu Gln Val
    1550                1555                1560

Cys Leu  Tyr Ala Leu Gly Glu  Ser Ile Glu Ser Ile  Arg Gln Lys
    1565                1570                1575

Cys Pro  Val Asp Asp Ala Asp  Ala Ser Ser Pro Pro  Lys Thr Val
    1580                1585                1590

Pro Cys  Leu Cys Arg Tyr Ala  Met Thr Pro Glu Arg  Val Thr Arg
    1595                1600                1605

Leu Arg  Met Asn His Val Thr  Ser Ile Ile Val Cys  Ser Ser Phe
    1610                1615                1620

Pro Leu  Pro Lys Tyr Lys Ile  Glu Gly Val Gln Lys  Val Lys Cys
    1625                1630                1635

Ser Lys  Val Met Leu Phe Asp  His Asn Val Pro Ser  Arg Val Ser
    1640                1645                1650

Pro Arg  Glu Tyr Arg Ser Ser  Gln Glu Ser Ala Gln  Glu Ala Ser
    1655                1660                1665

Thr Ile  Thr Ser Leu Thr His  Ser Gln Phe Asp Leu  Ser Val Asp
    1670                1675                1680

Gly Glu  Ile Leu Pro Val Pro  Ser Asp Leu Asp Ala  Asp Ala Pro
    1685                1690                1695

Ala Leu  Glu Pro Ala Leu Asp  Asp Gly Ala Thr His  Thr Leu Pro
    1700                1705                1710

Ser Thr  Thr Gly Asn Leu Ala  Ala Val Ser Asp Trp  Val Met Ser
    1715                1720                1725

Thr Val  Pro Val Ala Pro Pro  Arg Arg Arg Arg Gly  Arg Asn Leu
    1730                1735                1740

Thr Val  Thr Cys Asp Glu Arg  Glu Gly Asn Ile Thr  Pro Met Ala
    1745                1750                1755

Ser Val  Arg Phe Phe Arg Ala  Glu Leu Cys Pro Val  Val Gln Glu
    1760                1765                1770

Thr Ala  Glu Thr Arg Asp Thr  Ala Met Ser Leu Gln  Ala Pro Pro
    1775                1780                1785

Ser Thr  Ala Thr Glu Pro Asn  His Pro Pro Ile Ser  Phe Gly Ala
    1790                1795                1800

Ser Ser  Glu Thr Phe Pro Ile  Thr Phe Gly Asp Phe  Asn Glu Gly
    1805                1810                1815

Glu Ile  Glu Ser Leu Ser Ser  Glu Leu Leu Thr Phe  Gly Asp Phe
    1820                1825                1830

Leu Pro  Gly Glu Val Asp Asp  Leu Thr Asp Ser Asp  Trp Ser Thr
    1835                1840                1845

Cys Ser  Asp Thr Asp Asp Glu  Leu Leu Asp Arg Ala  Gly Gly Tyr
    1850                1855                1860

Ile Phe  Ser Ser Asp Thr Gly  Pro Gly His Leu Gln  Gln Lys Ser
    1865                1870                1875

Val Arg  Gln Ser Val Leu Pro  Val Asn Thr Leu Glu  Glu Val His
    1880                1885                1890

Glu Glu  Lys Cys Tyr Pro Pro  Lys Leu Asp Glu Ala  Lys Glu Gln
    1895                1900                1905

Leu Leu  Leu Lys Lys Leu Gln  Glu Ser Ala Ser Met  Ala Asn Arg
    1910                1915                1920

Ser Arg  Tyr Gln Ser Arg Lys  Val Glu Asn Met Lys  Ala Ala Ile
    1925                1930                1935
```

-continued

```
Ile Gln Arg Leu Lys Arg Gly Cys Arg Leu Tyr Leu Met Ser Glu
    1940                1945                1950

Thr Pro Lys Val Pro Thr Tyr Arg Thr Thr Tyr Pro Ala Pro Val
    1955                1960                1965

Tyr Ser Pro Pro Ile Asn Val Arg Leu Ser Asn Pro Glu Ser Ala
    1970                1975                1980

Val Ala Ala Cys Asn Glu Phe Leu Ala Arg Asn Tyr Pro Thr Val
    1985                1990                1995

Ser Ser Tyr Gln Ile Thr Asp Glu Tyr Asp Ala Tyr Leu Asp Met
    2000                2005                2010

Val Asp Gly Ser Glu Ser Cys Leu Asp Arg Ala Thr Phe Asn Pro
    2015                2020                2025

Ser Lys Leu Arg Ser Tyr Pro Lys Gln His Ala Tyr His Ala Pro
    2030                2035                2040

Ser Ile Arg Ser Ala Val Pro Ser Pro Phe Gln Asn Thr Leu Gln
    2045                2050                2055

Asn Val Leu Ala Ala Ala Thr Lys Arg Asn Cys Asn Val Thr Gln
    2060                2065                2070

Met Arg Glu Leu Pro Thr Leu Asp Ser Ala Val Phe Asn Val Glu
    2075                2080                2085

Cys Phe Lys Lys Phe Ala Cys Asn Gln Glu Tyr Trp Glu Glu Phe
    2090                2095                2100

Ala Ala Ser Pro Ile Arg Ile Thr Thr Glu Asn Leu Ala Thr Tyr
    2105                2110                2115

Val Thr Lys Leu Lys Gly Pro Lys Ala Ala Ala Leu Phe Ala Lys
    2120                2125                2130

Thr His Asn Leu Leu Pro Leu Gln Glu Val Pro Met Asp Arg Phe
    2135                2140                2145

Thr Val Asp Met Lys Arg Asp Val Lys Val Thr Pro Gly Thr Lys
    2150                2155                2160

His Thr Glu Glu Arg Pro Lys Val Gln Val Ile Gln Ala Ala Glu
    2165                2170                2175

Pro Leu Ala Thr Ala Tyr Leu Cys Gly Ile His Arg Glu Leu Val
    2180                2185                2190

Arg Arg Leu Asn Ala Val Leu Leu Pro Asn Val His Thr Leu Phe
    2195                2200                2205

Asp Met Ser Ala Glu Asp Phe Asp Ala Ile Ile Ala Ala His Phe
    2210                2215                2220

Lys Pro Gly Asp Thr Val Leu Glu Thr Asp Ile Ala Ser Phe Asp
    2225                2230                2235

Lys Ser Gln Asp Asp Ser Leu Ala Leu Thr Ala Leu Met Leu Leu
    2240                2245                2250

Glu Asp Leu Gly Val Asp His Ser Leu Leu Asp Leu Ile Glu Ala
    2255                2260                2265

Ala Phe Gly Glu Ile Ser Ser Cys His Leu Pro Thr Gly Thr Arg
    2270                2275                2280

Phe Lys Phe Gly Ala Met Met Lys Ser Gly Met Phe Leu Thr Leu
    2285                2290                2295

Phe Val Asn Thr Leu Leu Asn Ile Thr Ile Ala Ser Arg Val Leu
    2300                2305                2310

Glu Asp Arg Leu Thr Lys Ser Ala Cys Ala Ala Phe Ile Gly Asp
    2315                2320                2325
```

Asp Asn Ile Ile His Gly Val Val Ser Asp Glu Leu Met Ala Ala
    2330                2335                2340

Arg Cys Ala Thr Trp Met Asn Met Glu Val Lys Ile Ile Asp Ala
    2345                2350                2355

Val Val Ser Leu Lys Ala Pro Tyr Phe Cys Gly Gly Phe Ile Leu
    2360                2365                2370

His Asp Thr Val Thr Gly Thr Ala Cys Arg Val Ala Asp Pro Leu
    2375                2380                2385

Lys Arg Leu Phe Lys Leu Gly Lys Pro Leu Ala Ala Gly Asp Glu
    2390                2395                2400

Gln Asp Glu Asp Arg Arg Arg Ala Leu Ala Asp Glu Val Ile Arg
    2405                2410                2415

Trp Gln Arg Thr Gly Leu Ile Asp Glu Leu Glu Lys Ala Val Tyr
    2420                2425                2430

Ser Arg Tyr Glu Val Gln Gly Ile Ser Val Val Val Met Ser Met
    2435                2440                2445

Ala Thr Phe Ala Ser Ser Arg Ser Asn Phe Glu Lys Leu Arg Gly
    2450                2455                2460

Pro Val Ile Thr Leu Tyr Gly Gly Pro Lys
    2465                2470

<210> SEQ ID NO 31
<211> LENGTH: 2473
<212> TYPE: PRT
<213> ORGANISM: Chikungunya virus

<400> SEQUENCE: 31

Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Gly Lys Ile Gly Asp Leu Gln Ala Val Met Ala Val Pro Asp Thr
        115                 120                 125

Glu Thr Pro Thr Phe Cys Leu His Thr Asp Val Ser Cys Arg Gln Arg
    130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
        195                 200                 205

Asn Ile Gly Leu Cys Ser Thr Asp Leu Thr Glu Gly Arg Arg Gly Lys
    210                 215                 220

```
Leu Ser Ile Met Arg Gly Lys Lys Leu Lys Pro Cys Asp Arg Val Leu
225                 230                 235                 240

Phe Ser Val Gly Ser Thr Leu Tyr Pro Glu Ser Arg Lys Leu Leu Lys
                245                 250                 255

Ser Trp His Leu Pro Ser Val Phe His Leu Lys Gly Lys Leu Ser Phe
            260                 265                 270

Thr Cys Arg Cys Asp Thr Val Val Ser Cys Glu Gly Tyr Val Val Lys
        275                 280                 285

Arg Ile Thr Met Ser Pro Gly Leu Tyr Gly Lys Thr Thr Gly Tyr Ala
    290                 295                 300

Val Thr His His Ala Asp Gly Phe Leu Met Cys Lys Thr Thr Asp Thr
305                 310                 315                 320

Val Asp Gly Glu Arg Val Ser Phe Ser Val Cys Thr Tyr Val Pro Ala
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Lys Gln Lys Thr His Thr Val Tyr
            420                 425                 430

Lys Arg Pro Asp Thr Gln Ser Ile Gln Lys Val Gln Ala Glu Phe Asp
        435                 440                 445

Ser Phe Val Val Pro Ser Leu Trp Ser Ser Gly Leu Ser Ile Pro Leu
    450                 455                 460

Arg Thr Arg Ile Lys Trp Leu Leu Ser Lys Val Pro Lys Thr Asp Leu
465                 470                 475                 480

Ile Pro Tyr Ser Gly Asp Ala Arg Glu Ala Arg Asp Ala Glu Lys Glu
                485                 490                 495

Ala Glu Glu Glu Arg Glu Ala Glu Leu Thr Arg Glu Ala Leu Pro Pro
            500                 505                 510

Leu Gln Ala Ala Gln Glu Asp Val Gln Val Glu Ile Asp Val Glu Gln
        515                 520                 525

Leu Glu Asp Arg Ala Gly Ala Gly Ile Ile Glu Thr Pro Arg Gly Ala
    530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Asn Gly Arg Ala
            580                 585                 590

Gly Arg Tyr Ala Val Glu Ala Tyr Asp Gly Arg Val Leu Val Pro Ser
        595                 600                 605

Gly Tyr Ala Ile Ser Pro Glu Asp Phe Gln Ser Leu Ser Glu Ser Ala
    610                 615                 620

Thr Met Val Tyr Asn Glu Arg Glu Phe Val Asn Arg Lys Leu His His
625                 630                 635                 640
```

-continued

```
Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
            660                 665                 670

Gln Arg Arg Cys Cys Lys Lys Glu Glu Ala Ala Gly Leu Val Leu Val
        675                 680                 685

Gly Asp Leu Thr Asn Pro Pro Tyr His Glu Phe Ala Tyr Glu Gly Leu
    690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
            740                 745                 750

Thr Thr Asp Val Met Arg Gln Arg Gly Leu Glu Ile Ser Ala Arg Thr
        755                 760                 765

Val Asp Ser Leu Leu Leu Asn Gly Cys Asn Arg Pro Val Asp Val Leu
    770                 775                 780

Tyr Val Asp Glu Ala Phe Ala Cys His Ser Gly Thr Leu Leu Ala Leu
785                 790                 795                 800

Ile Ala Leu Val Arg Pro Arg Gln Lys Val Val Leu Cys Gly Asp Pro
                805                 810                 815

Lys Gln Cys Gly Phe Phe Asn Met Met Gln Met Lys Val Asn Tyr Asn
            820                 825                 830

His Asn Ile Cys Thr Gln Val Tyr His Lys Ser Ile Ser Arg Arg Cys
        835                 840                 845

Thr Leu Pro Val Thr Ala Ile Val Ser Ser Leu His Tyr Glu Gly Lys
    850                 855                 860

Met Arg Thr Thr Asn Glu Tyr Asn Lys Pro Ile Val Val Asp Thr Thr
865                 870                 875                 880

Gly Ser Thr Lys Pro Asp Pro Gly Asp Leu Val Leu Thr Cys Phe Arg
                885                 890                 895

Gly Trp Val Lys Gln Leu Gln Ile Asp Tyr Arg Gly Tyr Glu Val Met
            900                 905                 910

Thr Ala Ala Ala Ser Gln Gly Leu Thr Arg Lys Gly Val Tyr Ala Val
        915                 920                 925

Arg Gln Lys Val Asn Glu Asn Pro Leu Tyr Ala Ser Thr Ser Glu His
    930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975

Asn Phe Lys Ala Thr Ile Lys Glu Trp Glu Val Glu His Ala Ser Ile
            980                 985                 990

Met Ala Gly Ile Cys Ser His Gln  Met Thr Phe Asp Thr  Phe Gln Asn
        995                 1000                1005

Lys Ala  Asn Val Cys Trp Ala  Lys Ser Leu Val Pro  Ile Leu Glu
    1010                 1015                 1020

Thr Ala  Gly Ile Lys Leu Asn  Asp Arg Gln Trp Ser  Gln Ile Ile
    1025                 1030                 1035

Gln Ala  Phe Lys Glu Asp Lys  Ala Tyr Ser Pro Glu  Val Ala Leu
    1040                 1045                 1050

Asn Glu  Ile Cys Thr Arg Met  Tyr Gly Val Asp Leu  Asp Ser Gly
```

```
    1055                1060                1065

Leu Phe  Ser Lys Pro Leu Val  Ser Val Tyr Tyr Ala  Asp Asn His
    1070                1075                1080

Trp Asp  Asn Arg Pro Gly Gly  Lys Met Phe Gly Phe  Asn Pro Glu
    1085                1090                1095

Ala Ala  Ser Ile Leu Glu Arg  Lys Tyr Pro Phe Thr  Lys Gly Lys
    1100                1105                1110

Trp Asn  Ile Asn Lys Gln Ile  Cys Val Thr Thr Arg  Arg Ile Glu
    1115                1120                1125

Asp Phe  Asn Pro Thr Thr Asn  Ile Ile Pro Ala Asn  Arg Arg Leu
    1130                1135                1140

Pro His  Ser Leu Val Ala Glu  His Arg Pro Val Lys  Gly Glu Arg
    1145                1150                1155

Met Glu  Trp Leu Val Asn Lys  Ile Asn Gly His His  Val Leu Leu
    1160                1165                1170

Val Ser  Gly Tyr Asn Leu Ala  Leu Pro Thr Lys Arg  Val Thr Trp
    1175                1180                1185

Val Ala  Pro Leu Gly Val Arg  Gly Ala Asp Tyr Thr  Tyr Asn Leu
    1190                1195                1200

Glu Leu  Gly Leu Pro Ala Thr  Leu Gly Arg Tyr Asp  Leu Val Val
    1205                1210                1215

Ile Asn  Ile His Thr Pro Phe  Arg Ile His His Tyr  Gln Gln Cys
    1220                1225                1230

Val Asp  His Ala Met Lys Leu  Gln Met Leu Gly Gly  Asp Ser Leu
    1235                1240                1245

Arg Leu  Leu Lys Pro Gly Gly  Ser Leu Leu Ile Arg  Ala Tyr Gly
    1250                1255                1260

Tyr Ala  Asp Arg Thr Ser Glu  Arg Val Ile Cys Val  Leu Gly Arg
    1265                1270                1275

Lys Phe  Arg Ser Ser Arg Ala  Leu Lys Pro Pro Cys  Val Thr Ser
    1280                1285                1290

Asn Thr  Glu Met Phe Phe Leu  Phe Ser Asn Phe Asp  Asn Gly Arg
    1295                1300                1305

Arg Asn  Phe Thr Thr His Val  Met Asn Asn Gln Leu  Asn Ala Ala
    1310                1315                1320

Phe Val  Gly Gln Val Thr Arg  Ala Gly Cys Ala Pro  Ser Tyr Arg
    1325                1330                1335

Val Lys  Arg Met Asp Ile Ala  Lys Asn Asp Glu Glu  Cys Val Val
    1340                1345                1350

Asn Ala  Ala Asn Pro Arg Gly  Leu Pro Gly Asp Gly  Val Cys Lys
    1355                1360                1365

Ala Val  Tyr Lys Lys Trp Pro  Glu Ser Phe Lys Asn  Ser Ala Thr
    1370                1375                1380

Pro Val  Gly Thr Ala Lys Thr  Val Met Cys Gly Thr  Tyr Pro Val
    1385                1390                1395

Ile His  Ala Val Gly Pro Asn  Phe Ser Asn Tyr Ser  Glu Ser Glu
    1400                1405                1410

Gly Asp  Arg Glu Leu Ala Ala  Ala Tyr Arg Glu Val  Ala Lys Glu
    1415                1420                1425

Val Thr  Arg Leu Gly Val Asn  Ser Val Ala Ile Pro  Leu Leu Ser
    1430                1435                1440

Thr Gly  Val Tyr Ser Gly Gly  Lys Asp Arg Leu Thr  Gln Ser Leu
    1445                1450                1455
```

```
Asn His  Leu Phe Thr Ala Met  Asp Ser Thr Asp Ala  Asp Val Val
    1460                 1465                 1470

Ile Tyr  Cys Arg Asp Lys Glu  Trp Glu Lys Lys Ile  Ser Glu Ala
    1475                 1480                 1485

Ile Gln  Met Arg Thr Gln Val  Glu Leu Leu Asp Glu  His Ile Ser
    1490                 1495                 1500

Ile Asp  Cys Asp Ile Val Arg  Val His Pro Asp Ser  Ser Leu Ala
    1505                 1510                 1515

Gly Arg  Lys Gly Tyr Ser Thr  Thr Glu Gly Ala Leu  Tyr Ser Tyr
    1520                 1525                 1530

Leu Glu  Gly Thr Arg Phe His  Gln Thr Ala Val Asp  Met Ala Glu
    1535                 1540                 1545

Ile His  Thr Met Trp Pro Lys  Gln Thr Glu Ala Asn  Glu Gln Val
    1550                 1555                 1560

Cys Leu  Tyr Ala Leu Gly Glu  Ser Ile Glu Ser Ile  Arg Gln Lys
    1565                 1570                 1575

Cys Pro  Val Asp Asp Ala Asp  Ala Ser Ser Pro Pro  Lys Thr Val
    1580                 1585                 1590

Pro Cys  Leu Cys Arg Tyr Ala  Met Thr Pro Glu Arg  Val Thr Arg
    1595                 1600                 1605

Leu Arg  Met Asn His Val Thr  Ser Ile Ile Val Cys  Ser Ser Phe
    1610                 1615                 1620

Pro Leu  Pro Lys Tyr Lys Ile  Glu Gly Val Gln Lys  Val Lys Cys
    1625                 1630                 1635

Ser Lys  Val Met Leu Phe Asp  His Asn Val Pro Ser  Arg Val Ser
    1640                 1645                 1650

Pro Arg  Glu Tyr Arg Ser Ser  Gln Glu Ser Ala Gln  Glu Ala Ser
    1655                 1660                 1665

Thr Ile  Thr Ser Leu Thr His  Ser Gln Phe Asp Leu  Ser Val Asp
    1670                 1675                 1680

Gly Glu  Ile Leu Pro Val Pro  Pro Asp Leu Asp Ala  Asp Ala Pro
    1685                 1690                 1695

Ala Leu  Glu Pro Ala Leu Asp  Asp Gly Ala Thr His  Thr Leu Pro
    1700                 1705                 1710

Ser Thr  Thr Gly Asn Leu Ala  Ala Val Ser Asp Trp  Val Met Ser
    1715                 1720                 1725

Thr Val  Pro Val Ala Pro Pro  Arg Arg Arg Arg Gly  Arg Asn Leu
    1730                 1735                 1740

Thr Val  Thr Cys Asp Glu Arg  Glu Gly Asn Ile Thr  Pro Met Ala
    1745                 1750                 1755

Ser Val  Arg Phe Phe Arg Ala  Glu Leu Cys Pro Val  Val Gln Glu
    1760                 1765                 1770

Thr Ala  Glu Thr Arg Asp Thr  Ala Met Ser Leu Gln  Ala Pro Pro
    1775                 1780                 1785

Ser Thr  Ala Thr Glu Pro Asn  His Pro Pro Ile Ser  Phe Gly Ala
    1790                 1795                 1800

Ser Ser  Glu Thr Phe Pro Ile  Thr Phe Gly Asp Phe  Asn Glu Gly
    1805                 1810                 1815

Glu Ile  Glu Ser Leu Ser Ser  Glu Leu Leu Thr Phe  Gly Asp Phe
    1820                 1825                 1830

Leu Pro  Gly Glu Val Asp Asp  Leu Thr Asp Ser Asp  Trp Ser Thr
    1835                 1840                 1845
```

-continued

```
Cys Ser  Asp Thr Asp Asp Glu  Leu Leu Asp Arg Ala  Gly Gly Tyr
    1850                 1855                 1860

Ile Phe  Ser Ser Asp Thr Gly  Pro Gly His Leu Gln  Gln Lys Ser
    1865                 1870                 1875

Val Arg  Gln Ser Val Leu Pro  Val Asn Thr Leu Glu  Glu Val His
    1880                 1885                 1890

Glu Glu  Lys Cys Tyr Pro Pro  Lys Leu Asp Glu Ala  Lys Glu Gln
    1895                 1900                 1905

Leu Leu  Leu Lys Lys Leu Gln  Glu Ser Ala Ser Met  Ala Asn Arg
    1910                 1915                 1920

Ser Arg  Tyr Gln Ser Arg Lys  Val Glu Asn Met Lys  Ala Ala Ile
    1925                 1930                 1935

Ile Gln  Arg Leu Lys Arg Gly  Cys Arg Leu Tyr Leu  Met Ser Glu
    1940                 1945                 1950

Thr Pro  Lys Val Pro Thr Tyr  Arg Thr Thr Tyr Pro  Ala Pro Val
    1955                 1960                 1965

Tyr Ser  Pro Pro Ile Asn Val  Arg Leu Ser Asn Pro  Glu Ser Ala
    1970                 1975                 1980

Val Ala  Ala Cys Asn Glu Phe  Leu Ala Arg Asn Tyr  Pro Thr Val
    1985                 1990                 1995

Ser Ser  Tyr Gln Ile Thr Asp  Glu Tyr Asp Ala Tyr  Leu Asp Met
    2000                 2005                 2010

Val Asp  Gly Ser Glu Ser Cys  Leu Asp Arg Ala Thr  Phe Asn Pro
    2015                 2020                 2025

Ser Lys  Leu Arg Ser Tyr Pro  Lys Gln His Ala Tyr  His Ala Pro
    2030                 2035                 2040

Ser Ile  Arg Ser Ala Val Pro  Ser Pro Phe Gln Asn  Thr Leu Gln
    2045                 2050                 2055

Asn Val  Leu Ala Ala Ala Thr  Lys Arg Asn Cys Asn  Val Thr Gln
    2060                 2065                 2070

Met Arg  Glu Leu Pro Thr Leu  Asp Ser Ala Val Phe  Asn Val Glu
    2075                 2080                 2085

Cys Phe  Lys Lys Phe Ala Cys  Asn Gln Glu Tyr Trp  Glu Glu Phe
    2090                 2095                 2100

Ala Ala  Ser Pro Ile Arg Ile  Thr Thr Glu Asn Leu  Ala Thr Tyr
    2105                 2110                 2115

Val Thr  Lys Leu Lys Gly Pro  Lys Ala Ala Ala Leu  Phe Ala Lys
    2120                 2125                 2130

Thr His  Asn Leu Leu Pro Leu  Gln Glu Val Pro Met  Asp Arg Phe
    2135                 2140                 2145

Thr Val  Asp Met Lys Arg Asp  Val Lys Val Thr Pro  Gly Thr Lys
    2150                 2155                 2160

His Thr  Glu Glu Arg Pro Lys  Val Gln Val Ile Gln  Ala Ala Glu
    2165                 2170                 2175

Pro Leu  Ala Thr Ala Tyr Leu  Cys Gly Ile His Arg  Glu Leu Val
    2180                 2185                 2190

Arg Arg  Leu Asn Ala Val Leu  Leu Pro Asn Val His  Thr Leu Phe
    2195                 2200                 2205

Asp Met  Ser Ala Glu Asp Phe  Asp Ala Ile Ile Ala  Ala His Phe
    2210                 2215                 2220

Lys Pro  Gly Asp Thr Val Leu  Glu Thr Asp Ile Ala  Ser Phe Asp
    2225                 2230                 2235

Lys Ser  Gln Asp Asp Ser Leu  Ala Leu Thr Ala Leu  Met Leu Leu
```

```
    2240                2245                2250

Glu Asp  Leu Gly Val Asp His  Ser Leu Leu Asp Leu  Ile Glu Ala
    2255                2260                2265

Ala Phe  Gly Glu Ile Ser Ser  Cys His Leu Pro Thr  Gly Thr Arg
    2270                2275                2280

Phe Lys  Phe Gly Ala Met Met  Lys Ser Gly Met Phe  Leu Thr Leu
    2285                2290                2295

Phe Val  Asn Thr Leu Leu Asn  Ile Thr Ile Ala Ser  Arg Val Leu
    2300                2305                2310

Glu Asp  Arg Leu Thr Lys Ser  Ala Cys Ala Ala Phe  Ile Gly Asp
    2315                2320                2325

Asp Asn  Ile Ile His Gly Val  Val Ser Asp Glu Leu  Met Ala Ala
    2330                2335                2340

Arg Cys  Ala Thr Trp Met Asn  Met Glu Val Lys Ile  Ile Asp Ala
    2345                2350                2355

Val Val  Ser Leu Lys Ala Pro  Tyr Phe Cys Gly Gly  Phe Ile Leu
    2360                2365                2370

His Asp  Thr Val Thr Gly Thr  Ala Cys Arg Val Ala  Asp Pro Leu
    2375                2380                2385

Lys Arg  Leu Phe Lys Leu Gly  Lys Pro Leu Ala Ala  Gly Asp Glu
    2390                2395                2400

Gln Asp  Glu Asp Arg Arg Arg  Ala Leu Ala Asp Glu  Val Ile Arg
    2405                2410                2415

Trp Gln  Arg Thr Gly Leu Ile  Asp Glu Leu Glu Lys  Ala Val Tyr
    2420                2425                2430

Ser Arg  Tyr Glu Val Gln Gly  Ile Ser Val Val Val  Met Ser Met
    2435                2440                2445

Ala Thr  Phe Ala Ser Ser Arg  Ser Asn Phe Glu Lys  Leu Arg Gly
    2450                2455                2460

Pro Val  Ile Thr Leu Tyr Gly  Gly Pro Lys
    2465                2470


<210> SEQ ID NO 32
<211> LENGTH: 2473
<212> TYPE: PRT
<213> ORGANISM: Chikungunya virus

<400> SEQUENCE: 32

Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Gly Lys Ile Gly Asp Leu Gln Ala Val Met Ala Val Pro Asp Thr
        115                 120                 125
```

-continued

```
Glu Thr Pro Thr Phe Cys Leu His Thr Asp Val Ser Cys Arg Gln Arg
    130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
        195                 200                 205

Asn Ile Gly Leu Cys Ser Thr Asp Leu Thr Glu Gly Arg Arg Gly Lys
    210                 215                 220

Leu Ser Ile Met Arg Gly Lys Lys Leu Lys Pro Cys Asp Arg Val Leu
225                 230                 235                 240

Phe Ser Val Gly Ser Thr Leu Tyr Pro Glu Ser Arg Lys Leu Leu Lys
                245                 250                 255

Ser Trp His Leu Pro Ser Val Phe His Leu Lys Gly Lys Leu Ser Phe
            260                 265                 270

Thr Cys Arg Cys Asp Thr Val Val Ser Cys Glu Gly Tyr Val Val Lys
        275                 280                 285

Arg Ile Thr Met Ser Pro Gly Leu Tyr Gly Lys Thr Thr Gly Tyr Ala
    290                 295                 300

Val Thr His His Ala Asp Gly Phe Leu Met Cys Lys Thr Thr Asp Thr
305                 310                 315                 320

Val Asp Gly Glu Arg Val Ser Phe Ser Val Cys Thr Tyr Val Pro Ala
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Lys Gln Lys Thr His Thr Val Tyr
            420                 425                 430

Lys Arg Pro Asp Thr Gln Ser Ile Gln Lys Val Gln Ala Glu Phe Asp
        435                 440                 445

Ser Phe Val Val Pro Ser Leu Trp Ser Ser Gly Leu Ser Ile Pro Leu
    450                 455                 460

Arg Thr Arg Ile Lys Trp Leu Leu Ser Lys Val Pro Lys Thr Asp Leu
465                 470                 475                 480

Ile Pro Tyr Ser Gly Asp Ala Arg Glu Ala Arg Asp Ala Glu Lys Glu
                485                 490                 495

Ala Glu Glu Glu Arg Glu Ala Glu Leu Thr Arg Glu Ala Leu Pro Pro
            500                 505                 510

Leu Gln Ala Ala Gln Glu Asp Val Gln Val Glu Ile Asp Val Glu Gln
        515                 520                 525

Leu Glu Asp Arg Ala Gly Ala Gly Ile Ile Glu Thr Pro Arg Gly Ala
    530                 535                 540

Ile Lys Val Thr Ala Gln Pro Thr Asp His Val Val Gly Glu Tyr Leu
```

-continued

```
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Asn Gly Arg Ala
            580                 585                 590

Gly Arg Tyr Ala Val Glu Ala Tyr Asp Gly Arg Val Leu Val Pro Ser
        595                 600                 605

Gly Tyr Ala Ile Ser Pro Glu Asp Phe Gln Ser Leu Ser Glu Ser Ala
    610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
            660                 665                 670

Gln Arg Arg Cys Cys Lys Lys Glu Glu Ala Ala Gly Leu Val Leu Val
        675                 680                 685

Gly Asp Leu Thr Asn Pro Pro Tyr His Glu Phe Ala Tyr Glu Gly Leu
    690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
            740                 745                 750

Thr Thr Asp Val Met Arg Gln Arg Gly Leu Glu Ile Ser Ala Arg Thr
        755                 760                 765

Val Asp Ser Leu Leu Leu Asn Gly Cys Asn Arg Pro Val Asp Val Leu
    770                 775                 780

Tyr Val Asp Glu Ala Phe Ala Cys His Ser Gly Thr Leu Leu Ala Leu
785                 790                 795                 800

Ile Ala Leu Val Arg Pro Arg Gln Lys Val Val Leu Cys Gly Asp Pro
                805                 810                 815

Lys Gln Cys Gly Phe Phe Asn Met Met Gln Met Lys Val Asn Tyr Asn
            820                 825                 830

His Asn Ile Cys Thr Gln Val Tyr His Lys Ser Ile Ser Arg Arg Cys
        835                 840                 845

Thr Leu Pro Val Thr Ala Ile Val Ser Ser Leu His Tyr Glu Gly Lys
    850                 855                 860

Met Arg Thr Thr Asn Glu Tyr Asn Lys Pro Ile Val Val Asp Thr Thr
865                 870                 875                 880

Gly Ser Thr Lys Pro Asp Pro Gly Asp Leu Val Leu Thr Cys Phe Arg
                885                 890                 895

Gly Trp Val Lys Gln Leu Gln Ile Asp Tyr Arg Gly Tyr Glu Val Met
            900                 905                 910

Thr Ala Ala Ala Ser Gln Gly Leu Thr Arg Lys Gly Val Tyr Ala Val
        915                 920                 925

Arg Gln Lys Val Asn Glu Asn Pro Leu Tyr Ala Ser Thr Ser Glu His
    930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975
```

-continued

```
Asn Phe Lys Ala Thr Ile Lys Glu Trp Glu Val Glu His Ala Ser Ile
            980                 985                 990

Met Ala Gly Ile Cys Ser His Gln  Met Thr Phe Asp Thr  Phe Gln Asn
        995                 1000                 1005

Lys Ala  Asn Val Cys Trp Ala  Lys Ser Leu Val Pro  Ile Leu Glu
    1010                 1015                 1020

Thr Ala  Gly Ile Lys Leu Asn  Asp Arg Gln Trp Ser  Gln Ile Ile
    1025                 1030                 1035

Gln Ala  Phe Lys Glu Asp Lys  Ala Tyr Ser Pro Glu  Val Ala Leu
    1040                 1045                 1050

Asn Glu  Ile Cys Thr Arg Met  Tyr Gly Val Asp Leu  Asp Ser Gly
    1055                 1060                 1065

Leu Phe  Ser Lys Pro Leu Val  Ser Val Tyr Tyr Ala  Asp Asn His
    1070                 1075                 1080

Trp Asp  Asn Arg Pro Gly Gly  Lys Met Phe Gly Phe  Asn Pro Glu
    1085                 1090                 1095

Ala Ala  Ser Ile Leu Glu Arg  Lys Tyr Pro Phe Thr  Lys Gly Lys
    1100                 1105                 1110

Trp Asn  Ile Asn Lys Gln Ile  Cys Val Thr Thr Arg  Arg Ile Glu
    1115                 1120                 1125

Asp Phe  Asn Pro Thr Thr Asn  Ile Ile Pro Ala Asn  Arg Arg Leu
    1130                 1135                 1140

Pro His  Ser Leu Val Ala Glu  His Arg Pro Val Lys  Gly Glu Arg
    1145                 1150                 1155

Met Glu  Trp Leu Val Asn Lys  Ile Asn Gly His His  Val Leu Leu
    1160                 1165                 1170

Val Ser  Gly Tyr Asn Leu Ala  Leu Pro Thr Lys Arg  Val Thr Trp
    1175                 1180                 1185

Val Ala  Pro Leu Gly Val Arg  Gly Ala Asp Tyr Thr  Tyr Asn Leu
    1190                 1195                 1200

Glu Leu  Gly Leu Pro Ala Thr  Leu Gly Arg Tyr Asp  Leu Val Val
    1205                 1210                 1215

Ile Asn  Ile His Thr Pro Phe  Arg Ile His His Tyr  Gln Gln Cys
    1220                 1225                 1230

Val Asp  His Ala Met Lys Leu  Gln Met Leu Gly Gly  Asp Ser Leu
    1235                 1240                 1245

Arg Leu  Leu Lys Pro Gly Gly  Ser Leu Leu Ile Arg  Ala Tyr Gly
    1250                 1255                 1260

Tyr Ala  Asp Arg Thr Ser Glu  Arg Val Ile Cys Val  Leu Gly Arg
    1265                 1270                 1275

Lys Phe  Arg Ser Ser Arg Ala  Leu Lys Pro Pro Cys  Val Thr Ser
    1280                 1285                 1290

Asn Thr  Glu Met Phe Phe Leu  Phe Ser Asn Phe Asp  Asn Gly Arg
    1295                 1300                 1305

Arg Asn  Phe Thr Thr His Val  Met Asn Asn Gln Leu  Asn Ala Ala
    1310                 1315                 1320

Phe Val  Gly Gln Val Thr Arg  Ala Gly Cys Ala Pro  Ser Tyr Arg
    1325                 1330                 1335

Val Lys  Arg Met Asp Ile Ala  Lys Asn Asp Glu Glu  Cys Val Val
    1340                 1345                 1350

Asn Ala  Ala Asn Pro Arg Gly  Leu Pro Gly Asp Gly  Val Cys Lys
    1355                 1360                 1365
```

```
Ala Val Tyr Lys Lys Trp Pro Glu Ser Phe Lys Asn Ser Ala Thr
    1370                1375                1380

Pro Val Gly Thr Ala Lys Thr Val Met Cys Gly Thr Tyr Pro Val
    1385                1390                1395

Ile His Ala Val Gly Pro Asn Phe Ser Asn Tyr Ser Glu Ser Glu
    1400                1405                1410

Gly Asp Arg Glu Leu Ala Ala Ala Tyr Arg Glu Val Ala Lys Glu
    1415                1420                1425

Val Thr Arg Leu Gly Val Asn Ser Val Ala Ile Pro Leu Leu Ser
    1430                1435                1440

Thr Gly Val Tyr Ser Gly Gly Lys Asp Arg Leu Thr Gln Ser Leu
    1445                1450                1455

Asn His Leu Phe Thr Ala Met Asp Ser Thr Asp Ala Asp Val Val
    1460                1465                1470

Ile Tyr Cys Arg Asp Lys Glu Trp Glu Lys Lys Ile Ser Glu Ala
    1475                1480                1485

Ile Gln Met Arg Thr Gln Val Glu Leu Leu Asp Glu His Ile Ser
    1490                1495                1500

Ile Asp Cys Asp Ile Val Arg Val His Pro Asp Ser Ser Leu Ala
    1505                1510                1515

Gly Arg Lys Gly Tyr Ser Thr Thr Glu Gly Ala Leu Tyr Ser Tyr
    1520                1525                1530

Leu Glu Gly Thr Arg Phe His Gln Thr Ala Val Asp Met Ala Glu
    1535                1540                1545

Ile His Thr Met Trp Pro Lys Gln Thr Glu Ala Asn Glu Gln Val
    1550                1555                1560

Cys Leu Tyr Ala Leu Gly Glu Ser Ile Glu Ser Ile Arg Gln Lys
    1565                1570                1575

Cys Pro Val Asp Asp Ala Asp Ala Ser Ser Pro Pro Lys Thr Val
    1580                1585                1590

Pro Cys Leu Cys Arg Tyr Ala Met Thr Pro Glu Arg Val Thr Arg
    1595                1600                1605

Leu Arg Met Asn His Val Thr Ser Ile Ile Val Cys Ser Ser Phe
    1610                1615                1620

Pro Leu Pro Lys Tyr Lys Ile Glu Gly Val Gln Lys Val Lys Cys
    1625                1630                1635

Ser Lys Val Met Leu Phe Asp His Asn Val Pro Ser Arg Val Ser
    1640                1645                1650

Pro Arg Glu Tyr Arg Ser Ser Gln Glu Ser Ala Gln Glu Ala Ser
    1655                1660                1665

Thr Ile Thr Ser Leu Thr His Ser Gln Phe Asp Leu Ser Val Asp
    1670                1675                1680

Gly Glu Ile Leu Pro Val Pro Ser Asp Leu Asp Ala Asp Ala Pro
    1685                1690                1695

Ala Leu Glu Pro Ala Leu Asp Asp Gly Ala Thr His Thr Leu Pro
    1700                1705                1710

Ser Thr Thr Gly Asn Leu Ala Ala Val Ser Asp Trp Val Met Ser
    1715                1720                1725

Thr Val Pro Val Ala Pro Pro Arg Arg Arg Arg Gly Arg Asn Leu
    1730                1735                1740

Thr Val Thr Cys Asp Glu Arg Glu Gly Asn Ile Thr Pro Met Ala
    1745                1750                1755

Ser Val Arg Phe Phe Arg Ala Glu Leu Cys Pro Val Val Gln Glu
```

```
    1760                1765                1770

Thr Ala  Glu Thr Arg Asp Thr  Ala Met Ser Leu Gln  Ala Pro Pro
    1775                1780                1785

Ser Thr  Ala Thr Glu Pro Asn  His Pro Pro Ile Ser  Phe Gly Ala
    1790                1795                1800

Ser Ser  Glu Thr Phe Pro Ile  Thr Phe Gly Asp Phe  Asn Glu Gly
    1805                1810                1815

Glu Ile  Glu Ser Leu Ser Ser  Glu Leu Leu Thr Phe  Gly Asp Phe
    1820                1825                1830

Leu Pro  Gly Glu Val Asp Asp  Leu Thr Asp Ser Asp  Trp Ser Thr
    1835                1840                1845

Cys Ser  Asp Thr Asp Asp Glu  Leu Leu Asp Arg Ala  Gly Gly Tyr
    1850                1855                1860

Ile Phe  Ser Ser Asp Thr Gly  Pro Gly His Leu Gln  Gln Lys Ser
    1865                1870                1875

Val Arg  Gln Ser Val Leu Pro  Val Asn Thr Leu Glu  Glu Val His
    1880                1885                1890

Glu Glu  Lys Cys Tyr Pro Pro  Lys Leu Asp Glu Ala  Lys Glu Gln
    1895                1900                1905

Leu Leu  Leu Lys Lys Leu Gln  Glu Ser Ala Ser Met  Ala Asn Arg
    1910                1915                1920

Ser Arg  Tyr Gln Ser Arg Lys  Val Glu Asn Met Lys  Ala Ala Ile
    1925                1930                1935

Ile Gln  Arg Leu Lys Arg Gly  Cys Arg Leu Tyr Leu  Met Ser Glu
    1940                1945                1950

Thr Pro  Lys Val Pro Thr Tyr  Arg Thr Thr Tyr Pro  Ala Pro Val
    1955                1960                1965

Tyr Ser  Pro Pro Ile Asn Val  Arg Leu Ser Asn Pro  Glu Ser Ala
    1970                1975                1980

Val Ala  Ala Cys Asn Glu Phe  Leu Ala Arg Asn Tyr  Pro Thr Val
    1985                1990                1995

Ser Ser  Tyr Gln Ile Thr Asp  Glu Tyr Asp Ala Tyr  Leu Asp Met
    2000                2005                2010

Val Asp  Gly Ser Glu Ser Cys  Leu Asp Arg Ala Thr  Phe Asn Pro
    2015                2020                2025

Ser Lys  Leu Arg Ser Tyr Pro  Lys Gln His Ala Tyr  His Ala Pro
    2030                2035                2040

Ser Ile  Arg Ser Ala Val Pro  Ser Pro Phe Gln Asn  Thr Leu Gln
    2045                2050                2055

Asn Val  Leu Ala Ala Ala Thr  Lys Arg Asn Cys Asn  Val Thr Gln
    2060                2065                2070

Met Arg  Glu Leu Pro Thr Leu  Asp Ser Ala Val Phe  Asn Val Glu
    2075                2080                2085

Cys Phe  Lys Lys Phe Ala Cys  Asn Gln Glu Tyr Trp  Glu Glu Phe
    2090                2095                2100

Ala Ala  Ser Pro Ile Arg Ile  Thr Thr Glu Asn Leu  Ala Thr Tyr
    2105                2110                2115

Val Thr  Lys Leu Lys Gly Pro  Lys Ala Ala Ala Leu  Phe Ala Lys
    2120                2125                2130

Thr His  Asn Leu Leu Pro Leu  Gln Glu Val Pro Met  Asp Arg Phe
    2135                2140                2145

Thr Val  Asp Met Lys Arg Asp  Val Lys Val Thr Pro  Gly Thr Lys
    2150                2155                2160
```

```
His Thr  Glu Glu Arg Pro Lys  Val Gln Val Ile Gln  Ala Ala Glu
    2165                 2170                 2175

Pro Leu  Ala Thr Ala Tyr Leu  Cys Gly Ile His Arg  Glu Leu Val
    2180                 2185                 2190

Arg Arg  Leu Asn Ala Val Leu  Leu Pro Asn Val His  Thr Leu Phe
    2195                 2200                 2205

Asp Met  Ser Ala Glu Asp Phe  Asp Ala Ile Ile Ala  Ala His Phe
    2210                 2215                 2220

Lys Pro  Gly Asp Thr Val Leu  Glu Thr Asp Ile Ala  Ser Phe Asp
    2225                 2230                 2235

Lys Ser  Gln Asp Asp Ser Leu  Ala Leu Thr Ala Leu  Met Leu Leu
    2240                 2245                 2250

Glu Asp  Leu Gly Val Asp His  Ser Leu Leu Asp Leu  Ile Glu Ala
    2255                 2260                 2265

Ala Phe  Gly Glu Ile Ser Ser  Cys His Leu Pro Thr  Gly Thr Arg
    2270                 2275                 2280

Phe Lys  Phe Gly Ala Met Met  Lys Ser Gly Met Phe  Leu Thr Leu
    2285                 2290                 2295

Phe Val  Asn Thr Leu Leu Asn  Ile Thr Ile Ala Ser  Arg Val Leu
    2300                 2305                 2310

Glu Asp  Arg Leu Thr Lys Ser  Ala Cys Ala Ala Phe  Ile Gly Asp
    2315                 2320                 2325

Asp Asn  Ile Ile His Gly Val  Val Ser Asp Glu Leu  Met Ala Ala
    2330                 2335                 2340

Arg Cys  Ala Thr Trp Met Asn  Met Glu Val Lys Ile  Ile Asp Ala
    2345                 2350                 2355

Val Val  Ser Leu Lys Ala Pro  Tyr Phe Cys Gly Gly  Phe Ile Leu
    2360                 2365                 2370

His Asp  Thr Val Thr Gly Thr  Ala Cys Arg Val Ala  Asp Pro Leu
    2375                 2380                 2385

Lys Arg  Leu Phe Lys Leu Gly  Lys Pro Leu Ala Ala  Gly Asp Glu
    2390                 2395                 2400

Gln Asp  Glu Asp Arg Arg Arg  Ala Leu Ala Asp Glu  Val Ile Arg
    2405                 2410                 2415

Trp Gln  Arg Thr Gly Leu Ile  Asp Glu Leu Glu Lys  Ala Val Tyr
    2420                 2425                 2430

Ser Arg  Tyr Glu Val Gln Gly  Ile Ser Val Val Val  Met Ser Met
    2435                 2440                 2445

Ala Thr  Phe Ala Ser Ser Arg  Ser Asn Phe Glu Lys  Leu Arg Gly
    2450                 2455                 2460

Pro Val  Ile Thr Leu Tyr Gly  Gly Pro Lys
    2465                 2470
```

<210> SEQ ID NO 33
<211> LENGTH: 2473
<212> TYPE: PRT
<213> ORGANISM: Chikungunya virus

<400> SEQUENCE: 33

```
Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
```

-continued

```
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Gly Lys Ile Gly Asp Leu Gln Ala Val Met Ala Val Pro Asp Thr
        115                 120                 125

Glu Thr Pro Thr Phe Cys Leu His Thr Asp Val Ser Cys Arg Gln Arg
    130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
        195                 200                 205

Asn Ile Gly Leu Cys Ser Thr Asp Leu Thr Glu Gly Arg Arg Gly Lys
    210                 215                 220

Leu Ser Ile Met Arg Gly Lys Lys Leu Lys Pro Cys Asp Arg Val Leu
225                 230                 235                 240

Phe Ser Val Gly Ser Thr Leu Tyr Pro Glu Ser Arg Lys Leu Leu Lys
                245                 250                 255

Ser Trp His Leu Pro Ser Val Phe His Leu Lys Gly Lys Leu Ser Phe
            260                 265                 270

Thr Cys Arg Cys Asp Thr Val Val Ser Cys Glu Gly Tyr Val Val Lys
        275                 280                 285

Arg Ile Thr Met Ser Pro Gly Leu Tyr Gly Lys Thr Thr Gly Tyr Ala
    290                 295                 300

Val Thr His His Ala Asp Gly Phe Leu Met Cys Lys Thr Thr Asp Thr
305                 310                 315                 320

Val Asp Gly Glu Arg Val Ser Phe Ser Val Cys Thr Tyr Val Pro Ala
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Lys Gln Lys Thr His Thr Val Tyr
            420                 425                 430

Lys Arg Pro Asp Thr Gln Ser Ile Gln Lys Val Gln Ala Glu Phe Asp
        435                 440                 445

Ser Phe Val Val Pro Ser Leu Trp Ser Ser Gly Leu Ser Ile Pro Leu
    450                 455                 460
```

-continued

```
Arg Thr Arg Ile Lys Trp Leu Leu Ser Lys Val Pro Lys Thr Asp Leu
465                 470                 475                 480

Ile Pro Tyr Ser Gly Asp Ala Arg Glu Ala Arg Asp Ala Glu Lys Glu
                485                 490                 495

Ala Glu Glu Glu Arg Glu Ala Glu Leu Thr Arg Glu Ala Leu Pro Pro
            500                 505                 510

Leu Gln Ala Ala Gln Glu Asp Val Gln Val Glu Ile Asp Val Glu Gln
        515                 520                 525

Leu Glu Asp Arg Ala Gly Ala Gly Ile Ile Glu Thr Pro Arg Gly Ala
    530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Asn Gly Arg Ala
            580                 585                 590

Gly Arg Tyr Ala Val Glu Ala Tyr Asp Gly Arg Val Leu Val Pro Ser
        595                 600                 605

Gly Tyr Ala Ile Ser Pro Glu Asp Phe Gln Ser Leu Ser Glu Ser Ala
    610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
            660                 665                 670

Gln Arg Arg Cys Cys Lys Lys Glu Glu Ala Ala Gly Leu Val Leu Val
        675                 680                 685

Gly Asp Leu Thr Asn Pro Pro Tyr His Glu Phe Ala Tyr Glu Gly Leu
    690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
            740                 745                 750

Thr Thr Asp Val Met Arg Gln Arg Gly Leu Glu Ile Ser Ala Arg Thr
        755                 760                 765

Val Asp Ser Leu Leu Leu Asn Gly Cys Asn Arg Pro Val Asp Val Leu
    770                 775                 780

Tyr Val Asp Glu Ala Phe Ala Cys His Ser Gly Thr Leu Leu Ala Leu
785                 790                 795                 800

Ile Ala Leu Val Arg Pro Arg Gln Lys Val Val Leu Cys Gly Asp Pro
                805                 810                 815

Lys Gln Cys Gly Phe Phe Asn Met Met Gln Met Lys Val Asn Tyr Asn
            820                 825                 830

His Asn Ile Cys Thr Gln Val Tyr His Lys Ser Ile Ser Arg Arg Cys
        835                 840                 845

Thr Leu Pro Val Thr Ala Ile Val Ser Ser Leu His Tyr Glu Gly Lys
    850                 855                 860

Met Arg Thr Thr Asn Glu Tyr Asn Lys Pro Ile Val Val Asp Thr Thr
865                 870                 875                 880
```

-continued

```
Gly Ser Thr Lys Pro Asp Pro Gly Asp Leu Val Leu Thr Cys Phe Arg
                885                 890                 895

Gly Trp Val Lys Gln Leu Gln Ile Asp Tyr Arg Gly Tyr Glu Val Met
            900                 905                 910

Thr Ala Ala Ala Ser Gln Gly Leu Thr Arg Lys Gly Val Tyr Ala Val
        915                 920                 925

Arg Gln Lys Val Asn Glu Asn Pro Leu Tyr Ala Ser Thr Ser Glu His
    930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975

Asn Phe Lys Ala Thr Ile Lys Glu Trp Glu Val Glu His Ala Ser Ile
            980                 985                 990

Met Ala Gly Ile Cys Ser His Gln  Met Thr Phe Asp Thr  Phe Gln Asn
        995                 1000                1005

Lys Ala  Asn Val Cys Trp Ala  Lys Ser Leu Val Pro  Ile Leu Glu
    1010                 1015                1020

Thr Ala  Gly Ile Lys Leu Asn  Asp Arg Gln Trp Ser  Gln Ile Ile
    1025                 1030                1035

Gln Ala  Phe Lys Glu Asp Lys  Ala Tyr Ser Pro Glu  Val Ala Leu
    1040                 1045                1050

Asn Glu  Ile Cys Thr Arg Met  Tyr Gly Val Asp Leu  Asp Ser Gly
    1055                 1060                1065

Leu Phe  Ser Lys Pro Leu Val  Ser Val Tyr Tyr Ala  Asp Asn His
    1070                 1075                1080

Trp Asp  Asn Arg Pro Gly Gly  Lys Met Phe Gly Phe  Asn Pro Glu
    1085                 1090                1095

Ala Ala  Ser Ile Leu Glu Arg  Lys Tyr Pro Phe Thr  Lys Gly Lys
    1100                 1105                1110

Trp Asn  Ile Asn Lys Gln Ile  Cys Val Thr Thr Arg  Arg Ile Glu
    1115                 1120                1125

Asp Phe  Asn Pro Thr Thr Asn  Ile Ile Pro Ala Asn  Arg Arg Leu
    1130                 1135                1140

Pro His  Ser Leu Val Ala Glu  His Arg Pro Val Lys  Gly Glu Arg
    1145                 1150                1155

Met Glu  Trp Leu Val Asn Lys  Ile Asn Gly His His  Val Leu Leu
    1160                 1165                1170

Val Ser  Gly Tyr Asn Leu Ala  Leu Pro Thr Lys Arg  Val Thr Trp
    1175                 1180                1185

Val Ala  Pro Leu Gly Val Arg  Gly Ala Asp Tyr Thr  Tyr Asn Leu
    1190                 1195                1200

Glu Leu  Gly Leu Pro Ala Thr  Leu Gly Arg Tyr Asp  Leu Val Val
    1205                 1210                1215

Ile Asn  Ile His Thr Pro Phe  Arg Ile His His Tyr  Gln Gln Cys
    1220                 1225                1230

Val Asp  His Ala Met Lys Leu  Gln Met Leu Gly Gly  Asp Ser Leu
    1235                 1240                1245

Arg Leu  Leu Lys Pro Gly Gly  Ser Leu Leu Ile Arg  Ala Tyr Gly
    1250                 1255                1260

Tyr Ala  Asp Arg Thr Ser Glu  Arg Val Ile Cys Val  Leu Gly Arg
    1265                 1270                1275

Lys Phe  Arg Ser Ser Arg Ala  Leu Lys Pro Pro Cys  Val Thr Ser
```

```
    1280                1285                1290

Asn Thr  Glu Met Phe Phe Leu  Phe Ser Asn Phe Asp  Asn Gly Arg
    1295                1300                1305

Arg Asn  Phe Thr Thr His Val  Met Asn Asn Gln Leu  Asn Ala Ala
    1310                1315                1320

Phe Val  Gly Gln Val Thr Arg  Ala Gly Cys Ala Pro  Ser Tyr Arg
    1325                1330                1335

Val Lys  Arg Met Asp Ile Ala  Lys Asn Asp Glu Glu  Cys Val Val
    1340                1345                1350

Asn Ala  Ala Asn Pro Arg Gly  Leu Pro Gly Asp Gly  Val Cys Lys
    1355                1360                1365

Ala Val  Tyr Lys Lys Trp Pro  Glu Ser Phe Lys Asn  Ser Ala Thr
    1370                1375                1380

Pro Val  Gly Thr Ala Lys Thr  Val Met Cys Gly Thr  Tyr Pro Val
    1385                1390                1395

Ile His  Ala Val Gly Pro Asn  Phe Ser Asn Tyr Ser  Glu Ser Glu
    1400                1405                1410

Gly Asp  Arg Glu Leu Ala Ala  Ala Tyr Arg Glu Val  Ala Lys Glu
    1415                1420                1425

Val Thr  Arg Leu Gly Val Asn  Ser Val Ala Ile Pro  Leu Leu Ser
    1430                1435                1440

Thr Gly  Val Tyr Ser Gly Gly  Lys Asp Arg Leu Thr  Gln Ser Leu
    1445                1450                1455

Asn His  Leu Phe Thr Ala Met  Asp Ser Thr Asp Ala  Asp Val Val
    1460                1465                1470

Ile Tyr  Cys Arg Asp Lys Glu  Trp Glu Lys Lys Ile  Ser Glu Ala
    1475                1480                1485

Ile Gln  Met Arg Thr Gln Val  Glu Leu Leu Asp Glu  His Ile Ser
    1490                1495                1500

Ile Asp  Cys Asp Ile Val Arg  Val His Pro Asp Ser  Ser Leu Ala
    1505                1510                1515

Gly Arg  Lys Gly Tyr Ser Thr  Thr Glu Gly Ala Leu  Tyr Ser Tyr
    1520                1525                1530

Leu Glu  Gly Thr Arg Phe His  Gln Thr Ala Val Asp  Met Ala Glu
    1535                1540                1545

Ile His  Thr Met Trp Pro Lys  Gln Thr Glu Ala Asn  Glu Gln Val
    1550                1555                1560

Cys Leu  Tyr Ala Leu Gly Glu  Ser Ile Glu Ser Ile  Arg Gln Lys
    1565                1570                1575

Cys Pro  Val Asp Asp Ala Asp  Ala Ser Ser Pro Pro  Lys Thr Val
    1580                1585                1590

Pro Cys  Leu Cys Arg Tyr Ala  Met Thr Pro Glu Arg  Val Thr Arg
    1595                1600                1605

Leu Arg  Met Asn His Val Thr  Ser Ile Ile Val Cys  Ser Ser Phe
    1610                1615                1620

Pro Leu  Pro Lys Tyr Lys Ile  Glu Gly Val Gln Lys  Val Lys Cys
    1625                1630                1635

Ser Lys  Val Met Leu Phe Asp  His Asn Val Pro Ser  Arg Val Ser
    1640                1645                1650

Pro Arg  Glu Tyr Arg Ser Ser  Gln Glu Ser Ala Gln  Glu Ala Ser
    1655                1660                1665

Thr Ile  Thr Ser Leu Thr His  Ser Gln Phe Asp Leu  Ser Val Asp
    1670                1675                1680
```

```
Gly Glu  Ile Leu Pro Val Pro  Ser Asp Leu Asp Ala  Asp Ala Pro
    1685                 1690                 1695

Ala Leu  Glu Pro Ala Leu Asp  Asp Gly Ala Thr His  Thr Leu Pro
    1700                 1705                 1710

Ser Thr  Thr Gly Asn Leu Ala  Ala Val Ser Asp Trp  Val Met Ser
    1715                 1720                 1725

Thr Val  Pro Val Ala Pro Pro  Arg Arg Arg Arg Gly  Arg Asn Leu
    1730                 1735                 1740

Thr Val  Thr Cys Asp Glu Arg  Glu Gly Asn Ile Thr  Pro Met Ala
    1745                 1750                 1755

Ser Val  Arg Phe Phe Arg Ala  Glu Leu Cys Pro Val  Val Gln Glu
    1760                 1765                 1770

Thr Ala  Glu Thr Arg Asp Thr  Ala Met Ser Leu Gln  Ala Pro Pro
    1775                 1780                 1785

Ser Thr  Ala Thr Glu Pro Asn  His Pro Pro Ile Ser  Phe Gly Ala
    1790                 1795                 1800

Ser Ser  Glu Thr Phe Pro Ile  Thr Phe Gly Asp Phe  Asn Glu Gly
    1805                 1810                 1815

Glu Ile  Glu Ser Leu Ser Ser  Glu Leu Leu Thr Phe  Gly Asp Phe
    1820                 1825                 1830

Leu Pro  Gly Glu Val Asp Asp  Leu Thr Asp Ser Asp  Trp Ser Thr
    1835                 1840                 1845

Cys Ser  Asp Thr Asp Asp Glu  Leu Leu Asp Arg Ala  Gly Gly Tyr
    1850                 1855                 1860

Ile Phe  Ser Ser Asp Thr Gly  Pro Gly His Leu Gln  Gln Lys Ser
    1865                 1870                 1875

Val Arg  Gln Ser Val Leu Pro  Val Asn Thr Leu Glu  Glu Val His
    1880                 1885                 1890

Glu Glu  Lys Cys Tyr Pro Pro  Lys Leu Asp Glu Ala  Lys Glu Gln
    1895                 1900                 1905

Leu Leu  Leu Lys Lys Leu Gln  Glu Ser Ala Ser Met  Ala Asn Arg
    1910                 1915                 1920

Ser Arg  Tyr Gln Ser Arg Lys  Val Glu Asn Met Lys  Ala Ala Ile
    1925                 1930                 1935

Ile Gln  Arg Leu Lys Arg Gly  Cys Arg Leu Tyr Leu  Met Ser Glu
    1940                 1945                 1950

Thr Pro  Lys Val Pro Thr Tyr  Arg Thr Thr Tyr Pro  Ala Pro Val
    1955                 1960                 1965

Tyr Ser  Pro Pro Ile Asn Val  Arg Leu Ser Asn Pro  Glu Ser Ala
    1970                 1975                 1980

Val Ala  Ala Cys Asn Glu Phe  Leu Ala Arg Asn Tyr  Pro Thr Val
    1985                 1990                 1995

Ser Ser  Tyr Gln Ile Thr Asp  Glu Tyr Asp Ala Tyr  Leu Asp Met
    2000                 2005                 2010

Val Asp  Gly Ser Glu Ser Cys  Leu Asp Arg Ala Thr  Phe Asn Pro
    2015                 2020                 2025

Ser Lys  Leu Arg Ser Tyr Pro  Lys Gln His Ala Tyr  His Ala Pro
    2030                 2035                 2040

Ser Ile  Arg Ser Ala Val Pro  Ser Pro Phe Gln Asn  Thr Leu Gln
    2045                 2050                 2055

Asn Val  Leu Ala Ala Ala Thr  Lys Arg Asn Cys Asn  Val Thr Gln
    2060                 2065                 2070
```

-continued

```
Met Arg  Glu Leu Pro Thr Leu  Asp Ser Ala Val Phe  Asn Val Glu
    2075                 2080                 2085

Cys Phe  Lys Lys Phe Ala Cys  Asn Gln Glu Tyr Trp  Glu Glu Phe
    2090                 2095                 2100

Ala Ala  Ser Pro Ile Arg Ile  Thr Thr Glu Asn Leu  Ala Thr Tyr
    2105                 2110                 2115

Val Thr  Lys Leu Lys Gly Pro  Lys Ala Ala Ala Leu  Phe Ala Lys
    2120                 2125                 2130

Thr His  Asn Leu Leu Pro Leu  Gln Glu Val Pro Met  Asp Arg Phe
    2135                 2140                 2145

Thr Val  Asp Met Lys Arg Asp  Val Lys Val Thr Pro  Gly Thr Lys
    2150                 2155                 2160

His Thr  Glu Glu Arg Pro Lys  Val Gln Val Ile Gln  Ala Ala Glu
    2165                 2170                 2175

Pro Leu  Ala Thr Ala Tyr Leu  Cys Gly Ile His Arg  Glu Leu Val
    2180                 2185                 2190

Arg Arg  Leu Asn Ala Val Leu  Leu Pro Asn Val His  Thr Leu Phe
    2195                 2200                 2205

Asp Met  Ser Ala Glu Asp Phe  Asp Ala Ile Ile Ala  Ala His Phe
    2210                 2215                 2220

Lys Pro  Gly Asp Thr Val Leu  Glu Thr Asp Ile Ala  Ser Phe Asp
    2225                 2230                 2235

Lys Ser  Gln Asp Asp Ser Leu  Ala Leu Thr Ala Leu  Met Leu Leu
    2240                 2245                 2250

Glu Asp  Leu Gly Val Asp His  Ser Leu Leu Asp Leu  Ile Glu Ala
    2255                 2260                 2265

Ala Phe  Gly Glu Ile Ser Ser  Cys His Leu Pro Thr  Gly Thr Arg
    2270                 2275                 2280

Phe Lys  Phe Gly Ala Met Met  Lys Ser Gly Met Phe  Leu Thr Leu
    2285                 2290                 2295

Phe Val  Asn Thr Leu Leu Asn  Ile Thr Ile Ala Ser  Arg Val Leu
    2300                 2305                 2310

Glu Asp  Arg Leu Thr Lys Ser  Ala Cys Ala Ala Phe  Ile Gly Asp
    2315                 2320                 2325

Asp Asn  Ile Ile His Gly Val  Val Ser Asp Glu Leu  Met Ala Ala
    2330                 2335                 2340

Arg Cys  Ala Thr Trp Met Asn  Met Glu Val Lys Ile  Ile Asp Ala
    2345                 2350                 2355

Val Val  Ser Leu Lys Ala Pro  Tyr Phe Cys Gly Gly  Phe Ile Leu
    2360                 2365                 2370

His Asp  Thr Val Thr Gly Thr  Ala Cys Arg Val Ala  Asp Pro Leu
    2375                 2380                 2385

Lys Arg  Leu Phe Lys Leu Gly  Lys Pro Leu Ala Ala  Gly Asp Glu
    2390                 2395                 2400

Gln Asp  Glu Asp Arg Arg Arg  Ala Leu Ala Asp Glu  Val Ile Arg
    2405                 2410                 2415

Trp Gln  Arg Thr Gly Leu Ile  Asp Glu Leu Glu Lys  Ala Val Tyr
    2420                 2425                 2430

Ser Arg  Tyr Glu Val Gln Gly  Ile Ser Val Val Val  Met Ser Met
    2435                 2440                 2445

Ala Thr  Phe Ala Ser Ser Arg  Ser Asn Phe Glu Lys  Leu Arg Gly
    2450                 2455                 2460

Pro Val  Ile Thr Leu Tyr Gly  Gly Pro Lys
```

2465 2470

<210> SEQ ID NO 34
<211> LENGTH: 2472
<212> TYPE: PRT
<213> ORGANISM: Chikungunya virus

<400> SEQUENCE: 34

Met Asp Pro Val Tyr Val Asp Ile Asp Ala Asp Ser Ala Phe Leu Lys
1 5 10 15

Ala Leu Gln Arg Ala Tyr Pro Met Phe Glu Val Glu Pro Arg Gln Val
20 25 30

Thr Pro Asn Asp His Ala Asn Ala Arg Ala Phe Ser His Leu Ala Ile
35 40 45

Lys Leu Ile Glu Gln Glu Ile Asp Pro Asp Ser Thr Ile Leu Asp Ile
50 55 60

Gly Ser Ala Pro Ala Arg Arg Met Met Ser Asp Arg Lys Tyr His Cys
65 70 75 80

Val Cys Pro Met Arg Ser Ala Glu Asp Pro Glu Arg Leu Ala Asn Tyr
85 90 95

Ala Arg Lys Leu Ala Ser Ala Ala Gly Lys Val Leu Asp Arg Asn Ile
100 105 110

Ser Gly Lys Ile Gly Asp Leu Gln Ala Val Met Ala Val Pro Asp Thr
115 120 125

Glu Thr Pro Thr Phe Cys Leu His Thr Asp Val Ser Cys Arg Gln Arg
130 135 140

Ala Asp Val Ala Ile Tyr Gln Asp Val Tyr Ala Val His Ala Pro Thr
145 150 155 160

Ser Leu Tyr His Gln Ala Ile Lys Gly Val Arg Val Ala Tyr Trp Val
165 170 175

Gly Phe Asp Thr Thr Pro Phe Met Tyr Asn Ala Met Ala Gly Ala Tyr
180 185 190

Pro Ser Tyr Ser Thr Asn Trp Ala Asp Glu Gln Val Leu Lys Ala Lys
195 200 205

Asn Ile Gly Leu Cys Ser Thr Asp Leu Thr Glu Gly Arg Arg Gly Lys
210 215 220

Leu Ser Ile Met Arg Gly Lys Lys Leu Lys Pro Cys Asp Arg Val Leu
225 230 235 240

Phe Ser Val Gly Ser Thr Leu Tyr Pro Glu Ser Arg Lys Leu Leu Lys
245 250 255

Ser Trp His Leu Pro Ser Val Phe His Leu Lys Gly Lys Leu Ser Phe
260 265 270

Thr Cys Arg Cys Asp Thr Val Val Ser Cys Glu Gly Tyr Val Val Lys
275 280 285

Arg Ile Thr Met Ser Pro Gly Leu Tyr Gly Lys Thr Ile Gly Tyr Ala
290 295 300

Val Thr His His Ala Asp Gly Phe Leu Met Cys Lys Thr Thr Asp Thr
305 310 315 320

Val Asp Gly Glu Arg Val Ser Phe Ser Val Cys Thr Tyr Val Pro Ala
325 330 335

Thr Ile Cys Asp Gln Met Thr Gly Ile Leu Ala Thr Glu Val Thr Pro
340 345 350

Glu Asp Ala Gln Lys Leu Leu Val Gly Leu Asn Gln Arg Ile Val Val
355 360 365

```
Asn Gly Arg Thr Gln Arg Asn Thr Asn Thr Met Lys Asn Tyr Leu Leu
    370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Lys Gln Lys Thr His Thr Val Tyr
            420                 425                 430

Lys Arg Pro Asp Thr Gln Ser Ile Gln Lys Val Gln Ala Glu Phe Asp
        435                 440                 445

Ser Phe Val Val Pro Ser Leu Trp Ser Ser Gly Leu Ser Ile Pro Leu
    450                 455                 460

Arg Thr Arg Ile Lys Trp Leu Leu Ser Lys Val Pro Lys Thr Asp Leu
465                 470                 475                 480

Ile Pro Tyr Ser Gly Asp Ala Arg Glu Ala Arg Asp Ala Glu Lys Glu
                485                 490                 495

Ala Glu Glu Glu Arg Glu Ala Glu Leu Thr Arg Glu Ala Leu Pro Pro
            500                 505                 510

Leu Gln Ala Ala Gln Glu Asp Val Gln Val Glu Ile Asp Val Glu Gln
        515                 520                 525

Leu Glu Asp Arg Ala Gly Ala Gly Ile Ile Glu Thr Pro Arg Gly Ala
    530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Asn Gly Arg Ala
            580                 585                 590

Gly Arg Tyr Ala Val Glu Ala Tyr Asp Gly Arg Val Leu Val Pro Ser
        595                 600                 605

Gly Tyr Ala Ile Ser Pro Glu Asp Phe Gln Ser Leu Ser Glu Ser Ala
    610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
            660                 665                 670

Gln Arg Arg Cys Cys Lys Lys Glu Glu Ala Ala Gly Leu Val Leu Val
        675                 680                 685

Gly Asp Leu Thr Asn Pro Pro Tyr His Glu Phe Ala Tyr Glu Gly Leu
    690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
            740                 745                 750

Thr Thr Asp Val Met Arg Gln Arg Gly Leu Glu Ile Ser Ala Arg Thr
        755                 760                 765

Val Asp Ser Leu Leu Leu Asn Gly Cys Asn Arg Pro Val Asp Val Leu
    770                 775                 780

Tyr Val Asp Glu Ala Phe Ala Cys His Ser Gly Thr Leu Leu Ala Leu
```

```
785                 790                 795                 800

Ile Ala Leu Val Arg Pro Arg Gln Lys Val Val Leu Cys Gly Asp Pro
                805                 810                 815

Lys Gln Cys Gly Phe Phe Asn Met Met Gln Met Lys Val Asn Tyr Asn
            820                 825                 830

His Asn Ile Cys Thr Gln Val Tyr His Lys Ser Ile Ser Arg Arg Cys
        835                 840                 845

Thr Leu Pro Val Thr Ala Ile Val Ser Ser Leu His Tyr Glu Gly Lys
    850                 855                 860

Met Arg Thr Thr Asn Glu Tyr Asn Lys Pro Ile Val Val Asp Thr Thr
865                 870                 875                 880

Gly Ser Thr Lys Pro Asp Pro Gly Asp Leu Val Leu Thr Cys Phe Arg
                885                 890                 895

Gly Trp Val Lys Gln Leu Gln Ile Asp Tyr Arg Gly Tyr Glu Val Met
            900                 905                 910

Thr Ala Ala Ala Ser Gln Gly Leu Thr Arg Lys Gly Val Tyr Ala Val
        915                 920                 925

Arg Gln Lys Val Asn Glu Asn Pro Leu Tyr Ala Ser Thr Ser Glu His
    930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975

Asn Phe Lys Ala Thr Ile Lys Glu Trp Glu Val Glu His Ala Ser Ile
            980                 985                 990

Met Ala Gly Ile Cys Ser His Gln  Met Thr Phe Asp Thr  Phe Gln Asn
        995                 1000                 1005

Lys Ala  Asn Val Cys Trp Ala  Lys Ser Leu Val Pro  Ile Leu Glu
    1010                 1015                 1020

Thr Ala  Gly Ile Lys Leu Asn  Asp Arg Gln Trp Ser  Gln Ile Ile
    1025                 1030                 1035

Gln Ala  Phe Lys Glu Asp Lys  Ala Tyr Ser Pro Glu  Val Ala Leu
    1040                 1045                 1050

Asn Glu  Ile Cys Thr Arg Met  Tyr Gly Val Asp Leu  Asp Ser Gly
    1055                 1060                 1065

Leu Phe  Ser Lys Pro Leu Val  Ser Val Tyr Tyr Ala  Asp Asn His
    1070                 1075                 1080

Trp Asp  Asn Arg Pro Gly Gly  Lys Met Phe Gly Phe  Asn Pro Glu
    1085                 1090                 1095

Ala Ala  Ser Ile Leu Glu Arg  Lys Tyr Pro Phe Thr  Lys Gly Lys
    1100                 1105                 1110

Trp Asn  Ile Asn Lys Gln Ile  Cys Val Thr Thr Arg  Arg Ile Glu
    1115                 1120                 1125

Asp Phe  Asn Pro Thr Thr Asn  Ile Ile Pro Ala Asn  Arg Arg Leu
    1130                 1135                 1140

Pro His  Ser Leu Val Ala Glu  His Arg Pro Val Lys  Gly Glu Arg
    1145                 1150                 1155

Met Glu  Trp Leu Val Asn Lys  Ile Asn Gly His His  Val Leu Leu
    1160                 1165                 1170

Val Ser  Gly Asn Asn Leu Ala  Leu Pro Thr Lys Arg  Val Thr Trp
    1175                 1180                 1185

Val Ala  Pro Leu Gly Val Arg  Gly Ala Asp Tyr Thr  Tyr Asn Leu
    1190                 1195                 1200
```

```
Glu Leu  Gly Leu Pro Ala Thr  Leu Gly Arg Tyr Asp  Leu Val Val
    1205                 1210                 1215

Ile Asn  Ile His Thr Pro Phe  Arg Ile His His Tyr  Gln Gln Cys
    1220                 1225                 1230

Val Asp  His Ala Met Lys Leu  Gln Met Leu Gly Gly  Asp Ser Leu
    1235                 1240                 1245

Arg Leu  Leu Lys Pro Gly Gly  Ser Leu Leu Ile Arg  Ala Tyr Gly
    1250                 1255                 1260

Tyr Ala  Asp Arg Thr Ser Glu  Arg Val Ile Cys Val  Leu Gly Arg
    1265                 1270                 1275

Lys Phe  Arg Ser Ser Arg Ala  Leu Lys Pro Pro Cys  Val Thr Ser
    1280                 1285                 1290

Asn Thr  Glu Met Phe Phe Leu  Phe Ser Asn Phe Asp  Asn Gly Arg
    1295                 1300                 1305

Arg Asn  Phe Thr Thr His Val  Met Asn Asn Gln Leu  Asn Ala Ala
    1310                 1315                 1320

Phe Val  Gly Gln Val Thr Arg  Ala Gly Cys Ala Pro  Ser Tyr Arg
    1325                 1330                 1335

Val Lys  Arg Met Asp Ile Ala  Lys Asn Asp Glu Glu  Cys Val Val
    1340                 1345                 1350

Asn Ala  Ala Asn Pro Arg Gly  Leu Pro Gly Asp Gly  Val Cys Lys
    1355                 1360                 1365

Ala Val  Tyr Lys Lys Trp Pro  Glu Ser Phe Lys Asn  Ser Ala Thr
    1370                 1375                 1380

Pro Val  Gly Thr Ala Lys Thr  Val Met Cys Gly Thr  Tyr Pro Val
    1385                 1390                 1395

Ile His  Ala Val Gly Pro Asn  Phe Ser Asn Tyr Ser  Glu Ser Glu
    1400                 1405                 1410

Gly Asp  Arg Glu Leu Ala Ala  Ala Tyr Arg Glu Val  Ala Lys Glu
    1415                 1420                 1425

Val Thr  Arg Leu Gly Val Asn  Ser Val Ala Ile Pro  Leu Leu Ser
    1430                 1435                 1440

Thr Gly  Val Tyr Ser Gly Gly  Lys Asp Arg Leu Thr  Gln Ser Leu
    1445                 1450                 1455

Asn His  Leu Phe Thr Ala Met  Asp Ser Thr Asp Ala  Asp Val Val
    1460                 1465                 1470

Ile Tyr  Cys Arg Asp Lys Glu  Trp Glu Lys Lys Ile  Ser Glu Ala
    1475                 1480                 1485

Ile Gln  Met Arg Thr Gln Val  Glu Leu Leu Asp Glu  His Ile Ser
    1490                 1495                 1500

Ile Asp  Cys Asp Ile Val Arg  Val His Pro Asp Ser  Ser Leu Ala
    1505                 1510                 1515

Gly Arg  Lys Gly Tyr Ser Thr  Thr Glu Gly Ala Leu  Tyr Ser Tyr
    1520                 1525                 1530

Leu Glu  Gly Thr Arg Phe His  Gln Thr Ala Val Asp  Met Ala Glu
    1535                 1540                 1545

Ile His  Thr Met Trp Pro Lys  Gln Thr Glu Ala Asn  Glu Gln Val
    1550                 1555                 1560

Cys Leu  Tyr Ala Leu Gly Glu  Ser Ile Glu Ser Ile  Arg Gln Lys
    1565                 1570                 1575

Cys Pro  Val Asp Asp Ala Asp  Ala Ser Ser Pro Pro  Lys Thr Val
    1580                 1585                 1590
```

```
Pro Cys  Leu Cys Arg Tyr Ala  Met Thr Pro Glu Arg  Val Thr Arg
    1595                 1600                 1605

Leu Arg  Met Asn His Val Thr  Ser Ile Ile Val Cys  Ser Ser Phe
    1610                 1615                 1620

Pro Leu  Pro Lys Tyr Lys Ile  Glu Gly Val Gln Lys  Val Lys Cys
    1625                 1630                 1635

Ser Lys  Val Met Leu Phe Asp  His Asn Val Pro Ser  Arg Val Ser
    1640                 1645                 1650

Pro Arg  Glu Tyr Arg Ser Ser  Gln Glu Ser Ala Gln  Glu Ala Ser
    1655                 1660                 1665

Thr Ile  Thr Ser Leu Thr His  Ser Gln Phe Asp Leu  Ser Val Asp
    1670                 1675                 1680

Gly Glu  Ile Leu Pro Val Pro  Ser Asp Leu Asp Ala  Asp Ala Pro
    1685                 1690                 1695

Ala Leu  Glu Pro Ala Leu Asp  Asp Gly Ala Thr His  Thr Leu Pro
    1700                 1705                 1710

Ser Thr  Thr Gly Asn Leu Ala  Ala Val Ser Asp Trp  Val Met Ser
    1715                 1720                 1725

Thr Val  Pro Val Ala Pro Pro  Arg Arg Arg Arg Gly  Arg Asn Leu
    1730                 1735                 1740

Thr Val  Thr Cys Asp Glu Arg  Glu Gly Asn Ile Thr  Pro Met Ala
    1745                 1750                 1755

Ser Val  Arg Phe Phe Arg Ala  Glu Leu Cys Pro Val  Val Gln Glu
    1760                 1765                 1770

Thr Ala  Glu Thr Arg Asp Thr  Ala Met Ser Leu Gln  Ala Pro Pro
    1775                 1780                 1785

Ser Thr  Ala Thr Pro Asn His  Pro Pro Ile Ser Phe  Gly Ala Ser
    1790                 1795                 1800

Ser Glu  Thr Phe Pro Ile Thr  Phe Gly Asp Phe Asn  Glu Gly Glu
    1805                 1810                 1815

Ile Glu  Ser Leu Ser Ser Glu  Leu Leu Thr Phe Gly  Asp Phe Leu
    1820                 1825                 1830

Pro Gly  Glu Val Asp Asp Leu  Thr Asp Ser Asp Trp  Ser Thr Cys
    1835                 1840                 1845

Ser Asp  Thr Asp Asp Glu Leu  Leu Asp Arg Ala Gly  Gly Tyr Ile
    1850                 1855                 1860

Phe Ser  Ser Asp Thr Gly Pro  Gly His Leu Gln Gln  Lys Ser Val
    1865                 1870                 1875

Arg Gln  Ser Val Leu Pro Val  Asn Thr Leu Glu Glu  Val His Glu
    1880                 1885                 1890

Glu Lys  Cys Tyr Pro Pro Lys  Leu Asp Glu Ala Lys  Glu Gln Leu
    1895                 1900                 1905

Leu Leu  Lys Lys Leu Gln Glu  Ser Ala Ser Met Ala  Asn Arg Ser
    1910                 1915                 1920

Arg Tyr  Gln Ser Arg Lys Val  Glu Asn Met Lys Ala  Ala Ile Ile
    1925                 1930                 1935

Gln Arg  Leu Lys Arg Gly Cys  Arg Leu Tyr Leu Met  Ser Glu Thr
    1940                 1945                 1950

Pro Lys  Val Pro Thr Tyr Arg  Thr Thr Tyr Pro Ala  Pro Val Tyr
    1955                 1960                 1965

Ser Pro  Pro Ile Asn Val Arg  Leu Ser Asn Pro Glu  Ser Ala Val
    1970                 1975                 1980

Ala Ala  Cys Asn Glu Phe Leu  Ala Arg Asn Tyr Pro  Thr Val Ser
```

-continued

```
    1985                1990                1995

Ser Tyr  Gln Ile Thr Asp Glu  Tyr Asp Ala Tyr Leu  Asp Met Val
    2000                2005                2010

Asp Gly  Ser Glu Ser Cys Leu  Asp Arg Ala Thr Phe  Asn Pro Ser
    2015                2020                2025

Lys Leu  Arg Ser Tyr Pro Lys  Gln His Ala Tyr His  Ala Pro Ser
    2030                2035                2040

Ile Arg  Ser Ala Val Pro Ser  Pro Phe Gln Asn Thr  Leu Gln Asn
    2045                2050                2055

Val Leu  Ala Ala Ala Thr Lys  Arg Asn Cys Asn Val  Thr Gln Met
    2060                2065                2070

Arg Glu  Leu Pro Thr Leu Asp  Ser Ala Val Phe Asn  Val Glu Cys
    2075                2080                2085

Phe Lys  Lys Phe Ala Cys Asn  Gln Glu Tyr Trp Glu  Glu Phe Ala
    2090                2095                2100

Ala Ser  Pro Ile Arg Ile Thr  Thr Glu Asn Leu Ala  Thr Tyr Val
    2105                2110                2115

Thr Lys  Leu Lys Gly Pro Lys  Ala Ala Ala Leu Phe  Ala Lys Thr
    2120                2125                2130

His Asn  Leu Leu Pro Leu Gln  Glu Val Pro Met Asp  Arg Phe Thr
    2135                2140                2145

Val Asp  Met Lys Arg Asp Val  Lys Val Thr Pro Gly  Thr Lys His
    2150                2155                2160

Thr Glu  Glu Arg Pro Lys Val  Gln Val Ile Gln Ala  Ala Glu Pro
    2165                2170                2175

Leu Ala  Thr Ala Tyr Leu Cys  Gly Ile His Arg Glu  Leu Val Arg
    2180                2185                2190

Arg Leu  Asn Ala Val Leu Leu  Pro Asn Val His Thr  Leu Phe Asp
    2195                2200                2205

Met Ser  Ala Glu Asp Phe Asp  Ala Ile Ile Ala Ala  His Phe Lys
    2210                2215                2220

Pro Gly  Asp Thr Val Leu Glu  Thr Asp Ile Ala Ser  Phe Asp Lys
    2225                2230                2235

Ser Gln  Asp Asp Ser Leu Ala  Leu Thr Ala Leu Met  Leu Leu Glu
    2240                2245                2250

Asp Leu  Gly Val Asp His Ser  Leu Leu Asp Leu Ile  Glu Ala Ala
    2255                2260                2265

Phe Gly  Glu Ile Ser Ser Cys  His Leu Pro Thr Gly  Thr Arg Phe
    2270                2275                2280

Lys Phe  Gly Ala Met Met Lys  Ser Gly Met Phe Leu  Thr Leu Phe
    2285                2290                2295

Val Asn  Thr Leu Leu Asn Ile  Thr Ile Ala Ser Arg  Val Leu Glu
    2300                2305                2310

Asp Arg  Leu Thr Lys Ser Ala  Cys Ala Ala Phe Ile  Gly Asp Asp
    2315                2320                2325

Asn Ile  Ile His Gly Val Val  Ser Asp Glu Leu Met  Ala Ala Arg
    2330                2335                2340

Cys Ala  Thr Trp Met Asn Met  Glu Val Lys Ile Ile  Asp Ala Val
    2345                2350                2355

Val Ser  Leu Lys Ala Pro Tyr  Phe Cys Gly Gly Phe  Ile Leu His
    2360                2365                2370

Asp Thr  Val Thr Gly Thr Ala  Cys Arg Val Ala Asp  Pro Leu Lys
    2375                2380                2385
```

```
Arg Leu Phe Lys Leu Gly Lys Pro Leu Ala Ala Gly Asp Glu Gln
    2390                2395                2400

Asp Glu Asp Arg Arg Arg Ala Leu Ala Asp Glu Val Ile Arg Trp
    2405                2410                2415

Gln Arg Thr Gly Leu Ile Asp Glu Leu Glu Lys Ala Val Tyr Ser
    2420                2425                2430

Arg Tyr Glu Val Gln Gly Ile Ser Val Val Val Met Ser Met Ala
    2435                2440                2445

Thr Phe Ala Ser Ser Arg Ser Asn Phe Glu Lys Leu Arg Gly Pro
    2450                2455                2460

Val Ile Thr Leu Tyr Gly Gly Pro Lys
    2465                2470
```

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
cacgtagcct accagtttct ta 22

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
atggaacacc gatggtaggt g 21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
aaccccgttc atgtacaatg c 21

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cggtaccaca aagctgtcaa ac 22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 39
cactgacctg ctgctgtcta tg 22

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
agtcctgcag cttcttcctt c 21

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
cgagtttgac agctttgtgg ta 22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
atgactgcaa ttttgtatgg gc 22

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
caatctcgcc tgaagacttc c 21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
tccactacaa tcggcttgtt g 21

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 45

gtgcggcttc ttcaatatga tg                                          22


<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

tccaggccta ttatcccagt g                                           21


<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

aacatctgca cccaagtgta cc                                          22


<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

gtctcctgtt ggccggtata at                                          22


<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

taataggcct ggagggaaga tg                                          22


<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

ctacgcactc ttcatcgttc tt                                          22


<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
```

```
gaacgagtca tctgcgtatt gg                                          22


<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

atatctctgc catatccact gc                                          22


<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

tctttacagc catggactcg ac                                          22


<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

cgacaggtac ggtgctcatt ac                                          22


<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

tgtacaggaa gcgagtacga cc                                          22


<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

tctactttgc gcgactgata cc                                          22


<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
```

-continued

```
acggacgacg agttacgact ag                                              22


<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

cccagtattc ttggttgcat g                                               21


<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

aaaacagcac gcttaccacg                                                 20


<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

aacttgaagc gcgtacctgt c                                               21


<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

tcatagccgc acactttaag c                                               21


<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

aggaccgccg tacaaagtta c                                               21


<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63

gcaggtgacg aacaagatga g                                               21
```

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
ccgcttaaag gccaatttg 19

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
tcgaagtcaa gcacgaagg 19

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
gtctgtcgct tcatttctga tg 22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
tgcttgagga caacgtcatg ag 22

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
tttgtgattg gtgaccgcg 19

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
agtccggcaa cgtaaagatc ac 22

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
aaaggttgct gctcgttcca c 21

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
agttgtgtca gtggcctcgt tc 22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
taaaggacgc ggagcttagc tg 22

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
acaaaaccgt catcccgtct c 21

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
tgactatgtg gtccttcgga gg 22

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
cagcaagaaa ggcaagtgtg c 21

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
tttgccaatt atggtattca 20

<210> SEQ ID NO 77
<211> LENGTH: 17
<212> TYPE: PRT
<213> ORGANISM: Chikungunya virus

<400> SEQUENCE: 77

```
Met Leu Leu Ser Val Pro Leu Leu Leu Leu Gly Leu Leu Gly Leu Ala
1               5                   10                  15

Ala
```

<210> SEQ ID NO 78
<211> LENGTH: 2450
<212> TYPE: PRT
<213> ORGANISM: Chikungunya virus

<400> SEQUENCE: 78

```
Met Phe Glu Val Glu Pro Arg Gln Val Thr Pro Asn Asp His Ala Asn
1               5                   10                  15

Ala Arg Ala Phe Ser His Leu Ala Ile Lys Leu Ile Glu Gln Glu Ile
            20                  25                  30

Asp Pro Asp Ser Thr Ile Leu Asp Ile Gly Ser Ala Pro Ala Arg Arg
        35                  40                  45

Met Met Ser Asp Arg Lys Tyr His Cys Val Cys Pro Met Arg Ser Ala
    50                  55                  60

Glu Asp Pro Glu Arg Leu Ala Asn Tyr Ala Arg Lys Leu Ala Ser Ala
65                  70                  75                  80

Ala Gly Lys Val Leu Asp Arg Asn Ile Ser Gly Lys Ile Gly Asp Leu
                85                  90                  95

Gln Ala Val Met Ala Val Pro Asp Thr Glu Thr Pro Thr Phe Cys Leu
            100                 105                 110

His Thr Asp Val Ser Cys Arg Gln Arg Ala Asp Val Ala Ile Tyr Gln
        115                 120                 125

Asp Val Tyr Ala Val His Ala Pro Thr Ser Leu Tyr His Gln Ala Ile
    130                 135                 140

Lys Gly Val Arg Val Ala Tyr Trp Val Gly Phe Asp Thr Thr Pro Phe
145                 150                 155                 160

Met Tyr Asn Ala Met Ala Gly Ala Tyr Pro Ser Tyr Ser Thr Asn Trp
                165                 170                 175

Ala Asp Glu Gln Val Leu Lys Ala Lys Asn Ile Gly Leu Cys Ser Thr
            180                 185                 190

Asp Leu Thr Glu Gly Arg Arg Gly Lys Leu Ser Ile Met Arg Gly Lys
        195                 200                 205

Lys Leu Lys Pro Cys Asp Arg Val Leu Phe Ser Val Gly Ser Thr Leu
    210                 215                 220

Tyr Pro Glu Ser Arg Lys Leu Leu Lys Ser Trp His Leu Pro Ser Val
225                 230                 235                 240

Phe His Leu Lys Gly Lys Leu Ser Phe Thr Cys Arg Cys Asp Thr Val
```

-continued

```
                245                 250                 255

Val Ser Cys Glu Gly Tyr Val Val Lys Arg Ile Thr Met Ser Pro Gly
            260                 265                 270

Leu Tyr Gly Lys Thr Thr Gly Tyr Ala Val Thr His His Ala Asp Gly
        275                 280                 285

Phe Leu Met Cys Lys Thr Thr Asp Thr Val Asp Gly Glu Arg Val Ser
    290                 295                 300

Phe Ser Val Cys Thr Tyr Val Pro Ala Thr Ile Cys Asp Gln Met Thr
305                 310                 315                 320

Gly Ile Leu Ala Thr Glu Val Thr Pro Glu Asp Ala Gln Lys Leu Leu
                325                 330                 335

Val Gly Leu Asn Gln Arg Ile Val Val Asn Gly Arg Thr Gln Arg Asn
            340                 345                 350

Thr Asn Thr Met Lys Asn Tyr Leu Leu Pro Val Val Ala Gln Ala Phe
        355                 360                 365

Ser Lys Trp Ala Lys Glu Cys Arg Lys Asp Met Glu Asp Glu Lys Leu
    370                 375                 380

Leu Gly Val Arg Glu Arg Thr Leu Thr Cys Cys Cys Leu Trp Ala Phe
385                 390                 395                 400

Lys Lys Gln Lys Thr His Thr Val Tyr Lys Arg Pro Asp Thr Gln Ser
                405                 410                 415

Ile Gln Lys Val Gln Ala Glu Phe Asp Ser Phe Val Val Pro Ser Leu
            420                 425                 430

Trp Ser Ser Gly Leu Ser Ile Pro Leu Arg Thr Arg Ile Lys Trp Leu
        435                 440                 445

Leu Ser Lys Val Pro Lys Thr Asp Leu Ile Pro Tyr Ser Gly Asp Ala
    450                 455                 460

Arg Glu Ala Arg Asp Ala Glu Lys Glu Ala Glu Glu Glu Arg Glu Ala
465                 470                 475                 480

Glu Leu Thr Arg Glu Ala Leu Pro Pro Leu Gln Ala Ala Gln Glu Asp
                485                 490                 495

Val Gln Val Glu Ile Asp Val Glu Gln Leu Glu Asp Arg Ala Gly Ala
            500                 505                 510

Gly Ile Ile Glu Thr Pro Arg Gly Ala Ile Lys Val Thr Ala Gln Pro
        515                 520                 525

Thr Asp His Val Val Gly Glu Tyr Leu Val Leu Ser Pro Gln Thr Val
    530                 535                 540

Leu Arg Ser Gln Lys Leu Ser Leu Ile His Ala Leu Ala Glu Gln Val
545                 550                 555                 560

Lys Thr Cys Thr His Asn Gly Arg Ala Gly Arg Tyr Ala Val Glu Ala
                565                 570                 575

Tyr Asp Gly Arg Val Leu Val Pro Ser Gly Tyr Ala Ile Ser Pro Glu
            580                 585                 590

Asp Phe Gln Ser Leu Ser Glu Ser Ala Thr Met Val Tyr Asn Glu Arg
        595                 600                 605

Glu Phe Val Asn Arg Lys Leu His His Ile Ala Met His Gly Pro Ala
    610                 615                 620

Leu Asn Thr Asp Glu Glu Ser Tyr Glu Leu Val Arg Ala Glu Arg Thr
625                 630                 635                 640

Glu His Glu Tyr Val Tyr Asp Val Asp Gln Arg Arg Cys Cys Lys Lys
                645                 650                 655

Glu Glu Ala Ala Gly Leu Val Leu Val Gly Asp Leu Thr Asn Pro Pro
            660                 665                 670
```

-continued

```
Tyr His Glu Phe Ala Tyr Glu Gly Leu Lys Ile Arg Pro Ala Cys Pro
        675                 680                 685

Tyr Lys Ile Ala Val Ile Gly Val Phe Gly Val Pro Gly Ser Gly Lys
    690                 695                 700

Ser Ala Ile Ile Lys Asn Leu Val Thr Arg Gln Asp Leu Val Thr Ser
705                 710                 715                 720

Gly Lys Lys Glu Asn Cys Gln Glu Ile Thr Thr Asp Val Met Arg Gln
                725                 730                 735

Arg Gly Leu Glu Ile Ser Ala Arg Thr Val Asp Ser Leu Leu Leu Asn
            740                 745                 750

Gly Cys Asn Arg Pro Val Asp Val Leu Tyr Val Asp Glu Ala Phe Ala
        755                 760                 765

Cys His Ser Gly Thr Leu Leu Ala Leu Ile Ala Leu Val Arg Pro Arg
    770                 775                 780

Gln Lys Val Val Leu Cys Gly Asp Pro Lys Gln Cys Gly Phe Phe Asn
785                 790                 795                 800

Met Met Gln Met Lys Val Asn Tyr Asn His Asn Ile Cys Thr Gln Val
                805                 810                 815

Tyr His Lys Ser Ile Ser Arg Arg Cys Thr Leu Pro Val Thr Ala Ile
            820                 825                 830

Val Ser Ser Leu His Tyr Glu Gly Lys Met Arg Thr Thr Asn Glu Tyr
        835                 840                 845

Asn Lys Pro Ile Val Val Asp Thr Thr Gly Ser Thr Lys Pro Asp Pro
    850                 855                 860

Gly Asp Leu Val Leu Thr Cys Phe Arg Gly Trp Val Lys Gln Leu Gln
865                 870                 875                 880

Ile Asp Tyr Arg Gly Tyr Glu Val Met Thr Ala Ala Ala Ser Gln Gly
                885                 890                 895

Leu Thr Arg Lys Gly Val Tyr Ala Val Arg Gln Lys Val Asn Glu Asn
            900                 905                 910

Pro Leu Tyr Ala Ser Thr Ser Glu His Val Asn Val Leu Leu Thr Arg
        915                 920                 925

Thr Glu Gly Lys Leu Val Trp Lys Thr Leu Ser Gly Asp Pro Trp Ile
    930                 935                 940

Lys Thr Leu Gln Asn Pro Pro Lys Gly Asn Phe Lys Ala Thr Ile Lys
945                 950                 955                 960

Glu Trp Glu Val Glu His Ala Ser Ile Met Ala Gly Ile Cys Ser His
                965                 970                 975

Gln Met Thr Phe Asp Thr Phe Gln Asn Lys Ala Asn Val Cys Trp Ala
            980                 985                 990

Lys Ser Leu Val Pro Ile Leu Glu  Thr Ala Gly Ile Lys  Leu Asn Asp
        995                 1000                1005

Arg Gln  Trp Ser Gln Ile Ile  Gln Ala Phe Lys Glu  Asp Lys Ala
    1010                1015                1020

Tyr Ser  Pro Glu Val Ala Leu  Asn Glu Ile Cys Thr  Arg Met Tyr
    1025                1030                1035

Gly Val  Asp Leu Asp Ser Gly  Leu Phe Ser Lys Pro  Leu Val Ser
    1040                1045                1050

Val Tyr  Tyr Ala Asp Asn His  Trp Asp Asn Arg Pro  Gly Gly Lys
    1055                1060                1065

Met Phe  Gly Phe Asn Pro Glu  Ala Ala Ser Ile Leu  Glu Arg Lys
    1070                1075                1080
```

-continued

```
Tyr Pro  Phe Thr Lys Gly Lys  Trp Asn Ile Asn Lys  Gln Ile Cys
    1085                 1090                 1095

Val Thr  Thr Arg Arg Ile Glu  Asp Phe Asn Pro Thr  Thr Asn Ile
    1100                 1105                 1110

Ile Pro  Ala Asn Arg Arg Leu  Pro His Ser Leu Val  Ala Glu His
    1115                 1120                 1125

Arg Pro  Val Lys Gly Glu Arg  Met Glu Trp Leu Val  Asn Lys Ile
    1130                 1135                 1140

Asn Gly  His His Val Leu Leu  Val Ser Gly Tyr Asn  Leu Ala Leu
    1145                 1150                 1155

Pro Thr  Lys Arg Val Thr Trp  Val Ala Pro Leu Gly  Val Arg Gly
    1160                 1165                 1170

Ala Asp  Tyr Thr Tyr Asn Leu  Glu Leu Gly Leu Pro  Ala Thr Leu
    1175                 1180                 1185

Gly Arg  Tyr Asp Leu Val Val  Ile Asn Ile His Thr  Pro Phe Arg
    1190                 1195                 1200

Ile His  His Tyr Gln Gln Cys  Val Asp His Ala Met  Lys Leu Gln
    1205                 1210                 1215

Met Leu  Gly Gly Asp Ser Leu  Arg Leu Leu Lys Pro  Gly Gly Ser
    1220                 1225                 1230

Leu Leu  Ile Arg Ala Tyr Gly  Tyr Ala Asp Arg Thr  Ser Glu Arg
    1235                 1240                 1245

Val Ile  Cys Val Leu Gly Arg  Lys Phe Arg Ser Ser  Arg Ala Leu
    1250                 1255                 1260

Lys Pro  Pro Cys Val Thr Ser  Asn Thr Glu Met Phe  Phe Leu Phe
    1265                 1270                 1275

Ser Asn  Phe Asp Asn Gly Arg  Arg Asn Phe Thr Thr  His Val Met
    1280                 1285                 1290

Asn Asn  Gln Leu Asn Ala Ala  Phe Val Gly Gln Val  Thr Arg Ala
    1295                 1300                 1305

Gly Cys  Ala Pro Ser Tyr Arg  Val Lys Arg Met Asp  Ile Ala Lys
    1310                 1315                 1320

Asn Asp  Glu Glu Cys Val Val  Asn Ala Ala Asn Pro  Arg Gly Leu
    1325                 1330                 1335

Pro Gly  Asp Gly Val Cys Lys  Ala Val Tyr Lys Lys  Trp Pro Glu
    1340                 1345                 1350

Ser Phe  Lys Asn Ser Ala Thr  Pro Val Gly Thr Ala  Lys Thr Val
    1355                 1360                 1365

Met Cys  Gly Thr Tyr Pro Val  Ile His Ala Val Gly  Pro Asn Phe
    1370                 1375                 1380

Ser Asn  Tyr Ser Glu Ser Glu  Gly Asp Arg Glu Leu  Ala Ala Ala
    1385                 1390                 1395

Tyr Arg  Glu Val Ala Lys Glu  Val Thr Arg Leu Gly  Val Asn Ser
    1400                 1405                 1410

Val Ala  Ile Pro Leu Leu Ser  Thr Gly Val Tyr Ser  Gly Gly Lys
    1415                 1420                 1425

Asp Arg  Leu Thr Gln Ser Leu  Asn His Leu Phe Thr  Ala Met Asp
    1430                 1435                 1440

Ser Thr  Asp Ala Asp Val Val  Ile Tyr Cys Arg Asp  Lys Glu Trp
    1445                 1450                 1455

Glu Lys  Lys Ile Ser Glu Ala  Ile Gln Met Arg Thr  Gln Val Glu
    1460                 1465                 1470

Leu Leu  Asp Glu His Ile Ser  Ile Asp Cys Asp Ile  Val Arg Val
```

```
    1475                1480                1485

His Pro  Asp Ser Ser Leu Ala  Gly Arg Lys Gly Tyr  Ser Thr Thr
    1490                1495                1500

Glu Gly  Ala Leu Tyr Ser Tyr  Leu Glu Gly Thr Arg  Phe His Gln
    1505                1510                1515

Thr Ala  Val Asp Met Ala Glu  Ile His Thr Met Trp  Pro Lys Gln
    1520                1525                1530

Thr Glu  Ala Asn Glu Gln Val  Cys Leu Tyr Ala Leu  Gly Glu Ser
    1535                1540                1545

Ile Glu  Ser Ile Arg Gln Lys  Cys Pro Val Asp Asp  Ala Asp Ala
    1550                1555                1560

Ser Ser  Pro Pro Lys Thr Val  Pro Cys Leu Cys Arg  Tyr Ala Met
    1565                1570                1575

Thr Pro  Glu Arg Val Thr Arg  Leu Arg Met Asn His  Val Thr Ser
    1580                1585                1590

Ile Ile  Val Cys Ser Ser Phe  Pro Leu Pro Lys Tyr  Lys Ile Glu
    1595                1600                1605

Gly Val  Gln Lys Val Lys Cys  Ser Lys Val Met Leu  Phe Asp His
    1610                1615                1620

Asn Val  Pro Ser Arg Val Ser  Pro Arg Glu Tyr Arg  Ser Ser Gln
    1625                1630                1635

Glu Ser  Ala Gln Glu Ala Ser  Thr Ile Thr Ser Leu  Thr His Ser
    1640                1645                1650

Gln Phe  Asp Leu Ser Val Asp  Gly Glu Ile Leu Pro  Val Pro Ser
    1655                1660                1665

Asp Leu  Asp Ala Asp Ala Pro  Ala Leu Glu Pro Ala  Leu Asp Asp
    1670                1675                1680

Gly Ala  Thr His Thr Leu Pro  Ser Thr Thr Gly Asn  Leu Ala Ala
    1685                1690                1695

Val Ser  Asp Trp Val Met Ser  Thr Val Pro Val Ala  Pro Pro Arg
    1700                1705                1710

Arg Arg  Arg Gly Arg Asn Leu  Thr Val Thr Cys Asp  Glu Arg Glu
    1715                1720                1725

Gly Asn  Ile Thr Pro Met Ala  Ser Val Arg Phe Phe  Arg Ala Glu
    1730                1735                1740

Leu Cys  Pro Val Val Gln Glu  Thr Ala Glu Thr Arg  Asp Thr Ala
    1745                1750                1755

Met Ser  Leu Gln Ala Pro Pro  Ser Thr Ala Thr Glu  Pro Asn His
    1760                1765                1770

Pro Pro  Ile Ser Phe Gly Ala  Ser Ser Glu Thr Phe  Pro Ile Thr
    1775                1780                1785

Phe Gly  Asp Phe Asn Glu Gly  Glu Ile Glu Ser Leu  Ser Ser Glu
    1790                1795                1800

Leu Leu  Thr Phe Gly Asp Phe  Leu Pro Gly Glu Val  Asp Asp Leu
    1805                1810                1815

Thr Asp  Ser Asp Trp Ser Thr  Cys Ser Asp Thr Asp  Asp Glu Leu
    1820                1825                1830

Leu Asp  Arg Ala Gly Gly Tyr  Ile Phe Ser Ser Asp  Thr Gly Pro
    1835                1840                1845

Gly His  Leu Gln Gln Lys Ser  Val Arg Gln Ser Val  Leu Pro Val
    1850                1855                1860

Asn Thr  Leu Glu Glu Val His  Glu Glu Lys Cys Tyr  Pro Pro Lys
    1865                1870                1875
```

```
Leu Asp  Glu Ala Lys Glu Gln  Leu Leu Leu Lys Lys  Leu Gln Glu
    1880                 1885                 1890

Ser Ala  Ser Met Ala Asn Arg  Ser Arg Tyr Gln Ser  Arg Lys Val
    1895                 1900                 1905

Glu Asn  Met Lys Ala Ala Ile  Ile Gln Arg Leu Lys  Arg Gly Cys
    1910                 1915                 1920

Arg Leu  Tyr Leu Met Ser Glu  Thr Pro Lys Val Pro  Thr Tyr Arg
    1925                 1930                 1935

Thr Thr  Tyr Pro Ala Pro Val  Tyr Ser Pro Pro Ile  Asn Val Arg
    1940                 1945                 1950

Leu Ser  Asn Pro Glu Ser Ala  Val Ala Ala Cys Asn  Glu Phe Leu
    1955                 1960                 1965

Ala Arg  Asn Tyr Pro Thr Val  Ser Ser Tyr Gln Ile  Thr Asp Glu
    1970                 1975                 1980

Tyr Asp  Ala Tyr Leu Asp Met  Val Asp Gly Ser Glu  Ser Cys Leu
    1985                 1990                 1995

Asp Arg  Ala Thr Phe Asn Pro  Ser Lys Leu Arg Ser  Tyr Pro Lys
    2000                 2005                 2010

Gln His  Ala Tyr His Ala Pro  Ser Ile Arg Ser Ala  Val Pro Ser
    2015                 2020                 2025

Pro Phe  Gln Asn Thr Leu Gln  Asn Val Leu Ala Ala  Ala Thr Lys
    2030                 2035                 2040

Arg Asn  Cys Asn Val Thr Gln  Met Arg Glu Leu Pro  Thr Leu Asp
    2045                 2050                 2055

Ser Ala  Val Phe Asn Val Glu  Cys Phe Lys Lys Phe  Ala Cys Asn
    2060                 2065                 2070

Gln Glu  Tyr Trp Glu Glu Phe  Ala Ala Ser Pro Ile  Arg Ile Thr
    2075                 2080                 2085

Thr Glu  Asn Leu Ala Thr Tyr  Val Thr Lys Leu Lys  Gly Pro Lys
    2090                 2095                 2100

Ala Ala  Ala Leu Phe Ala Lys  Thr His Asn Leu Leu  Pro Leu Gln
    2105                 2110                 2115

Glu Val  Pro Met Asp Arg Phe  Thr Val Asp Met Lys  Arg Asp Val
    2120                 2125                 2130

Lys Val  Thr Pro Gly Thr Lys  His Thr Glu Glu Arg  Pro Lys Val
    2135                 2140                 2145

Gln Val  Ile Gln Ala Ala Glu  Pro Leu Ala Thr Ala  Tyr Leu Cys
    2150                 2155                 2160

Gly Ile  His Arg Glu Leu Val  Arg Arg Leu Asn Ala  Val Leu Leu
    2165                 2170                 2175

Pro Asn  Val His Thr Leu Phe  Asp Met Ser Ala Glu  Asp Phe Asp
    2180                 2185                 2190

Ala Ile  Ile Ala Ala His Phe  Lys Pro Gly Asp Thr  Val Leu Glu
    2195                 2200                 2205

Thr Asp  Ile Ala Ser Phe Asp  Lys Ser Gln Asp Asp  Ser Leu Ala
    2210                 2215                 2220

Leu Thr  Ala Leu Met Leu Leu  Glu Asp Leu Gly Val  Asp His Ser
    2225                 2230                 2235

Leu Leu  Asp Leu Ile Glu Ala  Ala Phe Gly Glu Ile  Ser Ser Cys
    2240                 2245                 2250

His Leu  Pro Thr Gly Thr Arg  Phe Lys Phe Gly Ala  Met Met Lys
    2255                 2260                 2265
```

-continued

```
Ser Gly  Met Phe Leu Thr Leu  Phe Val Asn Thr Leu  Leu Asn Ile
    2270                 2275                 2280

Thr Ile  Ala Ser Arg Val Leu  Glu Asp Arg Leu Thr  Lys Ser Ala
    2285                 2290                 2295

Cys Ala  Ala Phe Ile Gly Asp  Asp Asn Ile Ile His  Gly Val Val
    2300                 2305                 2310

Ser Asp  Glu Leu Met Ala Ala  Arg Cys Ala Thr Trp  Met Asn Met
    2315                 2320                 2325

Glu Val  Lys Ile Ile Asp Ala  Val Val Ser Leu Lys  Ala Pro Tyr
    2330                 2335                 2340

Phe Cys  Gly Gly Phe Ile Leu  His Asp Thr Val Thr  Gly Thr Ala
    2345                 2350                 2355

Cys Arg  Val Ala Asp Pro Leu  Lys Arg Leu Phe Lys  Leu Gly Lys
    2360                 2365                 2370

Pro Leu  Ala Ala Gly Asp Glu  Gln Asp Glu Asp Arg  Arg Arg Ala
    2375                 2380                 2385

Leu Ala  Asp Glu Val Ile Arg  Trp Gln Arg Thr Gly  Leu Ile Asp
    2390                 2395                 2400

Glu Leu  Glu Lys Ala Val Tyr  Ser Arg Tyr Glu Val  Gln Gly Ile
    2405                 2410                 2415

Ser Val  Val Val Met Ser Met  Ala Thr Phe Ala Ser  Ser Arg Ser
    2420                     2425                 2430

Asn Phe  Glu Lys Leu Arg Gly  Pro Val Ile Thr Leu  Tyr Gly Gly
    2435                 2440                 2445

Pro Lys
    2450
```

<210> SEQ ID NO 79
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
aaaaaagatc tgacaacttc aatgtctata aagccacaag acc 43

<210> SEQ ID NO 80
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
tttttgcggc cgcgtcatag tagggtacag ctcataatag tacaag 46

<210> SEQ ID NO 81
<211> LENGTH: 63
<212> TYPE: DNA
<213> ORGANISM: Chikungunya virus
<220> FEATURE:
<221> NAME/KEY: CDS
<222> LOCATION: (13)..(63)

<400> SEQUENCE: 81

```
cgcagcacca ag gac aac ttc aat gtc tat aaa gcc aca aga cca tac cta     51
              Asp Asn Phe Asn Val Tyr Lys Ala Thr Arg Pro Tyr Leu
              1               5                   10
```

```
gct cac tgt cca                                                      63
Ala His Cys Pro
        15


<210> SEQ ID NO 82
<211> LENGTH: 63
<212> TYPE: DNA
<213> ORGANISM: Chikungunya virus
<220> FEATURE:
<221> NAME/KEY: CDS
<222> LOCATION: (1)..(63)

<400> SEQUENCE: 82

ccg cat gag ata atc ttg tac tat tat gag ctg tac cct act atg act      48
Pro His Glu Ile Ile Leu Tyr Tyr Tyr Glu Leu Tyr Pro Thr Met Thr
1               5                   10                  15

gta gta gtt gtg tca                                                  63
Val Val Val Val Ser
            20


<210> SEQ ID NO 83
<211> LENGTH: 17
<212> TYPE: PRT
<213> ORGANISM: Chikungunya virus

<400> SEQUENCE: 83

Asp Asn Phe Asn Val Tyr Lys Ala Thr Arg Pro Tyr Leu Ala His Cys
1               5                   10                  15

Pro


<210> SEQ ID NO 84
<211> LENGTH: 21
<212> TYPE: PRT
<213> ORGANISM: Chikungunya virus

<400> SEQUENCE: 84

Pro His Glu Ile Ile Leu Tyr Tyr Tyr Glu Leu Tyr Pro Thr Met Thr
1               5                   10                  15

Val Val Val Val Ser
            20


<210> SEQ ID NO 85
<211> LENGTH: 1161
<212> TYPE: DNA
<213> ORGANISM: Chikungunya virus
<220> FEATURE:
<221> NAME/KEY: CDS
<222> LOCATION: (13)..(1155)

<400> SEQUENCE: 85

ggatccgcca cc atg ctg ctg agc gtg ccc ctg ctg ctg ggc ctg ctg ggc     51
              Met Leu Leu Ser Val Pro Leu Leu Leu Gly Leu Leu Gly
              1               5                   10

ctg gcc gtg gac aac ttc aac gtg tac aag gct acc aga ccc tac ctg      99
Leu Ala Val Asp Asn Phe Asn Val Tyr Lys Ala Thr Arg Pro Tyr Leu
    15                  20                  25

gcc cac tgc ccc gac tgc ggc gag gga cac agc tgc cac agc ccc gtg     147
Ala His Cys Pro Asp Cys Gly Glu Gly His Ser Cys His Ser Pro Val
30                  35                  40                  45

gcc ctg gag aga atc cgg aac gag gct acc gac ggc acc ctg aag atc     195
Ala Leu Glu Arg Ile Arg Asn Glu Ala Thr Asp Gly Thr Leu Lys Ile
                50                  55                  60

cag gtg agc ctg cag atc ggc atc aag acc gac gac agc cac gac tgg     243
```

-continued

```
Gln Val Ser Leu Gln Ile Gly Ile Lys Thr Asp Asp Ser His Asp Trp
            65                  70                  75

acc aag ctg aga tac atg gac aac cac atg ccc gcc gac gcc gag aga      291
Thr Lys Leu Arg Tyr Met Asp Asn His Met Pro Ala Asp Ala Glu Arg
        80                  85                  90

gcc ggc ctg ttc gtg aga acc agc gcc ccc tgc acc atc acc ggc acc      339
Ala Gly Leu Phe Val Arg Thr Ser Ala Pro Cys Thr Ile Thr Gly Thr
    95                  100                 105

atg ggc cac ttc atc ctg gcc aga tgc ccc aag ggc gag acc ctg acc      387
Met Gly His Phe Ile Leu Ala Arg Cys Pro Lys Gly Glu Thr Leu Thr
110                 115                 120                 125

gtg ggc ttc acc gac agc aga aag atc agc cac agc tgc acc cac ccc      435
Val Gly Phe Thr Asp Ser Arg Lys Ile Ser His Ser Cys Thr His Pro
                130                 135                 140

ttc cac cac gac cct ccc gtg atc ggc aga gag aag ttc cac agc aga      483
Phe His His Asp Pro Pro Val Ile Gly Arg Glu Lys Phe His Ser Arg
            145                 150                 155

ccc cag cac ggc aag gag ctg ccc tgc agc acc tac gtg cag agc acc      531
Pro Gln His Gly Lys Glu Leu Pro Cys Ser Thr Tyr Val Gln Ser Thr
        160                 165                 170

gcc gct aca acc gag gag atc gag gtg cac atg ccc ccc gac acc ccc      579
Ala Ala Thr Thr Glu Glu Ile Glu Val His Met Pro Pro Asp Thr Pro
    175                 180                 185

gac aga acc ctg atg agc cag cag agc ggc aac gtg aag atc acc gtg      627
Asp Arg Thr Leu Met Ser Gln Gln Ser Gly Asn Val Lys Ile Thr Val
190                 195                 200                 205

aac ggc cag acc gtg aga tac aag tgc aac tgc ggc ggc agc aac gag      675
Asn Gly Gln Thr Val Arg Tyr Lys Cys Asn Cys Gly Gly Ser Asn Glu
                210                 215                 220

ggc ctg acc aca acc gac aag gtg atc aac aac tgc aag gtg gac cag      723
Gly Leu Thr Thr Thr Asp Lys Val Ile Asn Asn Cys Lys Val Asp Gln
            225                 230                 235

tgc cac gcc gcc gtg acc aac cac aag aag tgg cag tac aac agc ccc      771
Cys His Ala Ala Val Thr Asn His Lys Lys Trp Gln Tyr Asn Ser Pro
        240                 245                 250

ctg gtg ccc aga aac gcc gag ctg ggc gac aga aag ggc aag atc cac      819
Leu Val Pro Arg Asn Ala Glu Leu Gly Asp Arg Lys Gly Lys Ile His
    255                 260                 265

atc ccc ttc ccc ctg gcc aac gtg acc tgc aga gtg ccc aag gcc aga      867
Ile Pro Phe Pro Leu Ala Asn Val Thr Cys Arg Val Pro Lys Ala Arg
270                 275                 280                 285

aac ccc acc gtg acc tac ggc aag aac cag gtg atc atg ctg ctg tac      915
Asn Pro Thr Val Thr Tyr Gly Lys Asn Gln Val Ile Met Leu Leu Tyr
                290                 295                 300

ccc gat cac ccc acc ctg ctg agc tac aga aac atg ggc gag gag ccc      963
Pro Asp His Pro Thr Leu Leu Ser Tyr Arg Asn Met Gly Glu Glu Pro
            305                 310                 315

aac tac cag gag gag tgg gtg atg cac aag aag gag gtg gtg ctg acc     1011
Asn Tyr Gln Glu Glu Trp Val Met His Lys Lys Glu Val Val Leu Thr
        320                 325                 330

gtg ccc acc gag ggc ctg gag gtg acc tgg ggc aac aac gag ccc tac     1059
Val Pro Thr Glu Gly Leu Glu Val Thr Trp Gly Asn Asn Glu Pro Tyr
    335                 340                 345

aag tac tgg ccc cag ctg agc acc aac ggc acc gcc cac gga cac ccc     1107
Lys Tyr Trp Pro Gln Leu Ser Thr Asn Gly Thr Ala His Gly His Pro
350                 355                 360                 365

cac gag atc atc ctg tac tac tac gag ctg tac ccc acc atg acc tga     1155
His Glu Ile Ile Leu Tyr Tyr Tyr Glu Leu Tyr Pro Thr Met Thr
                370                 375                 380
```

ctcgag 1161

<210> SEQ ID NO 86
<211> LENGTH: 380
<212> TYPE: PRT
<213> ORGANISM: Chikungunya virus

<400> SEQUENCE: 86

Met Leu Leu Ser Val Pro Leu Leu Leu Gly Leu Leu Gly Leu Ala Val
1 5 10 15

Asp Asn Phe Asn Val Tyr Lys Ala Thr Arg Pro Tyr Leu Ala His Cys
20 25 30

Pro Asp Cys Gly Glu Gly His Ser Cys His Ser Pro Val Ala Leu Glu
35 40 45

Arg Ile Arg Asn Glu Ala Thr Asp Gly Thr Leu Lys Ile Gln Val Ser
50 55 60

Leu Gln Ile Gly Ile Lys Thr Asp Asp Ser His Asp Trp Thr Lys Leu
65 70 75 80

Arg Tyr Met Asp Asn His Met Pro Ala Asp Ala Glu Arg Ala Gly Leu
85 90 95

Phe Val Arg Thr Ser Ala Pro Cys Thr Ile Thr Gly Thr Met Gly His
100 105 110

Phe Ile Leu Ala Arg Cys Pro Lys Gly Glu Thr Leu Thr Val Gly Phe
115 120 125

Thr Asp Ser Arg Lys Ile Ser His Ser Cys Thr His Pro Phe His His
130 135 140

Asp Pro Pro Val Ile Gly Arg Glu Lys Phe His Ser Arg Pro Gln His
145 150 155 160

Gly Lys Glu Leu Pro Cys Ser Thr Tyr Val Gln Ser Thr Ala Ala Thr
165 170 175

Thr Glu Glu Ile Glu Val His Met Pro Pro Asp Thr Pro Asp Arg Thr
180 185 190

Leu Met Ser Gln Gln Ser Gly Asn Val Lys Ile Thr Val Asn Gly Gln
195 200 205

Thr Val Arg Tyr Lys Cys Asn Cys Gly Gly Ser Asn Glu Gly Leu Thr
210 215 220

Thr Thr Asp Lys Val Ile Asn Asn Cys Lys Val Asp Gln Cys His Ala
225 230 235 240

Ala Val Thr Asn His Lys Lys Trp Gln Tyr Asn Ser Pro Leu Val Pro
245 250 255

Arg Asn Ala Glu Leu Gly Asp Arg Lys Gly Lys Ile His Ile Pro Phe
260 265 270

Pro Leu Ala Asn Val Thr Cys Arg Val Pro Lys Ala Arg Asn Pro Thr
275 280 285

Val Thr Tyr Gly Lys Asn Gln Val Ile Met Leu Leu Tyr Pro Asp His
290 295 300

Pro Thr Leu Leu Ser Tyr Arg Asn Met Gly Glu Glu Pro Asn Tyr Gln
305 310 315 320

Glu Glu Trp Val Met His Lys Lys Glu Val Val Leu Thr Val Pro Thr
325 330 335

Glu Gly Leu Glu Val Thr Trp Gly Asn Asn Glu Pro Tyr Lys Tyr Trp
340 345 350

Pro Gln Leu Ser Thr Asn Gly Thr Ala His Gly His Pro His Glu Ile
355 360 365

```
Ile Leu Tyr Tyr Tyr Glu Leu Tyr Pro Thr Met Thr
    370                 375                 380


<210> SEQ ID NO 87
<211> LENGTH: 59
<212> TYPE: DNA
<213> ORGANISM: Chikungunya virus

<400> SEQUENCE: 87

tatagatcaa agggctacgc aacccctgaa tagtaacaaa atacaaaatc actaaaaat      59


<210> SEQ ID NO 88
<211> LENGTH: 60
<212> TYPE: DNA
<213> ORGANISM: Chikungunya virus

<400> SEQUENCE: 88

tatagatcaa agggccgaat aacccctgaa tagtaacaaa atatgaaaat caataaaaat     60


<210> SEQ ID NO 89
<211> LENGTH: 59
<212> TYPE: DNA
<213> ORGANISM: Chikungunya virus

<400> SEQUENCE: 89

agtagttcaa agggctataa aacccctgaa tagtaacaaa acataaaatt aataaaaat      59


<210> SEQ ID NO 90
<211> LENGTH: 59
<212> TYPE: DNA
<213> ORGANISM: Chikungunya virus

<400> SEQUENCE: 90

tctagatcaa agggctatat aacccctgaa tagtaacaaa atacaaaatc actaaaaat      59


<210> SEQ ID NO 91
<211> LENGTH: 60
<212> TYPE: DNA
<213> ORGANISM: Chikungunya virus

<400> SEQUENCE: 91

tatagatcaa agggccgaac aacccctgaa tagtaacaaa atataaaaat taataaaaat     60


<210> SEQ ID NO 92
<211> LENGTH: 60
<212> TYPE: DNA
<213> ORGANISM: Chikungunya virus

<400> SEQUENCE: 92

agtagttcaa agggctataa aaacccctga atagtaacaa aacataaaac taataaaaat     60


<210> SEQ ID NO 93
<211> LENGTH: 60
<212> TYPE: DNA
<213> ORGANISM: Chikungunya virus

<400> SEQUENCE: 93

attagatcaa agggctatac aacccctgaa tagtaacaaa acacaaaaac caataaaaat     60


<210> SEQ ID NO 94
<211> LENGTH: 60
<212> TYPE: DNA
<213> ORGANISM: Chikungunya virus
```

<400> SEQUENCE: 94
tatagatcaa agggctatat taacccctga atagtaacaa aacacaaaaa caataaaaac 60

<210> SEQ ID NO 95
<211> LENGTH: 60
<212> TYPE: DNA
<213> ORGANISM: Chikungunya virus

<400> SEQUENCE: 95
agtagttcaa agggctacaa aacccctgaa tagtaacaaa acataaaatg taataaaaat 60

<210> SEQ ID NO 96
<211> LENGTH: 60
<212> TYPE: DNA
<213> ORGANISM: Chikungunya virus

<400> SEQUENCE: 96
agtagttcaa agggctataa aaacccctga atagtaacaa aacataaaac taataaaaat 60

<210> SEQ ID NO 97
<211> LENGTH: 60
<212> TYPE: DNA
<213> ORGANISM: Chikungunya virus

<400> SEQUENCE: 97
tatagatcaa aggcttgaat aacccctgaa taataataaa atataaaaat aaataagaat 60

<210> SEQ ID NO 98
<211> LENGTH: 59
<212> TYPE: DNA
<213> ORGANISM: Chikungunya virus

<400> SEQUENCE: 98
agatgttcaa agtggctata aaacccctgaa tagtaataaa acataaaatt aataaggat 59

<210> SEQ ID NO 99
<211> LENGTH: 59
<212> TYPE: DNA
<213> ORGANISM: Chikungunya virus

<400> SEQUENCE: 99
tgtagatcaa agggctatat aacccctgaa tagtaacaaa atacaaaatc actaaaaat 59

<210> SEQ ID NO 100
<211> LENGTH: 61
<212> TYPE: DNA
<213> ORGANISM: Chikungunya virus

<400> SEQUENCE: 100
agtagttcaa agggctataa aaacccctga atagtaacaa aacataaaac ctaataaaga 60
t 61

<210> SEQ ID NO 101
<211> LENGTH: 60
<212> TYPE: DNA
<213> ORGANISM: Chikungunya virus

<400> SEQUENCE: 101
agatgttcaa agtggctata aaacccctga atagtaataa aacataaaat taataaggat 60

<210> SEQ ID NO 102
<211> LENGTH: 26

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102

uaaguccca acgcaucggg aaacua                                          26


<210> SEQ ID NO 103
<211> LENGTH: 60
<212> TYPE: DNA
<213> ORGANISM: Chikungunya virus

<400> SEQUENCE: 103

ccgcatgaga taatcttgta ctattatgag ctgtacccta ctatgacgcg gccgcaaaaa     60
```